United States Patent
Glad et al.

(10) Patent No.: US 10,683,293 B2
(45) Date of Patent: Jun. 16, 2020

(54) OPTIONALLY FUSED HETEROCYCLYL-SUBSTITUTED DERIVATIVES OF PYRIMIDINE USEFUL FOR THE TREATMENT OF INFLAMMATORY, METABOLIC, ONCOLOGIC AND AUTOIMMUNE DISEASES

(71) Applicant: NUEVOLUTION A/S, Copenhagen (DK)

(72) Inventors: Sanne Schrøder Glad, Ballerup (DK); Niels Grøn Nørager, Copenhagen (DK); Ian Sarvary, Kristinehamn (SE); Alex Haahr Gouliaev, Veksø Sjælland (DK); Lene Teuber, Værløse (DK); Luigi Piero Stasi, Søllerød (DK)

(73) Assignee: NUEVOLUTION A/S, Copenhagen (DK)

( * ) Notice: Subject to any disclaimer, the term of this patent is extended or adjusted under 35 U.S.C. 154(b) by 0 days.

(21) Appl. No.: 15/501,226

(22) PCT Filed: Jul. 31, 2015

(86) PCT No.: PCT/EP2015/067692
§ 371 (c)(1),
(2) Date: Feb. 2, 2017

(87) PCT Pub. No.: WO2016/020288
PCT Pub. Date: Feb. 11, 2016

(65) Prior Publication Data
US 2017/0342074 A1    Nov. 30, 2017

(30) Foreign Application Priority Data

Aug. 4, 2014  (SE) ........................ 1450920
Nov. 21, 2014 (SE) ........................ 1451406

(51) Int. Cl.
| | | |
|---|---|---|
| C07D 417/12 | (2006.01) |
| C07D 413/12 | (2006.01) |
| C07D 411/12 | (2006.01) |
| C07D 409/14 | (2006.01) |
| C07D 405/14 | (2006.01) |
| C07D 239/48 | (2006.01) |
| C07D 405/12 | (2006.01) |
| C07D 403/14 | (2006.01) |
| C07D 401/12 | (2006.01) |
| C07D 401/14 | (2006.01) |
| C07D 409/12 | (2006.01) |
| C07D 487/04 | (2006.01) |
| C07D 403/12 | (2006.01) |
| C07D 413/14 | (2006.01) |
| C07D 403/04 | (2006.01) |
| C07D 413/04 | (2006.01) |
| C07D 417/14 | (2006.01) |
| C07D 451/04 | (2006.01) |
| C07D 471/10 | (2006.01) |
| C07D 401/04 | (2006.01) |
| C07D 471/04 | (2006.01) |

(52) U.S. Cl.
CPC ......... *C07D 487/04* (2013.01); *C07D 239/48* (2013.01); *C07D 401/04* (2013.01); *C07D 401/12* (2013.01); *C07D 401/14* (2013.01); *C07D 403/04* (2013.01); *C07D 403/12* (2013.01); *C07D 403/14* (2013.01); *C07D 405/12* (2013.01); *C07D 405/14* (2013.01); *C07D 409/12* (2013.01); *C07D 409/14* (2013.01); *C07D 411/12* (2013.01); *C07D 413/04* (2013.01); *C07D 413/12* (2013.01); *C07D 413/14* (2013.01); *C07D 417/12* (2013.01); *C07D 417/14* (2013.01); *C07D 451/04* (2013.01); *C07D 471/04* (2013.01); *C07D 471/10* (2013.01)

(58) Field of Classification Search
CPC .. C07D 417/12; C07D 413/12; C07D 411/12; C07D 409/14; C07D 405/14; C07D 239/48; C07D 405/12; C07D 403/14; C07D 401/12; C07D 401/14; C07D 409/12
See application file for complete search history.

(56) References Cited

U.S. PATENT DOCUMENTS

| | | | |
|---|---|---|---|
| 4,298,602 A | 11/1981 | Pawloski |
| 5,530,129 A | 6/1996 | Gallenkamp et al. |
| 8,338,439 B2 | 12/2012 | Singh et al. |
| 2003/0191121 A1 | 10/2003 | Miller et al. |
| 2004/0054173 A1 | 3/2004 | Kimura et al. |

(Continued)

FOREIGN PATENT DOCUMENTS

| | | |
|---|---|---|
| CL | 201700271 | 2/2017 |
| CL | 201701288 | 5/2017 |

(Continued)

OTHER PUBLICATIONS

Fin et al., Retinoic Acid Receptor-Related Orphan Receptors: Critical Roles in Tumorigenesis, Frontiers in Immunology, vol. 9, Article 1187, pp. 1-10 (Year: 2018).*

(Continued)

*Primary Examiner* — Brenda L Coleman
(74) *Attorney, Agent, or Firm* — Marshall, Gerstein & Borun LLP

(57) ABSTRACT

Disclosed are compounds active towards nuclear receptors, pharmaceutical compositions containing the compounds and use of the compounds in therapy.

42 Claims, 2 Drawing Sheets

(56) References Cited

U.S. PATENT DOCUMENTS

| | | |
|---|---|---|
| 2004/0087577 A1 | 5/2004 | Pratt et al. |
| 2004/0097492 A1 | 5/2004 | Pratt et al. |
| 2004/0180906 A1 | 9/2004 | Flynn et al. |
| 2005/0124623 A1 | 6/2005 | Bender et al. |
| 2005/0153989 A1 | 7/2005 | Grotzfeld et al. |
| 2005/0182045 A1 | 8/2005 | Nagase et al. |
| 2005/0245536 A1 | 11/2005 | Hao et al. |
| 2005/0288286 A1 | 12/2005 | Flynn et al. |
| 2006/0004018 A1 | 1/2006 | Xue et al. |
| 2006/0052374 A1 | 3/2006 | Carroll et al. |
| 2006/0069093 A1 | 3/2006 | Scarborough et al. |
| 2006/0235017 A1 | 10/2006 | Cirillo et al. |
| 2006/0241104 A1 | 10/2006 | Borzilleri et al. |
| 2006/0281712 A1 | 12/2006 | Yen et al. |
| 2008/0021063 A1 | 1/2008 | Kazantsev |
| 2008/0070319 A1 | 3/2008 | Makino |
| 2009/0018112 A1 | 1/2009 | Chapdelaine et al. |
| 2009/0018116 A1 | 1/2009 | Jin et al. |
| 2009/0018134 A1 | 1/2009 | Pike et al. |
| 2009/0018166 A1 | 1/2009 | Amin et al. |
| 2009/0029994 A1 | 1/2009 | Nakamura et al. |
| 2009/0036434 A1* | 2/2009 | Jones .................. C07D 239/48 514/227.8 |
| 2009/0069559 A1 | 3/2009 | Kazantsev |
| 2009/0143302 A1 | 6/2009 | Yen et al. |
| 2009/0163545 A1 | 6/2009 | Goldfarb |
| 2010/0152445 A1 | 6/2010 | Bolin et al. |
| 2010/0249153 A1 | 9/2010 | Tandon et al. |
| 2011/0135604 A1 | 6/2011 | Casarez et al. |
| 2011/0281842 A1 | 11/2011 | Michaelides et al. |
| 2012/0142714 A1 | 6/2012 | Yasuma et al. |
| 2012/0214762 A1 | 8/2012 | Staben et al. |
| 2012/0264798 A1 | 10/2012 | Sinha et al. |
| 2013/0158031 A1 | 6/2013 | Cai et al. |
| 2013/0190249 A1 | 7/2013 | Lemieux et al. |
| 2013/0231519 A1 | 9/2013 | Heinrich et al. |
| 2014/0018361 A1 | 1/2014 | Harriman et al. |

FOREIGN PATENT DOCUMENTS

| | | |
|---|---|---|
| CL | 201700287 | 11/2017 |
| CL | 201701289 | 3/2018 |
| CN | 102786512 A | 11/2012 |
| CN | 103588795 A | 2/2014 |
| DE | 3737748 A1 | 5/1989 |
| DE | 4124942 A1 | 1/1993 |
| DE | 10108480 A1 | 9/2002 |
| EP | 384244 A1 | 8/1990 |
| EP | 0419831 A2 | 4/1991 |
| EP | 0434341 A1 | 6/1991 |
| EP | 1396489 A1 | 3/2004 |
| FR | 2870541 A1 | 11/2005 |
| FR | 2926556 A1 | 7/2009 |
| JP | H04-348326 A | 12/1992 |
| JP | H06-220059 A | 8/1994 |
| JP | H10-251255 A | 9/1998 |
| JP | 2000-086663 A1 | 3/2000 |
| JP | 2002-284779 A | 10/2002 |
| JP | 2007-507529 A | 3/2007 |
| JP | 2007-119450 A | 5/2007 |
| JP | 2007-126551 A | 5/2007 |
| JP | 2007-186580 A | 7/2007 |
| JP | 2008-501698 A | 1/2008 |
| WO | 93/14082 A1 | 7/1993 |
| WO | 93/22311 A1 | 11/1993 |
| WO | 96/40142 A1 | 12/1996 |
| WO | 97/12878 A1 | 4/1997 |
| WO | 97/44038 A1 | 11/1997 |
| WO | 98/23613 A1 | 6/1998 |
| WO | 01/012601 A1 | 2/2001 |
| WO | 2001/030778 A1 | 5/2001 |
| WO | 2001047921 A1 | 7/2001 |
| WO | 01/57038 A1 | 8/2001 |
| WO | 2002/022584 A1 | 3/2002 |
| WO | 2003/011836 A1 | 2/2003 |
| WO | 2003/045941 A1 | 6/2003 |
| WO | 2003/066604 A2 | 8/2003 |
| WO | 2003/075828 A2 | 9/2003 |
| WO | 2003/094918 A1 | 11/2003 |
| WO | 2003/101959 A1 | 12/2003 |
| WO | 2004/000843 A1 | 12/2003 |
| WO | 2004/014384 A2 | 2/2004 |
| WO | 2004/039785 A1 | 5/2004 |
| WO | 2004/039786 A1 | 5/2004 |
| WO | 2004/039788 A1 | 5/2004 |
| WO | 2004/054987 A1 | 7/2004 |
| WO | 2004/060305 A2 | 7/2004 |
| WO | 2004/060306 A2 | 7/2004 |
| WO | 2004/083174 A2 | 9/2004 |
| WO | 2004/083185 A2 | 9/2004 |
| WO | 2004/101557 A1 | 11/2004 |
| WO | 2004/110350 A2 | 12/2004 |
| WO | 2005/033072 A2 | 4/2005 |
| WO | 2005/040119 A1 | 5/2005 |
| WO | 2005/067546 A2 | 7/2005 |
| WO | 2005/068457 A1 | 7/2005 |
| WO | 2005/084667 A1 | 9/2005 |
| WO | 2005/111003 A1 | 11/2005 |
| WO | 2005/117909 A2 | 12/2005 |
| WO | 2005/121121 A2 | 12/2005 |
| WO | 2005/123731 A2 | 12/2005 |
| WO | 2006/004741 A2 | 1/2006 |
| WO | 2006/045828 A1 | 5/2006 |
| WO | 2006/074057 A2 | 7/2006 |
| WO | 2006/076706 A1 | 7/2006 |
| WO | 2006/091963 A1 | 8/2006 |
| WO | 2006/122773 A1 | 11/2006 |
| WO | 2007/012661 A1 | 2/2007 |
| WO | 2007/021941 A2 | 2/2007 |
| WO | 2007/030574 A2 | 3/2007 |
| WO | 2007/068418 A1 | 6/2007 |
| WO | 2007/072163 A2 | 6/2007 |
| WO | 2007/072201 A2 | 6/2007 |
| WO | 2007/080382 A1 | 7/2007 |
| WO | 2007/088277 A1 | 8/2007 |
| WO | 2007/107545 A1 | 9/2007 |
| WO | 2007/121280 A1 | 10/2007 |
| WO | 2008/005368 A2 | 1/2008 |
| WO | 2008/005538 A2 | 1/2008 |
| WO | 2008/011476 A2 | 1/2008 |
| WO | 2008/023159 A1 | 2/2008 |
| WO | 2008/023180 A1 | 2/2008 |
| WO | 2008/074982 A1 | 6/2008 |
| WO | 2008/104077 A1 | 9/2008 |
| WO | 2008/115973 A2 | 9/2008 |
| WO | 2008/152093 A1 | 12/2008 |
| WO | 2009/007749 A1 | 1/2009 |
| WO | 2009/007750 A1 | 1/2009 |
| WO | 2009/007751 A2 | 1/2009 |
| WO | 2009/017664 A1 | 2/2009 |
| WO | 2009/055331 A2 | 4/2009 |
| WO | 2009/079683 A1 | 7/2009 |
| WO | 2009/099193 A1 | 8/2009 |
| WO | 2009/102736 A1 | 8/2009 |
| WO | 2009/103432 A2 | 8/2009 |
| WO | 2009/123221 A1 | 10/2009 |
| WO | 2009/128661 A2 | 10/2009 |
| WO | 2009/134384 A1 | 11/2009 |
| WO | 2009/149188 A1 | 12/2009 |
| WO | 2009/156484 A2 | 12/2009 |
| WO | 2010/012442 A1 | 2/2010 |
| WO | 2010/020432 A2 | 2/2010 |
| WO | 2010/022121 A1 | 2/2010 |
| WO | 2010/022125 A1 | 2/2010 |
| WO | 2010/022128 A1 | 2/2010 |
| WO | 2010/036316 A1 | 4/2010 |
| WO | 2010/048207 A2 | 4/2010 |
| WO | 2010/052569 A2 | 5/2010 |
| WO | 2010/080996 A1 | 7/2010 |
| WO | 2010/100127 A1 | 9/2010 |
| WO | 2010/114957 A1 | 10/2010 |
| WO | 2010/120994 A2 | 10/2010 |
| WO | 2010/129053 A2 | 11/2010 |

(56) References Cited

FOREIGN PATENT DOCUMENTS

| | | |
|---|---|---|
| WO | 2010/129242 A2 | 11/2010 |
| WO | 2010/135470 A1 | 11/2010 |
| WO | 2011/017513 A1 | 2/2011 |
| WO | 2011/022440 A2 | 2/2011 |
| WO | 2011/029043 A1 | 3/2011 |
| WO | 2011/029046 A1 | 3/2011 |
| WO | 2011/049946 A1 | 4/2011 |
| WO | 2011/055911 A1 | 5/2011 |
| WO | 2011/075684 A1 | 6/2011 |
| WO | 2011/078143 A1 | 6/2011 |
| WO | 2011/105572 A1 | 9/2011 |
| WO | 2011/115940 A1 | 9/2011 |
| WO | 2011/143129 A1 | 11/2011 |
| WO | 2011/153553 A2 | 12/2011 |
| WO | 2012/037226 A1 | 3/2012 |
| WO | 2012/041872 A1 | 4/2012 |
| WO | 2012/041873 A1 | 4/2012 |
| WO | 2012/046869 A1 | 4/2012 |
| WO | 2012/074022 A1 | 6/2012 |
| WO | 2012/103295 A2 | 8/2012 |
| WO | 2012/147516 A1 | 11/2012 |
| WO | 2012/147890 A1 | 11/2012 |
| WO | 2012/163773 A1 | 12/2012 |
| WO | 2012/166716 A1 | 12/2012 |
| WO | 2013/017461 A1 | 2/2013 |
| WO | 2013/019824 A2 | 2/2013 |
| WO | 2013/022766 A1 | 2/2013 |
| WO | WO-2013/036912 A2 | 3/2013 |
| WO | 2013/052526 A1 | 4/2013 |
| WO | 2013/068306 A1 | 5/2013 |
| WO | 2013/117649 A1 | 8/2013 |
| WO | 2013/134467 A1 | 9/2013 |
| WO | 2013/157022 A1 | 10/2013 |
| WO | 2013/178075 A1 | 12/2013 |
| WO | 2013/183673 A1 | 12/2013 |
| WO | 2014/005129 A1 | 1/2014 |
| WO | 2014/015523 A1 | 1/2014 |
| WO | 2014/015675 A1 | 1/2014 |
| WO | 2014/015830 A1 | 1/2014 |
| WO | 2014/015936 A1 | 1/2014 |
| WO | 2014/019908 A2 | 2/2014 |
| WO | WO-2016/020288 A1 | 2/2016 |
| WO | WO-2016/020320 A1 | 2/2016 |
| WO | WO-2016/081670 A2 | 5/2016 |
| WO | WO-2016/081918 A1 | 5/2016 |

OTHER PUBLICATIONS

Bronner S.M., et al. "RORγ antagonists and inverse agonists: a patent review", Expert Opinion on Therapeutics Patents, 27(1):101-112 (2017).

Cyr P. et al., "Recent progress on nuclear receptor RORγ modulators", Bioorganic & Medicinal Chemistry Letters 26:4387-4393 (2016).

Chang M.R. et al., "RORs in Autoimmune Disease", Sphingosine-1-Phosphate Signaling in Immunology and Infectious Diseases, Current Topics in Microbiology and Immunology 378:171-182 (2014).

Huh et al., "Small molecule inhibitors of RORγt: Targeting Th17 cells and other applications", NIH Public Access Author Manuscript, Eur J Immunol. 42(9):2232-2237 (2012).

Solt et al., "Action of RORs and their ligands in (patho) physiology", Trends in Endocrinology and Metabolism 23(12): 619-627 (2012).

Cook et al., "Retinoic Acid-Related Orphan Receptors (RORs): Regulatory Functions in Immunity, Development, Circadian Rhythm, and Metabolism", Nuclear Receptor Research 2, Article ID 101185:1-24 (2015).

Fauber et al., "Modulators of the Nuclear Receptor Retinoic Acid Receptor-Related Orphan Receptor-γ (RORγ or RORc)", J. Med. Chem. 57:5871-5892 (2014).

Kamenecka et al., "Synthetic modulators of the retinoic acid receptor-related orphan receptors", Med. Chem. Commun. 4:764-776 (2013).

Search Report for Swedish Patent Application No. 1451406-1, dated May 29, 2015.

Traverso J.J. et al., The Synthesis and Pharmacological Activities of Amide, Sulfamide, and Urea Derivatives of 4,6-Diaminopyrimidines, Journal of medical & pharmaceutical chemistry:808-815 (1962).

Montebugnoli D. et al., "Traceless solid-phase synthesis of 2,4,6-chlorodiamino and triaminopyrimidines", Tetrahedron, 59:7147-7156 (2003).

Kosary J. et al., "Preparation of pyrimidine derivatives with potential cardiotonic activity", Acta Pharmacetical Hungarica, 56,6:241-247 (abstract CA 112:216531), Retrieved from Chemical Abstmcts (1989).

International Search Report and Written Opinion for PCT/EP2015/067692, dated Sep. 21, 2015.

M.J. Kim et al., "Substituted pyrimidines as cannabinoid CB1 receptor ligands", Bioorganic & Medicinal Chemistry Letters, 19: 4692-4697 (2009).

M.R. Caira, "Crystalline Polymorphism of Organic Compounds", Topics in Current Chemistry, vol. 198: 163-208, 1998.

N.A. Tyukavkina et al., "Bioorganicheskaya himiya", Moskva, Drofa: 83-85 (2005) with partial English translation.

D.C. Pryde et al., "The discovery of a novel protoptype small molecule TLR7 agonist for the treatment of hepatitis C virus infection", Med.Chem.Commun 2: 185-189 (2011).

Shi-Xin FA et al., "Synthesis, Structure, and Fullerene-Complexing Property of Azacalix[6]aromatics". J. Org. Chem. v. 79: 3559-3571 (2014).

M. Klecka et al., "Direct C—H borylation and C—H arylation of pyrrolo[2,3d]pyrimidines: synthesis of 6,8-disubstituted 7-deazapurines", Org. Biomol. Chem., v.7: 866-868 (2009).

Y. Han et al., "Efficient and library-friendly synthesis of furo- and thienol[2,3-d] pyrimidin-4-amine derivatives by microwave irradiation", Tetrahedron Letters, v. 51: 629-632 (2010).

C.E. Müller et al.,"Chiral Pyrrolo[2,3d]pyrimidine and Pyrimido[4,5-b]indole Derivatives: Structure-Activity Relationships of Potent, Highly Stereoselective $A_1$-Adenosine Receptor Antagonists", J.Med. Chem. v.39: 2482-2491 (1996).

K.H. Yoo et al., "Synthesis of Mono-, Di-, and Triaminosubstituted-Pyrimidine Derivatives", Korean J. of Med. Chem. v.9: 83-86 (1999).

J.P. Marquet et al., "Sur une nouvelle série d'analogues puriques á action antimitotique: relations structure-activité", European Journal of medicinal chemistry—Chimie Therapeutique, v. 6: 427-438 (1971).

Y. Ma et al., "Combinatorial Synthesis of Substituted Biaryls and Heterocyclic Arylamines", J. Comb. Chem., 6(3): 426-430 (2004).

P. Upadhyaya et al. "Identification of Adducts Formed in the Reactions of 5'-Acetoxy-N'-nitrosonornicotine with Deoxyadenosine, Thymidine, and DNA.", Chem.Res.Toxicol. 21: 2164-2171 (2008).

Fan et al., "Retinoic Acid Receptor-Related Orphan Receptors: Critical Roles in Tumorigenesis", Frontiers in Immunology. vol. 9. Article 1187: 1-10 (2018).

D. Montebugnoli et al., "Traceless solid-phasse synthesis of 2,4,6-chlorodiamino and triaminopyrimidines", Tetrahedron 59: 7147-7153 (2003).

M.D. Mashkovskiy, "Lekarstvennie sredstva", Moscow, Medicina, part 1: 8 (1993) with partial English translation.

33 Substances CAS Registry Numbers: 1515972-57-2; 357614-47-2; 1537342-62-3; 357614-416; 1509319-43-0; 357614-39-2; 1508163-79-8; 1543241-09-3; 1507549-73-6; 1539058-95-1; 1504736-18-8; 1538881-49-0;1502546-73-7; 537342-62-3; 1502393-44-3; 1536916-94-5; 1501684-14-5; 1536417-79-4; 1500313-42-7; 1529040-93-4; 1499708-15-4; 1526739-06-9; 1020711-29-8; 1526652-58-3; 1020711-25-4; 1522387-54-7; 403668-62-2; 1522083-19-7; 357614-51-8; 1521680-88-5; 357614-49-4; 1519623-48-3; 357614-48-3 (2014).

Cas Reg. No. 1539496-16-6, STN Entry Date: Feb. 9, 2014; 4,6-Pyrimidinediamine, N6-ethyl-N4-methyl-5-(1-methylethyl)-N4-[(1-methyl-1H-pyrazol-4-yl)methyl]-.

Cas Reg. No. 1540192-80-0, STN Entry Date: Feb. 10, 2014; 4,6-Pyrimidinediamine, N4,N6-diethyl-2,5-dimethyl-N4-(2-thienylmethyl)-.

(56) References Cited

OTHER PUBLICATIONS

Cas Reg. No. 1542543-24-7, STN Entry Date: Feb. 14, 2014; 4,6-Pyrimidinediamine, N4-[(4-chlorophenyl)methyl]-N4,5-dimethyl-N6-propyl-.

Cas Reg. No. 1543250-40-3, STN Entry Date: Feb. 14, 2014; 4,6-Pyrimidinediamine, 5-methoxy-N4-methyl-N6-propyl-N4-[(tetrahydro-2H-pyran-3-yl)methyl]-.

Cas Reg. No. 1544786-92-6, STN Entry Date: Feb. 16, 2014; 4,6-Pyrimidinediamine, N6-ethyl-N4,2-dimethyl-N4-[(5-methyl-2-furanyl)methyl]-.

Database Registry,2013, RN 1445611 - 7, 1424439 [03, 2006.01, 01, 1, 1423758 - [35, 2006.01, 74] 3, 13118835, 1281111-22- 5, 1281111-13- 4; Retrieved from STN international [online] ;retrieved on Apr. 12, 2019.

Google patents translation, WO 2011105572, downloaded Sep. 22, 2017. I downloaded a copy on Nov. 14, 2019. Okay?.

International Search Report and Written Opinion for PCT/EP2015/067713, dated Sep. 22, 2015.

Ma et al., "Combinatorial Synthesis of Substituted Biaryls and Heterocyclic Arylamines", J. Comb. Chem, 6(3):426-430 ;2004).

PubChem (National Center for Biotechnology Information. PubChem Compound Database; CID=3236972, https://pubchem.ncbi.nlm.nih.gov/compound/3236972 (accessed Sep. 15, 2018), created Aug. 16, 2005, pp. 1-13).

Search Report for Swedish Patent Application No. 1450920-2, dated Feb. 17, 2015.

Wu et al., "Discovery of aminoheterocycles as potent and brain penetrant prolylcarboxypeptidase inhibitors", Bioorganic & Medicinal Chemistry Letters 22:1727-1730 (2012).

Yang et al., "Discovery of Tertiary Amine and Indole Derivatives as Potent RORγt Inverse Agonists", ACS Medical Chemistry Letters, 5:65-68 (2014).

* cited by examiner

A

OPTIONALLY FUSED HETEROCYCLYL-SUBSTITUTED DERIVATIVES OF PYRIMIDINE USEFUL FOR THE TREATMENT OF INFLAMMATORY, METABOLIC, ONCOLOGIC AND AUTOIMMUNE DISEASES

CROSS-REFERENCE TO RELATED APPLICATIONS

This application claims priority to the PCT Application PCT/EP2015/067692 filed on 31 Jul. 2015 which further claims the priority of Swedish Patent No. SE 1450920-2 filed on 4 Aug. 2014 and Swedish Patent No. SE 1451406-1 filed on 21 Nov. 2014 in the Swedish Patent and Trademark Office. The specifications of the above referenced patent applications are incorporated herein by reference in their entireties.

FIELD

Aspects and embodiments described herein relate to compounds active towards nuclear receptors, pharmaceutical compositions comprising the compounds, and methods of treating inflammatory, metabolic, oncologic and autoimmune diseases or disorders using the compounds.

BACKGROUND

Nuclear receptors are a family of transcription factors involved in the regulation of physiological functions, such as cell differentiation, embryonic development, and organ physiology. Nuclear receptors have also been identified as important pathological regulators in diseases such as cancer, diabetes, and autoimmune disorders.

Examples of nuclear receptors include the nuclear retinoic acid receptor-related orphan receptors (RORs). RORs contain four principal domains: an N-terminal A/B domain, a DNA-binding domain, a hinge domain and a ligand binding domain. Binding of ligands to the ligand-binding domain is believed to cause conformational changes in the domain resulting in downstream actions. Different isoforms exist and these isoforms differ in their N-terminal A/B domain only.

RORs consist of three members, namely ROR alpha (RORα), ROR beta (RORβ) and ROR gamma (RORγ or RORc).

RORα is expressed in many tissues such as cerebellar Purkinje cells, the liver, thymus, skeletal muscle, skin, lung, adipose tissue and kidney.

RORγ also has a broad expression pattern and was the most recently discovered of the three members. To date, five splice variants have been recorded for RORγ coding for two different protein isoforms: RORγ1 and RORγ2 (RORγ2 is also known as RORγt). Generally RORγ is used to describe RORγ1 and/or RORγt. RORγ1 is expressed in many tissues and is predominantly expressed in the kidneys, liver, and skeletal muscle. In contrast, expression of RORγt is restricted to lymphoid organs such as the thymus. RORγt has been identified as a key regulator of Th17 cell differentiation. Th17 cells are a subset of T helper cells which preferentially produce the cytokines IL-17A, IL-17F, IL-21 and IL-22. Th17 cells and their products have been shown to be associated with the pathology of many human inflammatory and autoimmune disorders.

There is thus evidence that RORα and RORγ play a role in the pathogenesis of many diseases.

It would be desirable to provide compounds that modulate the activity of RORα and/or RORγ for use in treating inflammatory, metabolic and autoimmune diseases.

SUMMARY

In one aspect provided herein are compounds of Formula (I)

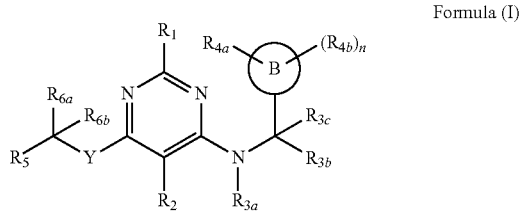

Formula (I)

or pharmaceutically acceptable salts, hydrates, solvates, polymorphs, and stereoisomers thereof, wherein:

Y is NR or O;

R is hydrogen or substituted or unsubstituted $C_{1-4}$ alkyl;

$R_1$ is selected from the group consisting of hydrogen, —OH, halogen, substituted or unsubstituted $C_{1-4}$ alkyl, substituted or unsubstituted $C_{1-4}$ alkoxy, and substituted or unsubstituted $C_{2-4}$ alkenyl;

$R_2$ is selected from the group consisting of hydrogen, halogen, substituted or unsubstituted $C_{1-4}$ alkyl, substituted or unsubstituted $C_{1-4}$ alkoxy, —CN, and —OH;

or R and $R_2$ are combined to form a substituted or unsubstituted fused ring; or $R_2$ and $R_{3a}$ are combined to form a substituted or unsubstituted fused ring;

$R_{4a}$ is selected from the group consisting of hydrogen, halogen, —OH, substituted or unsubstituted $C_{1-6}$ alkyl, substituted or unsubstituted $C_1$-$C_6$ alkoxy, substituted or unsubstituted $C_{1-6}$ alkenyl, substituted or unsubstituted aryl, substituted or unsubstituted aryl-$C_{1-6}$ alkyl, substituted or unsubstituted $C_3$-$C_6$ cycloalkyl, substituted or unsubstituted heteroaryl, and substituted or unsubstituted heteroaryl-$C_{1-6}$ alkyl;

$R_{4b}$ is selected from the group consisting of hydrogen, oxo, halogen, —OH, substituted or unsubstituted $C_{1-4}$ alkyl, substituted or unsubstituted $C_{1-4}$ alkoxy, and —C(=O)$R_{10}$;

$R_5$ is selected from the group consisting of —(CR$_8$R$_9$)pOR$_{12}$, —(CR$_8$R$_9$)p-CR$_{13}$R$_{14}$R$_{15}$, —(CR$_8$R$_9$)p-C(=O)OR$_7$, and —(CR$_8$R$_9$)p-C(=O)NR$_8$R$_9$;

n and p are integers independently selected from the group consisting of 0, 1, 2, 3 and 4;

$R_{6a}$, $R_{6b}$ are independently selected from the group consisting of hydrogen, halogen, substituted or unsubstituted $C_{1-6}$ alkyl, substituted or unsubstituted $C_{1-6}$ alkenyl, substituted or unsubstituted $C_{2-6}$ alkynyl, substituted or unsubstituted $C_{1-6}$ alkoxy, substituted or unsubstituted $C_{1-6}$ heteroalkyl, substituted or unsubstituted $C_{3-8}$ cycloalkyl, substituted or unsubstituted $C_{3-8}$ cycloalkenyl, substituted or unsubstituted $C_{2-9}$ heteroalicyclyl, substituted or unsubstituted aryl, and substituted or unsubstituted heteroaryl, or $R_{6a}$ and $R_{6b}$ are taken together to form an oxo group or a ring system selected from substituted or unsubstituted $C_{1-6}$ cycloalkyl, substituted or unsubstituted $C_{2-9}$ heteroalicyclyl, or $R_{6a}$ and $R_{13}$ are taken together to form a ring system selected from substituted or unsubstituted $C_{3-6}$ cycloalkyl, and substituted or unsubstituted $C_{2-5}$ heteroalicyclyl;

$R_7$, $R_8$, $R_9$, and $R_{12}$, are independently selected from the group consisting of hydrogen, substituted or unsubstituted $C_{1-6}$ alkyl, substituted or unsubstituted $C_{3-6}$ cycloalkyl, and substituted or unsubstituted $C_{2-9}$ heteroalicyclyl;

$R_{10}$ is selected from the group consisting of $C_{1-6}$ alkyl, $C_{1-6}$ alkoxy, —OH, —NH$_2$, —NH($C_{1-6}$ alkyl), —N($C_{1-6}$ alkyl)$_2$, and $C_{3-7}$ cycloalkyl;

$R_{13}$ is absent, or selected from the group consisting of hydrogen, —CN, —OH, substituted or unsubstituted $C_{1-6}$ alkyl, substituted or unsubstituted $C_{1-6}$ alkenyl, substituted or unsubstituted $C_{1-6}$ alkoxy, substituted or unsubstituted $C_{3-8}$ cycloalkyl, substituted or unsubstituted $C_{3-8}$ cycloalkenyl, and —(CR$_8$R$_9$)p-C(=O)OR$_7$, —(CR$_8$R$_9$)p-SO$_2$R$_7$, and —(CR$_8$R$_9$)p-C(=O)NR$_8$R$_9$;

$R_{14}$ and $R_{15}$ are independently selected from the group consisting of hydrogen, and substituted or unsubstituted $C_{1-6}$ alkyl, substituted or unsubstituted $C_{3-6}$ cycloalkyl, and substituted or unsubstituted $C_{2-9}$ heteroalicyclyl; or $R_{14}$ and $R_{15}$ are combined to form a ring system selected from the group consisting of substituted or unsubstituted $C_{3-8}$ cycloalkyl, substituted or unsubstituted $C_{3-8}$ cycloalkenyl, substituted or unsubstituted $C_{2-9}$ heteroalicyclyl, substituted or unsubstituted aryl, and substituted or unsubstituted heteroaryl;

B is a ring system selected from the group consisting of aryl, heteroaryl, and, $C_2$-$C_9$ heteroalicyclyl;

$R_{3a}$ is selected from the group consisting of substituted or unsubstituted $C_{1-6}$ alkyl, substituted or unsubstituted $C_{1-6}$ alkoxy, substituted or unsubstituted aryl, substituted or unsubstituted heteroaryl, substituted or unsubstituted $C_{3-8}$ cycloalkyl, substituted or unsubstituted $C_{3-8}$ cycloalkenyl, and substituted or unsubstituted $C_{2-9}$ heteroalicyclyl;

$R_{3b}$ and $R_{3c}$, are independently selected from the group consisting of hydrogen, —CN, substituted or unsubstituted $C_{1-6}$ alkyl, substituted or unsubstituted $C_{1-6}$ alkoxy, substituted or unsubstituted aryl, substituted or unsubstituted heteroaryl, substituted or unsubstituted $C_{3-8}$ cycloalkyl, substituted or unsubstituted $C_{3-8}$ cycloalkenyl, substituted or unsubstituted $C_{2-9}$ heteroalicyclyl, —(CR$_8$R$_9$)p-C(=O)OR$_7$, and —(CR$_8$R$_9$)p-C(=O)NR$_8$R$_9$, or $R_{3b}$ and $R_{3c}$ are combined to form an oxo group or a ring system selected from the group consisting of substituted or unsubstituted $C_{3-8}$ cycloalkyl substituted or unsubstituted $C_{3-8}$ cycloalkenyl, substituted or unsubstituted $C_{2-9}$ heteroalicyclyl; or $R_{3b}$ and $R_{4a}$ or $R_{4b}$ are combined to form a fused ring, and wherein whenever $R_2$ is hydrogen $R_1$ cannot be chloro, and with the proviso that the compound is not

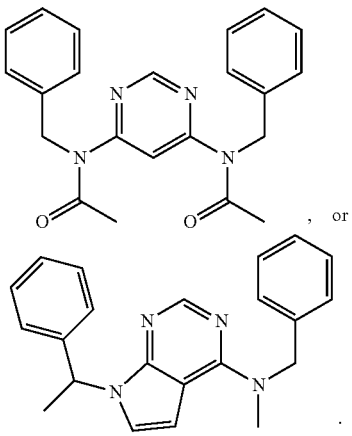

According to a further aspect, R and $R_2$ or $R_2$ and $R_{3a}$ are combined to form a fused ring. In another aspect, $R_5$ is —(CR$_8$R$_9$)p-C(=O)OR$_7$, or —(CR$_8$R$_9$)p-C(=O)NR$_8$R$_9$. Alternatively, $R_5$ is —(CR$_8$R$_9$)p-CR$_{13}$R$_{14}$R$_{15}$ wherein $R_{14}$ and $R_{15}$ are combined to form a ring system.

According to another aspect, there is provided a pharmaceutical composition comprising a compound of the herein above described type and at least one pharmaceutical acceptable excipient.

According to yet another aspect, the herein above described compound or pharmaceutical composition are for use in therapy.

According to another aspect, the herein above described compound or pharmaceutical composition are for use in the treatment and/or prevention of inflammatory, metabolic and autoimmune diseases or disorders.

In another aspect, the herein above described compound or pharmaceutical composition are for modulating the activity of a retinoic acid receptor-related orphan receptor (ROR).

Further, advantageous features of various embodiments are defined in the dependent claims and within the detailed description below.

DETAILED DESCRIPTION OF PREFERRED EMBODIMENTS

Definitions

Unless defined otherwise, all technical and scientific terms used herein have the same meaning as is commonly understood by one of ordinary skill in the art. All patents, applications, published applications and other publications referenced herein are incorporated by reference in their entirety. In the event that there are a plurality of definitions for a term herein, those in this section prevail unless stated otherwise.

As used herein, any "R" group(s) such as, without limitation, $R_1$, $R_2$, $R_3$, $R_4$, $R_5$, $R_8$, $R_9$, and $R_{10}$, represent substituents that can be attached to the indicated atom. A non-limiting list of R groups includes but is not limited to hydrogen, alkyl, alkenyl, alkynyl, cycloalkyl, cycloalkenyl, cycloalkynyl, aryl, heteroaryl, and heteroalicyclyl. If two "R" groups are covalently bonded to the same atom or to adjacent atoms, then they may be "taken together" or "combined" as defined herein to form a cycloalkyl, aryl, heteroaryl or heteroalicyclyl group. For example, without limitation, if $R_a$ and $R_b$ of an NR$_a$R$_b$ group are indicated to be "taken together" or "combined", it means that they are covalently bonded to one another at their terminal atoms to form a ring that includes the nitrogen:

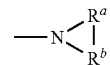

As readily recognized by the skilled person, any given group disclosed herein may comprise further hydrogen(s) than the one(s) provided by a R-group, being hydrogen, attached to the group.

Whenever a group is described as being "unsubstituted or substituted," if substituted, the substituent(s) (which may be present one or more times, such as 1, 2, 3 or 4 times) are independently selected from alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, oxo, alkoxy, aryloxy, acyl, ester, O-carboxy, mercapto, alkylthio, arylthio, cyano, halogen, carbonyl, thiocarbonyl, C-amido, N-amido, S-sulfonamido, N-sulfonamido, nitro, silyl, sulfenyl, sulfinyl, sulfonyl, haloalkyl, haloalkoxy, trihalomethanesulfonyl, trihalomethanesulfonamido, and amino, including mono- and di-substituted amino groups, and the protected derivatives thereof.

When a substituent on a group is deemed to be "substituted," the substitutent itself is substituted with one or more of the indicated substitutents. When the referenced substituent is substituted, it is meant that one or more hydrogen atoms on the referenced substituent may be replaced with a group(s) individually and independently selected from alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, oxo, alkoxy, aryloxy, acyl, ester, O-carboxy, mercapto, alkylthio, arylthio, cyano, halogen, carbonyl, thiocarbonyl, C-amido, N-amido, S-sulfonamido, N-sulfonamido, nitro, silyl, sulfenyl, sulfinyl, sulfonyl, haloalkyl, haloalkoxy, trihalomethanesulfonyl, trihalomethanesulfonamido, and amino, including mono- and di-substituted amino groups, and the protected derivatives thereof. The protecting groups that may form the protective derivatives of the above substituents are known to those of skill in the art and may be found in references Greene and Wuts, Protective Groups in Organic Synthesis, $3^{rd}$ Ed., John Wiley & Sons, New York, N.Y., 1999, which is hereby incorporated by reference in its entirety.

As used herein, "$C_m$ to $C_n$," "$C_m$-$C_n$" or "$C_{m-n}$" in which "m" and "n" are integers refers to the number of carbon atoms in the relevant group. That is, the group can contain from "m" to "n", inclusive, carbon atoms. Thus, for example, a "$C_1$ to $C_6$ alkyl" group refers to all alkyl groups having from 1 to 6 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$—, $CH_3CH(CH)_3CH_2$—, $CH_3CH(CH)_3CH_2$— and $(CH_3)_3C$—. If no "m" and "n" are designated with regard to a group, the broadest range described in these definitions is to be assumed.

As used herein, "alkyl" refers to a straight or branched hydrocarbon chain group that is fully saturated (no double or triple bonds). The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 10 carbon atoms, such as "$C_{1-6}$". The alkyl group could also be a lower alkyl having 1 to 4 carbon atoms. The alkyl group of the compounds may be designated as "$C_1$-$C_4$ alkyl," "$C_{1-4}$ alkyl" or similar designations. By way of example only, "$C_1$-$C_4$ alkyl" or "$C_{1-4}$ alkyl" indicates that there are one to four carbon atoms in the alkyl chain, i.e., the alkyl chain is selected from the group consisting of methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl, hexyl, and the like. When substituted, the substituent group(s) is(are) one or more group(s) individually and independently selected from alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, oxo, alkoxy, aryloxy, acyl, ester, O-carboxy, mercapto, alkylthio, arylthio, cyano, halogen, carbonyl, thiocarbonyl, C-amido, N-amido, S-sulfonamido, N-sulfonamido, nitro, silyl, sulfenyl, sulfinyl, sulfonyl, haloalkyl, haloalkoxy, trihalomethanesulfonyl, trihalomethanesulfonamido, and amino, including mono- and di-substituted amino groups, and the protected derivatives thereof.

As used herein, "alkenyl" refers to an alkyl group that contains in the straight or branched hydrocarbon chain one or more double bonds. If more than one double bond is present, the double bonds may be conjugated or not conjugated. The alkenyl group may have 2 to 20 carbon atoms (whenever it appears herein, a numerical range such as "2 to 20" refers to each integer in the given range; e.g., "2 to 20 carbon atoms" means that the alkenyl group may consist of 2 carbon atoms, 3 carbon atoms, 4 carbon atoms, etc., up to and including 20 carbon atoms, although the present definition also covers the occurrence of the term "alkenyl" where no numerical range is designated). When substituted, the substituent group(s) is(are) one or more group(s) individually and independently selected from alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, oxo, alkoxy, mercapto, alkylthio, cyano, halogen, nitro, haloalkyl, haloalkoxy, and amino, including mono- and di-substituted amino groups, and the protected derivatives thereof.

As used herein, "alkynyl" refers to an alkyl group that contains in the straight or branched hydrocarbon chain one or more triple bonds. The alkynyl group may have 2 to 20 carbon atoms (whenever it appears herein, a numerical range such as "2 to 20" refers to each integer in the given range; e.g., "2 to 20 carbon atoms" means that the alkynyl group may consist of 2 carbon atoms, 3 carbon atoms, 4 carbon atoms, etc., up to and including 20 carbon atoms, although the present definition also covers the occurrence of the term "alkynyl" where no numerical range is designated). An alkynyl group may be unsubstituted or substituted. When substituted, the substituent(s) may be selected from the same groups disclosed above with regard to alkenyl group substitution.

As used herein, "hetero" may be attached to a group and refers to one or more carbon atom(s) and the associated hydrogen atom(s) in the attached group have been independently replaced with the same or different heteroatoms selected from nitrogen, oxygen, phosphorus and sulfur.

As used herein, "heteroalkyl," by itself or in combination with another term, refers to a straight or branched alkyl group consisting of the stated number of carbon atoms, where one or more carbon atom(s), such as 1, 2, 3 or 4 carbon atom(s), and the associated hydrogen atom(s) have been independently replaced with the same or different heteroatoms selected from nitrogen, oxygen and sulfur. The carbon atom(s) being replace may be in the middle or at the end of the alkyl group. Examples of heteroalkyl include, but are not limited to, —S-alkyl, —O-alkyl, —NH-alkyl, -alkylene-O-alkyl, etc As used herein, "aryl" refers to a carbocyclic (all carbon) ring or two or more fused rings (rings that share two adjacent carbon atoms) that have a fully delocalized pi-electron system. Examples of aryl groups include, but are not limited to, benzene, naphthalene and azulene. An aryl group may be substituted. When substituted, hydrogen atoms are replaced by substituent group(s) that is(are) one or more group(s) independently selected from alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, oxo, alkoxy, aryloxy, acyl, ester, O-carboxy, mercapto, alkylthio, arylthio, cyano, halogen, carbonyl, thiocarbonyl, C-amido, N-amido, S-sulfonamido, N-sulfonamido, nitro, silyl, sulfenyl, sulfinyl, sulfonyl, haloalkyl, haloalkoxy, trihalomethanesulfonyl, trihalomethanesulfonamido, and amino, including mono- and di-substituted amino groups, and the protected derivatives thereof. When substituted, substituents on an aryl group may form a non-aromatic ring fused to the aryl group, including a cycloalkyl, cycloalkenyl, cycloalkynyl, and heterocyclyl.

As used herein, "heteroaryl" refers to a monocyclic or multicyclic aromatic ring system (a ring system with fully delocalized pi-electron system), in which at least one of the atoms in the ring system is a heteroatom, that is, an element other than carbon, including but not limited to, nitrogen, oxygen and sulfur. Examples of monocyclic "heteroaryl" include, but are not limited to, furan, thiophene, phthalazine, pyrrole, oxazole, thiazole, imidazole, pyrazole, isoxazole, isothiazole, triazole, thiadiazole, pyridine, pyridazine, pyrimidine, pyrazine, tetrazole, and triazine. Examples of multicyclic "heteroaryl" include, but are not limited to, quinoline, isoquinoline, quinazoline, quinoxaline, indole, purines, benzofuran, benzothiophene, benzopyranones (e.g. coumarin, chromone, and isocoumarin). A heteroaryl may be substituted. When substituted, hydrogen atoms are replaced by substituent group(s) that is(are) one or more group(s) independently selected from alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, oxo, alkoxy, aryloxy, acyl, ester, O-carboxy, mercapto, alkylthio, arylthio, cyano, halogen, carbonyl, thiocarbonyl, C-amido, N-amido, S-sulfonamido, N-sulfonamido, nitro, silyl, sulfenyl, sulfinyl, sulfonyl, haloalkyl, haloalkoxy, trihalomethanesulfonyl, trihalomethanesulfonamido, and amino, including mono- and di-substituted amino groups, and the protected derivatives thereof. When substituted, substituents on a heteroaryl group may form a non-aromatic ring fused to the aryl group, including a cycloalkyl, cycloalkenyl, cycloalkynyl, and heterocyclyl.

An "aralkyl" or "arylalkyl" is an aryl group connected, as a substituent, via an alkylene group. The alkylene and aryl group of an aralkyl may be substituted. Examples include but are not limited to benzyl, substituted benzyl, 2-phenylethyl, 3-phenylpropyl, and naphthylalkyl. In some cases, the alkylene group is a lower alkylene group.

A "heteroaralkyl" or "heteroarylalkyl" is heteroaryl group connected, as a substituent, via an alkylene group. The alkylene and heteroaryl group of heteroaralkyl may be substituted. Examples include but are not limited to 2-thienylmethyl, 3-thienylmethyl, furylmethyl, thienylethyl, pyrrolylalkyl, pyridylalkyl, isoxazolylalkyl, pyrazolylalkyl and imidazolylalkyl, and their substituted as well as benzo-fused analogs. In some cases, the alkylene group is a lower alkylene group.

An "alkylene" is a straight-chained tethering group, forming bonds to connect molecular fragments via their terminal carbon atoms. The alkylene may have 1 to 20 carbon atoms. The alkylene may also be a medium size alkylene having 1 to 10 carbon atoms, such as "$C_{1-6}$" The alkylene could also be a lower alkylene having 1 to 4 carbon atoms. The alkylene may be designated as "$C_1$-$C_4$ alkylene", "$C_{1-4}$ alkylene" or similar designations. Non-limiting examples include, methylene (—$CH_2$—), ethylene (—$CH_2CH_2$—), propylene (—$CH_2CH_2CH_2$—), and butylene (—$(CH_2)_4$—) groups. In the case of methylene, the two connected fragments are connected to the same carbon atom. A lower alkylene group may be substituted.

As used herein, "heteroalkylene" by itself or in combination with another term refers to an alkylene group consisting of the stated number of carbon atoms in which one or more of the carbon atoms, such as 1, 2, 3 or 4 carbon atom(s), are independently replaced with the same or different heteroatoms selected from oxygen, sulfur and nitrogen. Examples of heteroalkylene include, but not limited to —$CH_2$—O—, —$CH_2$—$CH_2$—O—, —$CH_2$—$CH_2$—$CH_2$—O—, —$CH_2$—NH—, —$CH_2$—$CH_2$—NH—, —$CH_2$—$CH_2$—$CH_2$—NH—, —$CH_2$—$CH_2$—NH—$CH_2$—, —O—$CH_2$—$CH_2$—O—$CH_2$—$CH_2$—O—, —O—$CH_2$—$CH_2$—O—$CH_2$—$CH_2$—, and the like.

As used herein, "alkylidene" refers to a divalent group, such as =CR'R", which is attached to one carbon of another group, forming a double bond. Alkylidene groups include, but are not limited to, methylidene (=$CH_2$) and ethylidene (=$CHCH_3$). As used herein, "arylalkylidene" refers to an alkylidene group in which either R' or R" is an aryl group. An alkylidene group may be substituted.

As used herein, "alkoxy" refers to the group —OR wherein R is an alkyl, e.g. methoxy, ethoxy, n-propoxy, cyclopropoxy, 1-methylethoxy (isopropoxy), n-butoxy, iso-butoxy, sec-butoxy, tert-butoxy, amoxy, tert-amoxy and the like. An alkoxy may be substituted.

As used herein, "alkylthio" refers to the formula —SR wherein R is an alkyl is defined as above, e.g. methylmercapto, ethylmercapto, n-propylmercapto, 1-methylethylmercapto (isopropylmercapto), n-butylmercapto, iso-butylmercapto, sec-butylmercapto, tert-butylmercapto, and the like. An alkylthio may be substituted.

As used herein, "aryloxy" and "arylthio" refers to RO— and RS—, in which R is an aryl as defined above, e.g., phenoxy, naphthalenyloxy, azulenyloxy, anthracenyloxy, naphthalenylthio, phenylthio and the like. Both an aryloxy and arylthio may be substituted.

As used herein, "alkenyloxy" refers to the formula —OR wherein R is an alkenyl as defined above, e.g., vinyloxy, propenyloxy, n-butenyloxy, iso-butenyloxy, sec-pentenyloxy, tert-pentenyloxy, and the like. The alkenyloxy may be substituted.

As used herein, "acyl" refers to a hydrogen, alkyl, alkenyl, alkynyl, or aryl connected, as substituents, via a carbonyl group. Examples include formyl, acetyl, propanoyl, benzoyl, and acryl. An acyl may be substituted.

As used herein, "cycloalkyl" refers to a completely saturated (no double bonds) mono- or multi-cyclic hydrocarbon ring system. When composed of two or more rings, the rings may be joined together in a fused, bridged or spiro-connected fashion. Cycloalkyl groups may range from $C_3$ to $C_{10}$, such as from $C_3$ to $C_6$. A cycloalkyl group may be unsubstituted or substituted. Typical cycloalkyl groups include, but are in no way limited to, cyclopropyl, cyclobutyl, cyclopentyl, cyclohexyl, and the like. If substituted, the substituent(s) may be an alkyl or selected from those indicated above with regard to substitution of an alkyl group unless otherwise indicated. When substituted, substituents on a cycloalkyl group may form an aromatic ring fused to the cycloalkyl group, including an aryl and a heteroaryl.

As used herein, "cycloalkenyl" refers to a cycloalkyl group that contains one or more double bonds in the ring although, if there is more than one, they cannot form a fully delocalized pi-electron system in the ring (otherwise the group would be "aryl," as defined herein). When composed of two or more rings, the rings may be connected together in a fused, bridged or spiro-connected fashion. Cycloalkenyl groups may range from $C_3$ to $C_{10}$, such as from $C_3$ to $C_8$ or from $C_5$ to $C_{10}$. For example, $C_{3-8}$ cycloalkenyl includes $C_{4-8}$ cycloalkenyl, $C_{5-8}$ cycloalkenyl or $C_{6-8}$ cycloalkenyl. A cycloalkenyl group may be unsubstituted or substituted. When substituted, the substituent(s) may be an alkyl or selected from the groups disclosed above with regard to alkyl group substitution unless otherwise indicated. When substituted, substituents on a cycloalkenyl group may form an aromatic ring fused to the cycloalkenyl group, including an aryl and a heteroaryl.

As used herein, "cycloalkynyl" refers to a cycloalkyl group that contains one or more triple bonds in the ring. When composed of two or more rings, the rings may be joined together in a fused, bridged or spiro-connected fashion. Cycloalkynyl groups may range from $C_8$ to $C_{12}$. A cycloalkynyl group may be unsubstituted or substituted. When substituted, the substituent(s) may be an alkyl or selected from the groups disclosed above with regard to alkyl group substitution unless otherwise indicated. When substituted, substituents on a cycloalkynyl group may form an aromatic ring fused to the cycloalkynyl group, including an aryl and a heteroaryl.

As used herein, "heteroalicyclic" or "heteroalicyclyl" refers to a 3- to 18 membered ring which consists of carbon atoms and from one to five heteroatoms selected from the group consisting of nitrogen, oxygen and sulfur. The heteroalicyclic or heteroalicyclyl groups may range from $C_2$ to $C_{10}$, in some embodiments it may range from $C_2$ to $C_9$, and in other embodiments it may range from $C_2$ to $C_8$. The "heteroalicyclic" or "heteroalicyclyl" may be monocyclic, bicyclic, tricyclic, or tetracyclic ring system, which may be joined together in a fused, bridged or spiro-connected fashion; and the nitrogen, carbon and sulfur atoms in the "heteroalicyclic" or "heteroalicyclyl" may be oxidized; the nitrogen may be quaternized; and the rings may also contain one or more double bonds provided that they do not form a fully delocalized pi-electron system throughout all the rings, examples are 2H-benzo[b][1,4]oxazin-3(4H)-one, 3,4-dihydroquinolin-2(1H)-one, 1,2,3,4-tetrahydroquino line, 3,4-dihydro-2H-benzo[b][1,4]oxazine, 2,3-dihydrobenzo[d]oxazole, 2,3-dihydro-1H-benzo[d]imidazole, indoline, and 1,3-dihydro-2H-benzo[d]imidazol-2-one, and benzo[d]oxazol-2(3H)-one. Heteroalicyclyl groups may be unsubstituted or substituted. When substituted, the substituent(s) may be one or more groups independently selected from the group consisting of alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, oxo, alkoxy, aryloxy, acyl, ester, O-carboxy, mercapto, alkylthio, arylthio, cyano, halogen, C-amido, N-amido, S-sulfonamido, N-sulfonamido, isocyanato, thiocyanato, isothiocyanato, nitro, silyl, haloalkyl, haloalkoxy, trihalomethanesulfonyl, trihalomethanesulfonamido, and amino, including mono- and di-substituted amino groups, and the protected derivatives thereof. Examples of such "heteroalicyclic" or "heteroalicyclyl" include but are not limited to, azepinyl, dioxolanyl, imidazolinyl, morpholinyl, oxetanyl, oxiranyl, piperidinyl N-Oxide, piperidinyl, piperazinyl, pyrrolidinyl, pyranyl, 4-piperidonyl, pyrazolidinyl, 2-oxopyrrolidinyl, tetrahydrofuranyl, tetrahydropyranyl, thiamorpholinyl, thiamorpholinyl sulfoxide, and thiamorpholinyl sulfone. When substituted, substituents on a heteroalicyclyl group may form an aromatic ring fused to the heteroalicyclyl group, including an aryl and a heteroaryl.

A "(cycloalkyl)alkyl" is a cycloalkyl group connected, as a substituent, via an alkylene group. The alkylene and cycloalkyl of a (cycloalkyl)alkyl may be substituted. Examples include but are not limited to cyclopropylmethyl, cyclobutylmethyl, cyclopropylethyl, cyclopropylbutyl, cyclobutylethyl, cyclopropylisopropyl, cyclopentylmethyl, cyclopentylethyl, cyclohexylmethyl, cyclohexylethyl, cycloheptylmethyl, and the like. In some cases, the alkylene group is a lower alkylene group.

A "(cycloalkenyl)alkyl" is a cycloalkenyl group connected, as a substituent, via an alkylene group. The alkylene and cycloalkenyl of a (cycloalkenyl)alkyl may be substituted. In some cases, the alkylene group is a lower alkylene group.

A "(cycloalkynyl)alkyl" is a cycloalkynyl group connected, as a substituent, via an alkylene group. The alkylene and cycloalkynyl of a (cycloalkynyl)alkyl may be substituted. In some cases, the alkylene group is a lower alkylene group.

As used herein, "halo" or "halogen" refers to F (fluoro), Cl (chloro), Br (bromo) or I (iodo).

As used herein, "haloalkyl" refers to an alkyl group in which one or more of the hydrogen atoms are replaced by halogen. Such groups include but are not limited to, chloromethyl, fluoromethyl, difluoromethyl, trifluoromethyl and 1-chloro-2-fluoromethyl, 2-fluoroisobutyl. A haloalkyl may be substituted.

As used herein, "haloalkoxy" refers to a RO-group in which R is a haloalkyl group. Such groups include but are not limited to, chloromethoxy, fluoromethoxy, difluoromethoxy, trifluoromethoxy and 1-chloro-2-fluoromethoxy, 2-fluoroisobutyoxy. A haloalkoxy may be substituted.

An "O-carboxy" group refers to a "RC(=O)O—" group in which R can be hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl, as defined herein. An O-carboxy may be substituted.

A "C-carboxy" group refers to a "—C(=O)OR" group in which R can be the same as defined with respect to O-carboxy. A C-carboxy may be substituted.

A "trihalomethanesulfonyl" group refers to an "$X_3CSO_2$—" group" wherein X is a halogen.

A dashed bond, ⋯, represents an optional unsaturation between the atoms forming the bond. This bond may be unsaturated (e.g. C=C, C=N, C=O) or saturated (e.g. C—C, C—N, C—O). When a dashed bond is present in a ring system it may form part of an aromatic ring system.

A "nitro" group refers to a "—$NO_2$" group

A "cyano" group refers to a "—CN" group.

A "cyanato" group refers to an "—OCN" group.

An "isocyanato" group refers to a "—NCO" group.

A "thiocyanato" group refers to a "—SCN" group.

A "carbonyl" group refers to a "—C(=O)—" group.

A "thiocarbonyl" group refers to a "—C(=S)—" group.

An "oxo" group refers to a "=O" group.

A "hydroxy" group or "hydroxyl" group refers to an "—OH" group.

An "isothiocyanato" group refers to an "—NCS" group.

A "sulfinyl" group refers to an "—S(=O)—R" group in which R can be the same as defined with respect to O-carboxy. A sulfinyl may be substituted.

A "sulfonyl" group refers to an "$SO_2R$" group in which R can be the same as defined with respect to O-carboxy. A sulfonyl may be substituted.

An "S-sulfonamido" group refers to a "—$SO_2NR_AR_B$" group in which $R_A$ and $R_B$ independently of each other can be the same as defined with respect to the R group as defined for O-carboxy, or combined to form a ring system selected from the group consisting of substituted or unsubstituted $C_{3-8}$ cycloalkyl, substituted or unsubstituted $C_{3-8}$ cycloalkenyl, substituted or unsubstituted $C_{3-8}$ cycloalkyl, substituted or unsubstituted $C_{3-8}$ cycloalkenyl substituted or unsubstituted heteroalicyclyl, substituted or unsubstituted aryl, and substituted or unsubstituted heteroaryl. A S-sulfonamido may be substituted.

An "N-sulfonamido" group refers to a "RSO$_2$N(R$_A$)—" group in which R and R$_A$ independently of each other can be the same as defined with respect to the R group as defined for O-carboxy. An N-sulfonamido may be substituted.

A "trihalomethanesulfonamido" group refers to an "X$_3$CSO$_2$N(R)—" group with X as halogen and R can be the same as defined with respect to O-carboxy. A trihalomethanesulfonamido may be substituted.

A "C-amido" group refers to a "—C(═O)NR$_A$R$_B$" group in which R$_A$ and R$_B$ independently of each other can be the same as defined with respect to the R group as defined for O-carboxy, or combined to form a ring system selected from the group consisting of substituted or unsubstituted C$_{3-8}$ cycloalkyl, substituted or unsubstituted C$_{3-8}$ cycloalkenyl, substituted or unsubstituted C$_{3-8}$ cycloalkyl, substituted or unsubstituted C$_{3-8}$ cycloalkenyl substituted or unsubstituted heteroalicyclyl, substituted or unsubstituted aryl, and substituted or unsubstituted heteroaryl. A C-amido may be substituted.

An "N-amido" group refers to a "RC(═O)NR$_A$—" group in which R and R$_A$ independently of each other can be the same as defined with respect to the R group as defined for O-carboxy. An N-amido may be substituted.

An "ester" refers to a "—C(═O)OR" group in which R can be the same as defined with respect to O-carboxy. An ester may be substituted.

A lower alkoxyalkyl refers to an alkoxy group connected via a lower alkylene group. A lower alkoxyalkyl may be substituted.

An "amine" or "amino" refers to "RNH$_2$" (a primary amine), "R$_2$NH" (a secondary amine), "R$_3$N" (a tertiary amine). An amino group may be substituted.

A lower aminoalkyl refers to an amino group connected via a lower alkylene group. A lower aminoalkyl may be substituted.

Any unsubstituted or monosubstituted amine group on a compound herein can be converted to an amide, any hydroxyl group can be converted to an ester and any carboxyl group can be converted to either an amide or ester using techniques well-known to those skilled in the art (see, for example, Greene and Wuts, Protective Groups in Organic Synthesis, 3$^{rd}$ Ed., John Wiley & Sons, New York, N.Y., 1999).

As used herein, the abbreviations for any protective groups, amino acids and other compounds, are, unless indicated otherwise, in accord with their common usage, recognized abbreviations, or the IUPAC-IUB Commission on Biochemical Nomenclature (See, Biochem. 11:942-944 (1972)).

As employed herein, the following terms have their accepted meaning in the chemical literature.

| | |
|---|---|
| CDCl$_3$ | deuterated chloroform |
| DCM | dichloromethane or CH$_2$Cl$_2$ |
| DIPEA | N,N-diisopropylethylamine |
| DMF | N,N-dimethylformamide |
| DMSO | dimethyl sulfoxide |
| EtOAc | ethyl acetate |
| h | hour(s) |
| MeOH | methanol |
| TFA | trifluoroacetic acid |

It is understood that, in any compound disclosed herein having one or more chiral centers, if an absolute stereochemistry is not expressly indicated, then each center may independently be of R-configuration or S-configuration or a mixture thereof. Thus, the compounds provided herein may be enatiomerically pure or be stereoisomeric mixtures. Further, compounds provided herein may be scalemic mixtures. In addition, it is understood that in any compound having one or more double bond(s) generating geometrical isomers that can be defined as E or Z each double bond may independently be E or Z or a mixture thereof. Likewise, all tautomeric forms are also intended to be included.

As used herein, "tautomer" and "tautomeric" refer to alternate forms of a compound disclosed herein that differ in the position of a proton. Non-limiting examples include enol-keto and imine-enamine tautomers, or the tautomeric forms of heteroaryl groups containing a ring atom attached to both a ring —NH— moiety and a ring ═N— moiety such as pyrazoles, imidazoles, benzimidazoles, triazoles, and tetrazoles.

It is understood that isotopes may be present in the compounds described herein. Each chemical element as represented in a compound structure may include any isotope of said element. For example, in a compound described herein a hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

As used herein, "pharmaceutically acceptable salt" refers to a salt of a compound that does not abrogate the biological activity and properties of the compound. Pharmaceutical salts can be obtained by reaction of a compound disclosed herein with an acid or base. Base-formed salts include, without limitation, ammonium salt (NH$_4$$^+$); alkali metal, such as, without limitation, sodium or potassium, salts; alkaline earth, such as, without limitation, calcium or magnesium, salts; salts of organic bases such as, without limitation, dicyclohexylamine, piperidine, piperazine, methylpiperazine, N-methyl-D-glucamine, diethylamine, ethylenediamine, tris(hydroxymethyl)methylamine; and salts with the amino group of amino acids such as, without limitation, arginine and lysine. Useful acid-based salts include, without limitation, acetates, adipates, aspartates, ascorbates, benzoates, butyrates, caparate, caproate, caprylate, camsylates, citrates, decanoates, formates, fumarates, gluconates, glutarate, glycolates, hexanoates, laurates, lactates, maleates, nitrates, oleates, oxalates, octanoates, propanoates, palmitates, phosphates, sebacates, succinates, stearates, sulfates, sulfonates, such as methanesulfonates, ethanesulfonates, p-toluenesulfonates, salicylates, tartrates, and tosylates.

Pharmaceutically acceptable solvates and hydrates are complexes of a compound with one or more solvent of water molecules, or 1 to about 100, or 1 to about 10, or one to about 2, 3 or 4, solvent or water molecules.

As used herein, a "prodrug" refers to a compound that may not be pharmaceutically active but that is converted into an active drug upon in vivo administration. The prodrug may be designed to alter the metabolic stability or the transport characteristics of a drug, to mask side effects or toxicity, to improve the flavor of a drug or to alter other characteristics or properties of a drug. Prodrugs are often useful because they may be easier to administer than the parent drug. They may, for example, be bioavailable by oral administration whereas the parent drug is not. The prodrug may also have better solubility than the active parent drug in pharmaceutical compositions. An example, without limitation, of a prodrug would be a compound disclosed herein, which is administered as an ester (the "prodrug") to facilitate absorption through a cell membrane where water solubility is detrimental to mobility but which then is metabolically hydrolyzed to a carboxylic acid (the active entity) once inside the cell where water-solubility is beneficial. A further example of a prodrug might be a short peptide (polyaminoacid) bonded to an acid group where the peptide is metabolized in vivo to release the active parent compound. By virtue of knowledge of pharmacodynamic processes and drug metabolism in vivo, those skilled in the art, once a pharmaceutically active compound is known, can design prodrugs of the compound (see, e.g. Nogrady (1985) *Medicinal Chemistry A Biochemical Approach*, Oxford University Press, New York, pages 388-392).

"Anti-drug" refers to a compound or composition acting against or opposing illicit drugs or their use. Compounds of the present application may act as anti-drugs.

As used herein, to "modulate" the activity of a receptor means either to activate it, i.e., to increase its cellular function over the base level measured in the particular environment in which it is found, or deactivate it, i.e., decrease its cellular function to less than the measured base level in the environment in which it is found and/or render it unable to perform its cellular function at all, even in the presence of a natural binding partner. A natural binding partner is an endogenous molecule that is an agonist for the receptor.

An "agonist" is defined as a compound that increases the basal activity of a receptor (i.e. signal transduction mediated by the receptor).

As used herein, "partial agonist" refers to a compound that has an affinity for a receptor but, unlike an agonist, when bound to the receptor it elicits only a fractional degree of the pharmacological response normally associated with the receptor even if a large number of receptors are occupied by the compound.

An "inverse agonist" is defined as a compound, which reduces, or suppresses the basal activity of a receptor, such that the compound is not technically an antagonist but, rather, is an agonist with negative intrinsic activity.

As used herein, "antagonist" refers to a compound that binds to a receptor to form a complex that does not give rise to any response, as if the receptor was unoccupied. An antagonist attenuates the action of an agonist on a receptor. An antagonist may bind reversibly or irreversibly, effectively eliminating the activity of the receptor permanently or at least until the antagonist is metabolized or dissociates or is otherwise removed by a physical or biological process.

As used herein, a "subject" refers to an animal that is the object of treatment, observation or experiment. "Animal" includes cold- and warm-blooded vertebrates and invertebrates such as birds, fish, shellfish, reptiles and, in particular, mammals. "Mammal" includes, without limitation, mice; rats; rabbits; guinea pigs; dogs; cats; sheep; goats; cows; horses; primates, such as monkeys, chimpanzees, and apes, and, in particular, humans.

As used herein, a "patient" refers to a subject that is being treated by a medical professional such as an M.D. or a D.V.M. to attempt to cure, or at least ameliorate the effects of, a particular disease or disorder or to prevent the disease or disorder from occurring in the first place.

As used herein, a "carrier" refers to a compound that facilitates the incorporation of a compound into cells or tissues. For example, without limitation, dimethyl sulfoxide (DMSO) is a commonly utilized carrier that facilitates the uptake of many organic compounds into cells or tissues of a subject.

As used herein, a "diluent" refers to an ingredient in a pharmaceutical composition that lacks pharmacological activity but may be pharmaceutically necessary or desirable. For example, a diluent may be used to increase the bulk of a potent drug whose mass is too small for manufacture or administration. It may also be a liquid for the dissolution of a drug to be administered by injection, ingestion or inhalation. A common form of diluent in the art is a buffered aqueous solution such as, without limitation, phosphate buffered saline that mimics the composition of human blood.

As used herein, an "excipient" refers to an inert substance that is added to a pharmaceutical composition to provide, without limitation, bulk, consistency, stability, binding ability, lubrication, disintegrating ability etc., to the composition. A "diluent" is a type of excipient.

A "receptor" is intended to include any molecule present inside or on the surface of a cell that may affect cellular physiology when it is inhibited or stimulated by a ligand. Typically, a receptor comprises an extracellular domain with ligand-binding properties, a transmembrane domain that anchors the receptor in the cell membrane, and a cytoplasmic domain that generates a cellular signal in response to ligand binding ("signal transduction"). A receptor also includes any intracellular molecule that in response to ligation generates a signal. A receptor also includes any molecule having the characteristic structure of a receptor, but with no identifiable ligand. In addition, a receptor includes a truncated, modified, mutated receptor, or any molecule comprising partial or all of the sequences of a receptor.

"Ligand" is intended to include any substance that interacts with a receptor.

"Selective" or "selectivity" is defined as a compound's ability to generate a desired response from a particular receptor type, subtype, class or subclass while generating less or little response from other receptor types. "Selective" or "selectivity" of one or more particular subtypes of a compound means a compound's ability to increase the activity of the subtypes while causing less, little or no increase in the activity of other subtypes.

As used herein, "coadministration" of pharmacologically active compounds refers to the delivery of two or more separate chemical entities, whether in vitro or in vivo. Coadministration means the simultaneous delivery of separate agents; the simultaneous delivery of a mixture of agents; as well as the delivery of one agent followed by delivery of a second agent or additional agents. Agents that are coadministered are typically intended to work in conjunction with each other.

The term "an effective amount" as used herein means an amount of active compound or pharmaceutical agent that elicits the biological or medicinal response in a tissue, system, animal or human that is being sought by a researcher, veterinarian, medical doctor or other clinician, which includes alleviation or palliation of the symptoms of the disease being treated.

When used herein, "prevent/preventing" should not be construed to mean that a condition and/or a disease never might occur again after use of a compound or pharmaceutical composition according to embodiments disclosed herein to achieve prevention. Further, the term should neither be construed to mean that a condition not might occur, at least to some extent, after such use to prevent said condition. Rather, "prevent/preventing" is intended to mean that the condition to be prevented, if occurring despite such use, will be less severe than without such use.

Compounds
According to one aspect compounds of Formula (I)

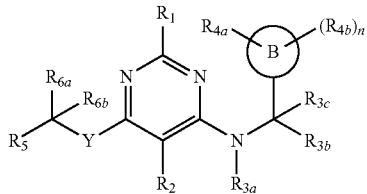

Formula (I)

or pharmaceutically acceptable salts, hydrates, solvates, polymorphs, and stereoisomers thereof, wherein:

Y is NR or O;

R is hydrogen or substituted or unsubstituted $C_{1-4}$ alkyl;

$R_1$ is selected from the group consisting of hydrogen, —OH, halogen, substituted or unsubstituted $C_{1-4}$ alkyl, substituted or unsubstituted $C_{1-4}$ alkoxy, and substituted or unsubstituted $C_{2-4}$ alkenyl;

$R_2$ is selected from the group consisting of hydrogen, halogen, substituted or unsubstituted $C_{1-4}$ alkyl, substituted or unsubstituted $C_{1-4}$ alkoxy, —CN, and —OH;

or R and $R_2$ are combined to form a substituted or unsubstituted fused ring; or $R_2$ and $R_{3a}$ are combined to form a substituted or unsubstituted fused ring;

$R_{4a}$ is selected from the group consisting of hydrogen, halogen, —OH, substituted or unsubstituted $C_{1-6}$ alkyl, substituted or unsubstituted $C_1$-$C_6$ alkoxy, substituted or unsubstituted $C_{1-6}$ alkenyl, substituted or unsubstituted $C_3$-$C_6$ cycloalkyl, substituted or unsubstituted aryl, substituted or unsubstituted aryl-$C_{1-6}$ alkyl, substituted or unsubstituted heteroaryl, substituted or unsubstituted heteroaryl-$C_{1-6}$ alkyl;

$R_{4b}$ is selected from the group consisting of hydrogen, halogen, —OH, substituted or unsubstituted $C_{1-4}$ alkyl, substituted or unsubstituted $C_{1-4}$ alkoxy, —C(=O)$R_{10}$;

$R_5$ is selected from the group consisting of —$(CR_8R_9)$p$OR_{12}$, —$(CR_8R_9)$p-$CR_{13}R_{14}R_{15}$, —$(CR_8R_9)$p-C(=O)$OR_7$, and —$(CR_8R_9)$p-C(=O)$NR_8R_9$;

n, and p are integers independently selected from the group consisting of 0, 1, 2, 3 and 4;

$R_{6a}$, $R_{6b}$ are independently selected from the group consisting of hydrogen, halogen substituted or unsubstituted $C_{1-6}$ alkyl, substituted or unsubstituted $C_{1-6}$ alkenyl, substituted or unsubstituted $C_{2-6}$ alkynyl, substituted or unsubstituted $C_{1-6}$ alkoxy, substituted or unsubstituted $C_{1-6}$ heteroalkyl, substituted or unsubstituted $C_{3-8}$ cycloalkyl, substituted or unsubstituted $C_{3-8}$ cycloalkenyl, substituted or unsubstituted $C_{2-9}$ heteroalicyclyl, substituted or unsubstituted aryl, and substituted or unsubstituted heteroaryl, or $R_{6a}$ and $R_{6b}$ are taken together to form an oxo group or a ring system selected from substituted or unsubstituted $C_{3-6}$ cycloalkyl, substituted or unsubstituted $C_{2-9}$ heteroalicyclyl, or $R_{6a}$ and $R_{13}$ are taken together to form a ring system selected from substituted or unsubstituted $C_{3-6}$ cycloalkyl, and substituted or unsubstituted $C_{2-9}$ heteroalicyclyl;

$R_7$, $R_8$, $R_9$, and $R_{12}$, are independently selected from the group consisting of hydrogen, substituted or unsubstituted $C_{1-6}$ alkyl, substituted or unsubstituted $C_{3-6}$ cycloalkyl, and substituted or unsubstituted $C_{2-9}$ heteroalicyclyl;

$R_{10}$ is selected from the group consisting of $C_{1-6}$ alkyl, $C_{1-6}$ alkoxy, —OH, —$NH_2$, —NH($C_{1-6}$ alkyl), —N($C_{1-6}$ alkyl)$_2$, and $C_{3-7}$ cycloalkyl;

$R_{13}$, if not to be taken together with $R_{6a}$, is absent, or selected from the group consisting of hydrogen, —CN, —OH, substituted or unsubstituted $C_{1-6}$ alkyl, substituted or unsubstituted $C_{1-6}$ alkenyl, substituted or unsubstituted $C_{1-6}$ alkoxy, substituted or unsubstituted $C_{3-8}$ cycloalkyl, substituted or unsubstituted $C_{3-8}$ cycloalkenyl, and —$(CR_8R_9)$p-C(=O)$OR_7$, —$(CR_8R_9)$p-$SO_2R_7$, and —$(CR_8R_9)$p-C(=O)$NR_8R_9$;

$R_{14}$ and $R_{15}$ are independently selected from the group consisting of hydrogen, and substituted or unsubstituted $C_{1-6}$ alkyl, substituted or unsubstituted $C_{3-6}$ cycloalkyl, and substituted or unsubstituted $C_{2-9}$ heteroalicyclyl; or $R_{14}$ and $R_{15}$ are combined to form a ring system selected from the group consisting of substituted or unsubstituted $C_{3-8}$ cycloalkyl, substituted or unsubstituted $C_{3-8}$ cycloalkenyl, substituted or unsubstituted $C_{2-9}$ heteroalicyclyl, substituted or unsubstituted aryl, and substituted or unsubstituted heteroaryl;

B is a ring system selected from the group consisting of aryl, heteroaryl, and $C_2$-$C_9$ heteroalicyclyl;

$R_{3a}$ is selected from the group consisting of substituted or unsubstituted $C_{1-6}$ alkyl, substituted or unsubstituted $C_{1-6}$ alkoxy, substituted or unsubstituted aryl, substituted or unsubstituted heteroaryl, substituted or unsubstituted $C_{3-8}$ cycloalkyl, substituted or unsubstituted $C_{3-8}$ cycloalkenyl, and substituted or unsubstituted $C_{2-9}$ heteroalicyclyl;

$R_{3b}$ and $R_{3c}$, are independently selected from the group consisting of hydrogen, —CN, substituted or unsubstituted $C_{1-6}$ alkyl, substituted or unsubstituted $C_{1-6}$ alkoxy, substituted or unsubstituted aryl, substituted or unsubstituted heteroaryl, substituted or unsubstituted $C_{3-8}$ cycloalkyl, substituted or unsubstituted $C_{3-8}$ cycloalkenyl, substituted or unsubstituted $C_{2-9}$ heteroalicyclyl, —$(CR_8R_9)$p-C(=O)$OR_7$, and —$(CR_8R_9)$p-C(=O)$NR_8R_9$, or $R_{3b}$ and $R_{3c}$ are combined to form an oxo group or a ring system selected from the group consisting of substituted or unsubstituted $C_{3-8}$ cycloalkyl substituted or unsubstituted $C_{3-8}$ cycloalkenyl, substituted or unsubstituted $C_{2-9}$ heteroalicyclyl; or $R_{3b}$ and $R_{4a}$ or $R_{4b}$ are combined to form a fused ring, and wherein whenever $R_2$ is hydrogen $R_1$ cannot be chloro, and with the proviso that the compound is not

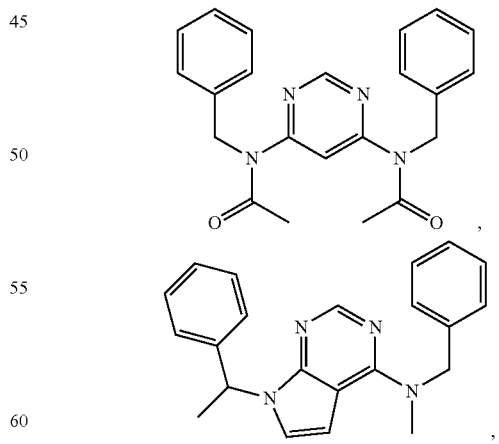

are provided herein.

As with any group of structurally related compounds which possess a particular utility, certain embodiments of variables of the compounds of Formula (I) may be particularly useful in their end use application.

In some embodiments of the compounds of Formula (I), R and $R_2$ in combination with the pyrimidine ring form a ring system selected from pyrrolo[2,3-d]pyrimidine, or 6,7-dihydro-5H-pyrrolo[2,3-d]pyrimidine. The ring system may be pyrrolo[2,3-d]pyrimidine.

In some embodiments of the compounds of Formula (I), R and $R_2$ in combination with the pyrimidine ring form a ring system selected from pyrrolo[2,3-d]pyrimidine or 6,7-dihydro-5H-pyrrolo[2,3-d]pyrimidine or $R_2$ and $R_{3a}$ in combination with the pyrimidine ring of formula (I) form ring system selected from a pyrrolo[2,3-d]pyrimidine or 6,7-dihydro-5H-pyrrolo[2,3-d]pyrimidine.

The compounds of Formula (I) may also have the Formula (IIa):

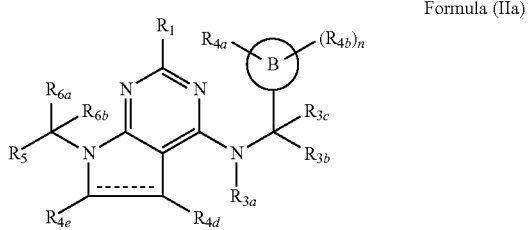

Formula (IIa)

wherein $R_{4e}$ and $R_{4d}$ are independently selected from the group consisting of hydrogen, halogen, substituted or unsubstituted $C_{1-4}$ alkyl, substituted or unsubstituted $C_{1-4}$ alkoxy, and —OH. Additional examples of compounds of Formula (IIa), $R_{4e}$ and $R_{4d}$ may be independently selected from the group consisting of hydrogen, methyl, and fluorine.

The compounds of Formula (I) may also have the Formula (IIab):

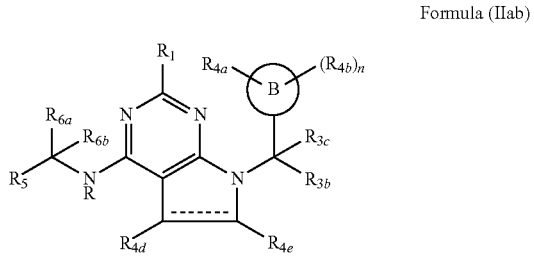

Formula (IIab)

wherein $R_{4e}$ and $R_{4d}$ are independently selected from the group consisting of hydrogen, halogen, substituted or unsubstituted $C_{1-4}$ alkyl, substituted or unsubstituted $C_{1-4}$ alkoxy, and —OH. Additional examples of compounds of Formula (IIa), $R_{4e}$ and $R_{4d}$ may be independently selected from the group consisting of hydrogen, methyl, and fluorine.

Embodiment disclosed herein below in relation to various groups, rings and substituents of compounds of Formula (I) are, as indicated, equally applicable to compounds of any one of the Formulae (IIa-IIf) provided below herein, provided that the relevant group, integer, ring and/or substituent is present in the Formula of concern, as readily appreciated by the skilled person.

According to another embodiment, the compounds of Formula (I) or compounds of any one of Formulae (IIa-IIf) have $R_5$ being —$(CR_8R_9)$p-C(=O)$OR_7$ or —$(CR_8R_9)$p-C(=O)$NR_8R_9$, unless otherwise specified. In an alternative embodiment, the compounds of Formula (I) or compounds of any one of Formulae (IIa-IIf) have $R_5$ being —$(CR_8R_9)$ p$OR_{12}$, unless otherwise specified. In these embodiments, $R_7$, $R_8$, $R_9$, and $R_{12}$ are independently selected of each other from hydrogen, substituted or unsubstituted $C_{1-6}$ alkyl, substituted or unsubstituted aryl-$C_{1-6}$ alkyl and substituted or unsubstituted aryl. Preferred groups of $R_7$, $R_8$, $R_9$, and $R_{12}$ are selected from hydrogen, $C_{1-6}$ alkyl, $C_{1-6}$ haloalkyl, $C_{1-6}$ hydroxyalkyl, and aryl, while even more preferred groups are selected from hydrogen, methyl, ethyl and tert-butyl. The integer p is preferably selected from 0, 1 or 2. In some embodiments, p is 0.

According to yet another embodiment, $R_5$ is —$(CR_8R_9)$ p-$CR_{13}R_{14}R_{15}$. In this embodiment it is preferred that $R_{14}$ and $R_{15}$ are combined to form a ring system. Further, the integer "p" may be 0 (zero). While it is not intended that the ring system be particular limited, preferred ring systems are selected from the group consisting of substituted or unsubstituted $C_{3-7}$ cycloalkyl, substituted or unsubstituted $C_{3-7}$ cycloalkenyl, substituted or unsubstituted $C_{2-6}$ heteroalicyclyl, substituted or unsubstituted aryl, and substituted or unsubstituted heteroaryl. For example, $R_{14}$ and $R_{15}$ may be combined to form a ring system selected from the group consisting of phenyl, naphthyl, cyclopropyl, cyclobutyl, cyclopentyl, cyclohexyl, cycloheptyl, azetidinyl, thietanyl, pyrrolyl, pyrazoleyl, imidazolyl, pyrrolidinyl, imidazolinyl, pyrazolidinyl, thiazolidinyl, isothiazolidinyl, triazolyl, tetrazolyl, oxazolyl, isoxazolyl, oxadiazolyl, oxathianyl, thiazolyl, isothiazolyl, pyridyl, pyridazinyl, pyrazinyl, pyrimidinyl, triazinyl, piperidinyl, piperazinyl, morpholinyl, thiomorpholinyl, dioxolanyl, dioxanyl, furyl, dihydrofuranyl, furazanyl, tetrahydrofuryl, pyranyl, tetrahydropyranyl, tetrahydrothiopyranyl, dithiolanyl, dithianyl, thiopyranyl, thianyl, thienyl, oxetanyl, quinolyl, isoquinolyl, indolyl, iso-indolyl, and tetrahydrothienyl, any of which may be substituted or unsubstituted. Preferably, $R_{14}$ and $R_{15}$ are combined to form a ring system selected from the group consisting of cycloheptyl, cyclohexyl, cyclopentyl, dioxanyl, furyl, imidazolyl, isothiazolyl, isoxazolyl, morpholinyl, oxazolyl, oxetanyl, oxathianyl, phenyl, piperidinyl, pyranyl, pyrazolidinyl, pyrazolyl, pyridyl, pyrimidyl, pyrrolidinyl, pyrrolyl, tetrahydrofuryl, tetrahydropyranyl, tetrazolyl, thianyl, thiazolyl, thienyl, thiomorpholinyl, thiopyryl, 1,4-oxathianyl 4,4-dioxide, thianyl-1,1-dioxide and triazolyl, all of which may be unsubstituted or substituted. Some embodiments relate to the ring system formed being phenyl, pyridyl, cyclopentyl, cyclohexyl, piperidyl, pyrrolidinyl, and oxetanyl, and tetrahydropyranyl, all which may be substituted by $(CH_2)_q(R_{5a})$ as defined below. Some embodiments relate to the ring system being phenyl, pyridyl, piperidinyl or cyclohexyl. In embodiments wherein the ring system formed by $R_{14}$ and $R_{15}$ is aromatic, $R_{13}$ is absent In a further embodiment, the ring system formed by the combination of $R_{14}$ and $R_{15}$ is substituted with one ore more —$(CH_2)q(R_{5a})$ wherein $R_{5a}$ is independently selected from the group consisting of —$CH_2COOR_{20}$, —$CH_2CONR_{21}R_{22}$, —CN, $C_{1-6}$ alkyl, —$CH_2$— imidazolyl, —$CH_2$—$SO_2R_{20}$, oxo —$CH_2C(CH_3)_2(OR_{20})$, —$OR_{20}$, —$CH_2$-triazolyl, —$CF_3$, dimethyl substituted-imidazolyl-2,4-dione, —$CH_2$—$SO_2NR_{21}R_{22}$, morpholinyl, —C(=O)-morpholinyl, piperidyl-$CH_2OR_{20}$, —$OCH_2$-tetrahydrofuryl, piperazinonyl, piperidinyl-$CONR_{21}R_{22}$, —OH, —$COR_{20}$, —$CONR_{21}R_{22}$, —$CH(OR_{20})CH_3$, —$COOR_{20}$, —$CH_2$-pyrrolidyl, $C_{1-6}$ alkylene-OH, cyclopentyl, pyrrolidonyl, tetrazolyl, —$CH_2$-tetrazolyl, —$CH_2OR_{20}$, acyl, —$SOR_{20}$, —$SO_2R_{20}$, —$COR_{20}$, —$NR_{21}SO_2R_{20}$, —$SO_2NR_{21}R_{22}$, and halogen;

$R_{20}$, $R_{21}$, and $R_{22}$ are independently of each other selected from the group consisting of hydrogen, substituted or unsubstituted $C_{1-6}$ alkyl, —CN, substituted or unsubstituted $C_{3-6}$ cycloalkyl, substituted or unsubstituted $C_{2-6}$ heteroalicyclyl or $R_{21}$ and $R_{22}$ are combined to form a $C_{3-6}$ cycloalkyl; and q is an integer selected from 0, 1 or 2.

Of course the ring system formed by the combination of $R_{14}$ and $R_{15}$ may, in alternative embodiments, be substituted with groups other than —$(CH_2)q(R_{5a})$.

According to some embodiments, $R_{13}$ is selected from the group consisting of hydrogen, —CN, —$CH_3$, fluorine, —OH, —$CH_2OH$, —$OCH_3$, —$CH_2CH_2OH$, —$CO_2H$, —$CO_2$—$C_{1-4}$-alkyl, —$CH_2$—$SO_2R_{20}$ and —$CONR_8R_9$ wherein $R_8$ and $R_9$ are independently of each other selected from hydrogen, $C_{1-4}$ alkyl and $C_{1-4}$ aminoalkyl or $R_8$ and $R_9$ are combined to form a $C_2$-$C_6$ heteroalicyclyl, and $R_{20}$ is selected from $C_{1-6}$ alkyl. Some embodiments relate to $R_{13}$ taken together with $R_{6a}$ to form a ring system selected from the group consisting of substituted or unsubstituted $C_{3-6}$ cycloalkyl and substituted or unsubstituted $C_{2-5}$ heteroalicyclyl. According to some embodiments, $R_{13}$ is absent or hydrogen.

In some embodiments of the compounds of Formula (I), Y is NR. Further, while R may be selected from the group consisting of hydrogen, $C_{1-4}$ alkyl, $C_{1-4}$ haloalkyl, and $C_{1-4}$ hydroxyalkyl. In one embodiment R is hydrogen.

According to some embodiments, $R_1$ is selected from the group consisting of hydrogen, halogen, substituted or unsubstituted $C_{1-4}$ alkyl, and substituted or unsubstituted $C_{1-4}$ alkoxy. $R_1$ may thus include $C_{1-4}$ haloalkyl and $C_{1-4}$ hydroxyalkyl groups. In some embodiment, $R_1$ is hydrogen.

According to some embodiments, $R_2$ is selected from the group consisting of hydrogen, halogen, $C_{1-4}$ alkyl, $C_{1-4}$ haloalkyl, and $C_{1-4}$ hydroxyalkyl. According to one embodiment $R_2$ is a halogen such as fluorine.

In some embodiments $R_{3a}$ is selected from the group consisting of $C_{1-4}$ alkyl, $C_{1-4}$ alkylene-$C_{3-6}$ cycloalkyl, $C_{1-4}$ alkylene-$C_{3-6}$ heteroalicyclyl, $C_{3-6}$ cycloalkyl, and $C_{3-5}$ heteroalicyclyl, any of which may be substituted or unsubstituted. Non limiting examples are methyl, methylenecyclopropyl, tetrahydrofuran-3-yl, cyclopropyl, cyclobutyl, and methylene-tetrahydrofuran-3-yl. Some embodiments relate to $R_{3a}$ being methyl, ethyl, propyl, butyl, isopropyl, t-butyl, cyclopropyl, cyclobutyl, cyclopentyl, or cyclohexyl, such as $R_{3a}$ being methyl, ethyl, cyclopropyl, or cyclobutyl. In one example, $R_{3a}$ is cyclopropyl. In some embodiments, $R_{3a}$ is cyclopropyl or cyclobutyl substituted by one or more substituents selected from the group consisting of methyl, chloro, and fluoro. When more than one substituent are present they may be bound to the same or separate carbon atom(s).

In some embodiments $R_{3b}$ is selected from the group consisting of hydrogen, substituted or unsubstituted $C_{1-4}$ alkyl, —$(CH_2)_{1-4}C(=O)R_{10}$, $C_{1-4}$ alkylene-$C_{3-6}$ cycloalkyl, $C_{1-4}$ alkylene-$C_{3-6}$ heteroalicyclyl, $C_{3-6}$ cycloalkyl, and $C_{3-6}$ heteroalicyclyl. Non limiting examples are methyl, $CH_2C$(O)OMe, cyclopropyl, and cyclobutyl. The substituents of substituted alkyls are, according to some embodiments, selected from the group consisting of: halogen, eg. fluorine, hydroxyl, $NH_2$, $NH(C_{1-4}$ alkyl), $N(C_{1-4}$ alkyl$)_2$, e.g. $NMe_2$, $NHC(O)C_{1-4}$ alkyl, $NC_{1-4}$ alkyl$C(O)C_{1-4}$ alkyl, substituted or unsubstituted aryl, and substituted and or unsubstituted heteroaryl.

In some embodiments $R_{3c}$ is selected from the group consisting of hydrogen, $C_{1-4}$ alkyl, and $C_{3-6}$ cycloalkyl.

In some embodiments $R_{3b}$ is hydrogen, and $R_{3c}$ is selected from the group consisting of hydrogen, methyl, cyclopropyl and cyclobutyl; or $R_{3b}$ and $R_{3c}$ are combined to form cyclopropyl.

In some embodiments $R_{3a}$ is selected from the group consisting of $C_{1-4}$ alkyl, $C_{1-4}$ alkyl-$C_{3-6}$ cycloalkyl, $C_{1-4}$ alkylene-$C_{3-6}$ heteroalicyclyl, $C_{3-6}$ cycloalkyl, and $C_{3-5}$ heteroalicyclyl, $R_{3b}$ is selected from the group consisting of hydrogen, substituted or unsubstituted $C_{1-4}$ alkyl, —$(CH_2)_mC(=O)R_{10}$, $C_{1-4}$ alkylene-$C_{3-6}$ cycloalkyl, $C_{1-4}$ alkylene-$C_{3-6}$ heteroalicyclyl, $C_{3-6}$ cycloalkyl and $C_{3-6}$ heteroalicyclyl, and $R_{3c}$ is selected from the group consisting of hydrogen, $C_{1-4}$ alkyl, and $C_{3-6}$ cycloalkyl.

In some embodiments $R_{3a}$ is selected from the group consisting of $C_{1-4}$ alkyl, $C_{1-4}$ alkylene-$C_{3-6}$ cycloalkyl, $C_{1-4}$ alkylene-$C_{3-6}$ heteroalicyclyl, $C_{3-6}$ cycloalkyl, and $C_{3-5}$ heteroalicyclyl, and $R_{3b}$ and $R_{3c}$ are hydrogen.

In some embodiments $R_{3a}$ is selected from the group consisting of methyl, ethyl, propyl, butyl, isopropyl, t-butyl, cyclopropyl, cyclobutyl, cyclopentyl, and cyclohexyl, such as from methyl, ethyl, cyclopropyl, and cyclobutyl, and $R_{3b}$ is hydrogen and $R_{3c}$ is selected from the group consisting of hydrogen, methyl, cyclopropyl and cyclobutyl; or $R_{3b}$ and $R_3c$ are combined to form a cyclopropyl.

According to some embodiments of the compounds of Formula (I) or compounds of any one of Formulae (IIa-IIf), $R_{4a}$ is selected from the group consisting of hydrogen, halogen, $C_{1-6}$ alkyl, $C_{1-6}$ haloalkyl, $C_{1-6}$ hydroxyalkyl, $C_1$-$C_6$ alkoxy, $C_{1-6}$ haloalkoxy, heteroaryl, and aryl. In some embodiments $R_{4a}$ groups are selected from the group consisting of methyl, ethyl, propyl, iso-propyl, tert-butyl, chlorine, bromine, fluorine, methoxy, ethoxy, $C_{1-2}$ haloalkyl, $C_{1-2}$ haloalkoxy, triazolyl. In some embodiments $R_{4a}$ groups are —$CF_3$, —$CF_2CF_3$, —$CHF_2$, —$OCF_3$, —$OCF_2CF_3$, and —$OCHF_2$. In some embodiments $R_{4a}$ is selected from the group consisting of isopropyl, —CN, ethoxy, —$CF_3$, —$OCF_3$, and triazolyl.

In some embodiments, wherein the ring system B is 6-membered aryl or heteroaryl, $R_{4a}$ is arranged in the para- or meta-position, in relation to the carbon carrying $R_{3b}$ and $R_{3c}$.

According to some embodiments, $R_{4b}$ is selected from hydrogen, oxo, halogen, $C_{1-4}$ alkyl, $C_{1-4}$ haloalkyl, $C_{1-4}$ hydroxyalkyl, $C_1$-$C_4$ alkoxy, and $C_{1-4}$ haloalkoxy. In this embodiment, $R_{4b}$ may be further selected from methyl, ethyl, propyl, iso-propyl, tert-butyl, chlorine, bromine, fluorine, methoxy, ethoxy, —OH, $C_{1-2}$ haloalkyl, and $C_{1-2}$ haloalkoxy. Examples of $R_{4b}$ groups comprise —$CF_3$, —$CHF_2$, —$OCF_3$, and —$OCHF_2$. In some embodiments $R_{4b}$ is hydrogen.

Some embodiments relate to $R_{4a}$ being selected from the group consisting of methyl, ethyl, propyl, iso-propyl, tert-butyl, chlorine, bromine, fluorine, methoxy, ethoxy, $C_{1-2}$ haloalkyl, $C_{1-2}$ haloalkoxy, and triazolyl arranged in the above mentioned para- or meta-position, and $R_{4b}$ being hydrogen.

In some embodiments of the compounds of Formula (I)) or compounds of any one of Formulae (IIa-IIf), $R_{6a}$ is selected from the group consisting of hydrogen, substituted or unsubstituted $C_{1-6}$ alkyl, substituted or unsubstituted $C_{1-6}$ alkoxy, and substituted or unsubstituted aryl, or $R_{6a}$ and $R_{13}$ are taken together to form a ring system selected from substituted or unsubstituted $C_{3-6}$ cycloalkyl, substituted or unsubstituted $C_{2-9}$ heteroalicyclyl. Further examples of groups of $R_{6a}$ are selected from hydrogen, $C_{1-6}$ alkyl, $C_{1-6}$ haloalkyl, $C_{1-6}$ hydroxyalkyl, $C_{1-6}$ alkoxy, $C_{1-6}$ haloalkoxy, and aryl. It is preferred however, that $R_{6a}$ is hydrogen.

According to some embodiments, $R_{6b}$ is selected from hydrogen, substituted or unsubstituted $C_{1-6}$ alkyl, substituted or unsubstituted $C_{1-6}$ alkoxy, substituted or unsubstituted aryl-$C_{1-6}$ alkyl, substituted or unsubstituted $C_{2-9}$ heteroalicyclyl-$C_{1-6}$ alkyl, and substituted or unsubstituted aryl in the compounds of Formula (I). Thus, $R_{6b}$ may be hydrogen, $C_{1-6}$ alkyl, $C_{1-6}$ haloalkyl, $C_{1-6}$ hydroxyalkyl, $C_1$-$C_6$ alkoxy, $C_{1-6}$ haloalkoxy, $C_{1-6}$-alkoxy-$C_{1-6}$-alkyl-, aryl-$C_{1-6}$ alkyl-, $C_{2-9}$ heteroalicyclyl-$C_{1-4}$ alkyl-, $C_{1-6}$-alkoxy-aryl-, haloaryl, and aryl. Particular examples are of compounds of Formula (I), or compounds of any one of Formulae (IIa-IIf), have, unless otherwise specified, an $R_{6b}$ group selected from hydrogen, —(CH$_2$)C(CH$_3$)$_3$, —(CH$_2$)CONH$_2$, phenyl, phenyl substituted with 1 to 3 halogens, —CH(CH$_3$)OC(CH$_3$)$_3$, —CH$_2$-phenyl-OCH$_3$, -phenyl-OCH$_3$, —CH$_2$-pyridyl, CH$_2$-cyclohexyl-CH$_2$CO$_2$H, —CH$_2$-cyclohexyl-CH$_2$CONH$_2$, CH$_2$-cyclohexyl-CH$_2$-tetrazolyl, —CH$_2$-cyclohexyl-CH$_2$OH, —CH$_2$-cyclohexyl-NHSO$_2$CH$_3$, —CH$_2$-cyclohexyl-NHSO$_2$CH$_2$CF$_3$, —CH$_2$-cyclohexyl-CH$_2$CN, —CH$_2$-phenyl-CH$_2$CO$_2$H, —CH$_2$-phenyl-CH$_2$CONH$_2$, —CH$_2$-phenyl-CH$_2$CONH$_2$CH$_3$, —CH$_2$-phenyl-CH$_2$-tetrazolyl, —CH$_2$-phenyl-CONH$_2$, —CH$_2$-phenyl-SO$_2$NH-cyclopropyl, —CH$_2$-phenyl-SO$_2$CH$_3$, —CH$_2$— phenyl-NHSO$_2$CF$_3$, —CH$_2$-phenyl-NHSO$_2$CH$_3$, —CH$_2$-phenyl-NHSO$_2$CHF$_2$, —CH$_2$-pyridyl-CH$_3$, —CH$_2$-pyridyl-SO$_2$CH$_3$, —CH$_2$-pyridyl-CH$_2$CONH$_2$, —CH$_2$-pyrimidyl-NHSO$_2$CH$_3$, —CH$_2$-piperidyl-COCH$_3$, —CH$_2$-piperidyl-SO$_2$CH$_3$, —CH$_2$-piperidyl-SO$_2$CF$_3$, —CH$_2$-thienyl-CH$_2$CO$_2$H, —CH$_2$-cyclobutyl-CH$_2$CO$_2$H, —CH$_2$-cyclobutyl-CH$_2$CONH$_2$, —CH$_2$-cyclobutyl-CO$_2$H, —CH$_2$-cyclobutyl-CONH$_2$, —CH$_2$-tetrahydrothiopyryl, —CH$_2$-cyclopentyl, —CH$_2$— cyclohexyl, —CH$_2$-tetrahydrofuranyl, —CH$_2$-tetrahydropyranyl, —CH$_2$-oxetanyl, and —CH$_2$— pyranyl.

Some embodiments relate to $R_{6a}$ and $R_{6b}$ being taken together to form a ring system selected from substituted or unsubstituted $C_{3-6}$ cycloalkyl, substituted or unsubstituted $C_{2-9}$ heteroalicyclyl.

Ring system B in compounds of Formula (I) or compounds of any one of Formulae (IIa-IIf) is not intended to be particularly limited, unless otherwise indicated.

In some embodiments, ring system B is a mono- or bicyclic aryl, a mono- or bicyclic heteroaryl, or a mono- or bicyclic heteroalicyclyl. Ring system B may, but need not, be substituted with at least one of $R_{4a}$ or $R_{4b}$ that is a non-hydrogen substituent. Compounds of Formula (I)) or compounds of any one of Formulae (IIa-IIf) may also have a ring system B that is a mono-cyclic, 6-membered aryl or heteroaryl substituted with $R_{4a}$. In some embodiments ring system B is selected from the group consisting of phenyl, pyridyl, pyridazinyl, pyrimidinyl, naphthyl and furanyl. In some embodiments ring system B is selected from the group consisting of phenyl, pyridyl and pyrimidinyl. Alternatively, n may be 0 and $R_{4a}$ hydrogen, i.e. the ring system B is unsubstituted.

In some embodiments, n is an integer selected from 1, 2, 3 and 4. Alternatively, n may be 0 meaning that $R_{4a}$ will be the only substituent on ring system B.

In some embodiments, the ring B is a bicyclic ring system, such as bicyclic aryl, bicyclic heteroaryl, or bicyclic heteroalicyclyl ring systems, e.g. benzazepine, benzazocines, benzimidazole, benzimidazoline, benzodioxin, benzodioxole, benzofuran, benzoisothiazole, benzothiadiazine, benzothiadiazole, benzothiazepine, benzothiazine, benzothiazole, benzothiophene, benzotriazole, benzoxadiazole, benzoxathiole, benzoxazepine, benzoxazine, benzoxazole, benzisoxazole, benzodioxole, chromane, chromene, coumarin, cyclopentapyridine, cyclopentapyrimidine, diazanaphthalene, dioxolopyridine, dioxolopyrimidine, dihydrobenzodioxine, dihydrobenzooxathiine, furofuran, furopyridine, furopyrimidine, imidazopyridine, imidazopyrimidines, indane, indazole, indene, indole, indoline, indolizines, isobenzofuran, isochromenes, isoindole, isoindoline, isoquinoline, naphthalene, naphthyridine, oxathiolopyridine, oxathiolopyrimidine, oxazolopyridine, oxazolopyrimidine, pteridine, purine, pyranopyridine, pyranopyrimidine, pyrazolodiazepines, pyrazolopyridine, pyrazolopyrimidine, pyridobenzthiazine, pyridodiazepene, pyridooxazine, pyridopyrazine, pyridopyrimidine, pyridothiazine, pyrimidooxazine, pyrimidopyrimidine, pyrimidothiazine, pyrrolizine, pyrroloimidazole, pyrrolopyrazine, pyrrolopyridine, pyrrolopyrimidine, quinazoline, quinoline, quinolone, quinolizidine, quinoxaline, tetralin, thiazolopyridine, thiazolopyrimidine, thienodiazepine, thienopyridine, thienopyrimidine, thiochromane, thiochromene, thiopyranopyridine, thiopyranopyrimidine, triazolopyridazine, triazolopyridine or triazolopyrimidine, all of which may be unsubstituted or substituted.

According to yet another embodiment, the compounds of Formula (I) or compounds of any one of Formulae (IIa-IIf) have $R_5$ being —(CR$_8$R$_9$)p-C(=O)NR$_8$R$_9$; $R_8$ and $R_9$ are independently of each other selected from H and substituted or unsubstituted $C_{1-6}$ alkyl; p is 0; and $R_{6b}$ is hydrogen or —(CH$_2$)C(CH$_3$)$_3$.

Compounds disclosed herein may also comprise compounds of Formula (IIb):

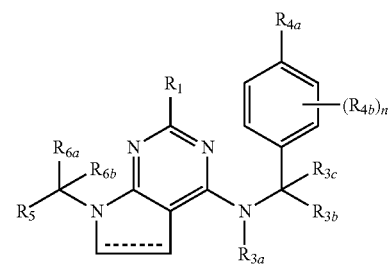

Formula (IIb)

wherein:
$R_1$ is selected from the group consisting of hydrogen, halogen, substituted or unsubstituted $C_{1-4}$ alkyl, and substituted or unsubstituted $C_{1-4}$ alkoxy; some compounds of Formula (IIb) have an $R_1$ that is hydrogen or —CF$_3$;

$R_{3a}$ is selected from the group consisting of substituted or unsubstituted $C_{1-6}$ alkyl, substituted or unsubstituted $C_{1-6}$ alkoxy, substituted or unsubstituted aryl, substituted or unsubstituted heteroaryl, substituted or unsubstituted $C_{3-8}$ cycloalkyl, substituted or unsubstituted $C_{3-8}$ cycloalkenyl, substituted or unsubstituted $C_{2-9}$ heteroalicyclyl;

$R_{3b}$ and $R_{3c}$, are independently selected from the group consisting of hydrogen, —CN, substituted or unsubstituted $C_{1-6}$ alkyl, substituted or unsubstituted $C_{1-6}$ alkoxy, substituted or unsubstituted aryl, substituted or unsubstituted heteroaryl, substituted or unsubstituted $C_{3-8}$ cycloalkyl, substituted or unsubstituted $C_{3-8}$ cycloalkenyl, substituted or unsubstituted $C_{2-9}$ heteroalicyclyl, —(CR$_8$R$_9$)p-C(=O)OR$_7$, and —(CR$_8$R$_9$)p-C(=O)NR$_8$R$_9$, or $R_{3b}$ and $R_{3c}$ are combined to form an oxo group or a ring system selected from the group consisting of substituted or unsubstituted $C_{3-8}$ cycloalkyl substituted or unsubstituted $C_{3-8}$ cycloalkenyl, substituted or unsubstituted $C_{2-9}$ heteroalicyclyl; or $R_{3b}$ and $R_{4b}$ are combined to form a fused ring;

$R_{4a}$ is selected from the group consisting of hydrogen, halogen, —OH, substituted or unsubstituted $C_{1-6}$ alkyl, substituted or unsubstituted $C_1$-$C_6$ alkoxy, substituted or unsubstituted $C_{1-6}$ alkenyl, substituted or unsubstituted aryl, substituted or unsubstituted aryl-$C_{1-6}$ alkyl, substituted or unsubstituted heteroaryl, substituted or unsubstituted heteroaryl-$C_{1-6}$ alkyl; some compounds of Formula (IIb) have an $R_{4a}$ that is selected from the group consisting of halogen, —$CF_3$, —$OCF_3$, iso-propyl, tert-butyl, —$C_{1-6}$ alkoxy, $C_{1-6}$ alkoxy substituted with one or more halogens, and phenyl;

$R_{4b}$ is independently selected from the group consisting of hydrogen, halogen, —OH, substituted or unsubstituted $C_{1-4}$ alkyl, substituted or unsubstituted $C_{1-4}$ alkoxy, —C(=O)$R_{10}$;

$R_5$ is selected from the group consisting of substituted or unsubstituted $C_{3-7}$ cycloalkyl, substituted or unsubstituted $C_{3-7}$ cycloalkenyl, substituted or unsubstituted $C_{2-6}$ heteroalicyclyl, unsubstituted or substituted aryl, and unsubstituted or substituted heteroaryl;

$R_{6a}$ are $R_{6b}$ are independently selected from the group consisting of hydrogen and substituted or unsubstituted $C_{1-6}$ alkyl;

n is an integer independently selected from the group consisting of 1, 2, 3, and 4; and p is an integer independently selected from the group consisting of 1, 2, 3, and 4.

In compounds of Formula (IIb), $R_5$ may be selected from the group consisting of substituted or unsubstituted $C_{4-7}$ cycloalkyl, substituted or unsubstituted $C_{6-12}$ membered aryl, substituted or unsubstituted 4-membered heteroalicyclyl, substituted or unsubstituted 5-membered heteroaryl, substituted or unsubstituted 5-membered heteroalicyclyl, substituted or unsubstituted 6-membered heteroaryl, a substituted or unsubstituted 6-membered heteroalicyclyl, substituted or unsubstituted 7-membered heteroaryl, and a substituted or unsubstituted 7-membered heteroalicyclyl. Thus, $R_5$ may be selected from the group consisting of phenyl, naphthyl, cyclopropyl, cyclobutyl, cyclopentyl, cyclohexyl, cycloheptyl, azetidinyl, thietanyl, pyrrolyl, pyrazolyl, imidazolyl, pyrrolidinyl, imidazolinyl, pyrazolidinyl, thiazolidinyl, isothiazolidinyl, triazolyl, tetrazolyl, oxazolyl, isoxazolyl, oxadiazolyl, oxathianyl, 1,4-oxathianyl, 4,4-dioxide, thiazolyl, isothiazolyl, pyridinyl, pyridazinyl, pyrazinyl, pyrimidinyl, triazinyl, piperidinyl, piperazinyl, morpholinyl, thiomorpholinyl, dioxolanyl, dioxanyl, furyl, dihydrofuranyl, furazanyl, tetrahydrofuryl, pyranyl, tetrahydropyranyl, tetrahydrothiopyranyl, dithiolanyl, dithianyl, thiopyranyl, thianyl, thianyl-1,1-dioxide, thienyl, oxetanyl, quinolyl, isoquinolyl, indolyl, iso-indolyl, and tetrahydrothienyl, any of which may be substituted or unsubstituted. Especially, $R_5$ may be selected from the group consisting of cycloheptyl, cyclohexyl, cyclopentyl, dioxanyl, furyl, imidazolyl, isothiazolyl, isoxazolyl, morpholinyl, oxazolyl, oxetanyl, oxathianyl, phenyl, piperidinyl, pyranyl, pyrazolidinyl, pyrazolyl, pyridyl, pyrimidyl, pyrrolidinyl, pyrrolyl, tetrahydrofuryl, tetrahydropyranyl, tetrazolyl, thianyl, thiazolyl, thienyl, thiomorpholinyl, thiopyryl, and triazolyl, any of which may be substituted or unsubstituted.

If substituted, $R_5$ may be substituted with one or more —$(CH_2)q(R5_a)$ wherein $R_{5a}$ is independently selected from the group consisting of —$CH_2COOR_{20}$, —$CH_2CONR_{21}R_{22}$, oxo, —CN, —$CH_2$—CN, $C_{1-6}$ alkyl, —$CH_2$-imidazolyl, —$CH_2$—$SO_2R_{20}$, —$CH_2C(CH_3)_2$(OR$_{20}$), —$OR_{20}$, —$CH_2$-triazolyl, —$CF_3$, dimethyl substituted-imidazolyl-2,4-dione, —$CH_2$—$SO_2NR_{21}R_{22}$, morpholinyl, —C(=O)-morpholinyl, piperidyl-$CH_2OR_{20}$, —$OCH_2$-tetrahydrofuryl, piperazinonyl, piperidinyl-$CONR_{21}R_{22}$, —OH, —$COR_{20}$, —$CONR_{21}R_{22}$, —CH(OR$_{20}$)CH$_3$, —$COOR_{20}$, —$CH_2$-pyrrolidyl, $C_{1-6}$ alkylene-OH, cyclopentyl, pyrrolidonyl, tetrazolyl, —$CH_2$-tetrazolyl, —$CH_2OR_{20}$, acyl, —$SOR_{20}$, —$SO_2R_{20}$, —$SO_2NR_{21}R_{22}$, —$NR_{21}SO_2R_{20}$, and halogen;

$R_{20}$, $R_{21}$, and $R_{22}$ are independently of each other selected from the group consisting of hydrogen, substituted or unsubstituted $C_{1-6}$ alkyl, —CN, substituted or unsubstituted $C_{3-6}$ cycloalkyl, substituted or unsubstituted $C_{2-6}$ heteroalicyclyl, or $R_{21}$ and $R_{22}$ are combined to form a $C_{3-6}$ cycloalkyl; and q is an integer selected from 0, 1 or 2.

Further, $R_5$ may be selected from the group consisting of unsubstituted aryl, unsubstituted heteroaryl, aryl substituted with one or more $C_{1-6}$ alkoxy, aryl substituted with —$CH_2COOC_{1-6}$ alkyl, aryl substituted with —$CH_2CONH$—($C_{1-6}$ alkyl), aryl substituted with —$CH_2CON(C_{1-6}$ alkyl)$_2$, —$(CH_2)$—C(=O)OR$_7$, —C(=O)OR$_7$, —$(CH_2)$—C(=O)NR$_8R_9$, or —C(=O)NR$_8R_9$, and heteroaryl substituted with —$(CH_2)$—C(=O)NR$_8R_9$ or $SO_2R_7$, and $C_{2-9}$ heteroalicyclyl substituted with —$(CH_2)$—C(=O)NR$_8R_9$ or $SO_2R_7$;

$R_7$, $R_8$, and $R_9$ are independently selected from the group consisting of hydrogen, unsubstituted $C_{1-6}$ alkyl, and $C_{1-6}$ alkylene substituted with furanyl.

Compounds disclosed herein may also comprise compounds of Formula (IIc):

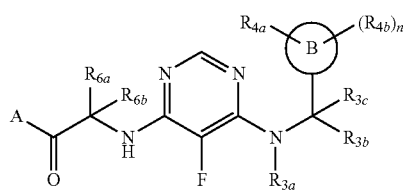

Formula (IIc)

wherein:

$R_{3a}$ is selected from the group consisting of substituted or unsubstituted $C_{1-6}$ alkyl, substituted or unsubstituted $C_{1-6}$ alkoxy, substituted or unsubstituted aryl, substituted or unsubstituted heteroaryl, substituted or unsubstituted $C_{3-8}$ cycloalkyl, substituted or unsubstituted $C_{3-8}$ cycloalkenyl, substituted or unsubstituted $C_{2-9}$ heteroalicyclyl;

$R_{3b}$ and $R_{3c}$, are independently selected from the group consisting of hydrogen, —CN, substituted or unsubstituted $C_{1-6}$ alkyl, substituted or unsubstituted $C_{1-6}$ alkoxy, substituted or unsubstituted aryl, substituted or unsubstituted heteroaryl, substituted or unsubstituted $C_{3-8}$ cycloalkyl, substituted or unsubstituted $C_{3-8}$ cycloalkenyl, substituted or unsubstituted $C_{2-9}$ heteroalicyclyl, —(CR$_8R_9$)p-C(=O)OR$_7$, and —(CR$_8R_9$)p-C(=O)NR$_8R_9$, or $R_{3b}$ and $R_{3c}$ are combined to form an oxo group or a ring system selected from the group consisting of substituted or unsubstituted $C_{3-8}$ cycloalkyl substituted or unsubstituted $C_{3-8}$ cycloalkenyl, substituted or unsubstituted $C_{2-9}$ heteroalicyclyl; or $R_{3b}$ and $R_{4a}$ are combined to form a ring system; or $R_{3b}$ and $R_{4b}$ are combined to form a ring system;

$R_{4a}$ is selected from the group consisting of hydrogen, fluorine, chlorine, —C(CH$_3$)$_3$, —CH$_2$(CH$_3$)$_2$, —CF$_3$, —OCH$_3$, —OC(CH$_3$)$_3$, and —OCF$_3$;

$R_{4b}$ is selected from the group consisting of hydrogen, fluorine, chlorine, and OCH$_3$;

n is an integer independently selected from 1 or 2;

p is an integer independently selected from the group consisting of 0, 1, and 2;

A is OR$_7$ or NR$_8R_9$;

$R_{6a}$, $R_{6b}$ are independently selected from the group consisting of hydrogen, substituted or unsubstituted $C_{1-6}$ alkyl, substituted or unsubstituted $C_{1-6}$ alkenyl, substituted or unsubstituted $C_{2-6}$ alkynyl, substituted or unsubstituted $C_{1-6}$ alkoxy, substituted or unsubstituted $C_{1-6}$ heteroalkyl, substituted or unsubstituted $C_{3-8}$ cycloalkyl, substituted or unsubstituted $C_{3-8}$ cycloalkenyl, substituted or unsubstituted $C_{2-9}$ heteroalicyclyl, substituted or unsubstituted aryl, and substituted or unsubstituted heteroaryl;

$R_7$, $R_8$, and $R_9$ are independently selected from H and $C_{1-6}$ alkyl; and B is selected from the group consisting of phenyl, pyridyl, pyrimidyl, 2-benzothiazolyl, quinolinyl, and 1,4-benzodioxanyl.

Compounds disclosed herein may also comprise compounds of Formula (IId):

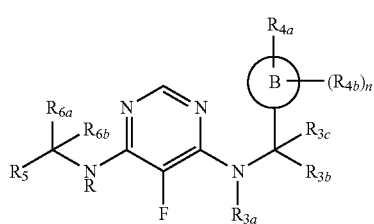

Formula (IId)

wherein:

B is selected from phenyl, pyridyl and pyrimidyl;

R is hydrogen or $C_{1-4}$ alkyl;

$R_{3a}$ is selected from the group consisting of substituted or unsubstituted $C_{1-6}$ alkyl, substituted or unsubstituted $C_{1-6}$ alkoxy, substituted or unsubstituted aryl, substituted or unsubstituted heteroaryl, substituted or unsubstituted $C_{3-8}$ cycloalkyl, substituted or unsubstituted $C_{3-8}$ cycloalkenyl, substituted or unsubstituted $C_{2-9}$ heteroalicyclyl;

$R_{3b}$ and $R_{3c}$, are independently selected from the group consisting of hydrogen, —CN, substituted or unsubstituted $C_{1-6}$ alkyl, substituted or unsubstituted $C_{1-6}$ alkoxy, substituted or unsubstituted aryl, substituted or unsubstituted heteroaryl, substituted or unsubstituted $C_{3-8}$ cycloalkyl, substituted or unsubstituted $C_{3-8}$ cycloalkenyl, substituted or unsubstituted $C_{2-9}$ heteroalicyclyl, —$(CR_8R_9)$p-C(=O)$OR_7$, and —$(CR_8R_9)$p-C(=O)$NR_8R_9$, or $R_{3b}$ and $R_{3c}$ are combined to form an oxo group or a ring system selected from the group consisting of substituted or unsubstituted $C_{3-8}$ cycloalkyl substituted or unsubstituted $C_{3-8}$ cycloalkenyl, substituted or unsubstituted $C_{2-9}$ heteroalicyclyl; or $R_{3b}$ and $R_{4b}$ are combined to form a fused ring;

$R_{4a}$ is selected from the group consisting of hydrogen, halogen, —OH, substituted or unsubstituted $C_{1-6}$ alkyl, substituted or unsubstituted $C_1$-$C_6$ alkoxy, substituted or unsubstituted $C_{1-6}$ alkenyl, substituted or unsubstituted aryl, substituted or unsubstituted aryl-$C_{1-6}$ alkyl, substituted or unsubstituted heteroaryl, substituted or unsubstituted heteroaryl-$C_{1-6}$ alkyl; for example $R_{4a}$ may be a substituent arrange in para- or meta-position compared to the carbon atom in the ring system C, and selected from the group consisting of hydrogen, halogen, $C_{1-4}$ alkyl, $C_{1-4}$ alkoxy, $C_{1-4}$ haloalkyl (for example —$CF_3$), $C_{1-4}$ haloalkoxy (for example —$OCF_3$), and heteroaryl;

$R_{4b}$ is independently selected from the group consisting of hydrogen, halogen, —OH, substituted or unsubstituted $C_{1-4}$ alkyl, substituted or unsubstituted $C_{1-4}$ alkoxy, —C(=O)$R_{10}$;

$R_{6a}$ are $R_{6b}$ are independently selected from the group consisting of hydrogen and substituted or unsubstituted $C_{1-6}$ alkyl $R_5$ is a ring selected from the group consisting of phenyl, pyrimidinyl, pyridyl, pyridinyl-N-oxide, cyclohexyl, pyrrolyl, pyrazolyl, furanyl, pyrrolidonyl, tetrahydrofuranyl, tetrahydropyranyl, benzopyrrolidonyl, cyclobutyl, oxetanyl, tetrahydrothiophenyl, tetrahydro-2H-thiopyranyl, cyclopentyl, cycloheptanyl, tetrahydrothiophenyl-1,1-dioxide, tetrahydro-2H-thiopyranyl-1,1-dioxide, 1,4-oxathianyl-4,4-dioxide, and piperidinyl, any of which may be unsubstituted or substituted with $(R_{5b})$t;

$R_{5b}$, when present, is independently selected from the group consisting of —$CH_2COOR_{20}$, —$CH_2CONR_{21}R_{22}$, —CN, —$CH_2CN$, —$C_{1-6}$ alkyl, —$CH_2$-imidazolyl, —$CH_2$—$SO_2CH_3$, —$CH_2C(CH_3)_2(OR_{20})$, —$OCH_3$, —$CH_2$-triazolyl, —$CF_3$, dimethyl substituted-imidazolidinyl-2,4-dione, —$NSO_2R_{20}$, —$CH_2$—$SO_2NR_{21}R_{22}$, morpholinyl, —C(=O)-morpholinyl, piperazinonyl, piperidinyl-$CONR_{21}R_{22}$, —OH, —$COR_{20}$, —$CONR_{21}R_{22}$, —CH$(OR_{20})CH_3$, —$COOR_{20}$, —$CH_2$-pyrrolidonyl, —$C_{1-6}$-alkylene-OH, -cyclopentyl, -pyrrolidonyl, -tetrazolyl, —$CH_2$-triazolyl, —$CH_2OR_{20}$, -acyl, —$SOR_{20}$, —$SO_2R_{20}$, —$SO_2NR_{21}R_{22}$, —$NR_{21}SO_2R_{20}$, and halogen; $R_7$, $R_8$, and $R_9$ are independently selected from the group consisting of hydrogen, unsubstituted $C_{1-6}$ alkyl, and $C_{1-6}$ alkylene substituted with furanyl;

$R_{10}$ is selected from the group consisting of $C_{1-6}$ alkyl, $C_{1-6}$ alkoxy, —$NH_2$, —$NH(C_{1-6}$ alkyl), —$N(C_{1-6}$ alkyl)$_2$, and $C_{3-7}$ cycloalkyl $R_{20}$, $R_{21}$, and $R_{22}$ are independently selected from H, —$C_{1-6}$ alkyl, —$C_{1-6}$ haloalkyl, —$C_{3-6}$ cycloalkyl, and —$C_{1-6}$ heteroalicyclyl;

p is an integer independently selected from the group consisting of 0, 1, and 2;

t is an integer selected from 1 or 2; and n is an integer selected from the group consisting of 1, 2, 3, and 4. In some embodiments of Formula (IId) $R_{3a}$ is selected from the group consisting of $C_{1-4}$ alkyl, $C_{1-4}$ alkyl-$C_{3-6}$ cycloalkyl, $C_{1-4}$ alkyl-$C_{3-6}$ heteroalicyclyl, $C_{3-6}$ cycloalkyl, and $C_{3-5}$ heteroalicyclyl, any of which may be substituted or unsubstituted; $R_{3b}$ is selected from the group consisting of hydrogen, substituted or unsubstituted $C_{1-4}$ alkyl, —$(CH_2)_mC(=O)R_{10}$, $C_{1-4}$ alkyl-$C_{3-6}$ cycloalkyl, $C_{1-4}$ alkyl-$C_{3-6}$ heteroalicyclyl, $C_{3-6}$ cycloalkyl and $C_{3-6}$ heteroalicyclyl; and $R_{3c}$ is selected from the group consisting of hydrogen, $C_{1-4}$ alkyl, and $C_{3-6}$ cycloalkyl.

Compounds disclosed herein may also comprise compounds of Formula (IIe):

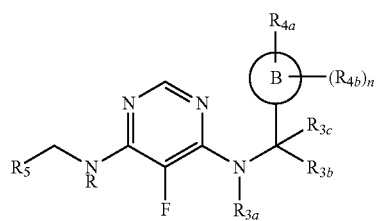

Formula (IIe)

or pharmaceutically acceptable salts, hydrates, solvates, polymorphs, and stereoisomers thereof, wherein:

n, and p are an integer selected from 0, 1 and 2;

B is selected from phenyl, pyridyl and pyrimidyl;

R is hydrogen or $C_{1-4}$ alkyl; $R_{3a}$ is selected from the group consisting of $C_{1-4}$ alkyl, $C_{3-6}$ cycloalkyl, $C_{1-3}$ alkylene-$C_{3-6}$ cycloalkyl, and $C_{2-5}$ heteroalicyclyl, any of which may be substituted or unsubstituted;

$R_{3b}$ and $R_{3c}$, are independently selected from the group consisting of hydrogen, —CN, substituted or unsubstituted $C_{1-6}$ alkyl, substituted or unsubstituted $C_{1-6}$ alkoxy, substituted or unsubstituted aryl, substituted or unsubstituted heteroaryl, substituted or unsubstituted $C_{3-8}$ cycloalkyl, substituted or unsubstituted $C_{3-8}$ cycloalkenyl, substituted or unsubstituted $C_{2-9}$ heteroalicyclyl, —$(CR_8R_9)p$-$C(=O)OR_7$, and —$(CR_8R_9)p$-$C(=O)NR_8R_9$, or $R_{3b}$ and $R_{3c}$ are combined to form an oxo group or a ring system selected from the group consisting of substituted or unsubstituted $C_{3-8}$ cycloalkyl substituted or unsubstituted $C_{3-8}$ cycloalkenyl, substituted or unsubstituted $C_{2-9}$ heteroalicyclyl;

$R_{4a}$ is selected from the group consisting of hydrogen, halogen, —OH, substituted or unsubstituted $C_{1-6}$ alkyl, substituted or unsubstituted $C_1$-$C_6$ alkoxy, substituted or unsubstituted $C_{1-6}$ alkenyl, substituted or unsubstituted aryl, substituted or unsubstituted aryl-$C_{1-6}$ alkyl, substituted or unsubstituted heteroaryl, substituted or unsubstituted heteroaryl-$C_{1-6}$ alkyl; for example $R_{4a}$ is —$CF_3$ or —$OCF_3$;

$R_{4b}$ is independently selected from the group consisting of hydrogen, halogen, —OH, substituted or unsubstituted $C_{1-4}$ alkyl, substituted or unsubstituted $C_{1-4}$ alkoxy, —$C(=O)R_{10}$;

$R_5$ is a ring selected from the group consisting of phenyl, pyrimidinyl, pyridyl, pyridinyl-N-oxide, cyclohexyl, pyrrolyl, pyrazolyl, furanyl, pyrrolidonyl, tetrahydrofuranyl, tetrahydropyranyl, benzopyrrolidonyl, cyclobutyl, oxetanyl, tetrahydrothiophenyl, tetrahydro-2H-thiopyranyl, cyclopentyl, cycloheptanyl, tetrahydrothiophenyl-1,1-dioxide, tetrahydro-2H-thiopyranyl-1,1-dioxide, 1,4-oxathianyl-4,4-dioxide, and piperidinyl, any of which may be unsubstituted or substituted with $(R_{5b})t$;

$R_{5b}$, when present, is independently selected from the group consisting of —$CH_2COOR_{20}$, —$CH_2CONR_{21}R_{22}$, oxo, —CN, —$CH_2CN$, —$C_{1-6}$ alkyl, —$CH_2$-imidazolyl, —$CH_2$—$SO_2CH_3$, —$CH_2C(CH_3)_2(OR_{20})$, —$OCH_3$, —$CH_2$-triazolyl, —$CF_3$, dimethyl substituted-imidazolidinyl-2,4-dione, —$NSO_2R_{20}$, —$CH_2$—$SO_2NR_{21}R_{22}$, morpholinyl, —$C(=O)$-morpholinyl, piperidinyl-$CH_2OR_{20}$, $OCH_2$-tetrahydrofuranyl, piperazinonyl, piperidinyl-$CONR_{21}R_{22}$, —OH, —$COR_{20}$, —$CONR_{21}R_{22}$, —$CH(OR_{20})CH_3$, —$COOR_{20}$, —$CH_2$— pyrrolidonyl, —$C_{1-6}$-alkylene-OH, -cyclopentyl, -pyrrolidonyl, -tetrazolyl, —$CH_2$-triazolyl, —$CH_2OR_{20}$, -acyl, —$SOR_{20}$, —$SO_2R_{20}$, —$SO_2NR_{21}R_{22}$, —$NR_{21}SO_2R_{20}$, and halogen;

$R_7$, $R_8$, and $R_9$ are independently selected from the group consisting of hydrogen, unsubstituted $C_{1-6}$ alkyl, and $C_{1-6}$ alkylene substituted with furanyl;

$R_{10}$ is selected from the group consisting of $C_{1-6}$ alkyl, $C_{1-6}$ alkoxy, —$NH_2$, —$NH(C_{1-6}$ alkyl), —$N(C_{1-6}$ alkyl)$_2$, and $C_{3-7}$ cycloalkyl $R_{20}$, $R_{21}$, and $R_{22}$ are independently selected from H, —$C_{1-6}$ alkyl, —$C_{1-6}$ haloalkyl, —$C_{3-6}$ cycloalkyl, and —$C_{1-6}$ heteroalicyclyl;

p is an integer independently selected from the group consisting of 0, 1, and 2;

t is an integer selected from 1 or 2; and n is an integer selected from the group consisting of 1, 2, 3, and 4.

In some embodiments of the compounds of formula (IIe), R and $R_{3b}$ are hydrogen, $R_{3a}$ is cyclopropyl, and $R_{4a}$ is —$CF_3$.

Compounds disclosed herein may also comprise compounds of Formula (IIf):

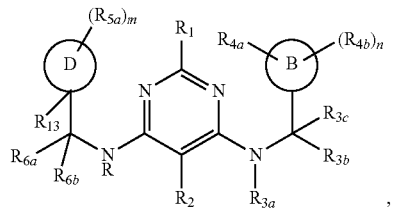

(IIf)

or pharmaceutically acceptable salts, hydrates, solvates, polymorphs, and stereoisomers thereof, wherein:

m, n and p are integers independently selected from the group consisting of 0, 1, and 2;

R is hydrogen or $C_{1-4}$ alkyl;

$R_1$ is selected from the group consisting of hydrogen, —OH, halogen, substituted or unsubstituted $C_{1-4}$ alkyl, and substituted or unsubstituted $C_{1-4}$ alkoxy;

$R_2$ is selected from the group consisting of hydrogen, halogen, $C_{1-4}$ alkyl, $C_{1-4}$ haloalkyl, and $C_{1-4}$ hydroxyalkyl;

or R and $R_2$ are combined to form a substituted or unsubstituted fused ring; or $R_2$ and $R_{3a}$ are combined to form a substituted or unsubstituted fused ring;

$R_{3a}$ is selected from the group consisting of substituted or unsubstituted $C_{1-6}$ alkyl, substituted or unsubstituted $C_{1-6}$ alkoxy, substituted or unsubstituted aryl, substituted or unsubstituted heteroaryl, substituted or unsubstituted $C_{3-8}$ cycloalkyl, substituted or unsubstituted $C_{3-8}$ cycloalkenyl, and substituted or unsubstituted $C_{2-9}$ heteroalicyclyl;

$R_{3b}$ and $R_{3c}$, are independently selected from the group consisting of hydrogen, —CN, substituted or unsubstituted $C_{1-6}$ alkyl, substituted or unsubstituted $C_{1-6}$ alkoxy, substituted or unsubstituted aryl, substituted or unsubstituted heteroaryl, substituted or unsubstituted $C_{3-8}$ cycloalkyl, substituted or unsubstituted $C_{3-8}$ cycloalkenyl, substituted or unsubstituted $C_{2-9}$ heteroalicyclyl, —$(CR_8R_9)p$-$C(=O)OR_7$, and —$(CR_8R_9)p$-$C(=O)NR_8R_9$, or $R_{3b}$ and $R_{3c}$ are combined to form an oxo group or a ring system selected from the group consisting of substituted or unsubstituted $C_{3-8}$ cycloalkyl substituted or unsubstituted $C_{3-8}$ cycloalkenyl, and substituted or unsubstituted $C_{2-9}$ heteroalicyclyl; or $R_{3b}$ and $R_{4a}$ or $R_{4b}$ are combined to form a fused ring, $R_{4a}$ is selected from the group consisting of hydrogen, halogen, —OH, substituted or unsubstituted $C_{1-6}$ alkyl, substituted or unsubstituted $C_1$-$C_6$ alkoxy, substituted or unsubstituted $C_{1-6}$ alkenyl, substituted or unsubstituted aryl, substituted or unsubstituted aryl-$C_{1-6}$ alkyl, substituted or unsubstituted $C_3$-$C_6$ cycloalkyl, substituted or unsubstituted heteroaryl, and substituted or unsubstituted heteroaryl-$C_{1-6}$ alkyl;

$R_{4b}$ is selected from the group consisting of hydrogen, oxo, halogen, —OH, substituted or unsubstituted $C_{1-4}$ alkyl, and substituted or unsubstituted $C_{1-4}$ alkoxy, —$C(=O)R_{10}$;

$R_{5a}$ is selected from the group consisting of hydrogen, halogen, oxo, —CN, —OH, substituted or unsubstituted $C_{1-6}$ alkyl, substituted or unsubstituted $C_{1-6}$ alkenyl, substituted or unsubstituted $C_{1-6}$ alkoxy, substituted or unsubstituted $C_{3-8}$ cycloalkyl, substituted or unsubstituted $C_{3-8}$ cycloalkenyl, substituted or unsubstituted aryl, substituted or unsubstituted aryl-$C_{1-6}$ alkyl, substituted or unsubstituted $C_2$-$C_8$ heteroalicyclyl, substituted or unsubstituted $C_2$-$C_8$ heteroalicyclyl-$C_{1-6}$ alkyl, substituted or unsubstituted heteroaryl, substituted or unsubstituted heteroaryl-$C_{1-6}$ alkyl, —(CH$_2$)$_q$CO$_2$R$_{20}$, —(CH$_2$)$_q$—CONR$_{20}$R$_{21}$, —(CH$_2$)$_q$—SOR$_{20}$, —(CH$_2$)$_q$—SO$_2$R$_{20}$, —(CH$_2$)$_q$—SO$_2$NR$_{21}$R$_{22}$, and —(CH$_2$)$_q$NR$_{21}$SO$_2$R$_{20}$;

q is an integer selected from 0 or 1;

R$_{20}$, R$_{21}$, and R$_{22}$ are independently of each other selected from the group consisting of hydrogen, substituted or unsubstituted C$_{1-6}$ alkyl, —CN, substituted or unsubstituted C$_{3-6}$ cycloalkyl, and substituted or unsubstituted C$_{2-6}$ heteroalicyclyl, or R$_{21}$ and R$_{22}$ are combined to form a C$_{3-6}$ cycloalkyl;

R$_{6a}$, R$_{6b}$ are independently selected from the group consisting of hydrogen, substituted or unsubstituted C$_{1-6}$ alkyl, substituted or unsubstituted C$_{1-6}$ alkenyl, substituted or unsubstituted C$_{2-6}$ alkynyl, substituted or unsubstituted C$_{1-6}$ alkoxy, substituted or unsubstituted C$_{1-6}$ heteroalkyl, substituted or unsubstituted C$_{3-8}$ cycloalkyl, substituted or unsubstituted C$_{3-8}$ cycloalkenyl, substituted or unsubstituted C$_{2-9}$ heteroalicyclyl, substituted or unsubstituted aryl, and substituted or unsubstituted heteroaryl, or R$_{6a}$ and R$_{6b}$ are taken together to form and oxo group or a ring system selected from substituted or unsubstituted C$_{3-6}$ cycloalkyl, and substituted or unsubstituted C$_{2-9}$ heteroalicyclyl, or R$_{6a}$ and R$_{13}$ are taken together to form a ring system selected from substituted or unsubstituted C$_{3-6}$ cycloalkyl, and substituted or unsubstituted C$_{2-5}$ heteroalicyclyl;

R$_{10}$ is selected from the group consisting of C$_{1-6}$ alkyl, C$_{1-6}$ alkoxy, —OH, —NH$_2$, —NH(C$_{1-6}$ alkyl), —N(C$_{1-6}$ alkyl)$_2$, and C$_{3-7}$ cycloalkyl;

R$_{13}$, if not to be taken together with R$_{6a}$, is absent, or selected from the group consisting of hydrogen, —CN, —OH, substituted or unsubstituted C$_{1-6}$ alkyl, substituted or unsubstituted C$_{1-6}$ alkenyl, substituted or unsubstituted C$_{1-6}$ alkoxy, substituted or unsubstituted C$_{3-8}$ cycloalkyl, substituted or unsubstituted C$_{3-8}$ cycloalkenyl, and —(CR$_8$R$_9$)p-C(=O)OR$_7$, —(CR$_8$R$_9$)p-SO$_2$R$_7$ and —(CR$_8$R$_9$)p-C(=O)NR$_8$R$_9$;

B is a ring system selected from the group consisting of aryl, heteroaryl, and, C$_2$-C$_9$ bicyclic heteroalicyclyl;

D is a ring system selected from the group consisting of aryl, heteroaryl, C$_{3-8}$ cycloalkyl and, C$_2$-C$_9$ heteroalicyclyl;

and wherein whenever R$_2$ is hydrogen R$_1$ cannot be chloro, and with the proviso that the compound is not

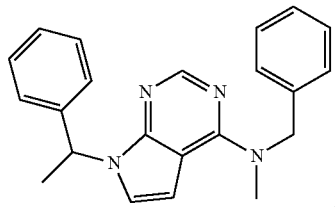

Some embodiments relates to the compound according to Formula (IIf) wherein

R$_{4a}$ is selected from the group consisting of hydrogen, halogen, C$_{1-4}$ alkyl, C$_{1-4}$ alkoxy, C$_{1-4}$ haloalkyl, C$_{1-4}$ haloalkoxy, and heteroaryl;

R$_{4b}$ is selected from the group consisting of hydrogen, oxo, halogen, C$_{1-4}$ alkyl, C$_{1-4}$ haloalkyl, C$_{1-4}$ hydroxyalkyl, C$_{1-4}$ alkoxy, and C$_{1-4}$ haloalkoxy;

R$_{6a}$ is selected from the group consisting of hydrogen, halogen, C$_{1-6}$ alkyl, C$_{1-6}$ haloalkyl, C$_{1-6}$ hydroxyalkyl, C$_{1-6}$ alkoxy, and C$_{1-6}$ haloalkoxy;

R$_{6b}$ is selected from the group consisting of hydrogen, C$_{1-6}$ alkyl, C$_{1-6}$ haloalkyl, C$_{1-6}$ hydroxyalkyl, C$_{1-6}$ alkoxy, C$_{1-6}$ alkoxy-C$_{1-6}$ alkyl, C$_{1-6}$ haloalkoxy, aryl-C$_{1-6}$ alkyl, substituted or unsubstituted C$_{2-9}$ heteroalicyclyl-C$_{1-6}$ alkyl, and substituted or unsubstituted aryl or R$_{6a}$ and R$_{6b}$ are taken together to form an oxo group or a ring system selected from substituted or unsubstituted C$_{3-6}$ cycloalkyl, and substituted or unsubstituted C$_{2-9}$ heteroalicyclyl, or R$_{6a}$ and R$_{13}$ are taken together to form a ring system selected from substituted or unsubstituted C$_{3-6}$ cycloalkyl, and substituted or unsubstituted C$_{2-5}$ heteroalicyclyl;

R$_{3a}$ is selected from the group consisting of C$_{1-4}$ alkyl, C$_{1-4}$ alkylene-C$_{3-6}$ cycloalkyl, C$_{1-4}$ alkylene-C$_{3-6}$ heteroalicyclyl, C$_{3-6}$ cycloalkyl, and C$_{3-5}$ heteroalicyclyl, any of which may be substituted or unsubstituted;

R$_{3b}$ and R$_{3c}$, are independently selected from the group consisting of hydrogen, substituted or unsubstituted C$_{1-4}$ alkyl, —(CH$_2$)$_{1-4}$—C(=O)R$_{10}$, C$_{1-4}$ alkylene-C$_{3-6}$ cycloalkyl, C$_{1-4}$ alkylene-C$_{3-6}$ heteroalicyclyl, C$_{3-6}$ cycloalkyl, and C$_{3-6}$ heteroalicyclyl, or R$_{3b}$ and R$_{3c}$ are combined to form an oxo group or a ring system selected from the group consisting of substituted or unsubstituted C$_{3-8}$ cycloalkyl, substituted or unsubstituted C$_{3-8}$ cycloalkenyl, substituted or unsubstituted C$_{2-9}$ heteroalicyclyl; or R$_{3b}$ and R$_{4a}$ or R$_{4b}$ are combined to form a fused ring.

In some embodiments compounds of Formula (I) or compounds of any one of Formulae (IIa-IIf), R$_{3a}$ is methyl, ethyl, cyclopropyl or cyclobutyl. When R$_{3a}$ is cyclopropyl or cyclobutyl it may substituted by one or more substituents selected from the group consisting of methyl, chloro, and fluoro. When more than one substituent are present they may be bound to the same or separate carbon atom(s).

In some embodiments compounds of Formula (I) or compounds of any one of Formulae (IIa-IIf), R$_{3b}$ and R$_{3c}$ are independently of each other selected from the group consisting of hydrogen, methyl, ethyl, or R$_{3b}$ and R$_{3c}$ are combined to form cyclopropyl or cyclobutyl.

In some embodiments compounds of Formula (I) or compounds of any one of Formulae (IIa-IIf), R$_{3a}$ is methyl, ethyl, cyclopropyl or cyclobutyl and R$_{3b}$ and R$_{3c}$ are independently of each other selected from the group consisting of hydrogen, methyl, ethyl, or R$_{3b}$ and R$_{3c}$ are combined to form cyclopropyl or cyclobutyl.

In some embodiments compounds of Formula (I) or compounds of any one of Formulae (IIa-IIf), B is aryl or heteroaryl, for example phenyl, pyridyl, pyrazolyl, pyridazinyl, pyrimidinyl, naphthyl and furanyl, unless otherwise specified. Some embodiments relates to B being phenyl, pyridyl or pyrimidyl.

In some embodiments compounds of Formula (I) or compounds of any one of Formulae (IIa-IIf), B is a 6-membered aryl, or a 6-membered heteroaryl substituted with R$_{4a}$ in the para-position or meta-position, or a 5-membered heteroaryl substituted with R$_{4a}$ in 2- or 3-position, unless otherwise specified. In some embodiments the 6-membered aryl is phenyl and the 6-membered heteroaryl is pyridyl or pyrimidyl. Some embodiments relate to R$_{4a}$ being selected from the group consisting of halogen, —CN, C$_{1-4}$ alkyl, C$_{1-4}$ haloalkyl, C$_1$-C$_4$ alkoxy, C$_{1-4}$ haloalkoxy and heteroaryl, for example isopropyl, —CN, ethoxy, CF$_3$, —OCF$_3$, and triazolyl. Some embodiments relate to R$_{4b}$ being selected from the group consisting of hydrogen, oxo, halogen, C$_{1-4}$ alkyl, C$_{1-4}$ haloalkyl, C$_{1-4}$ hydroxyalkyl, C$_1$-C$_4$ alkoxy, C$_{1-4}$ haloalkoxy, and heteroaryl. Some embodiments relate to R$_{4a}$ being selected from the group consisting of halogen, —CN, C$_{1-4}$ alkyl, C$_{1-4}$ haloalkyl, C$_1$-C$_4$ alkoxy, and C$_{1-4}$ haloalkoxy, for example isopropyl, —CF$_3$, —CHF$_2$, —OCF$_3$, and —OCHF$_2$ and R$_{4b}$ being hydrogen.

In some embodiments compounds of Formulae (IIf), D is selected from the group consisting of aryl, such as phenyl; heteroaryl, such as pyridyl, $C_{3-8}$ cycloalkyl, such as cyclohexyl; and $C_{2-8}$ heteroalicyclyl, such as piperidyl, tetrahydro-2H-pyranyl, thiopyranyl, tetrahydro-2H-thiopyranyl, tetrahydro-2H-thiopyranyl-1,1-dioxide, pyrrolidinyl, thianyl, and oxetanyl, all which may be substituted with one or more $R_{5a}$. Some embodiments relates to $R_{5a}$ being selected from hydrogen, $C_{1-6}$ alkyl, such as methyl and ethyl; $C_{1-6}$ hydroxyalkyl, such as methanol and ethanol; —$(CH_2)_q$—CN; oxo, —$(CH_2)_q$—$CO_2R_{20}$; —$(CH_2)_q$—$C_{1-6}$ alkoxy, such as methoxy and ethoxy and methoxyethyl; —$(CH_2)_q$-heteroaryl, such as —$(CH_2—)_q$-tetrazolyl, —$(CH_2—)_q$-imidazolyl, —$(CH_2—)_q$-triazolyl; —$(CH_2—)_q$—$CONR_{20}R_{21}$; —$(CH_2—)_q$—$COR_{20}$; —$(CH_2—)_q$—$SO_2R_{20}$; —$(CH_2—)_q$—$NR_{21}SOR_{20}$; —$(CH_2—)_q$—$SO_2NR_{21}R_{22}$;

$R_{20}$, $R_{21}$, and $R_{22}$ are independently of each other selected from the group consisting of hydrogen, —OH, substituted or unsubstituted $C_{1-6}$ alkyl, —CN, substituted or unsubstituted $C_{3-6}$ cycloalkyl, and substituted or unsubstituted $C_{2-6}$ heteroalicyclyl, or $R_{21}$ and $R_{22}$ are combined to form a $C_{3-6}$ cycloalkyl; and q is an integer selected from 0 or 1.

As for any given group disclosed herein, the ring system D may comprise further hydrogen(s) than the one(s) provided by $R_{5a}$ being hydrogen.

In some embodiments $R_{20}$, $R_{21}$, and $R_{22}$ are independently of each other selected from the group consisting of hydrogen, methyl, ethyl, cyclopropyl, —$CF_3$, and —$CHF_2$, In some embodiments according to Formula (I) or compounds of any one of Formulae (IIa-IIf), $R_{13}$ is absent, or selected from the group consisting of hydrogen, —OH, —CN, $C_{1-4}$ hydroxyalkyl, $C_{1-6}$ haloalkyl, —$(CH_2—)_qCO_2H$, —$(CH_2—)_q$—$SO_2R_{20}$, —$(CH_2—)_q$—$NR_{21}SO_2R_{20}$ and $C_{1-6}$ alkoxy, or $R_{13}$ combined with the atom to which it is attached and an adjacent $R_{5a}$ to form a $C_{3-5}$ cycloalkyl, or $C_{2-4}$ heteroalicyclyl.

In some embodiments compounds of Formula (I) or compounds of any one of Formulae (IIa-IIf), $R_{6a}$ is hydrogen, or combined with $R_{5a}$, $R_{6b}$ or $R_{13}$ to form ring system such as a $C_{3-6}$ cycloalkyl or $C_{2-5}$-heteroalicyclyl; $R_{6b}$ is hydrogen, combined with $R_{6a}$ to form ring system, or absent. In some embodiments both $R_{6a}$ and $R_{6b}$ are hydrogen.

In some embodiments according to Formula (IIf)

R is hydrogen; $R_2$ is selected from Cl or F; or R and $R_2$ are combined to form a pyrrolo[2,3-d]pyrimidine, 6,7-dihydro-5H-pyrrolo[2,3-d]pyrimidine;

m is an integer selected from 0 and 1;

n is an integer selected from 0 and 1;

$R_{3a}$ is methyl, ethyl, cyclopropyl or cyclobutyl;

$R_{3b}$ and $R_{3c}$ are independently of each other selected from the group consisting of hydrogen, methyl, ethyl, or $R_{3b}$ and $R_{3c}$ are combined to form cyclopropyl or cyclobutyl;

B is aryl or heteroaryl, for example phenyl, pyridyl, pyrazolyl, pyridazinyl, pyrimidinyl, naphthyl and furanyl.

$R_{4a}$ is selected from the group consisting of halogen, $C_{1-4}$ alkyl, $C_{1-4}$ haloalkyl, $C_1$-$C_4$ alkoxy, $C_{1-4}$ haloalkoxy and heteroaryl, for example $CF_3$, —$CHF_2$, —$OCF_3$, —$OCHF_2$, and triazolyl;

$R_{4b}$ is selected from the group consisting of hydrogen, oxo, halogen, $C_{1-4}$ alkyl, $C_{1-4}$ haloalkyl, $C_{1-4}$ hydroxyalkyl, $C_1$-$C_4$ alkoxy, $C_{1-4}$ haloalkoxy, and heteroaryl.

D is selected from the group consisting of aryl, such as phenyl; heteroaryl, such as pyridyl, and pyrimidyl; $C_{3-8}$ cycloalkyl, such as cyclopentyl and cyclohexyl; and $C_{2-8}$ heteroalicyclyl, such as a mono-cyclic or a bridged $C_{2-8}$ heteroalicyclyl, such as piperidyl, tetrahydro-2H-pyranyl, thiopyranyl, tetrahydro-2H-thiopyranyl, tetrahydro-2H-thiopyranyl-1,1-dioxide, oxetanyl, tropanyl and pyrrolidinyl, all which may be substituted with one or more $R_{5a}$;

$R_{5a}$ is selected from halogen, $C_{1-6}$ alkyl, such as methyl and ethyl; $C_{1-6}$ hydroxyalkyl, such as methanol and ethanol; $C_{1-6}$ haloalkyl, such as —$CF_3$, —$(CH_2)_q$—CN; —$(CH_2)_q$-acyl; —$(CH_2)_q$—$C_{1-6}$ alkoxy, such as methoxy and ethoxy and methoxyethyl; —$(CH_2)_q$-heteroaryl, such as —$(CH_2—)_q$-tetrazolyl, —$(CH_2—)_q$-imidazolyl, —$(CH_2—)_q$-triazolyl; —$(CH_2—)_q$—$CONR_{20}R_{21}$; —$(CH_2—)_q$—$COR_{20}$; —$(CH_2—)_q$—$SO_2R_{20}$; —$(CH_2—)_q$—$NR_{21}SOR_{20}$; —$(CH_2—)_q$—$SO_2NR_{21}R_{22}$;

$R_{20}$, $R_{21}$, and $R_{22}$ are independently of each other selected from the group consisting of hydrogen, —OH, substituted or unsubstituted $C_{1-6}$ alkyl, —CN, substituted or unsubstituted $C_{3-6}$ cycloalkyl, and substituted or unsubstituted $C_{2-6}$ heteroalicyclyl, or $R_{21}$ and $R_{22}$ are combined to form a $C_{3-6}$ cycloalkyl; and q is an integer selected from 0 or 1;

$R_{13}$ is absent, or selected from the group consisting of hydrogen, —OH, —CN, $C_{1-4}$ hydroxyalkyl, $C_{1-6}$ haloalkyl, —$(CH_2—)_q$—$SO_2R_{20}$, —$(CH_2—)_q$—$NR_{21}SO_2R_{20}$ and $C_{1-6}$ alkoxy, or $R_{13}$ combined with the atom to which it is attached and an adjacent $R_{5a}$ to form a $C_{3-5}$ cycloalkyl, or $C_{2-4}$ heteroalicyclyl; In some embodiments $R_{13}$ is absent or hydrogen;

$R_{6a}$ is hydrogen, or combined with $R_{5a}$, $R_{6b}$ or $R_{13}$ to form ring system such as a $C_{3-6}$ cycloalkyl or $C_{2-5}$-heteroalicyclyl; $R_b$ is hydrogen or absent; for example both $R_{6a}$ and $R_{6b}$ are hydrogen. In such embodiments, B may be phenyl or pyridyl. Further, B may be phenyl with $R_{4a}$ in the para-position or meta-position, or a 6-membered heteroaryl substituted with $R_{4a}$ in the para-position or meta-position, or a 5-membered heteroaryl substituted with $R_{4a}$ in 2- or 3-position, wherein $R_{4a}$ is selected from a group other than hydrogen.

According to one aspect disclosed herein are compounds of Formula (X)

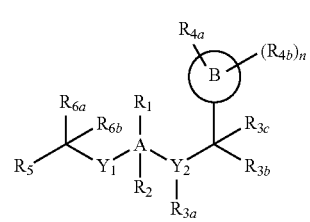

Formula (X)

or pharmaceutically acceptable salts, hydrates, solvates, polymorphs, and stereoisomers thereof, wherein:

$Y_1$ is NR or O;

$Y_2$ is N or C;

R is hydrogen or substituted or unsubstituted $C_{1-4}$ alkyl;

$R_1$ is selected from the group consisting of hydrogen, —OH, halogen, —CN, —$NO_2$, —$NH_2$, alkylamino, amide, acyl, ester, O-carboxy, mercapto, alkylthio, arylthio, carbonyl, thisocarbonyl, C amido, N amido, S-sulfonamido, N sulfonamide, silyl, sulfenyl, sulfinyl, sulfonyl, substituted or unsubstituted $C_{1-6}$ alkyl, substituted or unsubstituted $C_{1-6}$ alkoxy, substituted or unsubstituted $C_{1-6}$ alkenyl, substituted or unsubstituted $C_{2-6}$ alkynyl, substituted or unsubstituted $C_{1-6}$ heteroalkyl, substituted or unsubstituted aryl, substituted or unsubstituted heteroaryl, substituted or unsubstituted $C_{3-9}$ cycloalkyl, substituted or unsubstituted $C_{3-8}$ cycloalkenyl, substituted or unsubstituted $C_{2-9}$ heteroalicyclyl;

$R_2$ is selected from the group consisting of hydrogen, —OH, halogen, —CN, —NO$_2$, —NH$_2$, alkylamino, amide, acyl, ester, O-carboxy, mercapto, alkylthio, arylthio, carbonyl, thisocarbonyl, C amido, N amido, S-sulfonamido, N sulfonamide, silyl, sulfenyl, sulfinyl, sulfonyl, substituted or unsubstituted $C_{1-6}$ alkyl, substituted or unsubstituted $C_{1-6}$ alkoxy, substituted or unsubstituted $C_{1-6}$ alkenyl, substituted or unsubstituted $C_{2-6}$ alkynyl, substituted or unsubstituted $C_{1-6}$ heteroalkyl, substituted or unsubstituted aryl, substituted or unsubstituted heteroaryl, substituted or unsubstituted $C_{3-9}$ cycloalkyl, substituted or unsubstituted $C_{3-8}$ cycloalkenyl, substituted or unsubstituted $C_{2-9}$ heteroalicyclyl;

or R and $R_2$ are combined to form a fused ring; or $R_2$ and $R_{3a}$ are combined to form a fused ring;

$R_{3a}$ is selected from the group consisting of substituted or unsubstituted $C_{1-6}$ alkyl, substituted or unsubstituted $C_{1-6}$ alkoxy, substituted or unsubstituted aryl, substituted or unsubstituted heteroaryl, substituted or unsubstituted $C_{3-8}$ cycloalkyl, substituted or unsubstituted $C_{3-8}$ cycloalkenyl, substituted or unsubstituted $C_{2-9}$ heteroalicyclyl;

$R_{3b}$ and $R_{3c}$, are independently selected from the group consisting of hydrogen, —CN, substituted or unsubstituted $C_{1-6}$ alkyl, substituted or unsubstituted $C_{1-6}$ alkoxy, substituted or unsubstituted aryl, substituted or unsubstituted heteroaryl, substituted or unsubstituted $C_{3-8}$ cycloalkyl, substituted or unsubstituted $C_{3-8}$ cycloalkenyl, substituted or unsubstituted $C_{2-9}$ heteroalicyclyl, —(CR$_8$R$_9$)p-C(=O)OR$_7$, and —(CR$_8$R$_9$)p-C(=O)NR$_8$R$_9$, or $R_{3b}$ and $R_{3c}$ are combined to form an oxo group or a ring system selected from the group consisting of substituted or unsubstituted $C_{3-8}$ cycloalkyl substituted or unsubstituted $C_{3-8}$ cycloalkenyl, substituted or unsubstituted $C_{2-9}$ heteroalicyclyl; or $R_{3b}$ and $R_{4a}$ are combined to form a ring system; or $R_{3b}$ and $R_{4b}$ are combined to form a ring system;

$R_{4a}$ is selected from the group consisting of hydrogen, halogen, —OH, substituted or unsubstituted $C_{1-6}$ alkyl, substituted or unsubstituted $C_1$-$C_6$ alkoxy, substituted or unsubstituted $C_{1-6}$ alkenyl, substituted or unsubstituted aryl, substituted or unsubstituted aryl-$C_{1-6}$ alkyl, substituted or unsubstituted heteroaryl, substituted or unsubstituted heteroaryl-$C_{1-6}$ alkyl;

$R_{4b}$ is independently selected from the group consisting of hydrogen, halogen, —OH, substituted or unsubstituted $C_{1-4}$ alkyl, substituted or unsubstituted $C_{1-4}$ alkoxy, —C(=O)R$_{10}$;

$R_5$ is selected from the group consisting of —(CR$_8$R$_9$)pOR$_{12}$, —(CR$_8$R$_9$)p-CR$_{13}$R$_{14}$R$_{15}$, —(CR$_8$R$_9$)p-C(=O)OR$_7$, and —(CR$_8$R$_9$)p-C(=O)NR$_8$R$_9$;

n, and p are integers independently selected from the group consisting of 0, 1, 2, 3 and 4;

$R_{6a}$, $R_{6b}$ are independently selected from the group consisting of hydrogen, substituted or unsubstituted $C_{1-6}$ alkyl, substituted or unsubstituted $C_{1-6}$ alkenyl, substituted or unsubstituted $C_{1-6}$ alkynyl, substituted or unsubstituted $C_{1-6}$ alkoxy, substituted or unsubstituted $C_{1-6}$ heteroalkyl, substituted or unsubstituted $C_{3-8}$ cycloalkyl, substituted or unsubstituted $C_{3-8}$ cycloalkenyl, substituted or unsubstituted $C_{2-9}$ heteroalicyclyl, substituted or unsubstituted aryl, and substituted or unsubstituted heteroaryl;

$R_7$, $R_8$, $R_9$, and $R_{12}$, are independently selected from the group consisting of hydrogen, substituted or unsubstituted $C_{1-6}$ alkyl, substituted or unsubstituted $C_{3-6}$ cycloalkyl, and substituted or unsubstituted $C_{2-9}$ heteroalicyclyl;

$R_{10}$ is selected from the group consisting of $C_{1-6}$ alkyl, $C_{1-6}$ alkoxy, —NH$_2$, —NH($C_{1-6}$ alkyl), —N($C_{1-6}$ alkyl)$_2$, and $C_{3-7}$ cycloalkyl;

$R_{13}$ is absent, or selected from the group consisting of hydrogen, —OH, substituted or unsubstituted $C_{1-6}$ alkyl, substituted or unsubstituted $C_{1-6}$ alkenyl, substituted or unsubstituted $C_{1-6}$ alkoxy, substituted or unsubstituted $C_{3-8}$ cycloalkyl, substituted or unsubstituted $C_{3-8}$ cycloalkenyl, and —(CR$_8$R$_9$)p-C(=O)OR$_7$, and —(CR$_8$R$_9$)p-C(=O)NR$_8$R$_9$;

$R_{14}$ and $R_{15}$ are independently selected from the group consisting of hydrogen, and substituted or unsubstituted $C_{1-6}$ alkyl, substituted or unsubstituted $C_{3-6}$ cycloalkyl, substituted or unsubstituted $C_{2-9}$ heteroalicyclyl; or $R_{14}$ and $R_{15}$ are combined to form a ring system selected from the group consisting of substituted or unsubstituted $C_{3-8}$ cycloalkyl, substituted or unsubstituted $C_{3-8}$ cycloalkenyl, substituted or unsubstituted $C_{3-8}$ cycloalkyl, substituted or unsubstituted $C_{3-8}$ cycloalkenyl substituted or unsubstituted $C_{2-9}$ heteroalicyclyl, substituted or unsubstituted aryl, and substituted or unsubstituted heteroaryl;

A and B are independently of each other a ring system selected from the group consisting of mono- or bicyclic aryl, mono- or bicyclic heteroaryl, $C_{3-8}$ cycloalkyl, $C_{3-8}$ cycloalkenyl, and mono- or bicyclic $C_{2-9}$ heteroalicyclyl.-

In a related embodiment A is selected from the group consisting of Phenyl, pyridyl, pyrrolyl, furyl, pyranyl, thiopyranyl, thienyl, pyrazinyl, pyrimidinyl, triazinyl, naphthyl, indolyl, iso-indolyl, pyrazolyl, imidazolyl, triazolyl, tetrazolyl, and oxazolyl.

In yet a related embodiment A is selected from the group consisting of phenyl, pyridyl, pyrimidinyl, and wherein $R_1$ is arranged in position 1 of the 6 membered ring, $R_1$ is arranged in position 4 of the 6 membered ring, $Y_1$ arranged in position 3 of the 6 membered ring, $Y_2$ arranged in position 5 of the 6 membered ring. In a related embodiment $R_1$ is selected from the group consisting of hydrogen, —OH, halogen, substituted or unsubstituted $C_{1-4}$ alkyl, substituted or unsubstituted $C_{1-4}$ alkoxy, and substituted or unsubstituted $C_{2-4}$ alkenyl; and $R_2$ is selected from the group consisting of hydrogen, halogen, substituted or unsubstituted $C_{1-4}$ alkyl, substituted or unsubstituted $C_{1-4}$ alkoxy, —CN, —OH and —NO$_2$; or R and $R_2$ are combined to form a fused ring; In yet a related embodiment B is a ring system selected from the group consisting of aryl, heteroaryl, and bicyclic aryl or heteroalicyclyl, e.g. 11 or 12 membered bicyclic rings, e.g. benzazepine, benzazocines, benzimidazole, benzimidazo line, benzodioxin, benzodioxole, benzo furan, benzoisothiazole, benzothiadiazine, benzothiadiazole, benzothiazepine, benzothiazine, benzothiazole, benzothiophene, benzotriazole, benzoxadiazole, benzoxathiole, benzoxazepine, benzoxazine, benzoxazole, benzisoxazole, benzodioxole, chromane, chromene, coumarin, cyclopentapyridine, cyclopentapyrimidine, diazanaphthalene, dioxolopyridine, dioxolopyrimidine, dihydrobenzodioxine, dihydrobenzooxathiine, furofuran, furopyridine, furopyridine, furopyrimidine, imidazopyridine, imidazopyrimidines, indane, indazole, indene, indole, indoline, indolizines, isobenzofuran, isochromenes, isoindole, isoindoline, isoquinoline, naphthalene, naphthyridine, oxathiolopyridine, oxathiolopyrimidine, oxazolopyridine, oxazolopyrimidine, pteridine, purine, pyranopyridine, pyranopyrimidine, pyrazolodiazepines, pyrazolopyridine, pyrazolopyrimidine, pyridobenzthiazine, pyridodiazepene, pyridooxazine, pyridopyrazine, pyridopyrimidine, pyridothiazine, pyrimidooxazine, pyrimidopyrimidine, pyrimidothiazine, pyrrolizine, pyrroloimidazole, pyrrolopyrazine, pyrrolopyridine, pyrrolopyrimidine, quinazoline, quinoline, quinolone, quinolizidine, quinoxaline, tetralin, thiazolopyridine, thiazolopyrimidine, thienodiazepine, thienopyridine, thienopyrimidine, thiochromane, thiochromene, thiopyranopyridine, thiopyranopyrimidine, triazolopyridazine, triazolopyridine or triazolopyrimidine.

In some embodiments whenever a halogen is specified as a substituent the halogen is selected from fluoro or chloro. Specific examples of compounds are disclosed in Table 1 below.

TABLE 1

Example Compounds by Structure and Name.

| Ex. No. | Structure | Name |
|---|---|---|
| T1 | 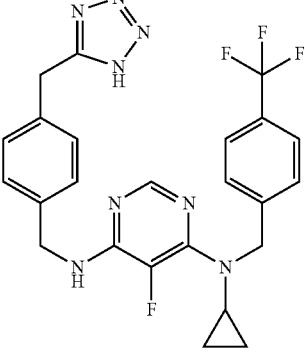 | N6-cyclopropyl-5-fluoro-N4-[[4-(1H-tetrazol-5-ylmethyl)phenyl]methyl]-N6-[[4-(trifluoromethyl)phenyl]methyl]pyrimidine-4,6-diamine |
| I1 | 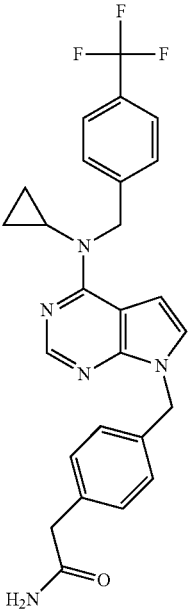 [SMILES: NC(=O)Cc1ccc(Cn2ccc3c(N(Cc4ccc(C(F)(F)F)cc4)C4CC4)ncnc32)cc1] | 2-[4-[[4-[cyclopropyl-[[4-(trifluoromethyl)phenyl]methyl]amino]pyrrolo[2,3-d]pyrimidin-7-yl]methyl]phenyl]acetamide |
| x | 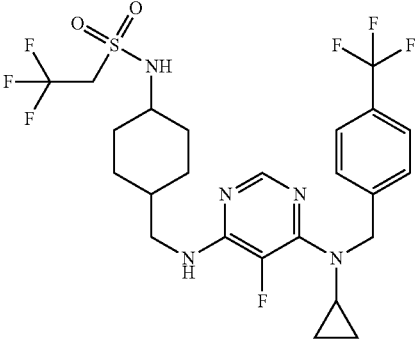 [SMILES: O=S(=O)(CC(F)(F)F)NC1CCC(CNc2ncnc(N(Cc3ccc(C(F)(F)F)cc3)C3CC3)c2F)CC1] | N-[4-[[[6-[cyclopropyl-[[4-(trifluoromethyl)phenyl]methyl]amino]-5-fluoro-pyrimidin-4-yl]amino]methyl]cyclohexyl]-2,2,2-trifluoro-ethanesulfonamide |

TABLE 1-continued

Example Compounds by Structure and Name.

| Ex. No. | Structure | Name |
|---|---|---|
| A1 | 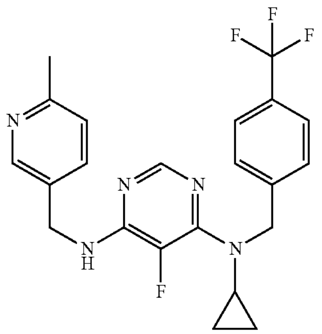 [SMILES: Cc1ccc(CNc2ncnc(N(Cc3ccc(C(F)(F)F)cc3)C3CC3)c2F)cn1] | N4-cyclopropyl-5-fluoro-N6-[(6-methyl-3-pyridyl)methyl]-N4-[[4-(trifluoromethyl)phenyl]methyl]pyrimidine-4,6-diamine |
| A2 | 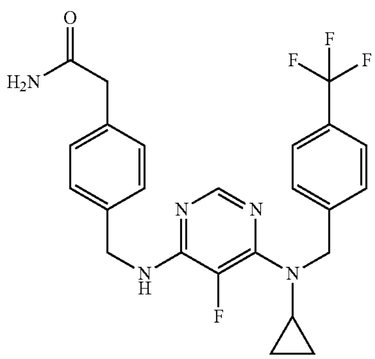 [SMILES: NC(=O)Cc1ccc(CNc2ncnc(N(Cc3ccc(C(F)(F)F)cc3)C3CC3)c2F)cc1] | 2-[4-[[[6-[cyclopropyl-[[4-(trifluoromethyl)phenyl]methyl]amino]-5-fluoro-pyrimidin-4-yl]amino]methyl]phenyl]acetamide |
| A3 | 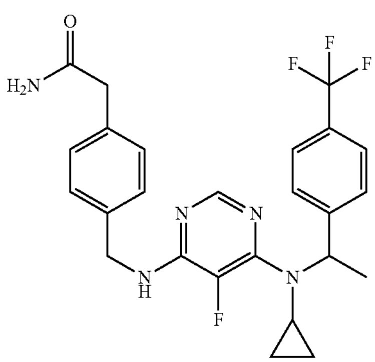 [SMILES: CC(c1ccc(C(F)(F)F)cc1)N(c1ncnc(NCc2ccc(CC(N)=O)cc2)c1F)C1CC1] | 2-[4-[[[6-[cyclopropyl-[1-[4-(trifluoromethyl)phenyl]ethyl]amino]-5-fluoro-pyrimidin-4-yl]amino]methyl]phenyl]acetamide |
| A4 | 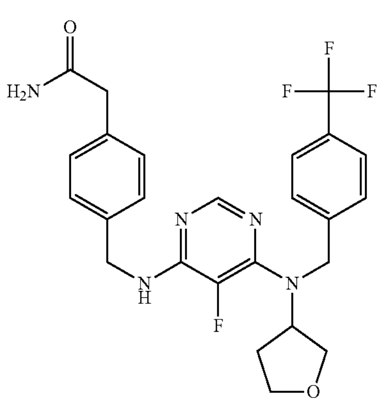 [SMILES: NC(=O)Cc1ccc(CNc2ncnc(N(Cc3ccc(C(F)(F)F)cc3)C3CCOC3)c2F)cc1] | 2-[4-[[[5-fluoro-6-[tetrahydrofuran-3-yl-[[4-(trifluoromethyl)phenyl]methyl]amino]pyrimidin-4-yl]amino]methyl]phenyl]acetamide |

TABLE 1-continued

Example Compounds by Structure and Name.

| Ex. No. | Structure | Name |
|---|---|---|
| A5 | 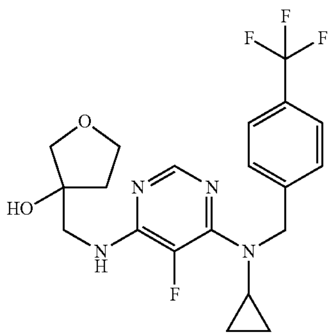 [SMILES: OC1(CNc2ncnc(N(Cc3ccc(C(F)(F)F)cc3)C3CC3)c2F)CCOC1] | 3-[[[6-[cyclopropyl-[[4-(trifluoromethyl)phenyl]methyl]amino]-5-fluoro-pyrimidin-4-yl]amino]methyl]tetrahydrofuran-3-ol |
| A6 | 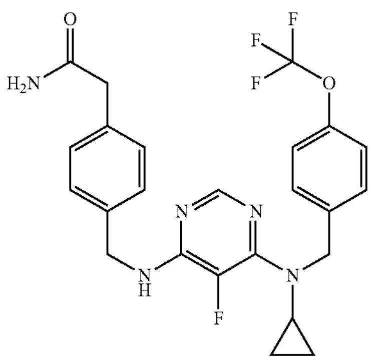 [SMILES: NC(=O)Cc1ccc(CNc2ncnc(N(Cc3ccc(OC(F)(F)F)cc3)C3CC3)c2F)cc1] | 2-[4-[[[6-[cyclopropyl-[[4-(trifluoromethoxy)phenyl]methyl]amino]-5-fluoro-pyrimidin-4-yl]amino]methyl]phenyl]acetamide |
| A7 | 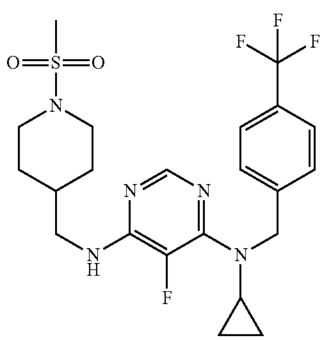 [SMILES: CS(=O)(=O)N1CCC(CNc2ncnc(N(Cc3ccc(C(F)(F)F)cc3)C3CC3)c2F)CC1] | N4-cyclopropyl-5-fluoro-N6-[(1-methylsulfonyl-4-piperidyl)methyl]-N4-[[4-(trifluoromethyl)phenyl]methyl]pyrimidine-4,6-diamine |
| A8 | 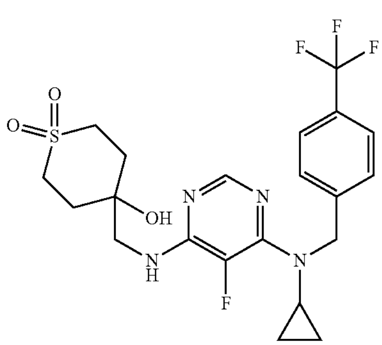 [SMILES: O=S1(=O)CCC(O)(CNc2ncnc(N(Cc3ccc(C(F)(F)F)cc3)C3CC3)c2F)CC1] | 4-[[[6-[cyclopropyl-[[4-(trifluoromethyl)phenyl]methyl]amino]-5-fluoro-pyrimidin-4-yl]amino]methyl]-1,1-dioxo-thian-4-ol |

TABLE 1-continued

Example Compounds by Structure and Name.

| Ex. No. | Structure | Name |
|---|---|---|
| A9 | 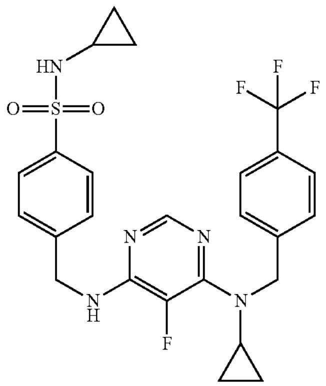 [SMILES: O=S(=O)(NC1CC1)c1ccc(CNc2ncnc(N(Cc3ccc(C(F)(F)F)cc3)C3CC3)c2F)cc1] | N-cyclopropyl-4-[[[6-[cyclopropyl-[[4-(trifluoromethyl)phenyl]methyl]amino]-5-fluoro-pyrimidin-4-yl]amino]methyl]benzenesulfonamide |
| A11 | 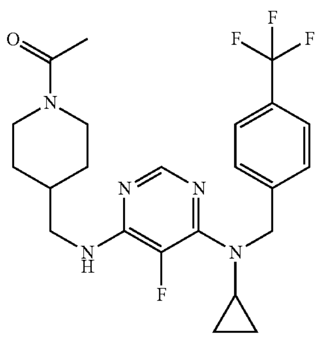 [SMILES: CC(=O)N1CCC(CNc2ncnc(N(Cc3ccc(C(F)(F)F)cc3)C3CC3)c2F)CC1] | 1-[4-[[[6-[cyclopropyl-[[4-(trifluoromethyl)phenyl]methyl]amino]-5-fluoro-pyrimidin-4-yl]amino]methyl]-1-piperidyl]ethanone |
| A12 | 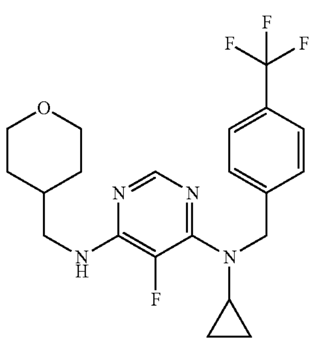 [SMILES: Fc1c(NCC2CCOCC2)ncnc1N(Cc1ccc(C(F)(F)F)cc1)C1CC1] | N4-cyclopropyl-5-fluoro-N6-(tetrahydropyran-4-ylmethyl)-N4-[[4-(trifluoromethyl)phenyl]methyl]pyrimidine-4,6-diamine |
| A13 | 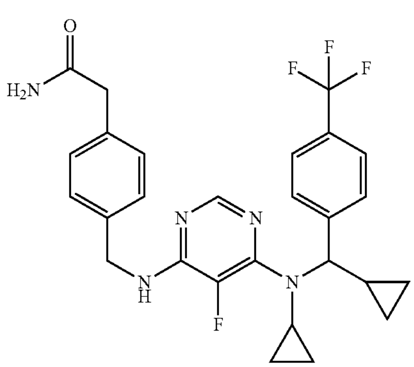 [SMILES: NC(=O)Cc1ccc(CNc2ncnc(N(C3CC3)C(c3ccc(C(F)(F)F)cc3)C3CC3)c2F)cc1] | 2-[4-[[[6-[cyclopropyl-[cyclopropyl-[4-(trifluoromethyl)phenyl]methyl]amino]-5-fluoro-pyrimidin-4-yl]amino]methyl]phenyl]acetamide |

TABLE 1-continued

Example Compounds by Structure and Name.

| Ex. No. | Structure | Name |
|---|---|---|
| A14 | 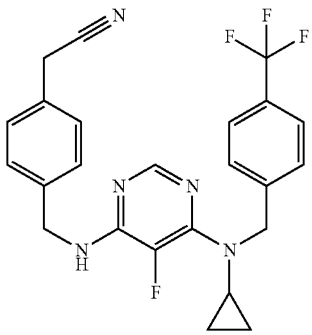 [SMILES: N#CCc1ccc(CNc2ncnc(N(Cc3ccc(C(F)(F)F)cc3)C3CC3)c2F)cc1] | 2-[4-[[[6-[cyclopropyl-[[4-(trifluoromethyl)phenyl]methyl]amino]-5-fluoro-pyrimidin-4-yl]amino]methyl]phenyl]acetonitrile |
| A15 | 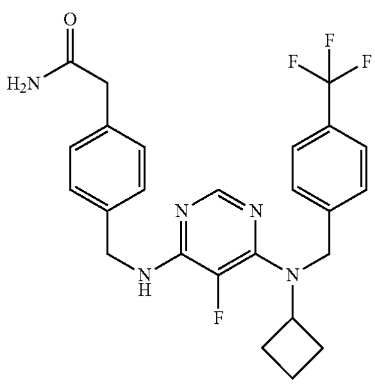 [SMILES: NC(=O)Cc1ccc(CNc2ncnc(N(Cc3ccc(C(F)(F)F)cc3)C3CCC3)c2F)cc1] | 2-[4-[[[6-[cyclobutyl-[[4-(trifluoromethyl)phenyl]methyl]amino]-5-fluoro-pyrimidin-4-yl]amino]methyl]phenyl]acetamide |
| A16 | 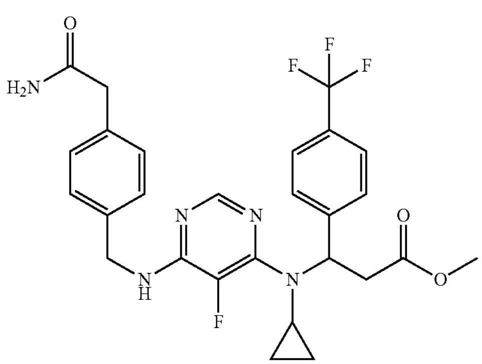 [SMILES: COC(=O)CC(c1ccc(C(F)(F)F)cc1)N(c1ncnc(NCc2ccc(CC(N)=O)cc2)c1F)C1CC1] | methyl 3-[[6-[[4-(2-amino-2-oxo-ethyl)phenyl]methylamino]-5-fluoro-pyrimidin-4-yl]-cyclopropyl-amino]-3-[4-(trifluoromethyl)phenyl]propanoate |
| A17 | 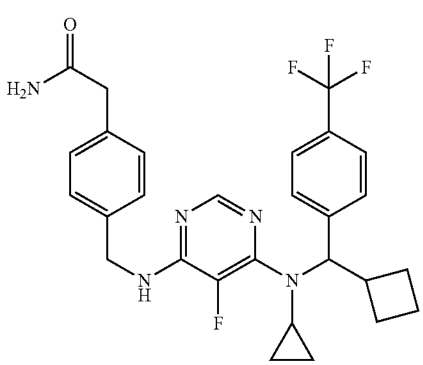 [SMILES: NC(=O)Cc1ccc(CNc2ncnc(N(C3CC3)C(c3ccc(C(F)(F)F)cc3)C3CCC3)c2F)cc1] | 2-[4-[[[6-[[cyclobutyl-[4-(trifluoromethyl)phenyl]methyl]-cyclopropyl-amino]-5-fluoro-pyrimidin-4-yl]amino]methyl]phenyl]acetamide |

TABLE 1-continued

Example Compounds by Structure and Name.

| Ex. No. | Structure | Name |
|---|---|---|
| A18 | 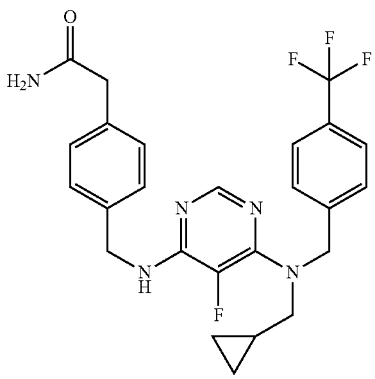 [SMILES: NC(=O)Cc1ccc(CNc2ncnc(N(Cc3ccc(C(F)(F)F)cc3)CC3CC3)c2F)cc1] | 2-[4-[[[6-[cyclopropylmethyl-[[4-(trifluoromethyl)phenyl]methyl]amino]-5-fluoro-pyrimidin-4-yl]amino]methyl]phenyl]acetamide |
| A19 | 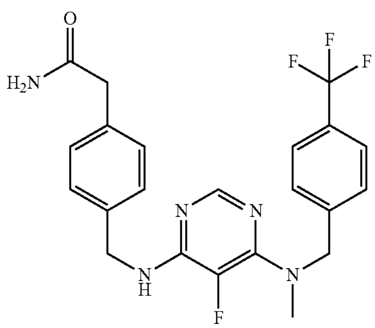 [SMILES: CN(Cc1ccc(C(F)(F)F)cc1)c1ncnc(NCc2ccc(CC(N)=O)cc2)c1F] | 2-[4-[[[5-fluoro-6-[methyl-[[4-(trifluoromethyl)phenyl]methyl]amino]pyrimidin-4-yl]amino]methyl]phenyl]acetamide |
| A20 | 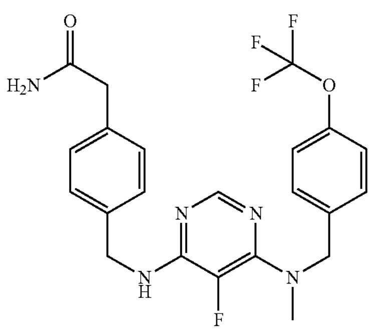 [SMILES: CN(Cc1ccc(OC(F)(F)F)cc1)c1ncnc(NCc2ccc(CC(N)=O)cc2)c1F] | 2-[4-[[[5-fluoro-6-[methyl-[[4-(trifluoromethoxy)phenyl]methyl]amino]pyrimidin-4-yl]amino]methyl]phenyl]acetamide |
| A21 | 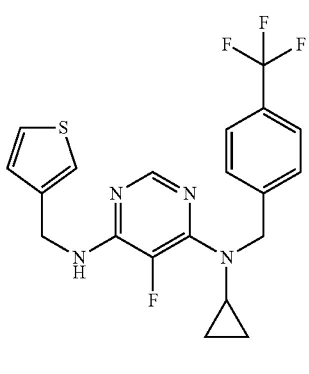 [SMILES: Fc1c(NCc2ccsc2)ncnc1N(Cc1ccc(C(F)(F)F)cc1)C1CC1] | N6-cyclopropyl-5-fluoro-N4-(3-thienylmethyl)-N6-[[4-(trifluoromethyl)phenyl]methyl]pyrimidine-4,6-diamine |

TABLE 1-continued

Example Compounds by Structure and Name.

| Ex. No. | Structure | Name |
|---|---|---|
| A22 | 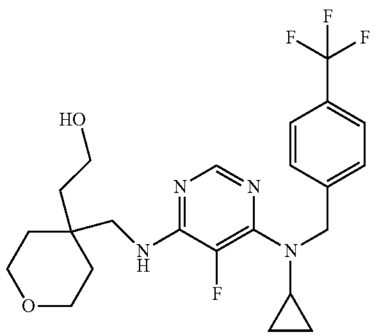 [SMILES: OCCC1(CNc2ncnc(N(Cc3ccc(C(F)(F)F)cc3)C3CC3)c2F)CCOCC1] | 2-[4-[[[6-[cyclopropyl-[[4-(trifluoromethyl)phenyl]methyl]amino]-5-fluoro-pyrimidin-4-yl]amino]methyl]tetrahydropyran-4-yl]ethanol |
| A23 | 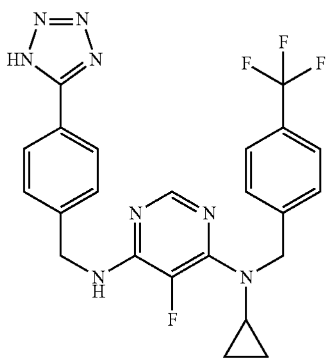 [SMILES: Fc1c(NCc2ccc(-c3nnn[nH]3)cc2)ncnc1N(Cc1ccc(C(F)(F)F)cc1)C1CC1] | N6-cyclopropyl-5-fluoro-N4-[[4-(1H-tetrazol-5-yl)phenyl]methyl]-N6-[[4-(trifluoromethyl)phenyl]methyl]pyrimidine-4,6-diamine |
| A24 | 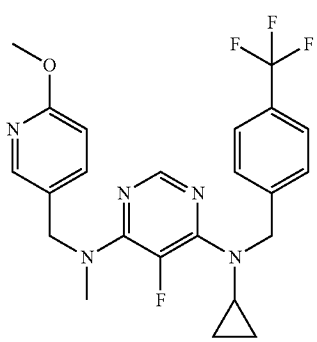 [SMILES: COc1ccc(CN(C)c2ncnc(N(Cc3ccc(C(F)(F)F)cc3)C3CC3)c2F)cn1] | N6-cyclopropyl-5-fluoro-N4-[(6-methoxy-3-pyridyl)methyl]-N4-methyl-N6-[[4-(trifluoromethyl)phenyl]methyl]pyrimidine-4,6-diamine |
| A25 | 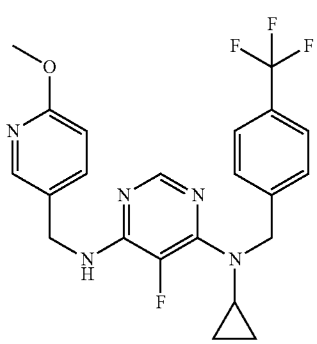 [SMILES: COc1ccc(CNc2ncnc(N(Cc3ccc(C(F)(F)F)cc3)C3CC3)c2F)cn1] | N6-cyclopropyl-5-fluoro-N4-[(6-methoxy-3-pyridyl)methyl]-N6-[[4-(trifluoromethyl)phenyl]methyl]pyrimidine-4,6-diamine |

TABLE 1-continued

Example Compounds by Structure and Name.

| Ex. No. | Structure | Name |
|---|---|---|
| A26 | 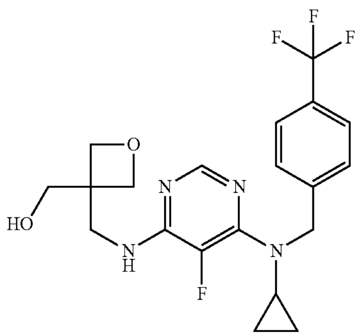 [SMILES: OCC1(CNc2ncnc(N(Cc3ccc(C(F)(F)F)cc3)C3CC3)c2F)COC1] | [3-[[[6-[cyclopropyl-[[4-(trifluoromethyl)phenyl]methyl]amino]-5-fluoro-pyrimidin-4-yl]amino]methyl]oxetan-3-yl]methanol |
| A27 | 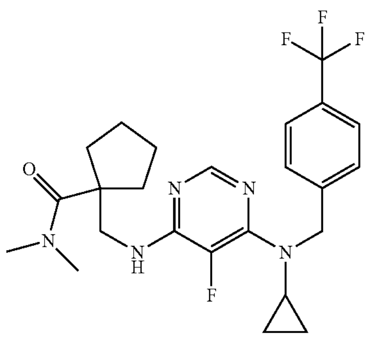 [SMILES: CN(C)C(=O)C1(CNc2ncnc(N(Cc3ccc(C(F)(F)F)cc3)C3CC3)c2F)CCCC1] | 1-[[[6-[cyclopropyl-[[4-(trifluoromethyl)phenyl]methyl]amino]-5-fluoro-pyrimidin-4-yl]amino]methyl]-N,N-dimethyl-cyclopentanecarboxamide |
| A28 | 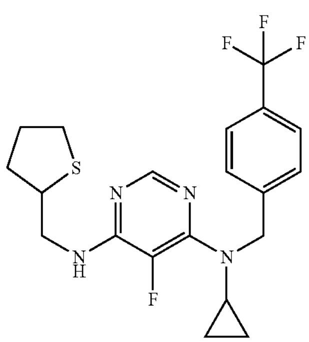 [SMILES: Fc1c(NCC2CCCS2)ncnc1N(Cc1ccc(C(F)(F)F)cc1)C1CC1] | N6-cyclopropyl-5-fluoro-N4-(tetrahydrothiophen-2-ylmethyl)-N6-[[4-(trifluoromethyl)phenyl]methyl]pyrimidine-4,6-diamine |
| A29 | 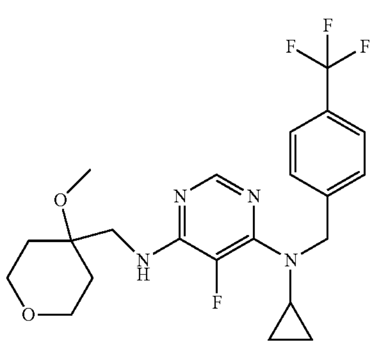 [SMILES: COC1(CNc2ncnc(N(Cc3ccc(C(F)(F)F)cc3)C3CC3)c2F)CCOCC1] | N6-cyclopropyl-5-fluoro-N4-[(4-methoxytetrahydropyran-4-yl)methyl]-N6-[[4-(trifluoromethyl)phenyl]methyl]pyrimidine-4,6-diamine |

TABLE 1-continued

Example Compounds by Structure and Name.

| Ex. No. | Structure | Name |
|---|---|---|
| A30 | 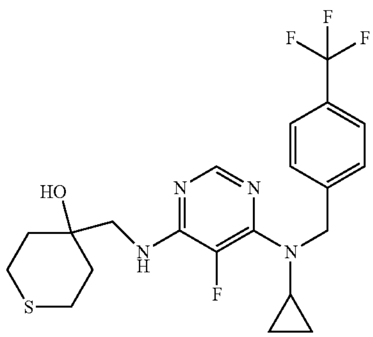 [SMILES: OC1(CNc2ncnc(N(Cc3ccc(C(F)(F)F)cc3)C3CC3)c2F)CCSCC1] | 4-[[[6-[cyclopropyl-[[4-(trifluoromethyl)phenyl]methyl]amino]-5-fluoro-pyrimidin-4-yl]amino]methyl]tetrahydrothiopyran-4-ol |
| A31 | 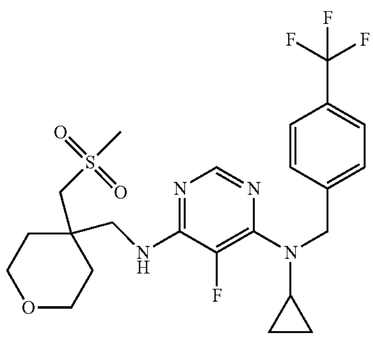 [SMILES: CS(=O)(=O)CC1(CNc2ncnc(N(Cc3ccc(C(F)(F)F)cc3)C3CC3)c2F)CCOCC1] | N6-cyclopropyl-5-fluoro-N4-[[4-(methylsulfonylmethyl)tetrahydropyran-4-yl]methyl]-N6-[[4-(trifluoromethyl)phenyl]methyl]pyrimidine-4,6-diamine |
| A32 | 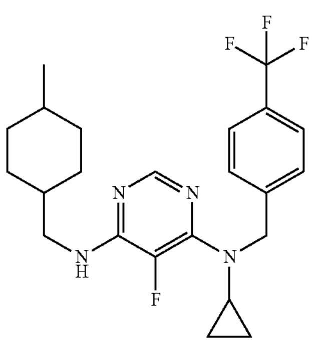 [SMILES: CC1CCC(CNc2ncnc(N(Cc3ccc(C(F)(F)F)cc3)C3CC3)c2F)CC1] | N6-cyclopropyl-5-fluoro-N4-[(4-methylcyclohexyl)methyl]-N6-[[4-(trifluoromethyl)phenyl]methyl]pyrimidine-4,6-diamine |
| A33 | 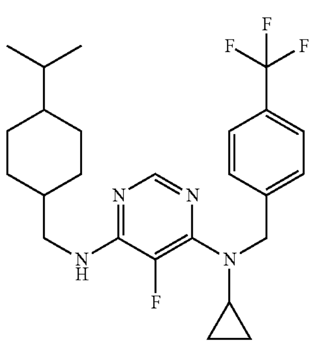 [SMILES: CC(C)C1CCC(CNc2ncnc(N(Cc3ccc(C(F)(F)F)cc3)C3CC3)c2F)CC1] | N6-cyclopropyl-5-fluoro-N4-[(4-isopropylcyclohexyl)methyl]-N6-[[4-(trifluoromethyl)phenyl]methyl]pyrimidine-4,6-diamine |

TABLE 1-continued

Example Compounds by Structure and Name.

| Ex. No. | Structure | Name |
|---|---|---|
| A34 | 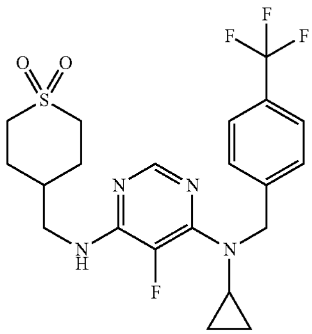 [SMILES: O=S1(=O)CCC(CNc2ncnc(N(Cc3ccc(C(F)(F)F)cc3)C3CC3)c2F)CC1] | N6-cyclopropyl-N4-[(1,1-dioxothian-4-yl)methyl]-5-fluoro-N6-[[4-(trifluoromethyl)phenyl]methyl]pyrimidine-4,6-diamine |
| A35 | 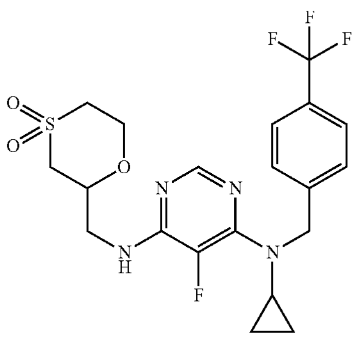 [SMILES: O=S1(=O)CCOC(CNc2ncnc(N(Cc3ccc(C(F)(F)F)cc3)C3CC3)c2F)C1] | N6-cyclopropyl-N4-[(4,4-dioxo-1,4-oxathian-2-yl)methyl]-5-fluoro-N6-[[4-(trifluoromethyl)phenyl]methyl]pyrimidine-4,6-diamine |
| A36 | 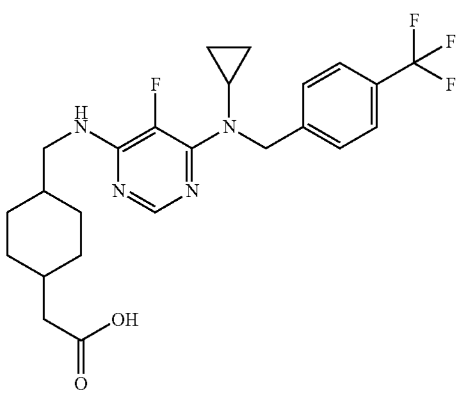 [SMILES: O=C(O)CC1CCC(CNc2ncnc(N(Cc3ccc(C(F)(F)F)cc3)C3CC3)c2F)CC1] | 2-[4-[[[6-[cyclopropyl-[[4-(trifluoromethyl)phenyl]methyl]amino]-5-fluoro-pyrimidin-4-yl]amino]methyl]cyclohexyl]acetic acid |
| A37 | 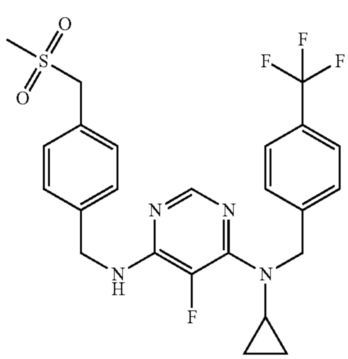 [SMILES: CS(=O)(=O)Cc1ccc(CNc2ncnc(N(Cc3ccc(C(F)(F)F)cc3)C3CC3)c2F)cc1] | N4-cyclopropyl-5-fluoro-N6-[[4-(methylsulfonylmethyl)phenyl]methyl]-N4-[[4-(trifluoromethyl)phenyl]methyl]pyrimidine-4,6-diamine |

TABLE 1-continued

Example Compounds by Structure and Name.

| Ex. No. | Structure | Name |
|---|---|---|
| A38 | 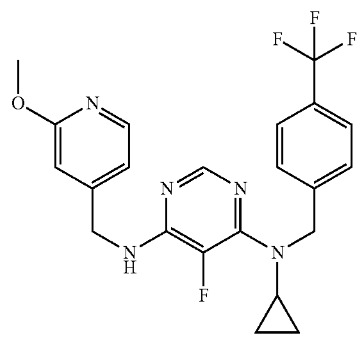 [SMILES: COc1cc(CNc2ncnc(N(Cc3ccc(C(F)(F)F)cc3)C3CC3)c2F)ccn1] | N4-cyclopropyl-5-fluoro-N6-[(2-methoxy-4-pyridyl)methyl]-N4-[[4-(trifluoromethyl)phenyl]methyl]pyrimidine-4,6-diamine |
| A39 | 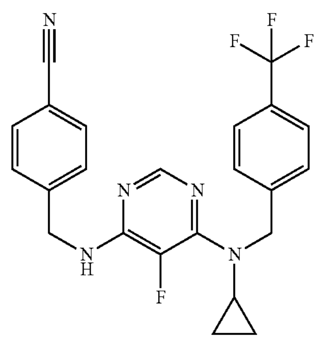 [SMILES: N#Cc1ccc(CNc2ncnc(N(Cc3ccc(C(F)(F)F)cc3)C3CC3)c2F)cc1] | 4-[[[6-[cyclopropyl-[[4-(trifluoromethyl)phenyl]methyl]amino]-5-fluoro-pyrimidin-4-yl]amino]methyl]benzonitrile |
| A40 | 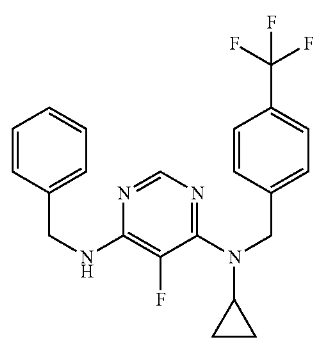 [SMILES: Fc1c(NCc2ccccc2)ncnc1N(Cc1ccc(C(F)(F)F)cc1)C1CC1] | N6-benzyl-N4-cyclopropyl-5-fluoro-N4-[[4-(trifluoromethyl)phenyl]methyl]pyrimidine-4,6-diamine |
| A41 | 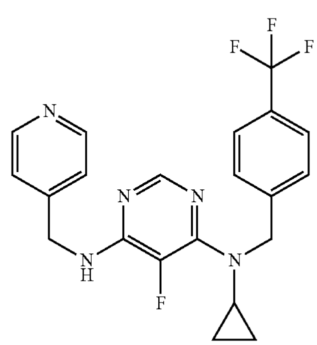 [SMILES: Fc1c(NCc2ccncc2)ncnc1N(Cc1ccc(C(F)(F)F)cc1)C1CC1] | N4-cyclopropyl-5-fluoro-N6-(4-pyridylmethyl)-N4-[[4-(trifluoromethyl)phenyl]methyl]pyrimidine-4,6-diamine |

TABLE 1-continued

Example Compounds by Structure and Name.

| Ex. No. | Structure | Name |
|---|---|---|
| A42 | 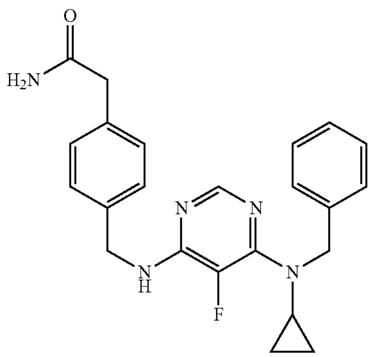 [SMILES: NC(=O)Cc1ccc(CNc2ncnc(N(Cc3ccccc3)C3CC3)c2F)cc1] | 2-[4-[[[6-[benzyl(cyclopropyl)amino]-5-fluoro-pyrimidin-4-yl]amino]methyl]phenyl]acetamide |
| A43 | 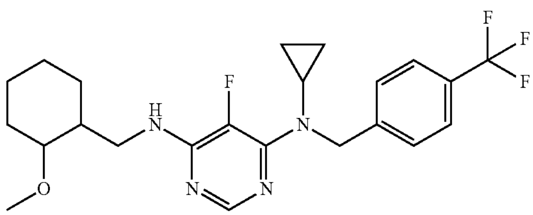 [SMILES: COC1CCCCC1CNc1ncnc(N(Cc2ccc(C(F)(F)F)cc2)C2CC2)c1F] | N4-cyclopropyl-5-fluoro-N6-[(2-methoxycyclohexyl)methyl]-N4-[[4-(trifluoromethyl)phenyl]methyl]pyrimidine-4,6-diamine |
| A44 | 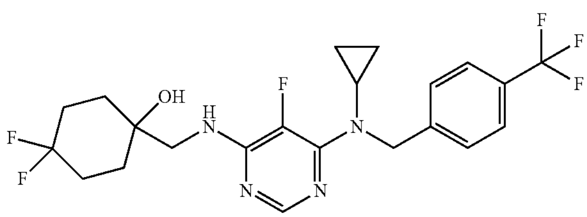 [SMILES: OC1(CNc2ncnc(N(Cc3ccc(C(F)(F)F)cc3)C3CC3)c2F)CCC(F)(F)CC1] | 1-[[[6-[cyclopropyl-[[4-(trifluoromethyl)phenyl]methyl]amino]-5-fluoro-pyrimidin-4-yl]amino]methyl]-4,4-difluoro-cyclohexanol |
| A45 | 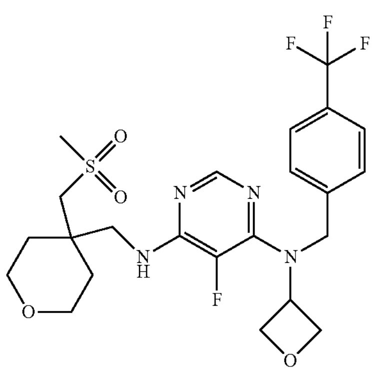 [SMILES: CS(=O)(=O)CC1(CNc2ncnc(N(Cc3ccc(C(F)(F)F)cc3)C3COC3)c2F)CCOCC1] | 5-fluoro-N6-[[4-(methylsulfonylmethyl)tetrahydro-pyran-4-yl]methyl]-N4-(oxetan-3-yl)-N4-[[4-(trifluoromethyl)phenyl]methyl]pyrimidine-4,6-diamine |
| A47 | 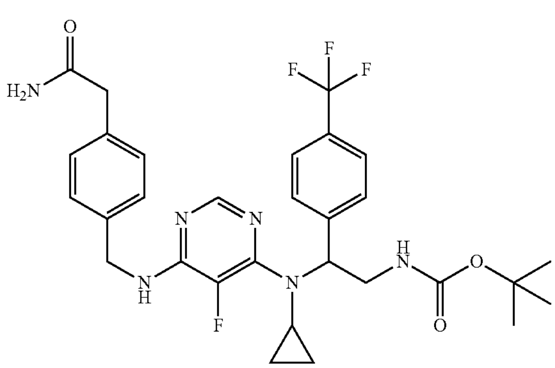 [SMILES: CC(C)(C)OC(=O)NCC(c1ccc(C(F)(F)F)cc1)N(c1ncnc(NCc2ccc(CC(N)=O)cc2)c1F)C1CC1] | tert-butyl N-[2-[[6-[[4-(2-amino-2-oxo-ethyl)phenyl]methylamino]-5-fluoro-pyrimidin-4-yl]-cyclopropyl-amino]-2-[4-(trifluoromethyl)phenyl]ethyl]carbamate |

TABLE 1-continued

Example Compounds by Structure and Name.

| Ex. No. | Structure | Name |
|---|---|---|
| A49 | 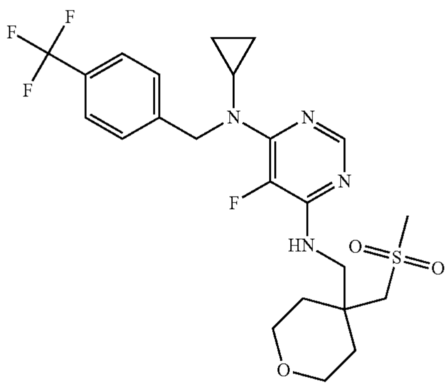 [SMILES: CS(=O)(=O)CC1(CNc2ncnc(N(Cc3ccc(C(F)(F)F)cc3)C3CC3)c2F)CCOCC1] | N6-cyclopropyl-5-fluoro-N4-[[4-(methylsulfonylmethyl)tetrahydro-pyran-4-yl]methyl]-N6-[[4-(trifluoromethyl)phenyl]methyl]pyrimidine-4,6-diamine |
| A52 | 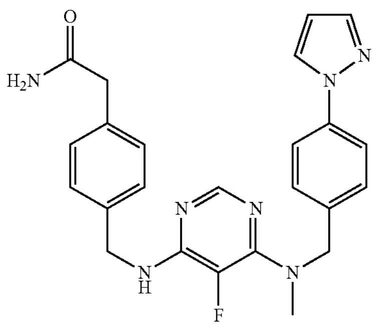 [SMILES: CN(Cc1ccc(-n2cccn2)cc1)c1ncnc(NCc2ccc(CC(N)=O)cc2)c1F] | 2-[4-[[[5-fluoro-6-[methyl-[(4-pyrazol-1-ylphenyl)methyl]amino]pyrimidin-4-yl]amino]methyl]phenyl]acetamide |
| A53 | 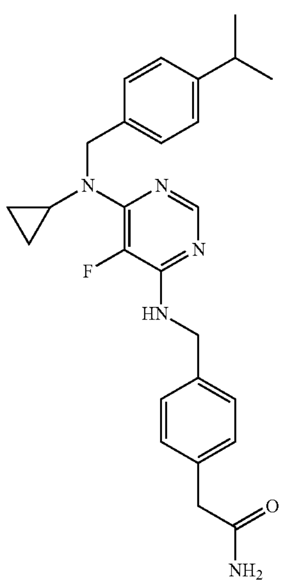 [SMILES: CC(C)c1ccc(CN(c2ncnc(NCc3ccc(CC(N)=O)cc3)c2F)C2CC2)cc1] | 2-[4-[[[6-[cyclopropyl-[(4-isopropylphenyl)methyl]amino]-5-fluoro-pyrimidin-4-yl]amino]methyl]phenyl]acetamide |

TABLE 1-continued
Example Compounds by Structure and Name.
| Ex. No. | Structure | Name |
|---|---|---|
| A54 | 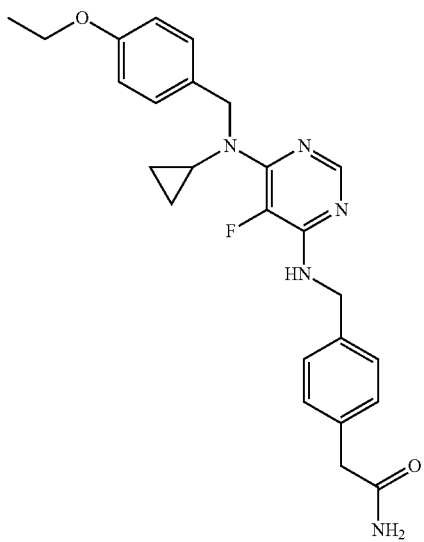 [SMILES: CCOc1ccc(CN(c2ncnc(NCc3ccc(CC(N)=O)cc3)c2F)C2CC2)cc1] | 2-[4-[[[6-[cyclopropyl-[(4-ethoxyphenyl)methyl]amino]-5-fluoro-pyrimidin-4-yl]amino]methyl]phenyl]acetamide |
| A55 | 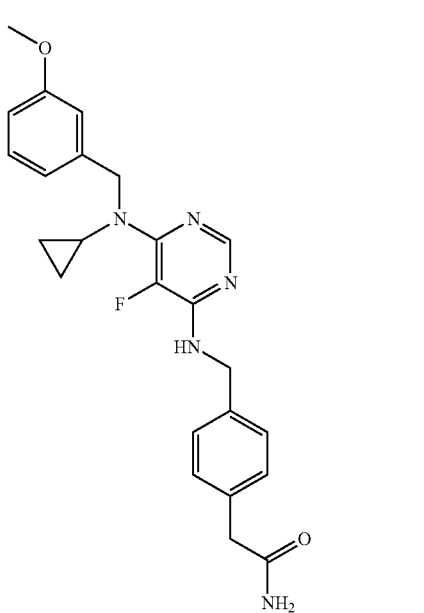 [SMILES: COc1cccc(CN(c2ncnc(NCc3ccc(CC(N)=O)cc3)c2F)C2CC2)c1] | 2-[4-[[[6-[cyclopropyl-[(3-methoxyphenyl)methyl]amino]-5-fluoro-pyrimidin-4-yl]amino]methyl]phenyl]acetamide |

TABLE 1-continued

Example Compounds by Structure and Name.

| Ex. No. | Structure | Name |
|---|---|---|
| A56 | 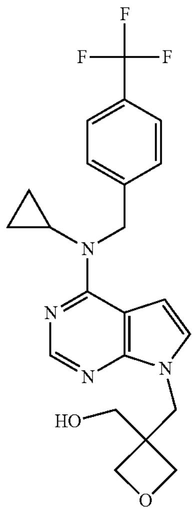 [SMILES: OCC1(Cn2ccc3c(N(Cc4ccc(C(F)(F)F)cc4)C4CC4)ncnc32)COC1] | [3-[[4-[cyclopropyl-[[4-(trifluoromethyl)phenyl]methyl]amino]pyrrolo[2,3-d]pyrimidin-7-yl]methyl]oxetan-3-yl]methanol |
| A57 | 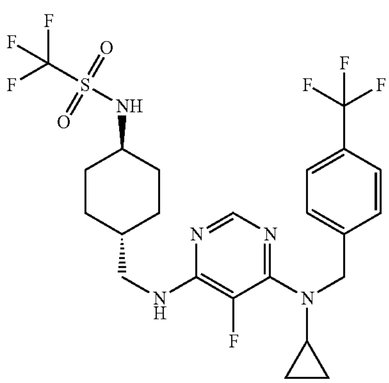 [SMILES: O=S(=O)(N[C@H]1CC[C@H](CNc2ncnc(N(Cc3ccc(C(F)(F)F)cc3)C3CC3)c2F)CC1)C(F)(F)F] | N-[4-[[[6-[cyclopropyl-[[4-(trifluoromethyl)phenyl]methyl]amino]-5-fluoro-pyrimidin-4-yl]amino]methyl]cyclohexyl]-1,1,1-trifluoro-methanesulfonamide |
| A58 | 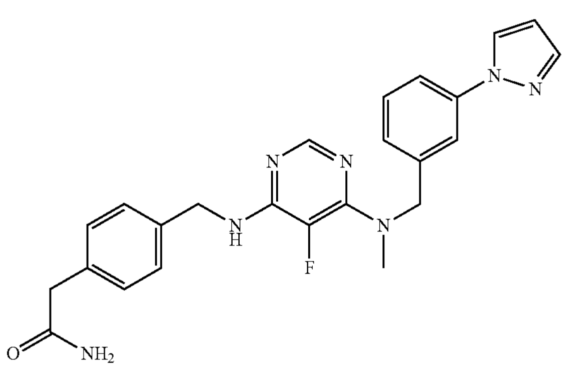 [SMILES: CN(Cc1cccc(-n2cccn2)c1)c1ncnc(NCc2ccc(CC(N)=O)cc2)c1F] | 2-[4-[[[5-fluoro-6-[methyl-[(3-pyrazol-1-ylphenyl)methyl]amino]pyrimidin-4-yl]amino]methyl]phenyl]acetamide |

TABLE 1-continued

Example Compounds by Structure and Name.

| Ex. No. | Structure | Name |
|---|---|---|
| A59 | 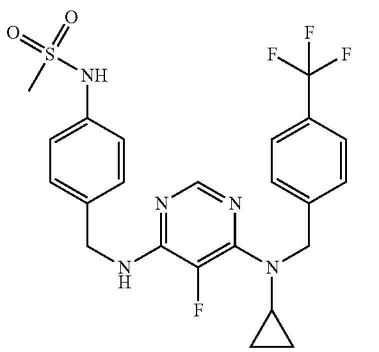 [SMILES: CS(=O)(=O)Nc1ccc(CNc2ncnc(N(Cc3ccc(C(F)(F)F)cc3)C3CC3)c2F)cc1] | N-[4-[[[6-[cyclopropyl-[[4-(trifluoromethyl)phenyl]methyl]amino]-5-fluoro-pyrimidin-4-yl]amino]methyl]phenyl]methane-sulfonamide |
| A60 | 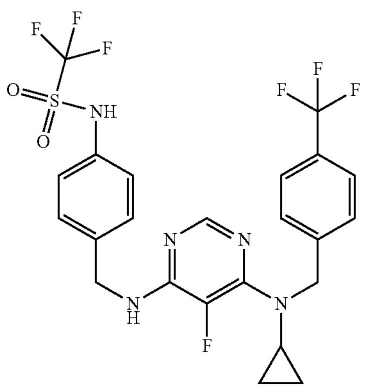 [SMILES: O=S(=O)(Nc1ccc(CNc2ncnc(N(Cc3ccc(C(F)(F)F)cc3)C3CC3)c2F)cc1)C(F)(F)F] | N-[4-[[[6-[cyclopropyl-[[4-(trifluoromethyl)phenyl]methyl]amino]-5-fluoro-pyrimidin-4-yl]amino]methyl]phenyl]-1,1,1-trifluoro-methanesulfonamide |
| A61 | 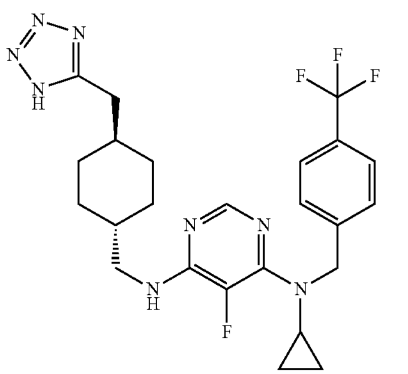 [SMILES: Fc1c(NC[C@H]2CC[C@H](Cc3nnn[nH]3)CC2)ncnc1N(Cc1ccc(C(F)(F)F)cc1)C1CC1] | N4-cyclopropyl-5-fluoro-N6-[[4-(1H-tetrazol-5-ylmethyl)cyclohexyl]methyl]-N4-[[4-(trifluoromethyl)phenyl]methyl]pyrimidine-4,6-diamine |
| A62 | 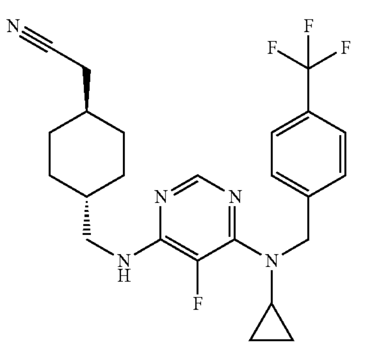 [SMILES: N#CC[C@H]1CC[C@H](CNc2ncnc(N(Cc3ccc(C(F)(F)F)cc3)C3CC3)c2F)CC1] | 2-[4-[[[6-[cyclopropyl-[[4-(trifluoromethyl)phenyl]methyl]amino]-5-fluoro-pyrimidin-4-yl]amino]methyl]cyclohexyl]acetonitrile |

TABLE 1-continued

Example Compounds by Structure and Name.

| Ex. No. | Structure | Name |
|---|---|---|
| A63 | 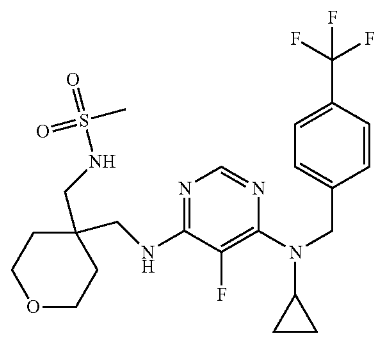 [SMILES: CS(=O)(=O)NCC1(CNc2ncnc(N(Cc3ccc(C(F)(F)F)cc3)C3CC3)c2F)CCOCC1] | N-[[4-[[[6-[cyclopropyl-[[4-(trifluoromethyl)phenyl]methyl]amino]-5-fluoro-pyrimidin-4-yl]amino]methyl]tetrahydropyran-4-yl]methyl]methanesulfonamide |
| A64 | 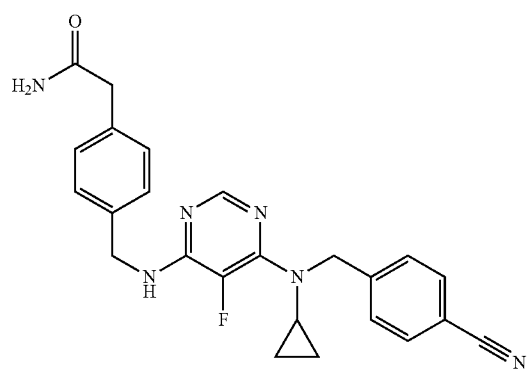 [SMILES: N#Cc1ccc(CN(c2ncnc(NCc3ccc(CC(N)=O)cc3)c2F)C2CC2)cc1] | 2-[4-[[[6-[(4-cyanophenyl)methyl-cyclopropyl-amino]-5-fluoro-pyrimidin-4-yl]amino]methyl]phenyl]acetamide |
| A65 | 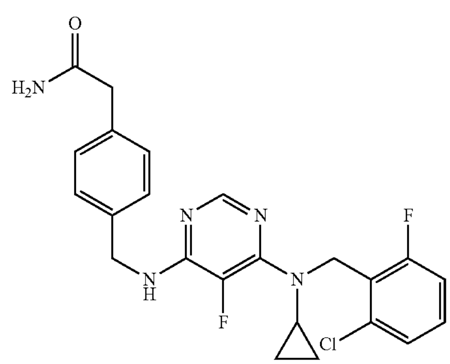 [SMILES: NC(=O)Cc1ccc(CNc2ncnc(N(Cc3c(F)cccc3Cl)C3CC3)c2F)cc1] | 2-[4-[[[6-[(2-chloro-6-fluoro-phenyl)methyl-cyclopropyl-amino]-5-fluoro-pyrimidin-4-yl]amino]methyl]phenyl]acetamide |
| A66 | 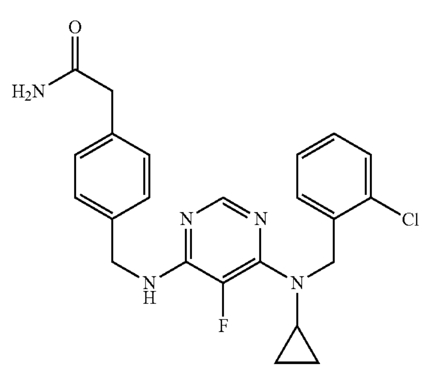 [SMILES: NC(=O)Cc1ccc(CNc2ncnc(N(Cc3ccccc3Cl)C3CC3)c2F)cc1] | 2-[4-[[[6-[(2-chlorophenyl)methyl-cyclopropyl-amino]-5-fluoro-pyrimidin-4-yl]amino]methyl]phenyl]acetamide |

TABLE 1-continued

Example Compounds by Structure and Name.

| Ex. No. | Structure | Name |
|---|---|---|
| A67 | 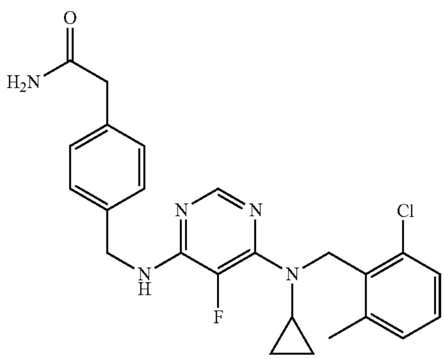 [SMILES: Cc1cccc(Cl)c1CN(c1ncnc(NCc2ccc(CC(N)=O)cc2)c1F)C1CC1] | 2-[4-[[[6-[(2-chloro-6-methyl-phenyl)methyl-cyclopropyl-amino]-5-fluoro-pyrimidin-4-yl]amino]methyl]phenyl]acetamide |
| A68 | 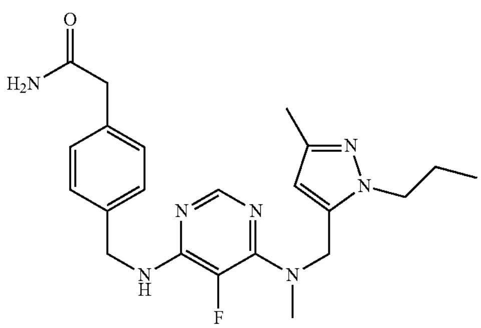 [SMILES: CCCn1nc(C)cc1CN(C)c1ncnc(NCc2ccc(CC(N)=O)cc2)c1F] | 2-[4-[[[5-fluoro-6-[methyl-[(5-methyl-2-propyl-pyrazol-3-yl)methyl]amino]pyrimidin-4-yl]amino]methyl]phenyl]acetamide |
| A69 | 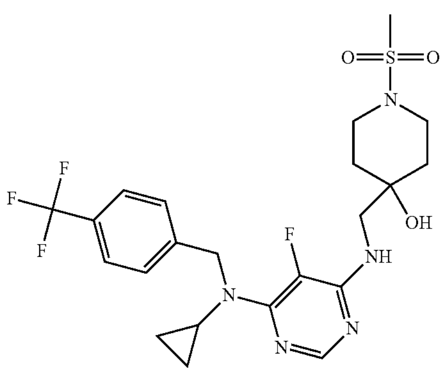 [SMILES: CS(=O)(=O)N1CCC(O)(CNc2ncnc(N(Cc3ccc(C(F)(F)F)cc3)C3CC3)c2F)CC1] | 4-[[[6-[cyclopropyl-[[4-(trifluoromethyl)phenyl]methyl]amino]-5-fluoro-pyrimidin-4-yl]amino]methyl]-1-methylsulfonyl-piperidin-4-ol |
| A72 | 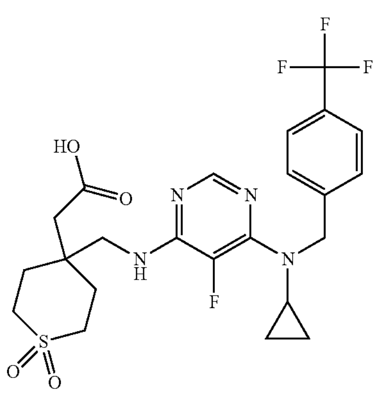 [SMILES: O=C(O)CC1(CNc2ncnc(N(Cc3ccc(C(F)(F)F)cc3)C3CC3)c2F)CCS(=O)(=O)CC1] | 2-[4-[[[6-[cyclopropyl-[[4-(trifluoromethyl)phenyl]methyl]amino]-5-fluoro-pyrimidin-4-yl]amino]methyl]-1,1-dioxo-thian-4-yl]acetic acid |

TABLE 1-continued
Example Compounds by Structure and Name.
| Ex. No. | Structure | Name |
|---|---|---|
| A73 | 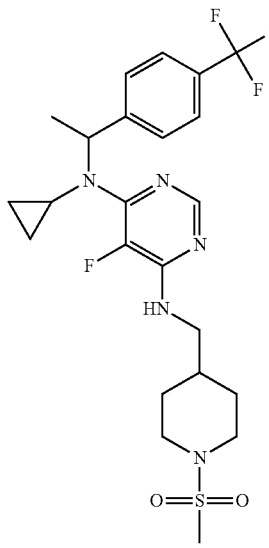 | N4-cyclopropyl-5-fluoro-N6-[(1-methylsulfonyl-4-piperidyl)methyl]-N4-[1-[4-(trifluoromethyl)phenyl]ethyl]pyrimidine-4,6-diamine |
| A74 | 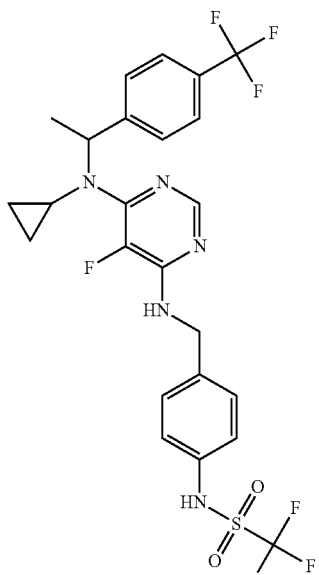 | N-[4-[[[6-[cyclopropyl-[1-[4-(trifluoromethyl)phenyl]ethyl]amino]-5-fluoro-pyrimidin-4-yl]amino]methyl]phenyl]-1,1,1-trifluoro-methanesulfonamide |

TABLE 1-continued

Example Compounds by Structure and Name.

| Ex. No. | Structure | Name |
|---|---|---|
| A75 | 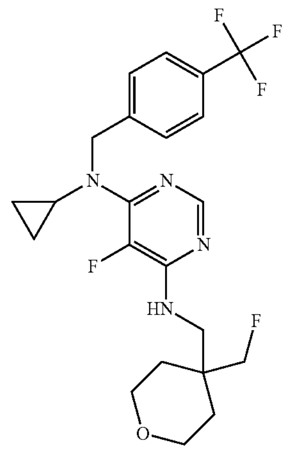 [SMILES: FCC1(CNc2ncnc(N(Cc3ccc(C(F)(F)F)cc3)C3CC3)c2F)CCOCC1] | N4-cyclopropyl-5-fluoro-N6-[[4-(fluoromethyl)tetrahydropyran-4-yl]methyl]-N4-[[4-(trifluoromethyl)phenyl]methyl]pyrimidine-4,6-diamine |
| A76 | 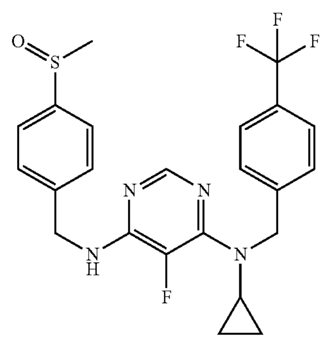 [SMILES: CS(=O)c1ccc(CNc2ncnc(N(Cc3ccc(C(F)(F)F)cc3)C3CC3)c2F)cc1] | N4-cyclopropyl-5-fluoro-N6-[(4-methylsulfinylphenyl)methyl]-N4-[[4-(trifluoromethyl)phenyl]methyl]pyrimidine-4,6-diamine |
| A77 | 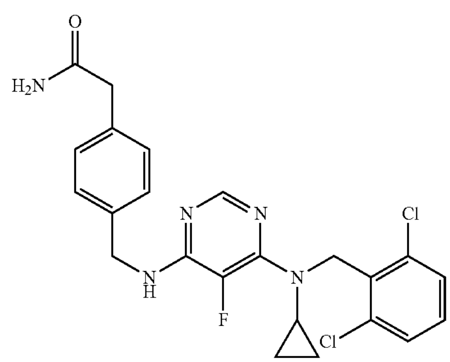 | 2-[4-[[[6-[cyclopropyl-[(2,6-dichlorophenyl)methyl]amino]-5-fluoro-pyrimidin-4-yl]amino]methyl]phenyl]acetamide |
| A78 | 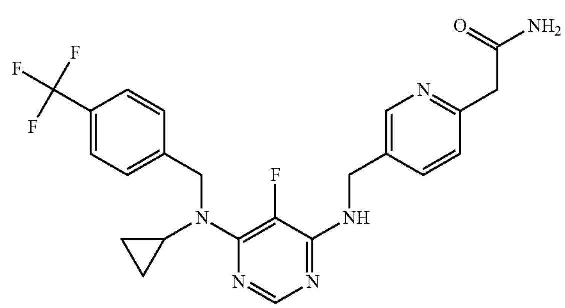 [SMILES: NC(=O)Cc1ccc(CNc2ncnc(N(Cc3ccc(C(F)(F)F)cc3)C3CC3)c2F)cn1] | 2-[5-[[[6-[cyclopropyl-[[4-(trifluoromethyl)phenyl]methyl]amino]-5-fluoro-pyrimidin-4-yl]amino]methyl]-2-pyridyl]acetamide |

TABLE 1-continued

Example Compounds by Structure and Name.

| Ex. No. | Structure | Name |
|---|---|---|
| A79 | 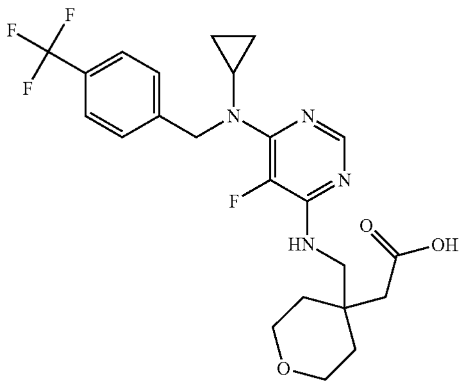 [SMILES: O=C(O)CC1(CNc2ncnc(N(Cc3ccc(C(F)(F)F)cc3)C3CC3)c2F)CCOCC1] | 2-[4-[[[6-[cyclopropyl-[[4-(trifluoromethyl)phenyl]methyl]amino]-5-fluoro-pyrimidin-4-yl]amino]methyl]tetrahydropyran-4-yl]acetic acid |
| A80 | 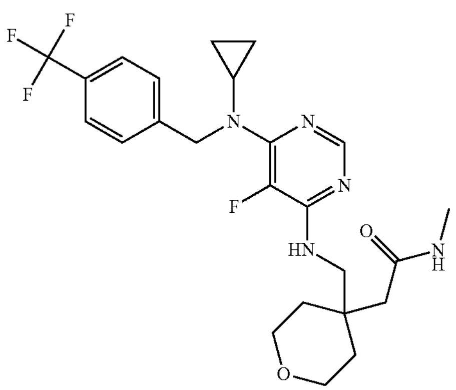 [SMILES: CNC(=O)CC1(CNc2ncnc(N(Cc3ccc(C(F)(F)F)cc3)C3CC3)c2F)CCOCC1] | 2-[4-[[[6-[cyclopropyl-[[4-(trifluoromethyl)phenyl]methyl]amino]-5-fluoro-pyrimidin-4-yl]amino]methyl]tetrahydropyran-4-yl]-N-methyl-acetamide |
| A81 | 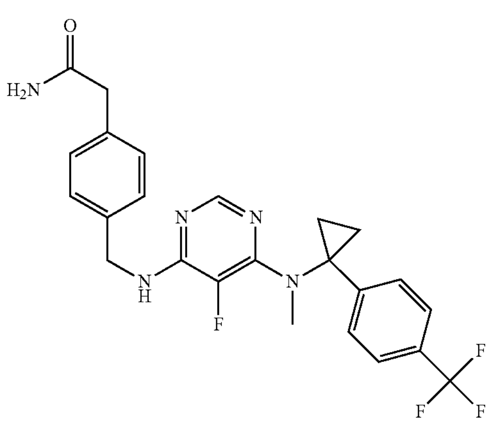 [SMILES: CN(c1ncnc(NCc2ccc(CC(N)=O)cc2)c1F)C1(c2ccc(C(F)(F)F)cc2)CC1] | 2-[4-[[[5-fluoro-6-[methyl-[1-[4-(trifluoromethyl)phenyl]cyclopropyl]amino]pyrimidin-4-yl]amino]methyl]phenyl]acetamide |

TABLE 1-continued

Example Compounds by Structure and Name.

| Ex. No. | Structure | Name |
|---|---|---|
| A82 | 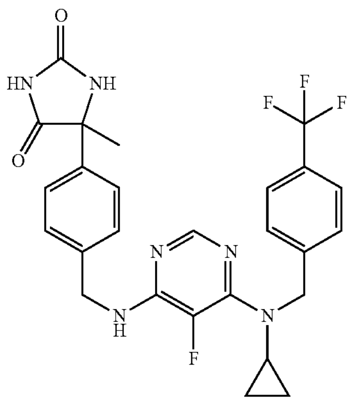 [SMILES: CC1(c2ccc(CNc3ncnc(N(Cc4ccc(C(F)(F)F)cc4)C4CC4)c3F)cc2)NC(=O)NC1=O] | 5-[4-[[[6-[cyclopropyl-[[4-(trifluoromethyl)phenyl]methyl]amino]-5-fluoro-pyrimidin-4-yl]amino]methyl]phenyl]-5-methyl-imidazolidine-2,4-dione |
| A83 | 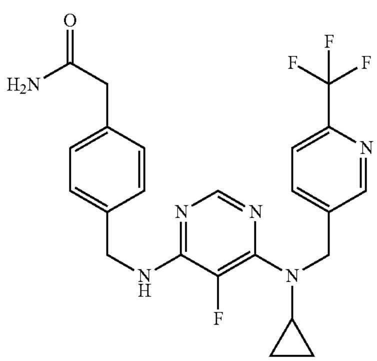 [SMILES: NC(=O)Cc1ccc(CNc2ncnc(N(Cc3ccc(C(F)(F)F)nc3)C3CC3)c2F)cc1] | 2-[4-[[[6-[cyclopropyl-[[6-(trifluoromethyl)-3-pyridyl]methyl]amino]-5-fluoro-pyrimidin-4-yl]amino]methyl]phenyl]acetamide |
| A84 | 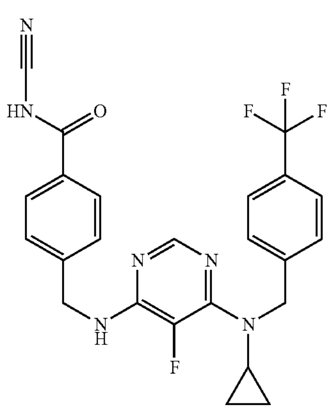 [SMILES: N#CNC(=O)c1ccc(CNc2ncnc(N(Cc3ccc(C(F)(F)F)cc3)C3CC3)c2F)cc1] | N-cyano-4-[[[6-[cyclopropyl-[[4-(trifluoromethyl)phenyl]methyl]amino]-5-fluoro-pyrimidin-4-yl]amino]methyl]benzamide |

TABLE 1-continued

Example Compounds by Structure and Name.

| Ex. No. | Structure | Name |
|---|---|---|
| A85 | 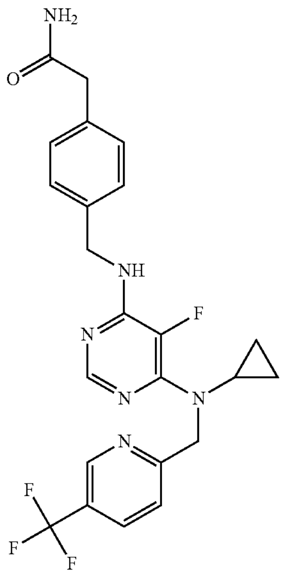 [SMILES: NC(=O)Cc1ccc(CNc2ncnc(N(Cc3ccc(C(F)(F)F)cn3)C3CC3)c2F)cc1] | 2-[4-[[[6-[cyclopropyl-[[5-(trifluoromethyl)-2-pyridyl]methyl]amino]-5-fluoro-pyrimidin-4-yl]amino]methyl]phenyl]acetamide |
| A88 | 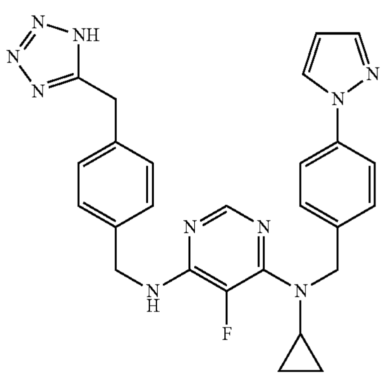 [SMILES: Fc1c(NCc2ccc(Cc3nnn[nH]3)cc2)ncnc1N(Cc1ccc(-n2cccn2)cc1)C1CC1] | N4-cyclopropyl-5-fluoro-N4-[(4-pyrazol-1-ylphenyl)methyl]-N6-[[4-(1H-tetrazol-5-ylmethyl)phenyl]methyl]pyrimidine-4,6-diamine |
| A89 | 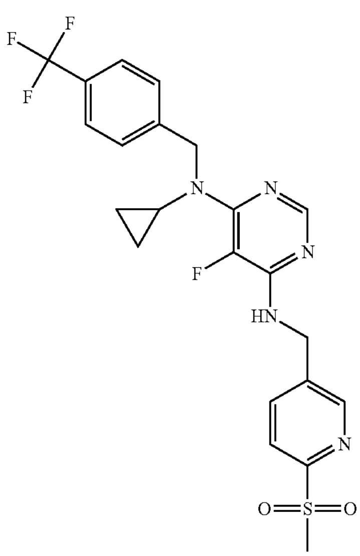 [SMILES: CS(=O)(=O)c1ccc(CNc2ncnc(N(Cc3ccc(C(F)(F)F)cc3)C3CC3)c2F)cn1] | N6-cyclopropyl-5-fluoro-N4-[(6-methylsulfonyl-3-pyridyl)methyl]-N6-[[4-(trifluoromethyl)phenyl]methyl]pyrimidine-4,6-diamine |

TABLE 1-continued

Example Compounds by Structure and Name.

| Ex. No. | Structure | Name |
|---|---|---|
| A90 | 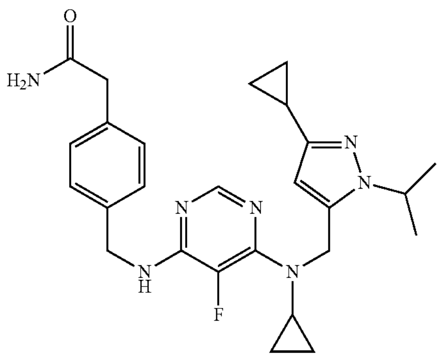 [SMILES: CC(C)n1nc(C2CC2)cc1CN(c1ncnc(NCc2ccc(CC(N)=O)cc2)c1F)C1CC1] | 2-[4-[[[6-[cyclopropyl-[(5-cyclopropyl-2-isopropyl-pyrazol-3-yl)methyl]amino]-5-fluoro-pyrimidin-4-yl]amino]methyl]phenyl]acetamide |
| A91 | 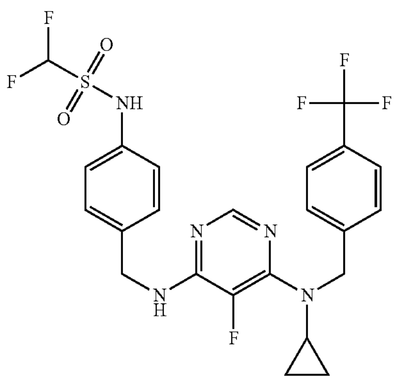 [SMILES: O=S(=O)(Nc1ccc(CNc2ncnc(N(Cc3ccc(C(F)(F)F)cc3)C3CC3)c2F)cc1)C(F)F] | N-[4-[[[6-[cyclopropyl-[[4-(trifluoromethyl)phenyl]methyl]amino]-5-fluoro-pyrimidin-4-yl]amino]methyl]phenyl]-1,1-difluoro-methanesulfonamide |
| A92 | 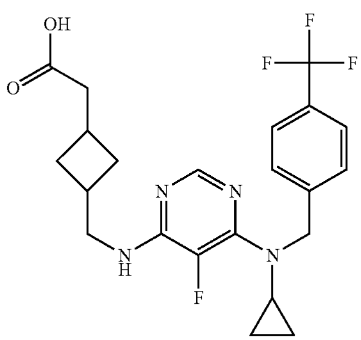 [SMILES: O=C(O)CC1CC(CNc2ncnc(N(Cc3ccc(C(F)(F)F)cc3)C3CC3)c2F)C1] | 2-[3-[[[6-[cyclopropyl-[[4-(trifluoromethyl)phenyl]methyl]amino]-5-fluoro-pyrimidin-4-yl]amino]methyl]cyclobutyl]acetic acid |
| A93 | 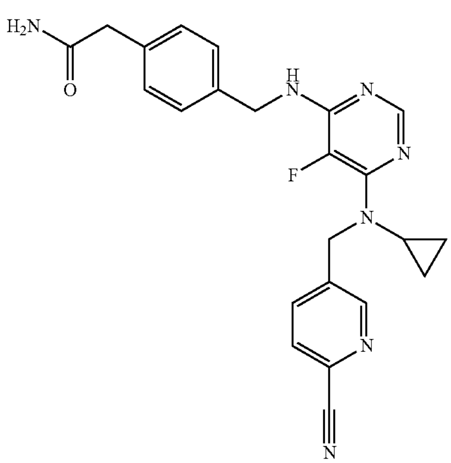 [SMILES: N#Cc1ccc(CN(c2ncnc(NCc3ccc(CC(N)=O)cc3)c2F)C2CC2)cn1] | 2-[4-[[[6-[(6-cyano-3-pyridyl)methyl-cyclopropyl-amino]-5-fluoro-pyrimidin-4-yl]amino]methyl]phenyl]acetamide |

TABLE 1-continued

Example Compounds by Structure and Name.

| Ex. No. | Structure | Name |
|---|---|---|
| A95 | 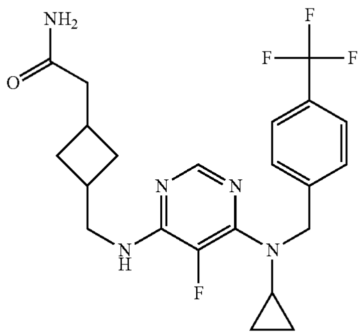 [SMILES: NC(=O)CC1CC(CNc2ncnc(N(Cc3ccc(C(F)(F)F)cc3)C3CC3)c2F)C1] | 2-[3-[[[6-[cyclopropyl-[[4-(trifluoromethyl)phenyl]methyl]amino]-5-fluoro-pyrimidin-4-yl]amino]methyl]cyclobutyl]acetamide |
| A96 | 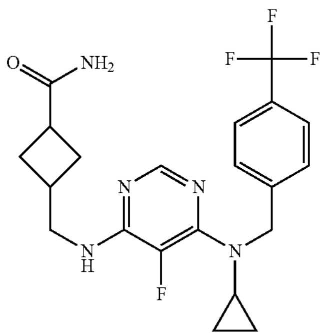 [SMILES: NC(=O)C1CC(CNc2ncnc(N(Cc3ccc(C(F)(F)F)cc3)C3CC3)c2F)C1] | 3-[[[6-[cyclopropyl-[[4-(trifluoromethyl)phenyl]methyl]amino]-5-fluoro-pyrimidin-4-yl]amino]methyl]cyclobutane-carboxamide |
| A97 | 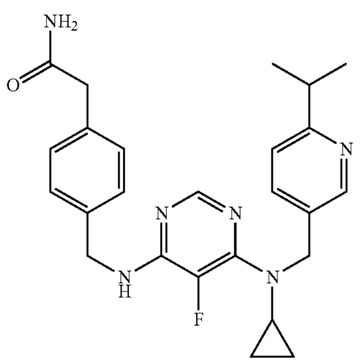 [SMILES: CC(C)c1ccc(CN(c2ncnc(NCc3ccc(CC(N)=O)cc3)c2F)C2CC2)cn1] | 2-[4-[[[6-[cyclopropyl-[(6-isopropyl-3-pyridyl)methyl]amino]-5-fluoro-pyrimidin-4-yl]amino]methyl]phenyl]acetamide |
| A98 | 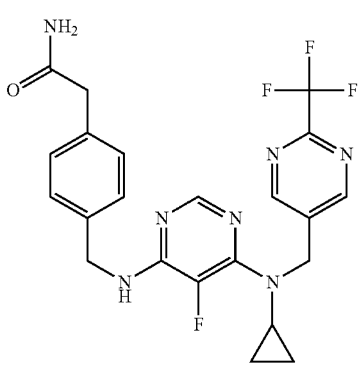 [SMILES: NC(=O)Cc1ccc(CNc2ncnc(N(Cc3cnc(C(F)(F)F)nc3)C3CC3)c2F)cc1] | 2-[4-[[[6-[cyclopropyl-[[2-(trifluoromethyl)pyrimidin-5-yl]methyl]amino]-5-fluoro-pyrimidin-4-yl]amino]methyl]phenyl]acetamide |

TABLE 1-continued

Example Compounds by Structure and Name.

| Ex. No. | Structure | Name |
|---|---|---|
| A99 | 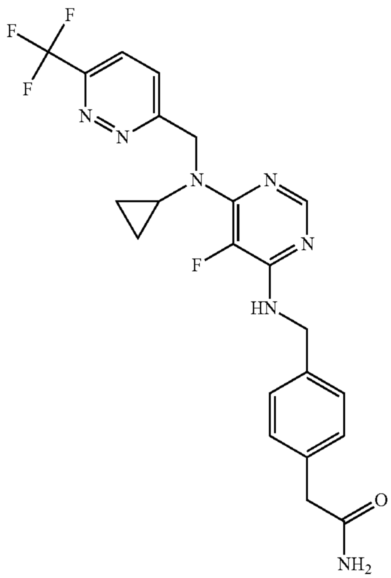 [SMILES: NC(=O)Cc1ccc(CNc2ncnc(N(Cc3ccc(C(F)(F)F)nn3)C3CC3)c2F)cc1] | 2-[4-[[[6-[cyclopropyl-[[6-(trifluoromethyl)pyridazin-3-yl]methyl]amino]-5-fluoro-pyrimidin-4-yl]amino]methyl]phenyl]acetamide |
| A100 | 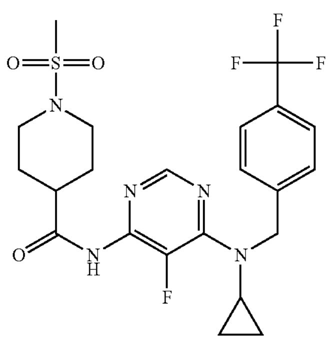 [SMILES: CS(=O)(=O)N1CCC(C(=O)Nc2ncnc(N(Cc3ccc(C(F)(F)F)cc3)C3CC3)c2F)CC1] | N-[6-[cyclopropyl-[[4-(trifluoromethyl)phenyl]methyl]amino]-5-fluoro-pyrimidin-4-yl]-1-methylsulfonyl-piperidine-4-carboxamide |
| A101 | 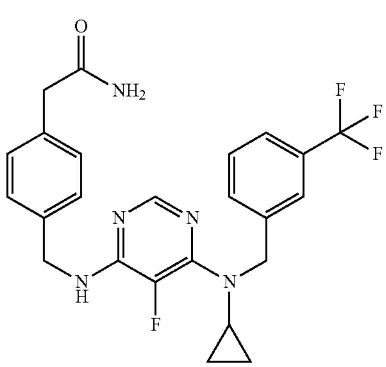 [SMILES: NC(=O)Cc1ccc(CNc2ncnc(N(Cc3cccc(C(F)(F)F)c3)C3CC3)c2F)cc1] | 2-[4-[[[6-[cyclopropyl-[[3-(trifluoromethyl)phenyl]methyl]amino]-5-fluoro-pyrimidin-4-yl]amino]methyl]phenyl]acetamide |

TABLE 1-continued

Example Compounds by Structure and Name.

| Ex. No. | Structure | Name |
|---|---|---|
| A102 | 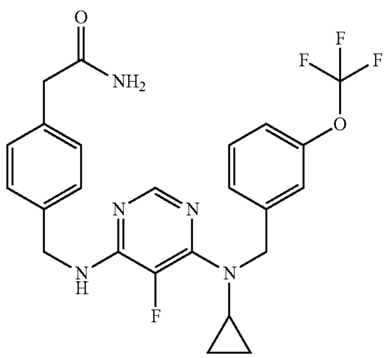 [SMILES: NC(=O)Cc1ccc(CNc2ncnc(N(Cc3cccc(OC(F)(F)F)c3)C3CC3)c2F)cc1] | 2-[4-[[[6-[cyclopropyl-[[3-(trifluoromethyl)phenyl]methyl]amino]-5-fluoro-pyrimidin-4-yl]amino]methyl]phenyl]acetamide |
| A103 | 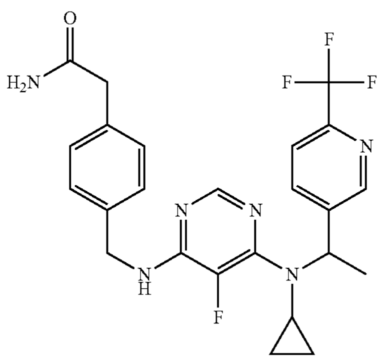 [SMILES: CC(c1ccc(C(F)(F)F)nc1)N(c1ncnc(NCc2ccc(CC(N)=O)cc2)c1F)C1CC1] | 2-[4-[[[6-[cyclopropyl-[1-[6-(trifluoromethyl)-3-pyridyl]ethyl]amino]-5-fluoro-pyrimidin-4-yl]amino]methyl]phenyl]acetamide |
| A104 | 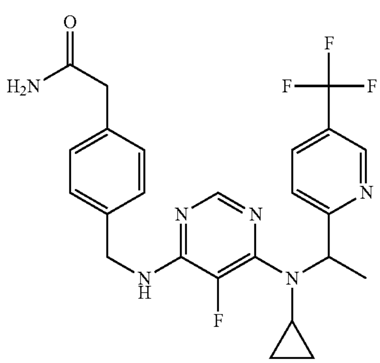 [SMILES: CC(c1ccc(C(F)(F)F)cn1)N(c1ncnc(NCc2ccc(CC(N)=O)cc2)c1F)C1CC1] | 2-[4-[[[6-[cyclopropyl-[1-[5-(trifluoromethyl)-2-pyridyl]ethyl]amino]-5-fluoro-pyrimidin-4-yl]amino]methyl]phenyl]acetamide |
| A105 | 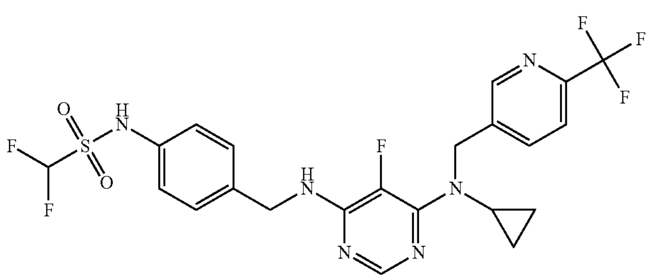 [SMILES: O=S(=O)(Nc1ccc(CNc2ncnc(N(Cc3ccc(C(F)(F)F)nc3)C3CC3)c2F)cc1)C(F)F] | N-[4-[[[6-[cyclopropyl-[[6-(trifluoromethyl)-3-pyridyl]methyl]amino]-5-fluoro-pyrimidin-4-yl]amino]methyl]phenyl]-1,1-difluoro-methanesulfonamide |

TABLE 1-continued

Example Compounds by Structure and Name.

| Ex. No. | Structure | Name |
|---|---|---|
| A106 | 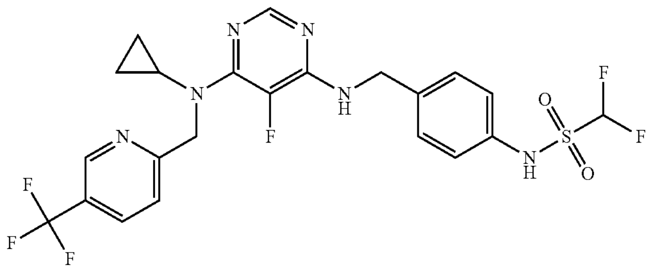 [SMILES: O=S(=O)(Nc1ccc(CNc2ncnc(N(Cc3ccc(C(F)(F)F)cn3)C3CC3)c2F)cc1)C(F)F] | N-[4-[[[6-[cyclopropyl-[[5-(trifluoromethyl)-2-pyridyl]methyl]amino]-5-fluoro-pyrimidin-4-yl]amino]methyl]phenyl]-1,1-difluoro-methanesulfonamide |
| A107 | 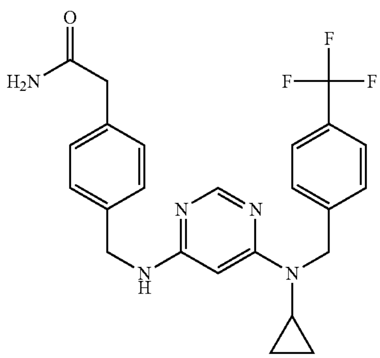 [SMILES: NC(=O)Cc1ccc(CNc2cc(N(Cc3ccc(C(F)(F)F)cc3)C3CC3)ncn2)cc1] | 2-[4-[[[6-[cyclopropyl-[[4-(trifluoromethyl)phenyl]methyl]amino]pyrimidin-4-yl]amino]methyl]phenyl]acetamide |
| A108 | 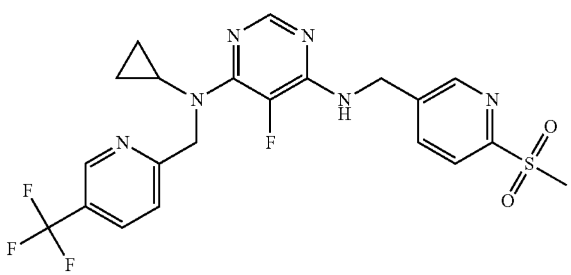 [SMILES: CS(=O)(=O)c1ccc(CNc2ncnc(N(Cc3ccc(C(F)(F)F)cn3)C3CC3)c2F)cn1] | N4-cyclopropyl-5-fluoro-N6-[(6-methylsulfonyl-3-pyridyl)methyl]-N4-[[5-(trifluoromethyl)-2-pyridyl]methyl]pyrimidine-4,6-diamine |
| A109 | 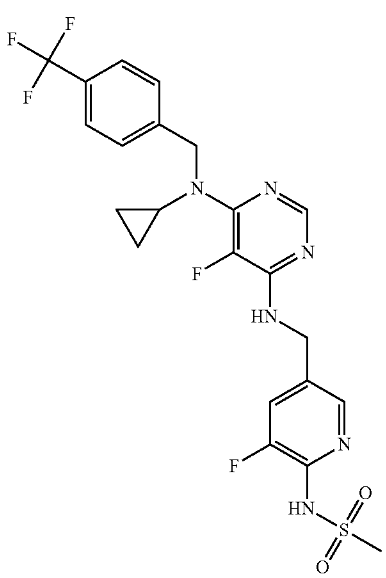 [SMILES: CS(=O)(=O)Nc1ncc(CNc2ncnc(N(Cc3ccc(C(F)(F)F)cc3)C3CC3)c2F)cc1F] | N-[5-[[[6-[cyclopropyl-[[4-(trifluoromethyl)phenyl]methyl]amino]-5-fluoro-pyrimidin-4-yl]amino]methyl]-3-fluoro-2-pyridyl]methanesulfonamide |

TABLE 1-continued

Example Compounds by Structure and Name.

| Ex. No. | Structure | Name |
|---|---|---|
| A110 | 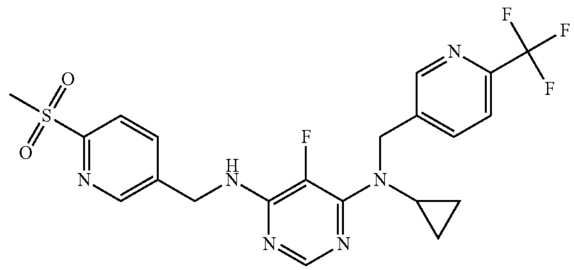 [SMILES: CS(=O)(=O)c1ccc(CNc2ncnc(N(Cc3ccc(C(F)(F)F)nc3)C3CC3)c2F)cn1] | N4-cyclopropyl-5-fluoro-N6-[(6-methylsulfonyl-3-pyridyl)methyl]-N4-[[6-(trifluoromethyl)-3-pyridyl]methyl]pyrimidine-4,6-diamine |
| A111 | 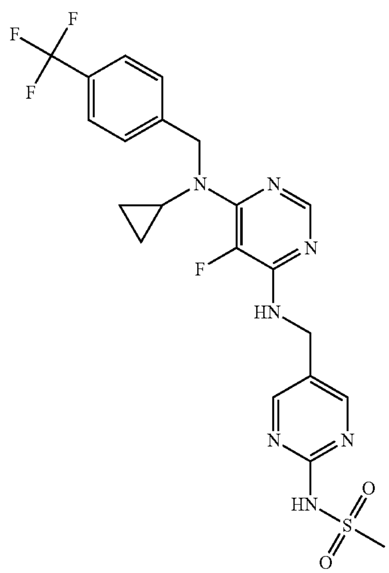 [SMILES: CS(=O)(=O)Nc1ncc(CNc2ncnc(N(Cc3ccc(C(F)(F)F)cc3)C3CC3)c2F)cn1] | N-[5-[[[6-[cyclopropyl-[[4-(trifluoromethyl)phenyl]methyl]amino]-5-fluoro-pyrimidin-4-yl]amino]methyl]pyrimidin-2-yl]methanesulfonamide |
| A112 | 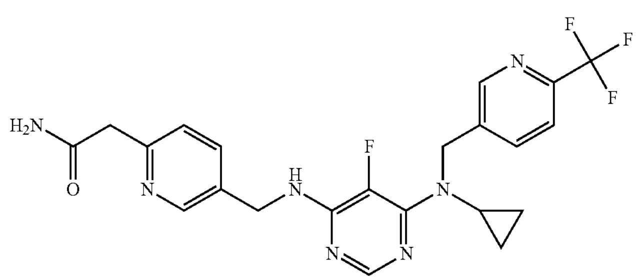 [SMILES: NC(=O)Cc1ccc(CNc2ncnc(N(Cc3ccc(C(F)(F)F)nc3)C3CC3)c2F)cn1] | 2-[5-[[[6-[cyclopropyl-[[6-(trifluoromethyl)-3-pyridyl]methyl]amino]-5-fluoro-pyrimidin-4-yl]amino]methyl]-2-pyridyl]acetamide |
| A113 | 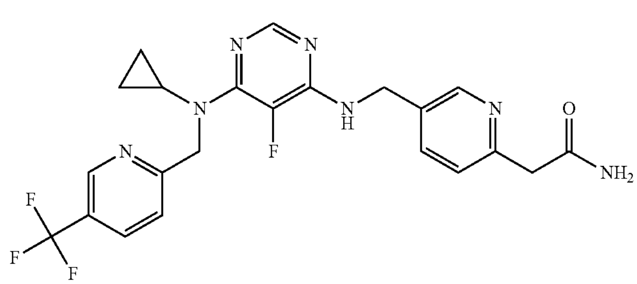 [SMILES: NC(=O)Cc1ccc(CNc2ncnc(N(Cc3ccc(C(F)(F)F)cn3)C3CC3)c2F)cn1] | 2-[5-[[[6-[cyclopropyl-[[5-(trifluoromethyl)-2-pyridyl]methyl]amino]-5-fluoro-pyrimidin-4-yl]amino]methyl]-2-pyridyl]acetamide |

TABLE 1-continued

Example Compounds by Structure and Name.

| Ex. No. | Structure | Name |
|---|---|---|
| A114 | 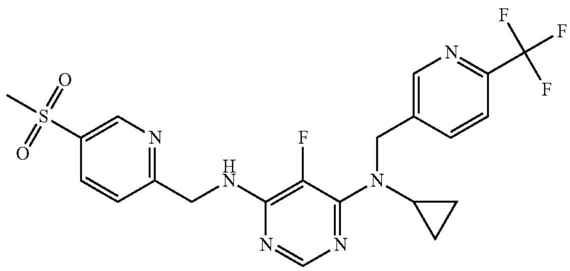 [SMILES: CS(=O)(=O)c1ccc(CNc2ncnc(N(Cc3ccc(C(F)(F)F)nc3)C3CC3)c2F)nc1] | N4-cyclopropyl-5-fluoro-N6-[(5-methylsulfonyl-2-pyridyl)methyl]-N4-[[6-(trifluoromethyl)-3-pyridyl]methyl]pyrimidine-4,6-diamine |
| A115 | 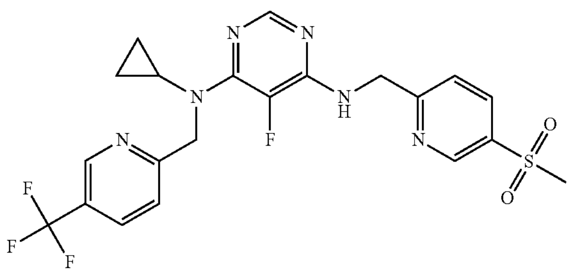 [SMILES: CS(=O)(=O)c1ccc(CNc2ncnc(N(Cc3ccc(C(F)(F)F)cn3)C3CC3)c2F)nc1] | N4-cyclopropyl-5-fluoro-N6-[(5-methylsulfonyl-2-pyridyl)methyl]-N4-[[5-(trifluoromethyl)-2-pyridyl]methyl]pyrimidine-4,6-diamine |
| A118 | 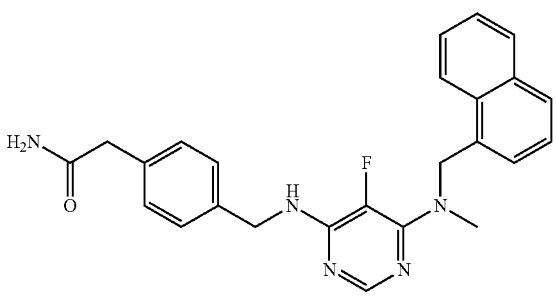 [SMILES: CN(Cc1cccc2ccccc12)c1ncnc(NCc2ccc(CC(N)=O)cc2)c1F] | 2-[4-[[[5-fluoro-6-[methyl(1-naphthylmethyl)amino]pyrimidin-4-yl]amino]methyl]phenyl]acetamide |
| A119 | 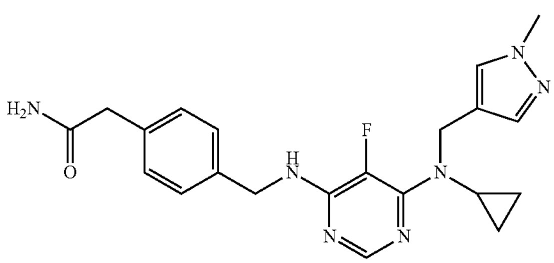 [SMILES: Cn1cc(CN(c2ncnc(NCc3ccc(CC(N)=O)cc3)c2F)C2CC2)cn1] | 2-[4-[[[6-[cyclopropyl-[(1-methylpyrazol-4-yl)methyl]amino]-5-fluoro-pyrimidin-4-yl]amino]methyl]phenyl]acetamide |
| A120 | 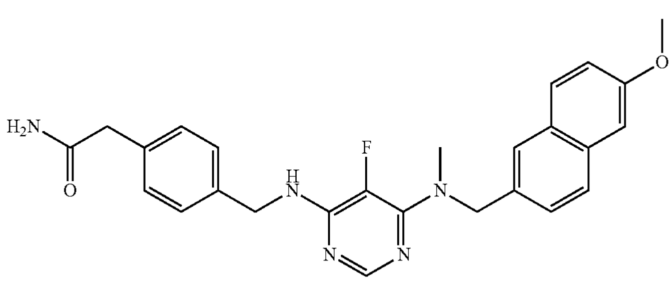 [SMILES: COc1ccc2cc(CN(C)c3ncnc(NCc4ccc(CC(N)=O)cc4)c3F)ccc2c1] | 2-[4-[[[5-fluoro-6-[(6-methoxy-2-naphthyl)methyl-methyl-amino]pyrimidin-4-yl]amino]methyl]phenyl]acetamide |

TABLE 1-continued

Example Compounds by Structure and Name.

| Ex. No. | Structure | Name |
|---|---|---|
| A121 | 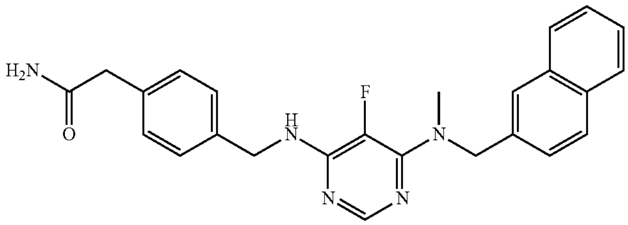 [SMILES: CN(Cc1ccc2ccccc2c1)c1ncnc(NCc2ccc(CC(N)=O)cc2)c1F] | 2-[4-[[[5-fluoro-6-[methyl(2-naphthylmethyl)amino]pyrimidin-4-yl]amino]methyl]phenyl]acetamide |
| A122 | 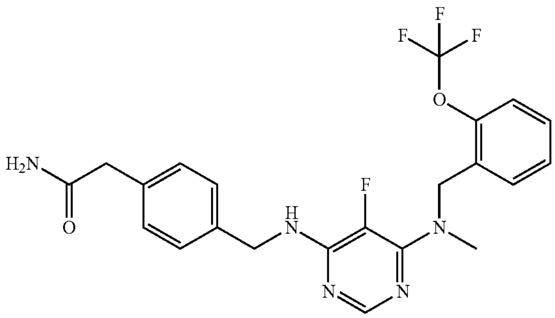 [SMILES: CN(Cc1ccccc1OC(F)(F)F)c1ncnc(NCc2ccc(CC(N)=O)cc2)c1F] | 2-[4-[[[5-fluoro-6-[methyl-[[2-(trifluoromethoxy)phenyl]methyl]amino]pyrimidin-4-yl]amino]methyl]phenyl]acetamide |
| A123 | 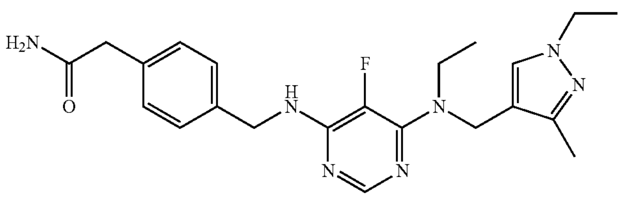 [SMILES: CCN(Cc1cn(CC)nc1C)c1ncnc(NCc2ccc(CC(N)=O)cc2)c1F] | 2-[4-[[[6-[ethyl-[(1-ethyl-3-methyl-pyrazol-4-yl)methyl]amino]-5-fluoro-pyrimidin-4-yl]amino]methyl]phenyl]acetamide |
| A124 | 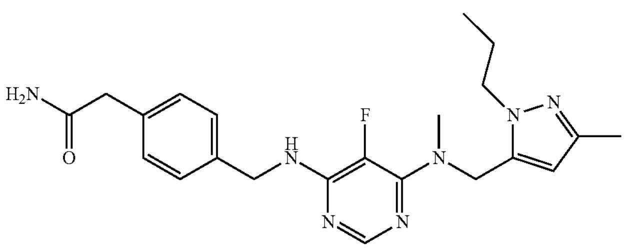 [SMILES: CCCn1nc(C)cc1CN(C)c1ncnc(NCc2ccc(CC(N)=O)cc2)c1F] | 2-[4-[[[5-fluoro-6-[methyl-[(5-methyl-2-propyl-pyrazol-3-yl)methyl]amino]pyrimidin-4-yl]amino]methyl]phenyl]acetamide |
| A125 | 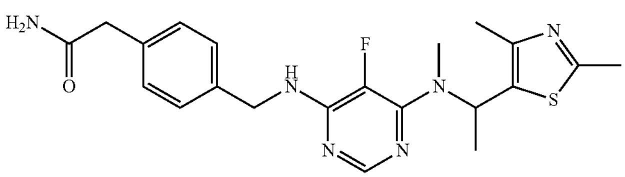 [SMILES: Cc1nc(C)c(C(C)N(C)c2ncnc(NCc3ccc(CC(N)=O)cc3)c2F)s1] | 2-[4-[[[6-[1-(2,4-dimethylthiazol-5-yl)ethyl-methyl-amino]-5-fluoro-pyrimidin-4-yl]amino]methyl]phenyl]acetamide |
| A126 | 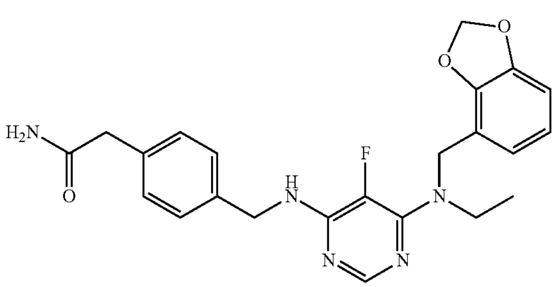 [SMILES: CCN(Cc1cccc2c1OCO2)c1ncnc(NCc2ccc(CC(N)=O)cc2)c1F] | 2-[4-[[[6-[1,3-benzodioxol-4-ylmethyl(ethyl)amino]-5-fluoro-pyrimidin-4-yl]amino]methyl]phenyl]acetamide |

TABLE 1-continued

Example Compounds by Structure and Name.

| Ex. No. | Structure | Name |
|---|---|---|
| A127 | 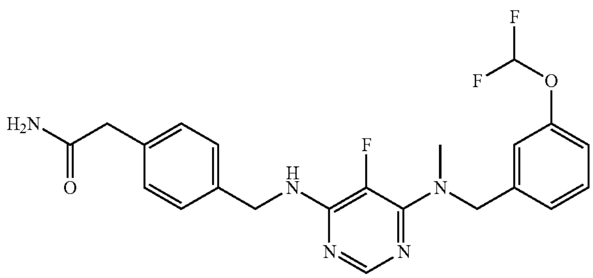 [SMILES: CN(Cc1cccc(OC(F)F)c1)c1ncnc(NCc2ccc(CC(N)=O)cc2)c1F] | 2-[4-[[[6-[[3-(difluoromethoxy)phenyl]methyl-methyl-amino]-5-fluoro-pyrimidin-4-yl]amino]methyl]phenyl]acetamide |
| A128 | 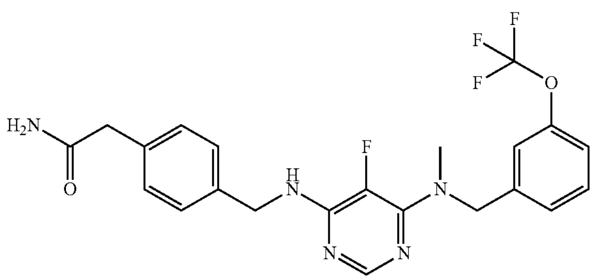 [SMILES: CN(Cc1cccc(OC(F)(F)F)c1)c1ncnc(NCc2ccc(CC(N)=O)cc2)c1F] | 2-[4-[[[5-fluoro-6-[methyl-[[3-(trifluoromethoxy)phenyl]methyl]amino]pyrimidin-4-yl]amino]methyl]phenyl]acetamide |
| A129 | 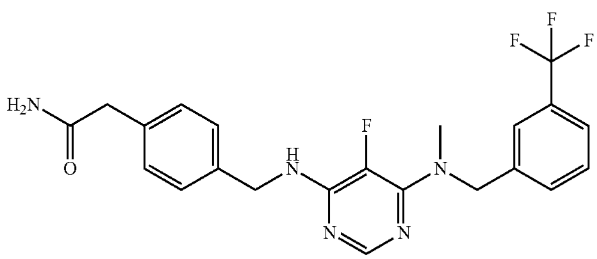 [SMILES: CN(Cc1cccc(C(F)(F)F)c1)c1ncnc(NCc2ccc(CC(N)=O)cc2)c1F] | 2-[4-[[[5-fluoro-6-[methyl-[[3-(trifluoromethyl)phenyl]methyl]amino]pyrimidin-4-yl]amino]methyl]phenyl]acetamide |
| A130 | 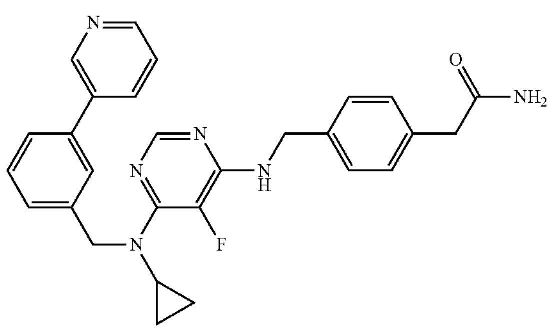 [SMILES: NC(=O)Cc1ccc(CNc2ncnc(N(Cc3cccc(-c4cccnc4)c3)C3CC3)c2F)cc1] | 2-[4-[[[6-[cyclopropyl-[[3-(3-pyridyl)phenyl]methyl]amino]-5-fluoro-pyrimidin-4-yl]amino]methyl]phenyl]acetamide |
| A131 | 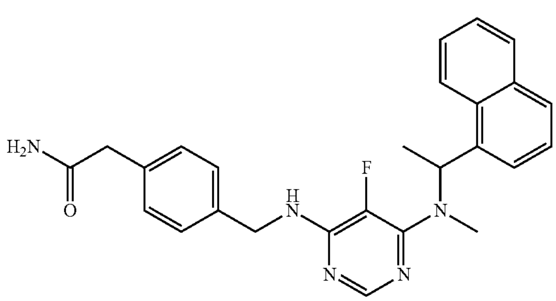 [SMILES: CC(c1cccc2ccccc12)N(C)c1ncnc(NCc2ccc(CC(N)=O)cc2)c1F] | 2-[4-[[[5-fluoro-6-[methyl-[1-(1-naphthyl)ethyl]amino]pyrimidin-4-yl]amino]methyl]phenyl]acetamide |

TABLE 1-continued

Example Compounds by Structure and Name.

| Ex. No. | Structure | Name |
|---|---|---|
| A132 | 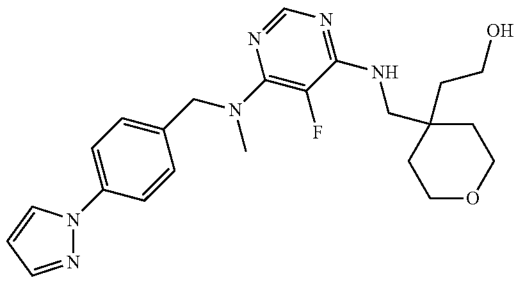 [SMILES: CN(Cc1ccc(-n2cccn2)cc1)c1ncnc(NCC2(CCO)CCOCC2)c1F] | 2-[4-[[[5-fluoro-6-[methyl-[(4-pyrazol-1-ylphenyl)methyl]amino]pyrimidin-4-yl]amino]methyl]tetrahydropyran-4-yl]ethanol |
| A133 | 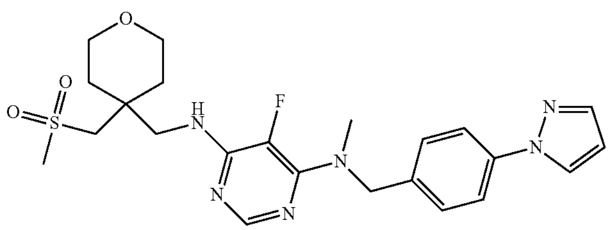 [SMILES: CN(Cc1ccc(-n2cccn2)cc1)c1ncnc(NCC2(CS(C)(=O)=O)CCOCC2)c1F] | 5-fluoro-N6-methyl-N4-[[4-(methylsulfonylmethyl)tetrahydropyran-4-yl]methyl]-N6-[(4-pyrazol-1-ylphenyl)methyl]pyrimidine-4,6-diamine |
| A134 | 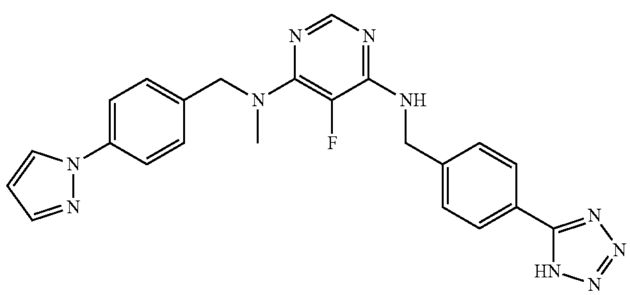 [SMILES: CN(Cc1ccc(-n2cccn2)cc1)c1ncnc(NCc2ccc(-c3nnn[nH]3)cc2)c1F] | 5-fluoro-N6-methyl-N6-[(4-pyrazol-1-ylphenyl)methyl]-N4-[[4-(1H-tetrazol-5-yl)phenyl]methyl]pyrimidine-4,6-diamine |
| A135 | 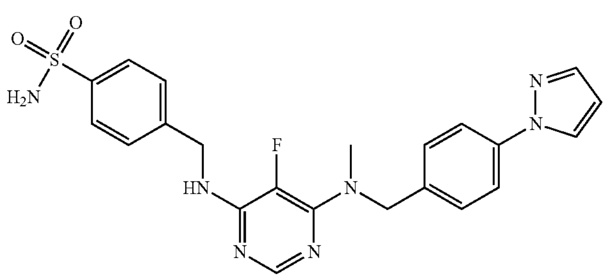 [SMILES: CN(Cc1ccc(-n2cccn2)cc1)c1ncnc(NCc2ccc(S(N)(=O)=O)cc2)c1F] | 4-[[[5-fluoro-6-[methyl-[(4-pyrazol-1-ylphenyl)methyl]amino]pyrimidin-4-yl]amino]methyl]benzenesulfonamide |
| A136 | 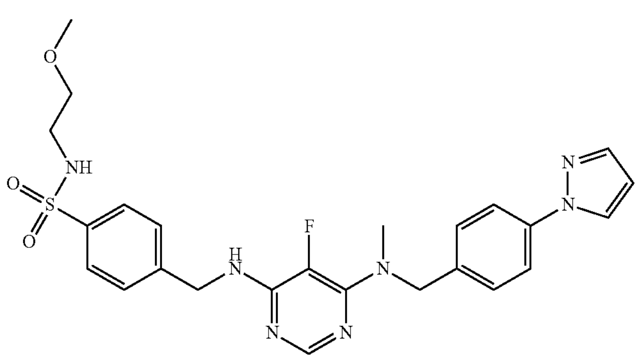 [SMILES: COCCNS(=O)(=O)c1ccc(CNc2ncnc(N(C)Cc3ccc(-n4cccn4)cc3)c2F)cc1] | 4-[[[5-fluoro-6-[methyl-[(4-pyrazol-1-ylphenyl)methyl]amino]pyrimidin-4-yl]amino]methyl]-N-(2-methoxyethyl)benzenesulfonamide |

TABLE 1-continued

Example Compounds by Structure and Name.

| Ex. No. | Structure | Name |
|---|---|---|
| A137 | 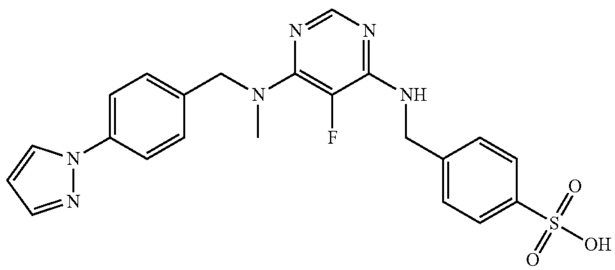 [SMILES: CN(Cc1ccc(-n2cccn2)cc1)c1ncnc(NCc2ccc(S(=O)(=O)O)cc2)c1F] | 4-[[[5-fluoro-6-[methyl-[(4-pyrazol-1-ylphenyl)methyl]amino]pyrimidin-4-yl]amino]methyl]benzenesulfonic acid |
| A138 | 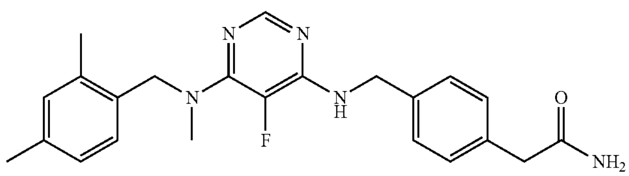 [SMILES: Cc1ccc(CN(C)c2ncnc(NCc3ccc(CC(N)=O)cc3)c2F)c(C)c1] | 2-[4-[[[6-[(2,4-dimethylphenyl)methyl-methyl-amino]-5-fluoro-pyrimidin-4-yl]amino]methyl]phenyl]acetamide |
| A139 | 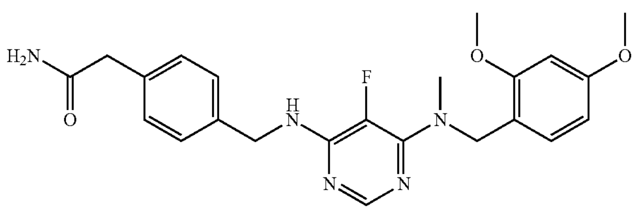 [SMILES: COc1ccc(CN(C)c2ncnc(NCc3ccc(CC(N)=O)cc3)c2F)c(OC)c1] | 2-[4-[[[6-[(2,4-dimethoxyphenyl)methyl-methyl-amino]-5-fluoro-pyrimidin-4-yl]amino]methyl]phenyl]acetamide |
| A140 | 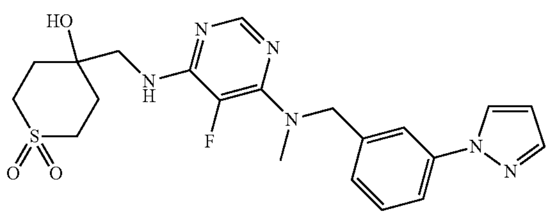 [SMILES: CN(Cc1cccc(-n2cccn2)c1)c1ncnc(NCC2(O)CCS(=O)(=O)CC2)c1F] | 4-[[[5-fluoro-6-[methyl-[(3-pyrazol-1-ylphenyl)methyl]amino]pyrimidin-4-yl]amino]methyl]-1,1-dioxo-thian-4-ol |
| A141 | 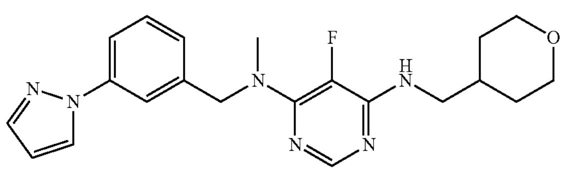 [SMILES: CN(Cc1cccc(-n2cccn2)c1)c1ncnc(NCC2CCOCC2)c1F] | 5-fluoro-N6-methyl-N6-[(3-pyrazol-1-ylphenyl)methyl]-N4-(tetrahydropyran-4-ylmethyl)pyrimidine-4,6-diamine |
| A142 | 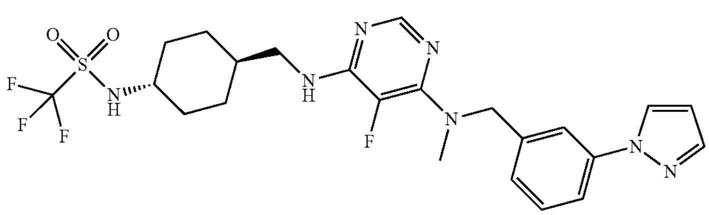 [SMILES: CN(Cc1cccc(-n2cccn2)c1)c1ncnc(NC[C@H]2CC[C@H](NS(=O)(=O)C(F)(F)F)CC2)c1F] | 1,1,1-trifluoro-N-[4-[[[5-fluoro-6-[methyl-[(3-pyrazol-1-ylphenyl)methyl]amino]pyrimidin-4-yl]amino]methyl]cyclohexyl]methanesulfonamide |
| A143 | 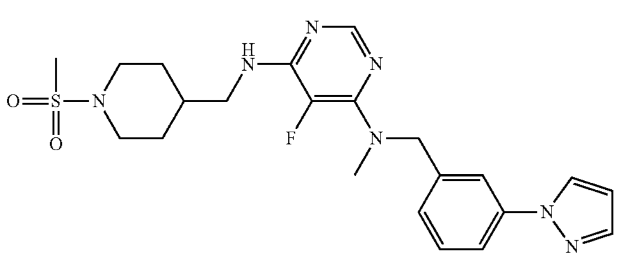 [SMILES: CN(Cc1cccc(-n2cccn2)c1)c1ncnc(NCC2CCN(S(C)(=O)=O)CC2)c1F] | 5-fluoro-N6-methyl-N4-[(1-methylsulfonyl-4-piperidyl)methyl]-N6-[(3-pyrazol-1-ylphenyl)methyl]pyrimidine-4,6-diamine |

TABLE 1-continued

Example Compounds by Structure and Name.

| Ex. No. | Structure | Name |
|---|---|---|
| A144 | 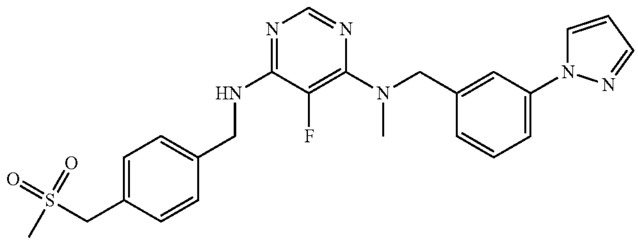 [SMILES: CN(Cc1cccc(-n2cccn2)c1)c1ncnc(NCc2ccc(CS(C)(=O)=O)cc2)c1F] | 5-fluoro-N6-methyl-N4-[[4-(methylsulfonylmethyl)phenyl]methyl]-N6-[(3-pyrazol-1-ylphenyl)methyl]pyrimidine-4,6-diamine |
| A145 | 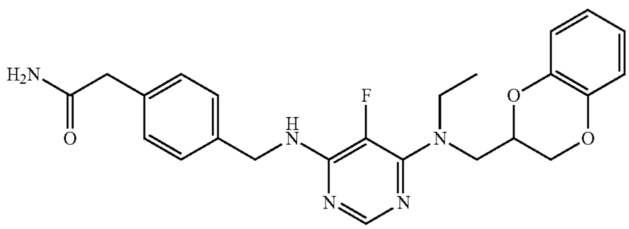 [SMILES: CCN(CC1COc2ccccc2O1)c1ncnc(NCc2ccc(CC(N)=O)cc2)c1F] | 2-[4-[[[6-[2,3-dihydro-1,4-benzodioxin-3-ylmethyl(ethyl)amino]-5-fluoro-pyrimidin-4-yl]amino]methyl]phenyl]acetamide |
| A147 | 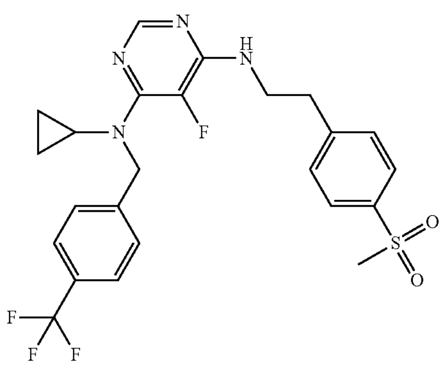 [SMILES: CS(=O)(=O)c1ccc(CCNc2ncnc(N(Cc3ccc(C(F)(F)F)cc3)C3CC3)c2F)cc1] | N4-cyclopropyl-5-fluoro-N6-[2-(4-methylsulfonylphenyl)ethyl]-N4-[[4-(trifluoromethyl)phenyl]methyl]pyrimidine-4,6-diamine |
| A148 | 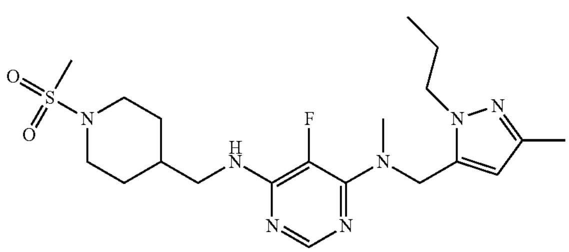 [SMILES: CCCn1nc(C)cc1CN(C)c1ncnc(NCC2CCN(S(C)(=O)=O)CC2)c1F] | 5-fluoro-N4-methyl-N4-[(5-methyl-2-propyl-pyrazol-3-yl)methyl]-N6-[(1-methylsulfonyl-4-piperidyl)methyl]pyrimidine-4,6-diamine |
| A149 | 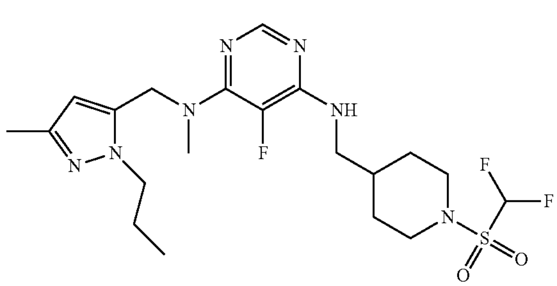 [SMILES: CCCn1nc(C)cc1CN(C)c1ncnc(NCC2CCN(S(=O)(=O)C(F)F)CC2)c1F] | N6-[[1-(difluoromethylsulfonyl)-4-piperidyl]methyl]-5-fluoro-N4-methyl-N4-[(5-methyl-2-propyl-pyrazol-3-yl)methyl]pyrimidine-4,6-diamine |

TABLE 1-continued

Example Compounds by Structure and Name.

| Ex. No. | Structure | Name |
|---|---|---|
| A150 | 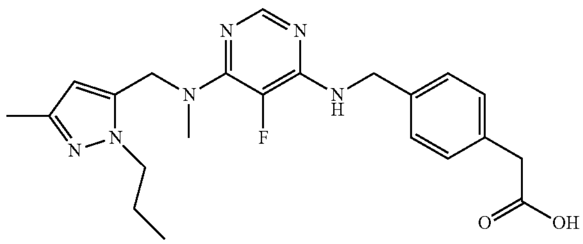 [SMILES: CCCn1nc(C)cc1CN(C)c1ncnc(NCc2ccc(CC(=O)O)cc2)c1F] | 2-[4-[[[5-fluoro-6-[methyl-[(5-methyl-2-propyl-pyrazol-3-yl)methyl]amino]pyrimidin-4-yl]amino]methyl]phenyl]acetic acid |
| A151 | 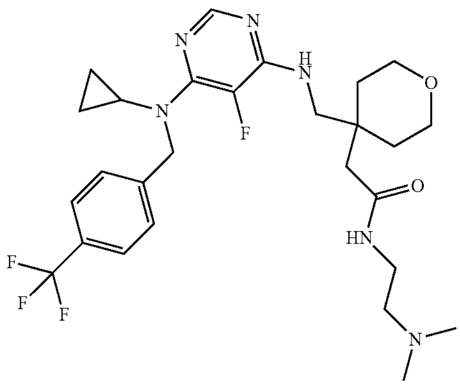 [SMILES: CN(C)CCNC(=O)CC1(CNc2ncnc(N(Cc3ccc(C(F)(F)F)cc3)C3CC3)c2F)CCOCC1] | 2-[4-[[[6-[cyclopropyl-[[4-(trifluoromethyl)phenyl]methyl]amino]-5-fluoro-pyrimidin-4-yl]amino]methyl]tetrahydropyran-4-yl]-N-(2-dimethylaminoethyl)acetamide |
| A152 | 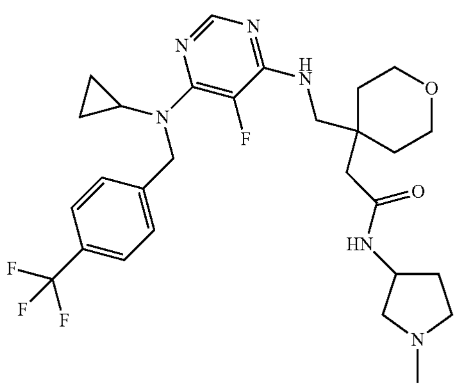 [SMILES: CN1CCC(NC(=O)CC2(CNc3ncnc(N(Cc4ccc(C(F)(F)F)cc4)C4CC4)c3F)CCOCC2)C1] | 2-[4-[[[6-[cyclopropyl-[[4-(trifluoromethyl)phenyl]methyl]amino]-5-fluoro-pyrimidin-4-yl]amino]methyl]tetrahydropyran-4-yl]-N-(1-methylpyrrolidin-3-yl)acetamide |
| A153 | 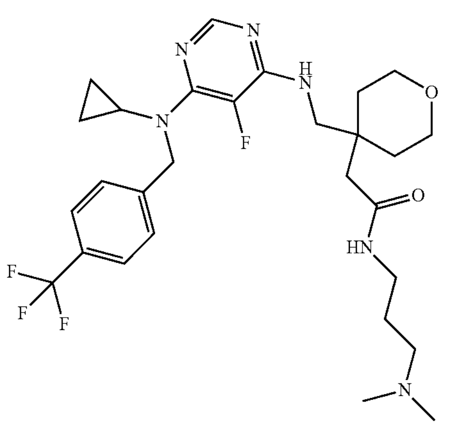 [SMILES: CN(C)CCCNC(=O)CC1(CNc2ncnc(N(Cc3ccc(C(F)(F)F)cc3)C3CC3)c2F)CCOCC1] | 2-[4-[[[6-[cyclopropyl-[[4-(trifluoromethyl)phenyl]methyl]amino]-5-fluoro-pyrimidin-4-yl]amino]methyl]tetrahydropyran-4-yl]-N-[3-(dimethylamino)propyl]acetamide |

TABLE 1-continued

Example Compounds by Structure and Name.

| Ex. No. | Structure | Name |
|---|---|---|
| A154 | 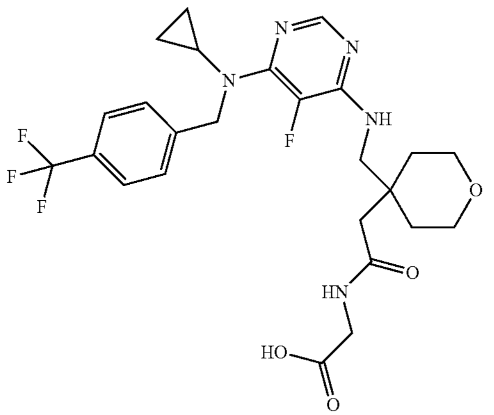 [SMILES: O=C(O)CNC(=O)CC1(CNc2ncnc(N(Cc3ccc(C(F)(F)F)cc3)C3CC3)c2F)CCOCC1] | 2-[[2-[4-[[[6-[cyclopropyl-[[4-(trifluoromethyl)phenyl]methyl]amino]-5-fluoro-pyrimidin-4-yl]amino]methyl]tetrahydropyran-4-yl]acetyl]amino]acetic acid |
| A155 | 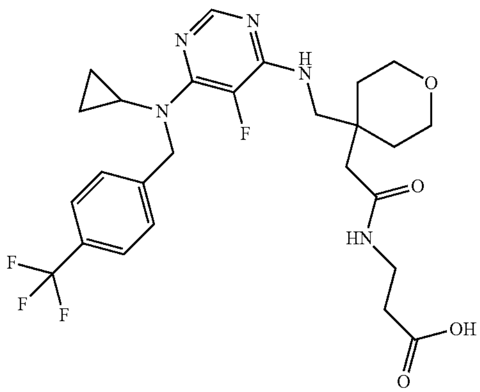 [SMILES: O=C(O)CCNC(=O)CC1(CNc2ncnc(N(Cc3ccc(C(F)(F)F)cc3)C3CC3)c2F)CCOCC1] | 3-[[2-[4-[[[6-[cyclopropyl-[[4-(trifluoromethyl)phenyl]methyl]amino]-5-fluoro-pyrimidin-4-yl]amino]methyl]tetrahydropyran-4-yl]acetyl]amino]propanoic acid |
| A156 | 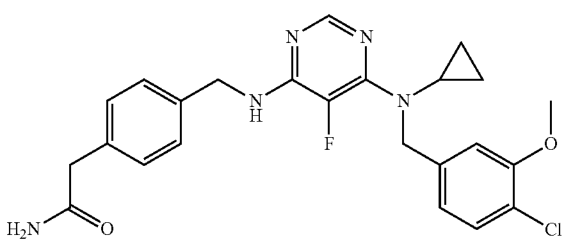 [SMILES: COc1cc(CN(c2ncnc(NCc3ccc(CC(N)=O)cc3)c2F)C2CC2)ccc1Cl] | 2-[4-[[[6-[(4-chloro-3-methoxy-phenyl)methyl-cyclopropyl-amino]-5-fluoro-pyrimidin-4-yl]amino]methyl]phenyl]acetamide |
| A157 | 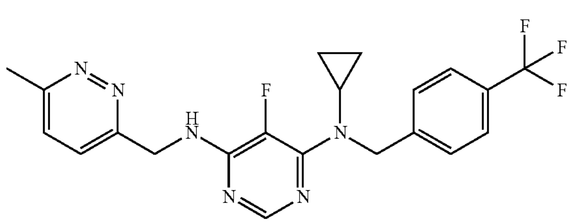 [SMILES: Cc1ccc(CNc2ncnc(N(Cc3ccc(C(F)(F)F)cc3)C3CC3)c2F)nn1] | N4-cyclopropyl-5-fluoro-N6-[(6-methylpyridazin-3-yl)methyl]-N4-[[4-(trifluoromethyl)phenyl]methyl]pyrimidine-4,6-diamine |
| A158 | 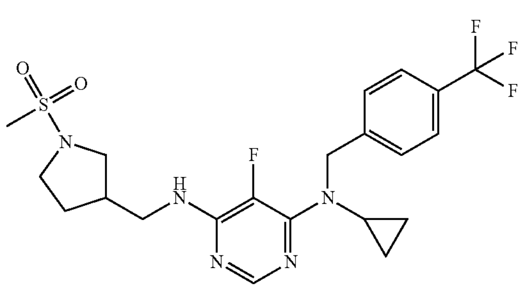 [SMILES: CS(=O)(=O)N1CCC(CNc2ncnc(N(Cc3ccc(C(F)(F)F)cc3)C3CC3)c2F)C1] | N4-cyclopropyl-5-fluoro-N6-[(1-methylsulfonylpyrrolidin-3-yl)methyl]-N4-[[4-(trifluoromethyl)phenyl]methyl]pyrimidine-4,6-diamine |

TABLE 1-continued

Example Compounds by Structure and Name.

| Ex. No. | Structure | Name |
|---|---|---|
| A159 | 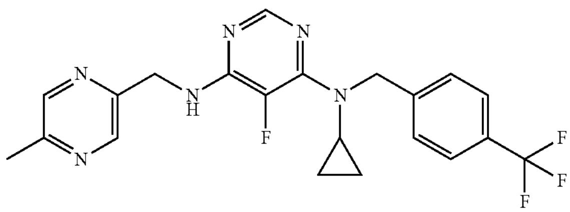 [SMILES: Cc1cnc(CNc2ncnc(N(Cc3ccc(C(F)(F)F)cc3)C3CC3)c2F)cn1] | N4-cyclopropyl-5-fluoro-N6-[(5-methylpyrazin-2-yl)methyl]-N4-[[4-(trifluoromethyl)phenyl]methyl]pyrimidine-4,6-diamine |
| A160 | 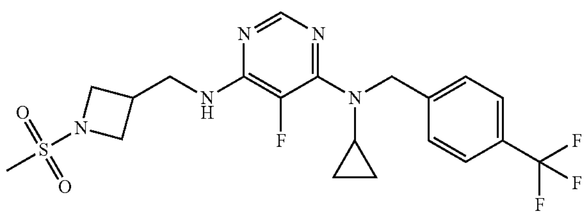 [SMILES: CS(=O)(=O)N1CC(CNc2ncnc(N(Cc3ccc(C(F)(F)F)cc3)C3CC3)c2F)C1] | N4-cyclopropyl-5-fluoro-N6-[(1-methylsulfonylazetidin-3-yl)methyl]-N4-[[4-(trifluoromethyl)phenyl]methyl]pyrimidine-4,6-diamine |
| A161 | 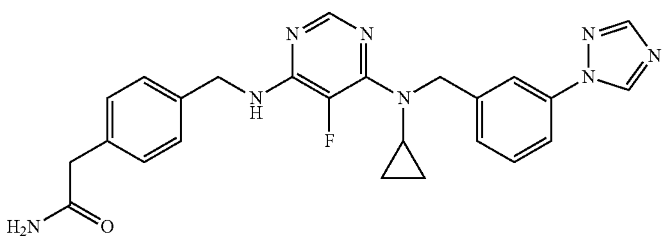 [SMILES: NC(=O)Cc1ccc(CNc2ncnc(N(Cc3cccc(-n4cncn4)c3)C3CC3)c2F)cc1] | 2-[4-[[[6-[cyclopropyl-[[3-(1,2,4-triazol-1-yl)phenyl]methyl]amino]-5-fluoro-pyrimidin-4-yl]amino]methyl]phenyl]acetamide |
| A162 | 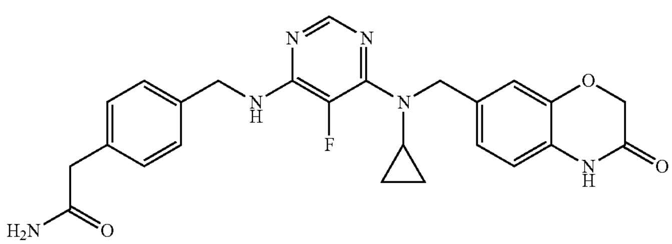 [SMILES: NC(=O)Cc1ccc(CNc2ncnc(N(Cc3ccc4c(c3)OCC(=O)N4)C3CC3)c2F)cc1] | 2-[4-[[[6-[cyclopropyl-[(3-oxo-4H-1,4-benzoxazin-7-yl)methyl]amino]-5-fluoro-pyrimidin-4-yl]amino]methyl]phenyl]acetamide |
| A163 | 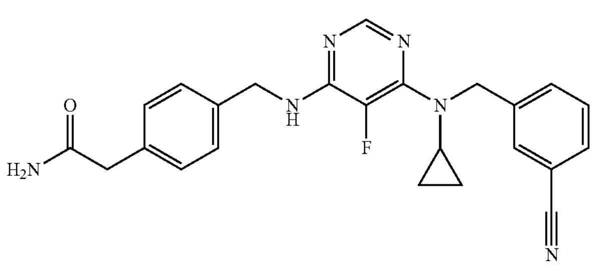 [SMILES: N#Cc1cccc(CN(c2ncnc(NCc3ccc(CC(N)=O)cc3)c2F)C2CC2)c1] | 2-[4-[[[6-[(3-cyanophenyl)methyl-cyclopropyl-amino]-5-fluoro-pyrimidin-4-yl]amino]methyl]phenyl]acetamide |

TABLE 1-continued

Example Compounds by Structure and Name.

| Ex. No. | Structure | Name |
|---|---|---|
| A164 | 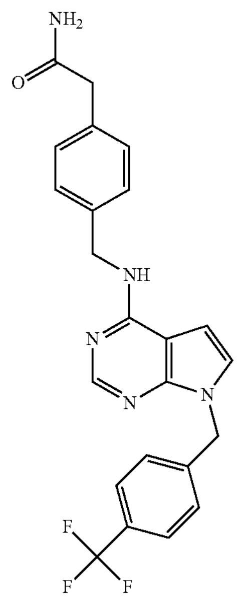 [SMILES: NC(=O)Cc1ccc(CNc2ncnc3c2ccn3Cc2ccc(C(F)(F)F)cc2)cc1] | 2-[4-[[[7-[[4-(trifluoromethyl)phenyl]methyl]pyrrolo[2,3-d]pyrimidin-4-yl]amino]methyl]phenyl]acetamide |
| A165 | 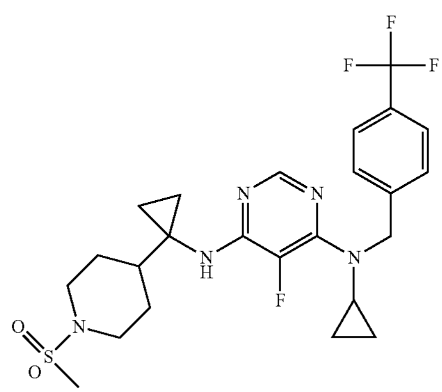 | N6-cyclopropyl-5-fluoro-N4-[1-(1-methylsulfonyl-4-piperidyl)cyclopropyl]-N6-[[4-(trifluoromethyl)phenyl]methyl]pyrimidine-4,6-diamine |
| A166 | 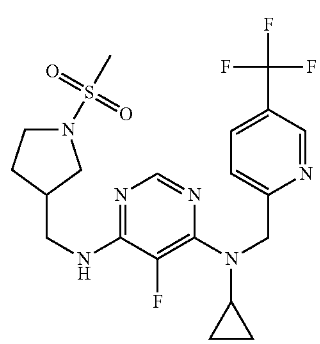 [SMILES: CS(=O)(=O)N1CCC(CNc2ncnc(N(Cc3ccc(C(F)(F)F)cn3)C3CC3)c2F)C1] | N6-cyclopropyl-5-fluoro-N4-[(1-methylsulfonylpyrrolidin-3-yl)methyl]-N6-[[5-(trifluoromethyl)-2-pyridyl]methyl]pyrimidine-4,6-diamine |

TABLE 1-continued

Example Compounds by Structure and Name.

| Ex. No. | Structure | Name |
|---|---|---|
| A167 | 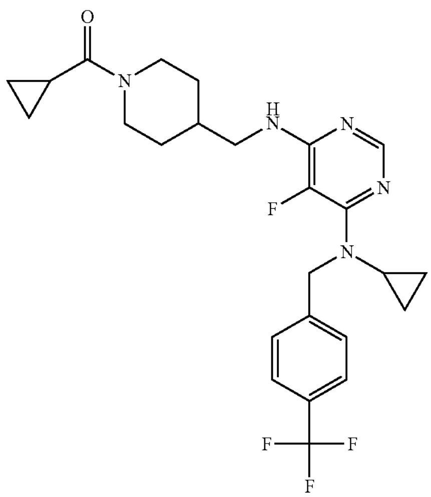 [SMILES: O=C(C1CC1)N1CCC(CNc2ncnc(N(Cc3ccc(C(F)(F)F)cc3)C3CC3)c2F)CC1] | cyclopropyl-[4-[[[6-[cyclopropyl-[[4-(trifluoromethyl)phenyl]methyl]amino]-5-fluoro-pyrimidin-4-yl]amino]methyl]-1-piperidyl]methanone |
| A168 | 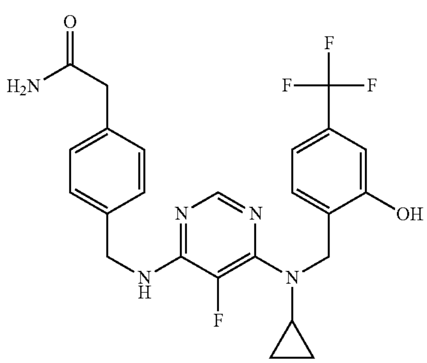 [SMILES: NC(=O)Cc1ccc(CNc2ncnc(N(Cc3ccc(C(F)(F)F)cc3O)C3CC3)c2F)cc1] | 2-[4-[[[6-[cyclopropyl-[[2-hydroxy-4-(trifluoromethyl)phenyl]methyl]amino]-5-fluoro-pyrimidin-4-yl]amino]methyl]phenyl]acetamide |
| A169 | 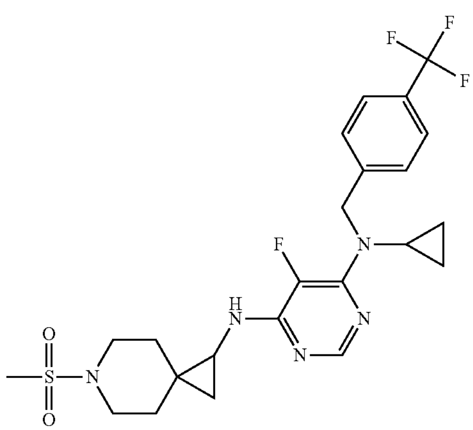 [SMILES: CS(=O)(=O)N1CCC2(CC1)CC2Nc1ncnc(N(Cc2ccc(C(F)(F)F)cc2)C2CC2)c1F] | N6-cyclopropyl-5-fluoro-N4-(6-methylsulfonyl-6-azaspiro[2.5]octan-2-yl)-N6-[[4-(trifluoromethyl)phenyl]methyl]pyrimidine-4,6-diamine |

TABLE 1-continued

Example Compounds by Structure and Name.

| Ex. No. | Structure | Name |
|---|---|---|
| A170 | 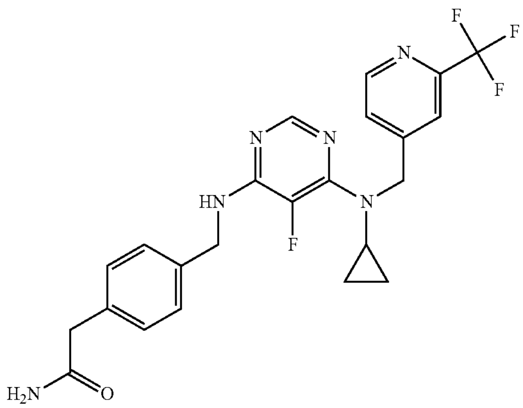 [SMILES: NC(=O)Cc1ccc(CNc2ncnc(N(Cc3ccnc(C(F)(F)F)c3)C3CC3)c2F)cc1] | 2-[4-[[[6-[cyclopropyl-[[2-(trifluoromethyl)-4-pyridyl]methyl]amino]-5-fluoro-pyrimidin-4-yl]amino]methyl]phenyl]acetamide |
| A171 | 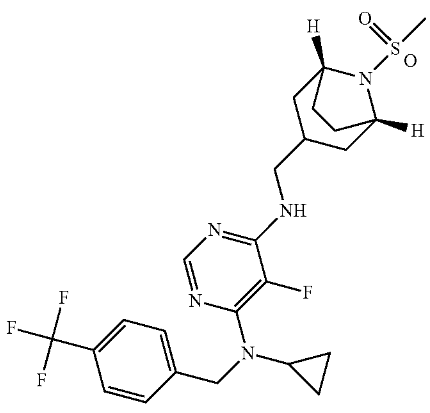 | N6-cyclopropyl-5-fluoro-N4-[[(1S,5R)-8-methylsulfonyl-8-azabicyclo[3.2.1]octan-3-yl]methyl]-N6-[[4-(trifluoromethyl)phenyl]methyl]pyrimidine-4,6-diamine |
| A172 | 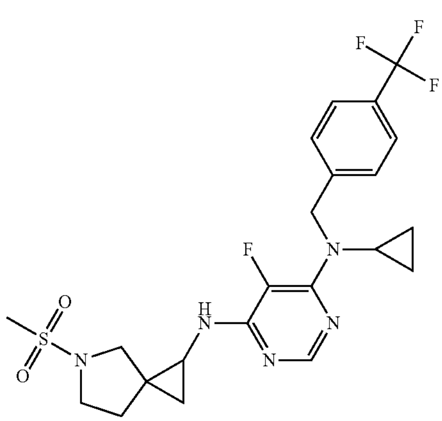 [SMILES: CS(=O)(=O)N1CCC2(CC2Nc2ncnc(N(Cc3ccc(C(F)(F)F)cc3)C3CC3)c2F)C1] | N6-cyclopropyl-5-fluoro-N4-(6-methylsulfonyl-6-azaspiro[2.4]heptan-2-yl)-N6-[[4-(trifluoromethyl)phenyl]methyl]pyrimidine-4,6-diamine |

TABLE 1-continued

Example Compounds by Structure and Name.

| Ex. No. | Structure | Name |
|---|---|---|
| A173 | 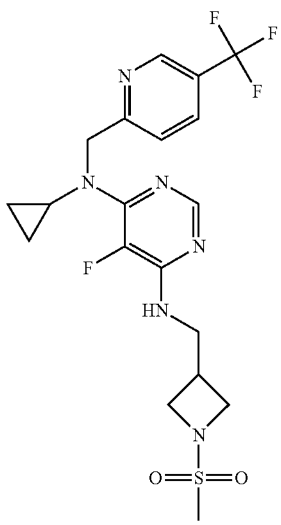 [SMILES: CS(=O)(=O)N1CC(CNc2ncnc(N(Cc3ccc(C(F)(F)F)cn3)C3CC3)c2F)C1] | N4-cyclopropyl-5-fluoro-N6-[(1-methylsulfonylazetidin-3-yl)methyl]-N4-[[5-(trifluoromethyl)-2-pyridyl]methyl]pyrimidine-4,6-diamine |
| A174 | 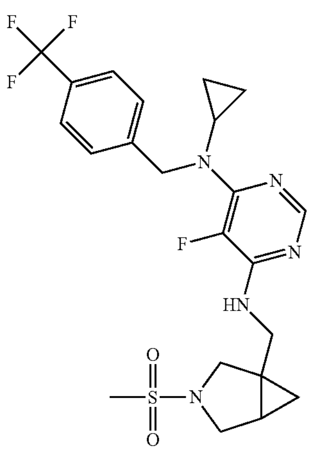 [SMILES: CS(=O)(=O)N1CC2CC2(CNc2ncnc(N(Cc3ccc(C(F)(F)F)cc3)C3CC3)c2F)C1] | N6-cyclopropyl-5-fluoro-N4-[(3-methylsulfonyl-3-azabicyclo[3.1.0]hexan-5-yl)methyl]-N6-[[4-(trifluoromethyl)phenyl]methyl]pyrimidine-4,6-diamine |
| A175 | 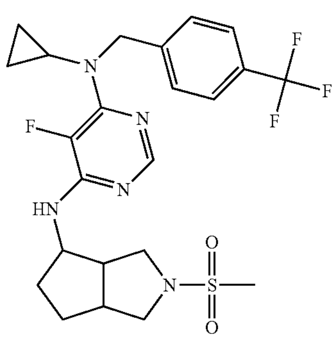 [SMILES: CS(=O)(=O)N1CC2CCC(Nc3ncnc(N(Cc4ccc(C(F)(F)F)cc4)C4CC4)c3F)C2C1] | N6-cyclopropyl-5-fluoro-N4-(2-methylsulfonyl-3,3a,4,5,6,6a-hexahydro-1H-cyclopenta[c]pyrrol-4-yl)-N6-[[4-(trifluoromethyl)phenyl]methyl]pyrimidine-4,6-diamine |

TABLE 1-continued

Example Compounds by Structure and Name.

| Ex. No. | Structure | Name |
|---|---|---|
| A176 | 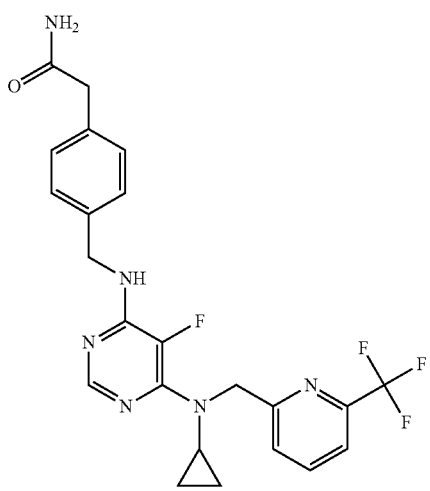 [SMILES: NC(=O)Cc1ccc(CNc2ncnc(N(Cc3cccc(C(F)(F)F)n3)C3CC3)c2F)cc1] | 2-[4-[[[6-[cyclopropyl-[[6-(trifluoromethyl)-2-pyridyl]methyl]amino]-5-fluoro-pyrimidin-4-yl]amino]methyl]phenyl]acetamide |
| A177 | 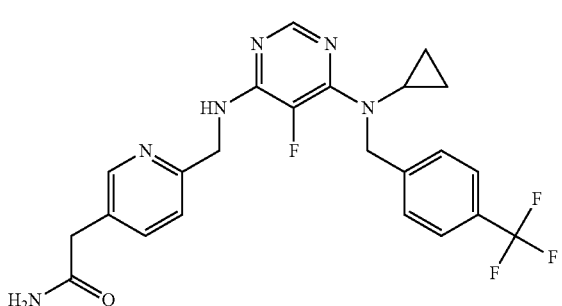 | 2-[6-[[[6-[cyclopropyl-[[4-(trifluoromethyl)phenyl]methyl]amino]-5-fluoro-pyrimidin-4-yl]amino]methyl]-3-pyridyl]acetamide |
| A178 | 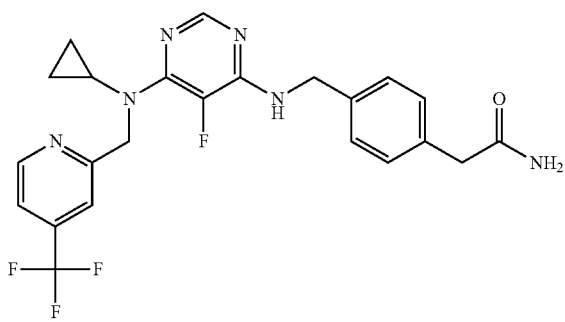 [SMILES: NC(=O)Cc1ccc(CNc2ncnc(N(Cc3cc(C(F)(F)F)ccn3)C3CC3)c2F)cc1] | 2-[4-[[[6-[cyclopropyl-[[4-(trifluoromethyl)-2-pyridyl]methyl]amino]-5-fluoro-pyrimidin-4-yl]amino]methyl]phenyl]acetamide |
| A179 | 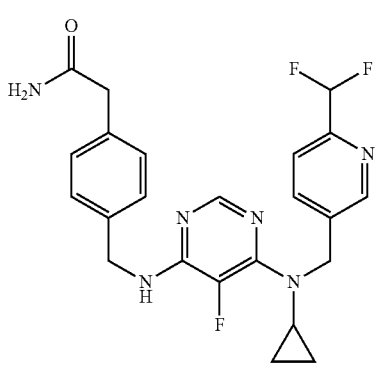 [SMILES: NC(=O)Cc1ccc(CNc2ncnc(N(Cc3ccc(C(F)F)nc3)C3CC3)c2F)cc1] | 2-[4-[[[6-[cyclopropyl-[[6-(difluoromethyl)-3-pyridyl]methyl]amino]-5-fluoro-pyrimidin-4-yl]amino]methyl]phenyl]acetamide |

TABLE 1-continued

Example Compounds by Structure and Name.

| Ex. No. | Structure | Name |
|---|---|---|
| A180 | 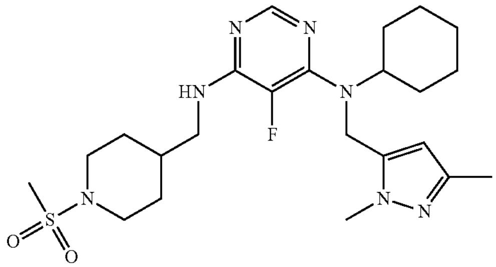 [SMILES: Cc1cc(CN(c2ncnc(NCC3CCN(S(C)(=O)=O)CC3)c2F)C2CCCCC2)n(C)n1] | N6-cyclohexyl-N6-[(2,5-dimethylpyrazol-3-yl)methyl]-5-fluoro-N4-[(1-methylsulfonyl-4-piperidyl)methyl]pyrimidine-4,6-diamine |
| A181 | 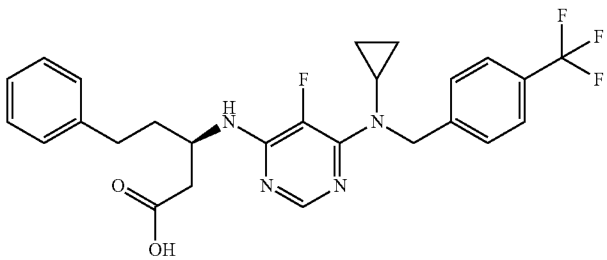 [SMILES: O=C(O)C[C@@H](CCc1ccccc1)Nc1ncnc(N(Cc2ccc(C(F)(F)F)cc2)C2CC2)c1F] | (3R)-3-[[6-[cyclopropyl-[[4-(trifluoromethyl)phenyl]methyl]amino]-5-fluoro-pyrimidin-4-yl]amino]-5-phenyl-pentanoic acid |
| A182 | 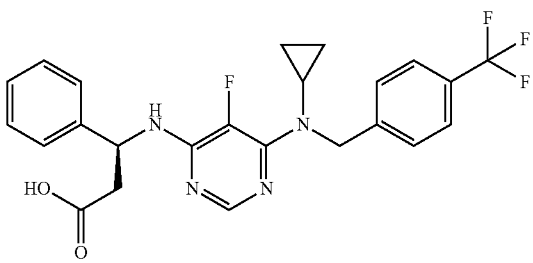 [SMILES: O=C(O)C[C@H](Nc1ncnc(N(Cc2ccc(C(F)(F)F)cc2)C2CC2)c1F)c1ccccc1] | (3S)-3-[[6-[cyclopropyl-[[4-(trifluoromethyl)phenyl]methyl]amino]-5-fluoro-pyrimidin-4-yl]amino]-3-phenyl-propanoic acid |
| A183 | 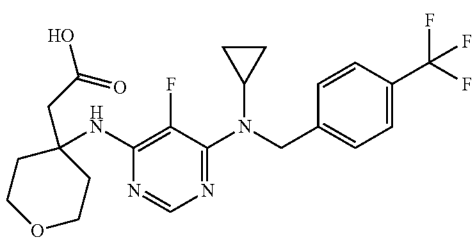 [SMILES: O=C(O)CC1(Nc2ncnc(N(Cc3ccc(C(F)(F)F)cc3)C3CC3)c2F)CCOCC1] | 2-[4-[[6-[cyclopropyl-[[4-(trifluoromethyl)phenyl]methyl]amino]-5-fluoro-pyrimidin-4-yl]amino]tetrahydropyran-4-yl]acetic acid |
| A184 | 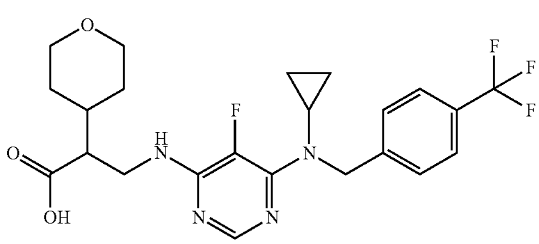 [SMILES: O=C(O)C(CNc1ncnc(N(Cc2ccc(C(F)(F)F)cc2)C2CC2)c1F)C1CCOCC1] | 3-[[6-[cyclopropyl-[[4-(trifluoromethyl)phenyl]methyl]amino]-5-fluoro-pyrimidin-4-yl]amino]-2-tetrahydropyran-4-yl-propanoic acid |
| A185 | 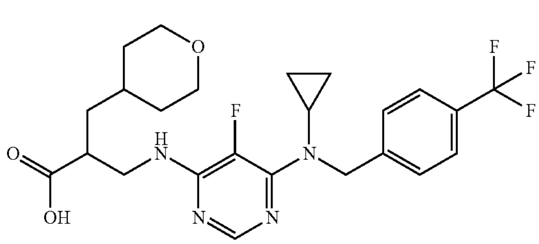 [SMILES: O=C(O)C(CNc1ncnc(N(Cc2ccc(C(F)(F)F)cc2)C2CC2)c1F)CC1CCOCC1] | 2-[[[6-[cyclopropyl-[[4-(trifluoromethyl)phenyl]methyl]amino]-5-fluoro-pyrimidin-4-yl]amino]methyl]-3-tetrahydropyran-4-yl-propanoic acid |

In a related aspect there is provided a prodrug of a compound of Formula (I) as described herein.

Pharmaceutical Compositions

In another aspect, the present disclosure relates to a pharmaceutical composition comprising physiologically acceptable surface active agents, carriers, diluents, excipients, smoothing agents, suspension agents, film forming substances, and coating assistants, or a combination thereof; and a compound of Formula (I) as disclosed herein. The compound of Formula (I) included in the pharmaceutical composition may also be any compound of the preferred embodiments described above. In another aspect, the present disclosure relates to a pharmaceutical composition comprising physiologically acceptable surface active agents, carriers, diluents, excipients, smoothing agents, suspension agents, film forming substances, and coating assistants, or a combination thereof; and a compound of any one of Formulae (IIa), (IIb), (IIc), or (IId) as disclosed herein. Acceptable carriers or diluents, as well as other additives to be combined with a compound of Formula (I) as disclosed herein to provide a pharmaceutical composition, for therapeutic use are well known in the pharmaceutical art, and are described, for example, in Remington's Pharmaceutical Sciences, 18th Ed., Mack Publishing Co., Easton, Pa. (1990) which is incorporated herein by reference in its entirety. Preservatives, stabilizers, dyes, sweeteners, fragrances, flavoring agents, taste masking agents, and the like may be provided in the pharmaceutical composition. For example, sodium benzoate, ascorbic acid and esters of p-hydroxybenzoic acid may be added as preservatives. In addition, antioxidants and suspending agents may be used. In various embodiments, alcohols, esters, sulfated aliphatic alcohols, and the like may be used as surface active agents; sucrose, glucose, lactose, starch, crystallized cellulose, mannitol, light anhydrous silicate, magnesium aluminate, magnesium methasilicate aluminate, synthetic aluminum silicate, calcium carbonate, sodium acid carbonate, calcium hydrogen phosphate, calcium carboxymethyl cellulose, and the like may be used as excipients; magnesium stearate, talc, hardened oil and the like may be used as smoothing agents; coconut oil, olive oil, sesame oil, peanut oil, soya may be used as suspension agents or lubricants; cellulose acetate phthalate as a derivative of a carbohydrate such as cellulose or sugar, or methylacetate-methacrylate copolymer as a derivative of polyvinyl may be used as suspension agents; and plasticizers such as ester phthalates and the like may be used as suspension agents.

The term "pharmaceutical composition" refers to a mixture of a compound disclosed herein with other chemical components, such as diluents or carriers. The pharmaceutical composition facilitates administration of the compound to an organism. Multiple techniques of administering a compound exist in the art including, but not limited to, oral, injection, aerosol, parenteral, and topical administration. Pharmaceutical compositions can also be obtained by reacting compounds with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid and the like. Similar, pharmaceutical compositions can also be obtained by reacting compounds with inorganic or organic bases, such as ammonia, sodium carbonate, sodium hydrogen carbonate, sodium hydroxide, and the like.

The term "carrier" defines a chemical compound that facilitates the incorporation of a compound into cells or tissues. For example dimethyl sulfoxide (DMSO) is a commonly utilized carrier as it facilitates the uptake of many organic compounds into the cells or tissues of an organism.

The term "diluent" defines chemical compounds diluted in water that will dissolve the compound of interest as well as stabilize the biologically active form of the compound. Salts dissolved in buffered solutions are utilized as diluents in the art. One commonly used buffered solution is phosphate buffered saline because it mimics the salt conditions of human blood. Since buffer salts can control the pH of a solution at low concentrations, a buffered diluent rarely modifies the biological activity of a compound.

The term "physiologically acceptable" defines a carrier or diluent that does not abrogate the biological activity and properties of the compound.

The pharmaceutical compositions described herein can be administered to a human patient per se, or in pharmaceutical compositions where they are mixed with other active ingredients, as in combination therapy, or suitable carriers or excipient(s).

Techniques for formulation and administration of the compounds of the instant application may be found in "Remington's Pharmaceutical Sciences," Mack Publishing Co., Easton, Pa., 18th edition, 1990.

Suitable routes of administration may, for example, include oral, rectal, transmucosal, topical, or intestinal administration; parenteral delivery, including intramuscular, subcutaneous, intravenous, intramedullary injections, as well as intrathecal, direct intraventricular, intraperitoneal, intranasal, or intraocular injections.

The compounds can also be administered in sustained or controlled release dosage forms, including depot injections, osmotic pumps, pills, transdermal (including electrotransport) patches, and the like, for prolonged and/or timed, pulsed administration at a predetermined rate.

The pharmaceutical compositions may be manufactured in a manner that is itself known, e.g., by means of conventional mixing, dissolving, granulating, dragee-making, levigating, emulsifying, encapsulating, entrapping or tabletting processes.

Pharmaceutical compositions for use as described herein may be formulated in conventional manner using one or more physiologically acceptable carriers comprising excipients and auxiliaries which facilitate processing of the active compounds into preparations which can be used pharmaceutically. Proper formulation is dependent upon the route of administration chosen. Any of the well-known techniques, carriers, and excipients may be used as suitable and as understood in the art; e.g., in Remington's Pharmaceutical Sciences, above.

Injectables can be prepared in conventional forms, either as liquid solutions or suspensions, solid forms suitable for solution or suspension in liquid prior to injection, or as emulsions. Suitable excipients are, for example, water, saline, dextrose, mannitol, lactose, lecithin, albumin, sodium glutamate, cysteine hydrochloride, and the like. In addition, if desired, the injectable pharmaceutical compositions may contain minor amounts of nontoxic auxiliary substances, such as wetting agents, pH buffering agents, and the like. Physiologically compatible buffers include, but are not limited to, Hanks's solution, Ringer's solution, or physiological saline buffer. If desired, absorption enhancing preparations (for example, liposomes), may be utilized.

For transmucosal administration, penetrants appropriate to the barrier to be permeated may be used in the formulation.

Pharmaceutical formulations for parenteral administration, e.g., by bolus injection or continuous infusion, include aqueous solutions of the active compounds in water-soluble form. Additionally, suspensions of the active compounds may be prepared as appropriate oily injection suspensions. Suitable lipophilic solvents or vehicles include fatty oils such as sesame oil, or other organic oils such as soybean, grapefruit or almond oils, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

For oral administration, the compounds can be formulated readily by combining the active compounds with pharmaceutically acceptable carriers well known in the art.

Such carriers enable the compounds disclosed herein to be formulated as tablets, pills, dragees, capsules, liquids, gels, syrups, slurries, suspensions and the like, for oral ingestion by a patient to be treated. Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use as described herein are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas.

In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

Further disclosed herein are various pharmaceutical compositions well known in the pharmaceutical art for uses that include intraocular, intranasal, and intraauricular delivery. Suitable penetrants for these uses are generally known in the art. Topical ophthalmic compositions may be formulated as a solution in water buffered at a pH of 5.0 to 8.0. Other ingredients that may be desirable to use in the ophthalmic preparations include preservatives (such as benzalkonium chloride, stabilized oxychloro complex, which is sold as Purite™, or stabilized chlorine dioxide), cosolvents (such as polysorbate 20, 60 and 80, Pluronic® F-68, F-84 and P-103, cyclodextrin, or Solutol) and viscosity-building agents (such as polyvinyl alcohol, polyvinyl pyrrolidone, methyl cellulose, hydroxypropyl methyl cellulose, hydroxyethyl cellulose, carboxymethyl cellulose, or hydroxypropyl cellulose). The compounds disclosed herein may also be used in an intraocular implant as described in U.S. Pat. No. 7,931,909 which is hereby incorporated by reference. Pharmaceutical compositions for intraocular delivery include aqueous ophthalmic solutions of the active compounds in water-soluble form, such as eyedrops, or in gellan gum (Shedden et al., *Clin. Ther.*, 23(3):440-50 (2001)) or hydrogels (Mayer et al., *Ophthalmologica*, 210(2):101-3 (1996)); ophthalmic ointments; ophthalmic suspensions, such as microparticulates, drug-containing small polymeric particles that are suspended in a liquid carrier medium (Joshi, A., *J. Ocul. Pharmacol.*, 10(1):29-45 (1994)), lipid-soluble formulations (Alm et al., *Prog. Clin. Biol. Res.*, 312:447-58 (1989)), and microspheres (Mordenti, *Toxicol. Sci.*, 52(1):101-6 (1999)); and ocular inserts. All of the above-mentioned references, are incorporated herein by reference in their entireties. Such suitable pharmaceutical formulations for intraocular delivery are most often and preferably formulated to be sterile, isotonic and buffered for stability and comfort. Pharmaceutical compositions for intranasal delivery may also include drops and sprays often prepared to simulate in many respects nasal secretions to ensure maintenance of normal ciliary action. As disclosed in Remington's Pharmaceutical Sciences, 18th Ed., Mack Publishing Co., Easton, Pa. (1990), which is incorporated herein by reference in its entirety, and well-known to those skilled in the art, suitable formulations are most often and preferably isotonic, slightly buffered to maintain a pH of 5.5 to 6.5, and most often and preferably include antimicrobial preservatives and appropriate drug stabilizers. Pharmaceutical formulations for intraauricular delivery include suspensions and ointments for topical application in the ear. Common solvents for such aural formulations include glycerin and water.

The compounds disclosed herein may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For hydrophobic compounds, a suitable pharmaceutical carrier may be a cosolvent system comprising benzyl alcohol, a nonpolar surfactant, a water-miscible organic polymer, and an aqueous phase. A common cosolvent system used is the VPD co-solvent system, which is a solution of 3% w/v benzyl alcohol, 8% w/v of the nonpolar surfactant Polysorbate 80™, and 65% w/v polyethylene glycol 300, made up to volume in absolute ethanol. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of POLYSORBATE 80™; the fraction size of polyethylene glycol may be varied; other biocompatible polymers may replace polyethylene glycol, e.g., polyvinyl pyrrolidone; and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. Certain organic solvents such as dimethylsulfoxide also may be employed. Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

Agents intended to be administered intracellularly may be administered using techniques well known to those of ordinary skill in the art. For example, such agents may be encapsulated into liposomes. All molecules present in an aqueous solution at the time of liposome formation are incorporated into the aqueous interior. The liposomal contents are both protected from the external micro-environment and, because liposomes fuse with cell membranes, are efficiently delivered into the cell cytoplasm. The liposome may be coated with a tissue-specific antibody. The liposomes will be targeted to and taken up selectively by the desired organ. Alternatively, small hydrophobic organic molecules may be directly administered intracellularly.

Additional therapeutic or diagnostic agents may be incorporated into the pharmaceutical compositions. Alternatively or additionally, pharmaceutical compositions may be combined with other compositions that contain other therapeutic or diagnostic agents.

Uses

The compounds or pharmaceutical compositions disclosed herein as described above may be used to modulate the activity of a retinoic acid receptor-related orphan receptor (ROR), such as a RORα, RORβ and/or RORγ (RORc) receptor. Modulators of RORγ have been reviewed by B. Fauber and S. Magnuson in J. Med. Chem., Feb. 6, 2014, which hereby is incorporated by reference in its entirety. Examples of RORγ receptors are RORγ1 and RORγt receptors. The compounds or pharmaceutical compositions as described above may also display selective modulation of a particular ROR receptor relative to a different ROR receptor. For example, according to some embodiments disclosed herein some compounds or pharmaceutical compositions modulate the activity of an RORγ receptor to a larger extent than they modulate the activity of RORα and/or RORP receptors.

The compounds or pharmaceutical compositions disclosed herein may also be used to modulate the activity of regulatory T cells (Tregs).

The compounds or pharmaceutical compositions disclosed herein may also be used to modulate the activity of cells producing IL17 in a RORγt dependent manner, for example, γδT cells, Th17 cells and ILC3 cells.

Publications providing useful background information are Arthritis & Rheumatism, 2014, 66, 579-588; Curr Top Microbial Immun, 2014, 378, 171-182; Drug Disc. Today, 2014, May; Nature Rev. Drug Disc. 2012, 11, 763-776, and Nature Rev. Drug Disc., 2014, 13, 197-216, all of which are hereby incorporated by reference in their entirety.

The compounds or pharmaceutical compositions as described herein and above may also be used in therapy or may be used to treat inflammatory, metabolic, oncologic and autoimmune diseases or disorders. Examples of such diseases or disorders are inflammatory, metabolic, oncologic and autoimmune diseases or disorders mediated or affected by IL17 and/or RORγ (RORc). The role of RORγ in the pathogenesis of autoimmune or inflammatory diseases has been disclosed in Immunity 2007, 26, 643-654; Nat. Rev. Immunol. 2006, 6, 205-217; J. Immunol. 2009, 183, 7169-7177; Brain Pathol. 2004, 14, 164-174; Brain 2007, 130, 1089-1104; and Nat Rev. Immunol. 2008, 8, 183-192 all of which are hereby incorporated by reference in their entirety.

More specific examples of diseases or disorders include asthma, chronic obstructive pulmonary disease (COPD), bronchitis, atherosclerosis, *Helicobacter pylori* infection, allergic diseases including allergic rhinitis, allergic conjunctivitis and uveitis, sprue and food allergy, atopic dermatitis, cystic fibrosis, lung allograph rejection, multiple sclerosis, rheumatoid arthritis, juvenile rheumatoid arthritis, osteoarthritis, ankylosing spondylitis, psoriasis, psoriatic arthritis, steatosis, steatohepatitis, non-alcoholic fatty liver disease (NAFLD), non-alcoholic steatohepatitis (NASH), lupus erythematosus, Hashimoto's disease, pancreatitis, autoimmune diabetes, autoimmune ocular disease, ulcerative colitis, colitis, Crohn's disease, inflammatory bowel disease (IBD), inflammatory bowel syndrome (IBS), Sjogren's syndrome, optic neuritis, type I diabetes, neuromyelitis optica, Myasthenia Gravis, Guillain-Barre syndrome, Graves' disease, scleritis, obesity, obesity-induced insulin resistance and type II diabetes and cancer.

More specifically, compounds or pharmaceutical compositions having an antagonistic or inverse agonistic effect on RORγ may be used to reduce levels of IL17 and/or other gene products, such as interleukins, and cytokines, regulated RORγ. This may for example be in subjects suffering from for example, asthma, chronic obstructive pulmonary disease (COPD), bronchitis, atherosclerosis, *Helicobacter pylori* infection, allergic diseases including allergic rhinitis, allergic conjunctivitis and uveitis, sprue and food allergy, atopic dermatitis, cystic fibrosis, lung allograph rejection, multiple sclerosis, rheumatoid arthritis, juvenile rheumatoid arthritis, osteoarthritis, ankylosing spondylitis, psoriasis, psoriatic arthritis, steatosis, steatohepatitis, non-alcoholic fatty liver disease (NAFLD), non-alcoholic steatohepatitis (NASH), lupus erythematosus, Hashimoto's disease, pancreatitis, autoimmune diabetes, autoimmune ocular disease, ulcerative colitis, colitis, Crohn's disease, inflammatory bowel disease (IBD), inflammatory bowel syndrome (IBS), Sjogren's syndrome, optic neuritis, type I diabetes, neuromyelitis optica, Myasthenia Gravis, Guillain-Barre syndrome, Graves' disease, scleritis, obesity, obesity-induced insulin resistance and type II diabetes.

Conversely, compounds or pharmaceutical compositions having an agonistic effect on RORγ may be used to increase IL17 levels. Increasing IL17 levels may be particularly useful in immune compromised conditions or boosting the immune system response for example during infections and in cancer.

Methods of Administration

The compounds or pharmaceutical compositions may be administered to the patient by any suitable means. Non-limiting examples of methods of administration include, among others, (a) administration though oral pathways, which administration includes administration in capsule, tablet, granule, spray, syrup, or other such forms; (b) administration through non-oral pathways such as rectal, vaginal, intraurethral, intraocular, intranasal, or intraauricular, which administration includes administration as an aqueous suspension, an oily preparation or the like or as a drip, spray, suppository, salve, ointment or the like; (c) administration via injection, subcutaneously, intraperitoneally, intravenously, intramuscularly, intradermally, intraorbitally, intracapsularly, intraspinally, intrasternally, or the like, including infusion pump delivery; (d) administration locally such as by injection directly in the renal or cardiac area, e.g., by depot implantation, by intratumoral injection, or by intralymph node injection; (e) administration topically; as well as well as (f) administration to cells ex vivo followed by insertion of said cells into the patient; as deemed appropriate by those of skill in the art for bringing the compound disclosed herein into contact with living tissue.

Pharmaceutical compositions suitable for administration include compositions where the active ingredients are contained in an amount effective to achieve its intended purpose. The therapeutically effective amount of the compounds disclosed herein required as a dose will depend on the route of administration, the type of animal, including mammal, e.g. human, being treated, and the physical characteristics of the specific animal under consideration. The dose can be tailored to achieve a desired effect, but will depend on such factors as weight, diet, concurrent medication and other factors which those skilled in the medical arts will recognize. More specifically, a therapeutically effective amount means an amount of compound effective to prevent, alleviate or ameliorate symptoms of disease or prolong the survival of the subject being treated. Determination of a therapeutically effective amount is well within the capability of those skilled in the art, especially in light of the detailed disclosure provided herein.

As will be readily apparent to one skilled in the art, the useful in vivo dosage to be administered and the particular mode of administration will vary depending upon the age, weight and mammalian species treated, the particular compounds employed, and the specific use for which these compounds are employed. The determination of effective dosage levels, that is the dosage levels necessary to achieve the desired result, can be accomplished by one skilled in the art using routine pharmacological methods. Typically, human clinical applications of products are commenced at lower dosage levels, with dosage level being increased until the desired effect is achieved. Alternatively, acceptable in vitro studies can be used to establish useful doses and routes of administration of the compositions identified by the present methods using established pharmacological methods.

In non-human animal studies, applications of potential products are commenced at higher dosage levels, with dosage being decreased until the desired effect is no longer achieved or adverse side effects disappear. The dosage may range broadly, depending upon the desired effects and the therapeutic indication.

Typically, dosages may be between about 10 microgram/kg and 100 mg/kg body weight, preferably between about 100 microgram/kg and 10 mg/kg body weight. Alternatively dosages may be based and calculated upon the surface area of the patient, as understood by those of skill in the art.

The exact formulation, route of administration and dosage for the pharmaceutical compositions disclosed herein can be chosen by the individual physician in view of the patient's condition. (See e.g., Fingl et al. 1975, in "The Pharmacological Basis of Therapeutics", which is hereby incorporated herein by reference in its entirety, with particular reference to Ch. 1, p. 1). Typically, the dose range of the composition administered to the patient can be from about 0.5 to 1000 mg/kg of the patient's body weight. The dosage may be a single one or a series of two or more given in the course of one or more days, as is needed by the patient. In instances where human dosages for compounds have been established for at least some condition, those same dosages may be used, or dosages that are between about 0.1% and 500%, more preferably between about 25% and 250% of the established human dosage. Where no human dosage is established, as will be the case for newly-discovered pharmaceutical compounds, a suitable human dosage can be inferred from $ED_{50}$ or $ID_{50}$ values, or other appropriate values derived from in vitro or in vivo studies, as qualified by toxicity studies and efficacy studies in animals.

It should be noted that the attending physician would know how to and when to terminate, interrupt, or adjust administration due to toxicity or organ dysfunctions. Conversely, the attending physician would also know to adjust treatment to higher levels if the clinical response were not adequate (precluding toxicity). The magnitude of an administrated dose in the management of the disorder of interest will vary with the severity of the condition to be treated and to the route of administration. The severity of the condition may, for example, be evaluated, in part, by standard prognostic evaluation methods. Further, the dose and perhaps the dose frequency will also vary according to the age, body weight, and response of the individual patient. A program comparable to that discussed above may be used in veterinary medicine.

Although the exact dosage will be determined on a drug-by-drug basis, in most cases, some generalizations regarding the dosage can be made. The daily dosage regimen for an adult human patient may be, for example, an oral dose of between 0.1 mg and 2000 mg of each active ingredient, preferably between 1 mg and 500 mg, e.g. 5 to 200 mg. An ocular eye drop may range in concentration between 0.005 and 5 percent. In one embodiment, an eye drop may range between 0.01 and 1 percent, or between 0.01 and 0.3 percent in another embodiment. In other embodiments, an intravenous, subcutaneous, or intramuscular dose of each active ingredient of between 0.01 mg and 100 mg, preferably between 0.1 mg and 60 mg, e.g. 1 to 40 mg is used. In cases of administration of a pharmaceutically acceptable salt, dosages may be calculated as the free base. In some embodiments, the composition is administered 1 to 4 times per day. Alternatively the compositions disclosed herein may be administered by continuous intravenous infusion, preferably at a dose of each active ingredient up to 1000 mg per day. As will be understood by those of skill in the art, in certain situations it may be necessary to administer the compounds disclosed herein in amounts that exceed, or even far exceed, the above-stated, preferred dosage range or frequency in order to effectively and aggressively treat particularly aggressive diseases or infections. In some embodiments, the compounds will be administered for a period of continuous therapy, for example for a week or more, or for months or years.

Dosage amount and interval may be adjusted individually to provide plasma or tissue levels of the active moiety which are sufficient to maintain the modulating effects, or minimal effective concentration (MEC). The MEC will vary for each compound but can be estimated from in vitro data. Dosages necessary to achieve the MEC will depend on individual characteristics and route of administration. However, HPLC assays or bioassays can be used to determine plasma concentrations.

Dosage intervals can also be determined using MEC value. Compositions should be administered using a regimen which maintains plasma levels above the MEC for 10-90% of the time, preferably between 30-90% and most preferably between 50-90%.

In cases of local or ex vivo administration or selective uptake, the effective local concentration of the drug may not be related to plasma concentration.

The amount of composition administered may be dependent on the subject being treated, on the subject's weight, the severity of the affliction, the manner of administration and the judgment of the prescribing physician.

Compounds disclosed herein can be evaluated for efficacy and toxicity using known methods. For example, the toxicology of a particular compound, or of a subset of the compounds, sharing certain chemical moieties, may be established by determining in vitro toxicity towards a cell line, such as a mammalian, and preferably human, cell line. The results of such studies are often predictive of toxicity in animals, such as mammals, or more specifically, humans. Alternatively, the toxicity of particular compounds in an animal model, such as mice, rats, rabbits, or monkeys, may be determined using known methods. The efficacy of a particular compound may be established using several recognized methods, such as in vitro methods, animal models, or human clinical trials. Recognized in vitro models exist for nearly every class of condition, including but not limited to cancer, cardiovascular disease, and various immune dysfunction. Similarly, acceptable animal models may be used to establish efficacy of chemicals to treat such conditions. When selecting a model to determine efficacy, the skilled artisan can be guided by the state of the art to choose an appropriate model, dose, and route of administration, and regime. Of course, human clinical trials can also be used to determine the efficacy of a compound in humans.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions comprising a compound disclosed herein formulated in a compatible pharmaceutical carrier may also be prepared, placed in an appropriate container, and labeled for treatment of an indicated condition.

GENERAL REMARKS

Figure 1:
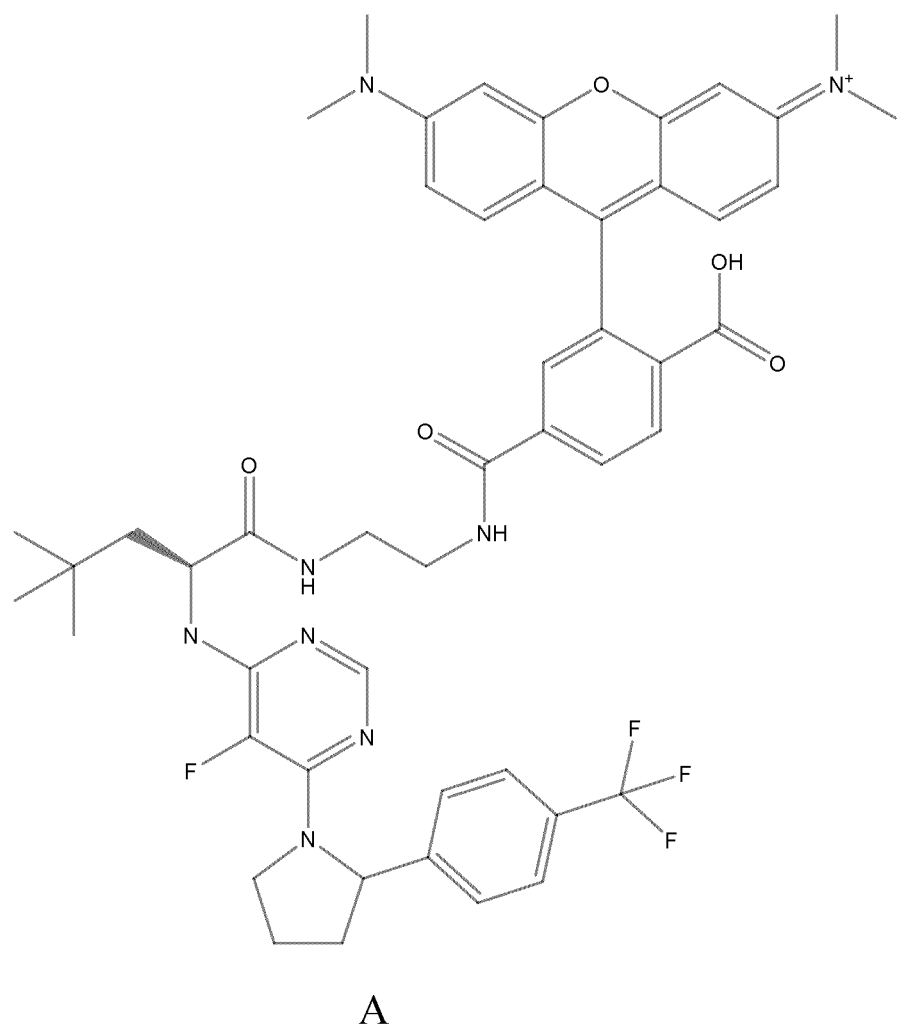
FIG. 1 illustrates the TAMRA-labelled probe.

As described above with reference to specific illustrative embodiments, it is not intended to be limited to the specific form set forth herein. Any combination of the above mentioned embodiments should be appreciated as being within the scope of the invention. Rather, the invention is limited only by the accompanying claims and other embodiments than the specific above are equally possible within the scope of these appended claims.

In the claims, the term "comprises/comprising" does not exclude the presence of other species or steps. Additionally, although individual features may be included in different claims, these may possibly advantageously be combined, and the inclusion in different claims does not imply that a combination of features is not feasible and/or advantageous. In addition, singular references do not exclude a plurality. The terms "a", "an", "first", "second" etc. do not preclude a plurality. The phrases "at least one" or "one or more" refer to 1 or a number greater than 1, such as to 1, 2, 3, 4, 5, 6, 7, 8, 9, or 10.

Whenever a chemical name or structure has been given it has been generated by conventional means or by means of a suitable software such as ChemDraw Ultra 8.0.7 or Accelrys Draw 4.0 .NET.

Experimental

The following examples are mere examples and should by no mean be interpreted to limit the scope of the invention. Rather, the invention is limited only by the accompanying claims.

General Chemical Procedures

Unless otherwise stated, starting materials were obtained from commercial suppliers, such as (but not limited to); ABchem, ABCR, Alfa Aesar, Anaspec, Anichem, Apollo Scientific, ASDI-Inter, Asiba Pharmatech, Astatech, Bachem, Chem-Impex, ChemCollect, Chembridge, Combi-Blocks, Enamine, Fluka, Fluorochem, Frontier Scientific, HDH Pharma, InFarmatik, InterBioScreen, Life Chemicals, Manchester organics, Matrix, MercaChem, NetChem, Oakwood Chemical, PepTech, Pharmcore, PrincetonBio, Sigma-Aldrich, TRC, Tyger Scientific and Ukrorgsyn. N,N-dimethylformamide (DMF), dimethyl sulfoxide (DMSO) and dichloromethane (DCM) were dried over molecular sieves. Analytical HPLC was performed on a Waters Acquity system using a C18 reverse phase column (Merck Chromolith Speedrod RP-18E) with a linear gradient of the binary solvent system water/acetonitrile/formic acid (A: 100/0/0.1% and B: 0/100/0.1%) with a flow rate of 3.0 mL/min and UV detection at 254 nm at ambient temperature, combined with MS detection on a Waters Micromass QZ Quadrupole Mass Spectrometer instrument using electron spray ionization, or on a Shimadzu Nexera X2 system using a C18 reverse phase column (Acquity UPLC BEH C18 1.7 μm, 2.1×50 mm), with a linear gradient of the binary solvent system water/methanol/formic acid (A: 100/0/0.1% and B: 0/100/0.1%) with a flow rate of 0.78 mL/min and UV detection at 254 nm, combined with MS detecting on a Shimadzu LCMS-2020 Spectrometer instrument using electron spray ionization. Preparative HPLC was performed on a Waters Acquity system using a C18 reverse phase column (Supelco ASCENTIS C18 581358-U, 15 cm×21.2 mm), with a linear gradient of the binary solvent system water/acetonitrile/formic acid (A: 100/0/0.1% and B: 0/100/0.1%) with a flow rate of 15 mL/min and UV detection at 254 nm, combined with MS detection on a Waters Micromass QZ Quadrupole Mass Spectrometer instrument using electron spray ionization. Chiral resolution was performed on a Lux Cellulose2 (250×21 mm) column using a mobile phase of 0.2% diethyamine in hexane/ethanol, with a flow of 20 mL/min and UV detection at 290 nm. $^1$H NMR spectra were recorded on a Bruker Avance 300 spectrometer (at 300 MHz), using CD$_3$OD, CDCl$_3$ or DMSO-d6 solvents. Chemical shifts are reported in ppm (δ) using residual solvent as an internal standard; CDCl$_3$: 7.26 ppm; CD$_3$OD: 3.31; DMSO-d$_6$: 2.50 ppm. Coupling constants (J) are given in Hz.

Synthetic Methods

The compounds disclosed herein may be made by one of the following four general methods. Further, additional guidance for preparing building blocks to be used in providing compounds disclosed herein is present in the co-pending international application also claiming priority from SE 1450920-2 and SE 1451406-1.

General Method 1

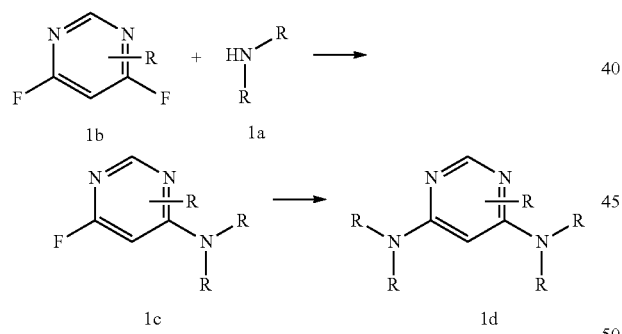

A compound containing a free amino group 1a, e.g. N-[[4-(trifluoromethyl)phenyl]methyl]cyclopropanamine, was coupled to a fluorinated aromatic compound 1b, e.g. 4,5,6-trifluoro-pyrimidine, upon treatment with a suitable base in an appropriate solvent, e.g. N,N-Diisopropylethylamine (DIPEA) or cesium carbonate in dry DMSO or dioxane. Conversion to 1c was typically achieved after stirring at room temperature (i.e. 20-25° C.) overnight. The reaction may for example be monitored by thin layer chromatography. The desired product was obtained upon work-up, e.g. by extraction with EtOAc, washing with water at a suitable pH and brine, drying over an appropriate drying agent, e.g. Na$_2$SO$_4$, and purification by flash column chromatography (CC) using an appropriate eluent combination on a suitable column material, e.g. heptane/EtOAc or DCM/MeOH on silica gel, or recrystallization from a suitable solvent or solvent mixture, e.g. toluene/heptane. Subsequent nucleophilic aromatic substitution of 1c with a building block containing a free amino group was achieved upon treatment with a suitable base in an appropriate solvent. An example of treatment conditions is cesium carbonate in dry DMSO under microwave irradiation during a period of time, e.g. at 80-150° C. for 1 hour. The reaction may for example be monitored by thin layer chromatography. The desired compound 1d was obtained upon work-up, for example by extraction with EtOAc, washing with water at a suitable pH and brine, drying over an appropriate drying agent, e.g. Na$_2$SO$_4$, and purification by flash column chromatography (CC) using an appropriate eluent combination on a suitable column material, e.g. heptane/EtOAc or DCM/MeOH on silica gel, or recrystallization from a suitable solvent or solvent mixture, e.g. toluene/heptane.

Use of General Method 1 to Prepare Example No. A5

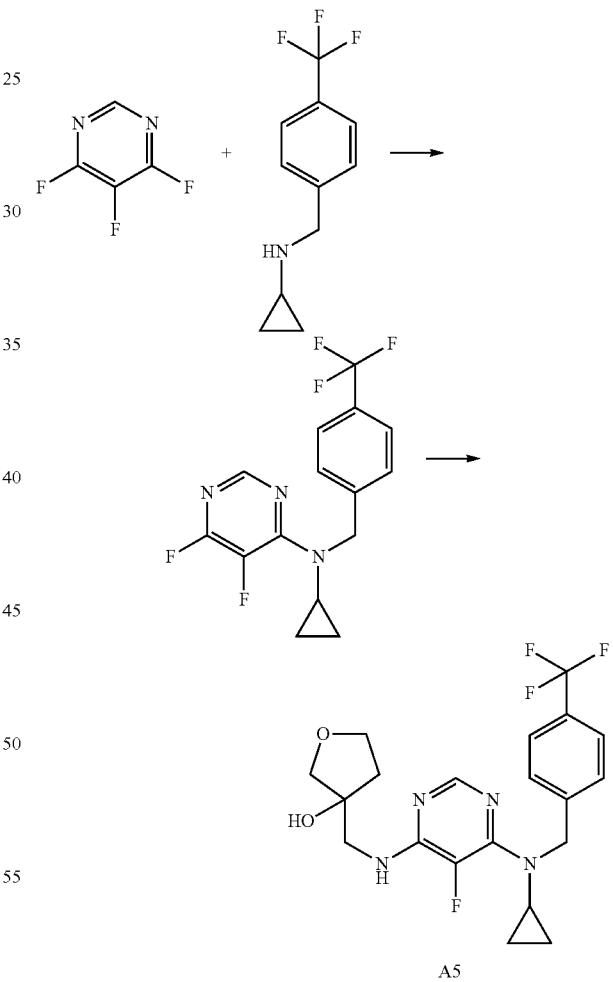

4,5,6-Trifluoro-pyrimidine (0.27 g, 2.0 mmol) and N-[[4-(trifluoromethyl)phenyl]methyl]cyclopropanamine (0.43 g, 2.0 mmol) were dissolved in dry DMSO (4 mL) and DIPEA (0.7 mL, 4.0 mmol) was added. The reaction was stirred at room temperature overnight, poured into 3M aq. calcium chloride, extracted with EtOAc, washed with brine, dried over sodium sulfate, filtered and concentrated in vacuo. The crude product was purified by flash CC (eluent: DCM/MeOH, on silica gel) yielding N-cyclopropyl-5,6-difluoro-N-[[4-(trifluoromethyl)phenyl]methyl]pyrimidin-4-amine (0.50 g, 76% yield). 4,5-difluoro-6-[2-[4-(trifluoromethyl)phenyl]pyrrolidin-1-yl]pyrimidine (0.33 g, 1.0 mmol) and 3-(aminomethyl)tetrahydrofuran-3-ol (0.12 g, 1.0 mmol) were dissolved in dry DMSO (2 mL) and cesium carbonate (0.65 g, 2.0 mmol) was added. The reaction was heated in a microwave reactor for 1 hour at 100° C., poured into 3M aq. calcium chloride, extracted with EtOAc, washed with brine, dried over sodium sulfate, filtered and concentrated in vacuo. The crude product was purified by flash CC (eluent: DCM/MeOH, on silica gel), yielding 3-[[[6-[cyclopropyl-[[4-(trifluoromethyl)phenyl]methyl]amino]-5-fluoro-pyrimidin-4-yl]amino]methyl]tetrahydrofuran-3-ol A5 (290 mg, 68% yield). $^1$H NMR (400 MHz, CDCl$_3$) δ 7.94 (d, J=1.5 Hz, 1H), 7.56 (d, J=7.9 Hz, 2H), 7.35 (d, J=8.0 Hz, 2H), 5.25 (s, 1H), 4.87 (s, 2H), 4.07-3.99 (m, 1H), 3.98-3.89 (m, 1H), 3.79 (d, J=9.2 Hz, 1H), 3.70-3.61 (m, 3H), 3.18-2.49 (m, 1H), 2.03-1.99 (m, 2H), 0.80 (d, J=6.6 Hz, 2H), 0.76-0.68 (m, 2H). m/z 427 (M+H).

General method 1 was used to prepare the following example numbers using the shown starting materials:

| Ex. No. | Free amine (1) | Free amine (2) | Fluorinated aromatic compound |
|---|---|---|---|
| T1 | 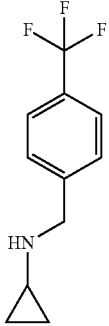<br>N-[[4-(trifluoromethyl)phenyl]methyl]cyclopropanamine | 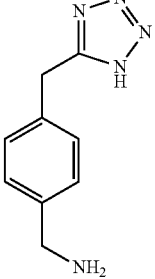<br>[4-(1H-tetrazol-5-ylmethyl)phenyl]methanamine | 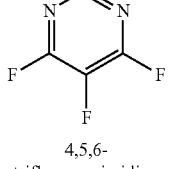<br>4,5,6-trifluoropyrimidine |
| X | 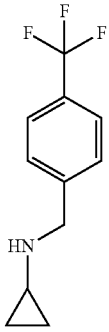<br>N-[[4-(trifluoromethyl)phenyl]methyl]cyclopropanamine | 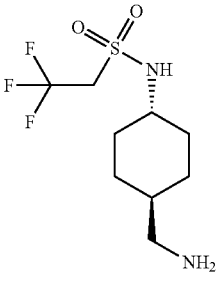<br>N-[4-(aminomethyl)cyclohexyl]-2,2,2-trifluoro-ethanesulfonamide | 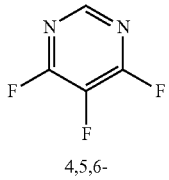<br>4,5,6-trifluoropyrimidine |

-continued

| Ex. No. | Free amine (1) | Free amine (2) | Fluorinated aromatic compound |
|---|---|---|---|
| A1 | 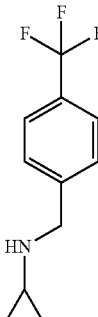<br>N-[[4-(trifluoromethyl)phenyl]methyl]cyclopropanamine | 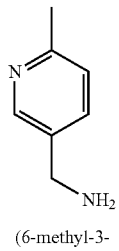<br>(6-methyl-3-pyridyl)methanamine | 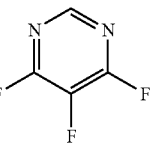<br>4,5,6-trifluoropyrimidine |
| A2 | 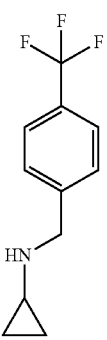<br>N-[[4-(trifluoromethyl)phenyl]methyl]cyclopropanamine | 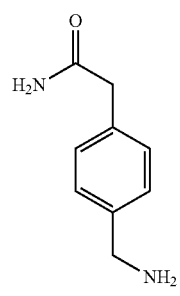<br>2-[4-(aminomethyl)phenyl]acetamide | 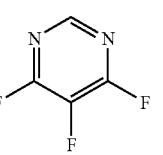<br>4,5,6-trifluoropyrimidine |
| A3 | 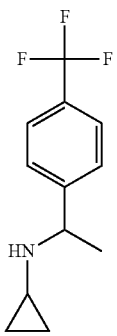<br>N-[1-[4-(trifluoromethyl)phenyl]ethyl]cyclopropanamine | 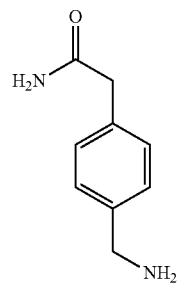<br>2-[4-(aminomethyl)phenyl]acetamide | 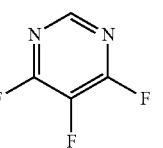<br>4,5,6-trifluoropyrimidine |

-continued

| Ex. No. | Free amine (1) | Free amine (2) | Fluorinated aromatic compound |
|---|---|---|---|
| A4 | 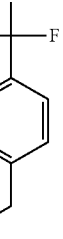<br>N-[[4-(trifluoromethyl)phenyl]methyl]tetrahydrofuran-3-amine | 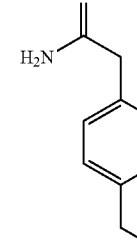<br>2-[4-(aminomethyl)phenyl]acetamide | 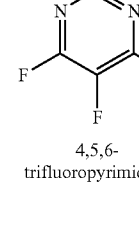<br>4,5,6-trifluoropyrimidine |
| A5 | 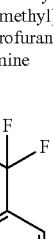<br>N-[[4-(trifluoromethyl)phenyl]methyl]cyclopropanamine | 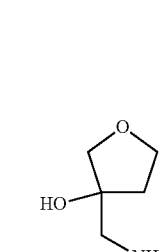<br>3-(aminomethyl)tetrahydrofuran-3-ol | 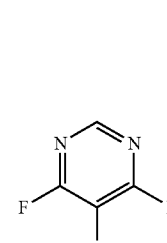<br>4,5,6-trifluoropyrimidine |
| A6 | 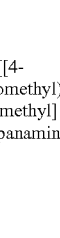<br>N-[[4-(trifluoromethoxy)phenyl]methyl]cyclopropanamine | <br>2-[4-(aminomethyl)phenyl]acetamide | <br>4,5,6-trifluoropyrimidine |

-continued

| Ex. No. | Free amine (1) | Free amine (2) | Fluorinated aromatic compound |
|---|---|---|---|
| A7 | 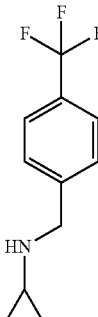<br>N-[[4-(trifluoromethyl)phenyl]methyl]cyclopropanamine | 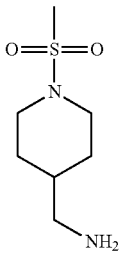<br>(1-methylsulfonyl-4-piperidyl)methanamine | 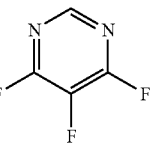<br>4,5,6-trifluoropyrimidine |
| A8 | 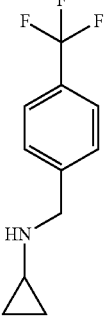<br>N-[[4-(trifluoromethyl)phenyl]methyl]cyclopropanamine | 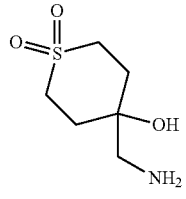<br>4-(aminomethyl)-1,1-dioxo-thian-4-ol | 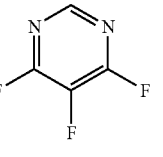<br>4,5,6-trifluoropyrimidine |
| A9 | 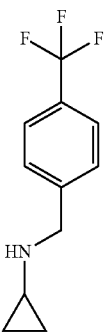<br>N-[[4-(trifluoromethyl)phenyl]methyl]cyclopropanamine | 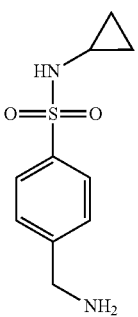<br>4-(aminomethyl)-N-cyclopropyl-benzenesulfonamide | 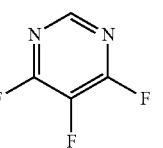<br>4,5,6-trifluoropyrimidine |

-continued

| Ex. No. | Free amine (1) | Free amine (2) | Fluorinated aromatic compound |
|---|---|---|---|
| A11 | N-[[4-(trifluoromethyl)phenyl]methyl]cyclopropanamine | 1-[4-(aminomethyl)-1-piperidyl]ethanone | 4,5,6-trifluoropyrimidine |
| A12 | N-[[4-(trifluoromethyl)phenyl]methyl]cyclopropanamine | tetrahydropyran-4-ylmethanamine | 4,5,6-trifluoropyrimidine |
| A13 | N-[cyclopropyl-[4-(trifluoromethyl)phenyl]methyl]cyclopropanamine | 2-[4-(aminomethyl)phenyl]acetamide | 4,5,6-trifluoropyrimidine |

-continued

| Ex. No. | Free amine (1) | Free amine (2) | Fluorinated aromatic compound |
|---|---|---|---|
| A14 | 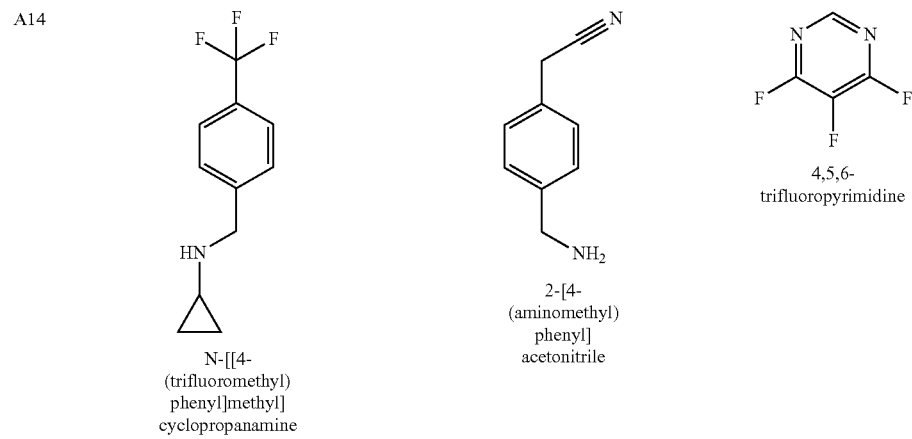 N-[[4-(trifluoromethyl)phenyl]methyl]cyclopropanamine | 2-[4-(aminomethyl)phenyl]acetonitrile | 4,5,6-trifluoropyrimidine |
| A15 | 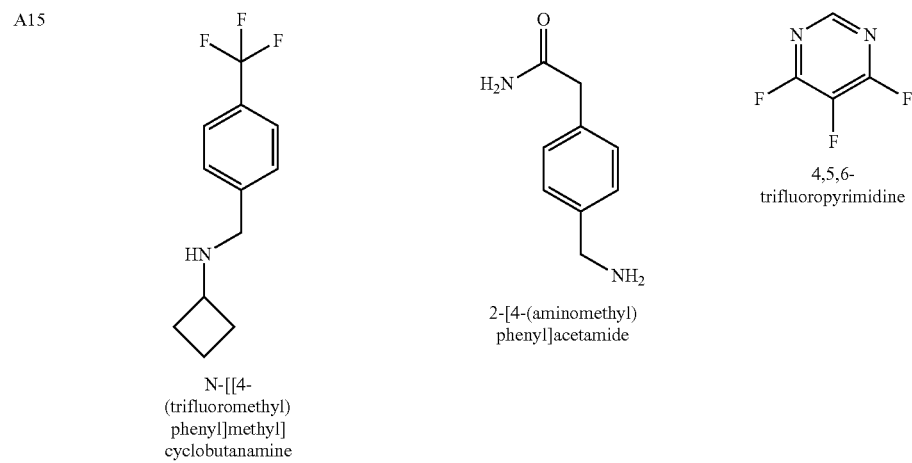 N-[[4-(trifluoromethyl)phenyl]methyl]cyclobutanamine | 2-[4-(aminomethyl)phenyl]acetamide | 4,5,6-trifluoropyrimidine |
| A16 | 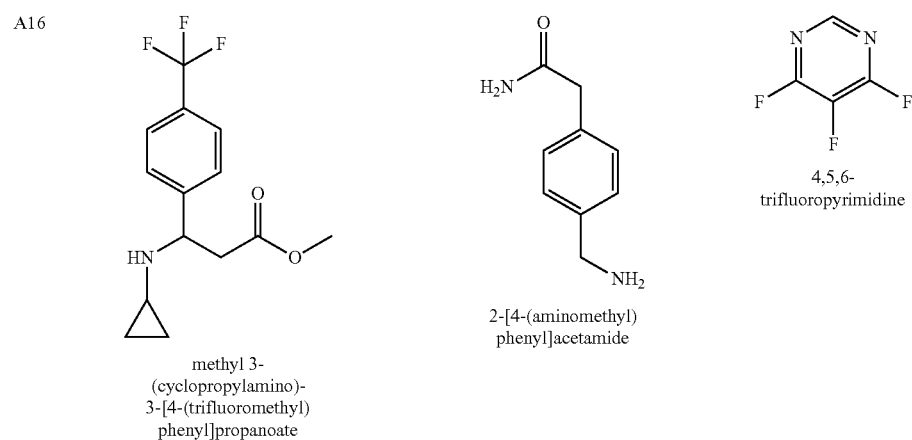 methyl 3-(cyclopropylamino)-3-[4-(trifluoromethyl)phenyl]propanoate | 2-[4-(aminomethyl)phenyl]acetamide | 4,5,6-trifluoropyrimidine |

-continued

| Ex. No. | Free amine (1) | Free amine (2) | Fluorinated aromatic compound |
|---|---|---|---|
| A17 | 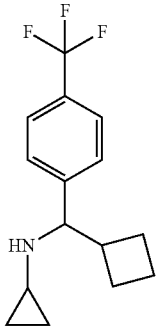<br>N-[cyclobutyl-[4-(trifluoromethyl)phenyl]methyl]cyclopropanamine | 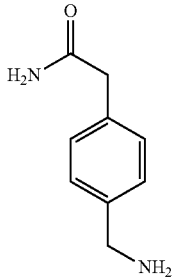<br>2-[4-(aminomethyl)phenyl]acetamide | 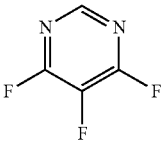<br>4,5,6-trifluoropyrimidine |
| A18 | 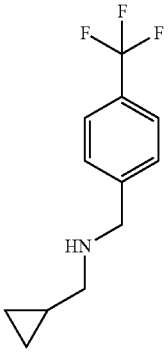<br>N-(cyclopropylmethyl)-1-[4-(trifluoromethyl)phenyl]methanamine | 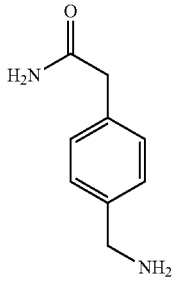<br>2-[4-(aminomethyl)phenyl]acetamide | 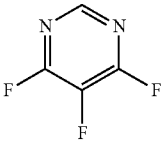<br>4,5,6-trifluoropyrimidine |
| A19 | 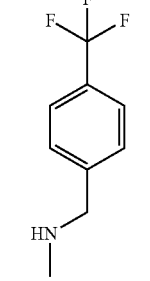<br>N-methyl-1-[4-(trifluoromethyl)phenyl]methanamine | 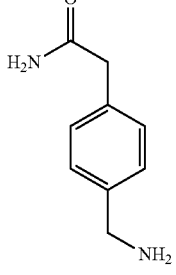<br>2-[4-(aminomethyl)phenyl]acetamide | <br>4,5,6-trifluoropyrimidine |

-continued

| Ex. No. | Free amine (1) | Free amine (2) | Fluorinated aromatic compound |
|---|---|---|---|
| A20 | 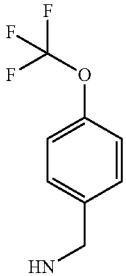<br>N-methyl-1-[4-(trifluoromethoxy)phenyl]methanamine | 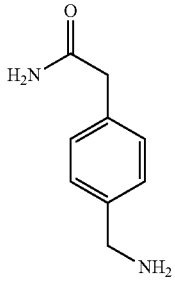<br>2-[4-(aminomethyl)phenyl]acetamide | 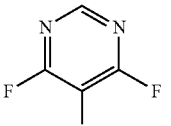<br>4,5,6-trifluoropyrimidine |
| A21 | 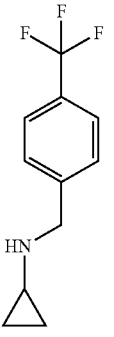<br>N-[[4-(trifluoromethyl)phenyl]methyl]cyclopropanamine | 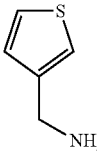<br>3-thienylmethanamine | 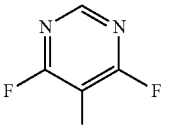<br>4,5,6-trifluoropyrimidine |
| A22 | 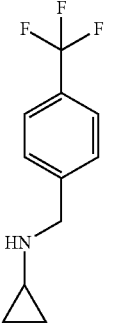<br>N-[[4-(trifluoromethyl)phenyl]methyl]cyclopropanamine | 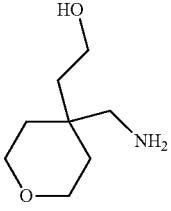<br>2-[4-(aminomethyl)tetrahydropyran-4-yl]ethanol | 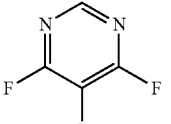<br>4,5,6-trifluoropyrimidine |

-continued

| Ex. No. | Free amine (1) | Free amine (2) | Fluorinated aromatic compound |
|---|---|---|---|
| A23 | 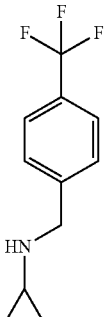 N-[[4-(trifluoromethyl)phenyl]methyl]cyclopropanamine | 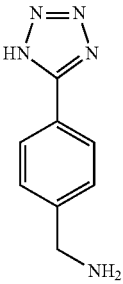 [4-(1H-tetrazol-5-yl)phenyl]methanamine | 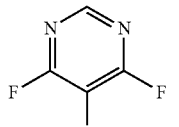 4,5,6-trifluoropyrimidine |
| A24 | 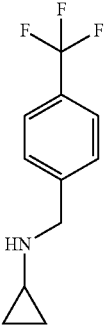 N-[[4-(trifluoromethyl)phenyl]methyl]cyclopropanamine | 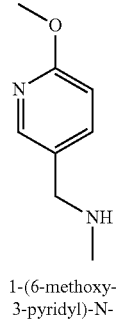 1-(6-methoxy-3-pyridyl)-N-methyl-methanamine | 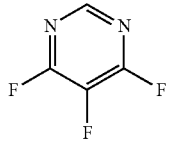 4,5,6-trifluoropyrimidine |
| A25 | 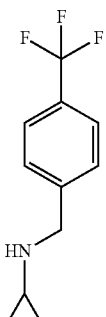 N-[[4-(trifluoromethyl)phenyl]methyl]cyclopropanamine | 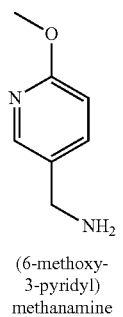 (6-methoxy-3-pyridyl)methanamine | 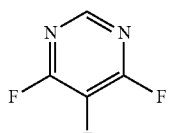 4,5,6-trifluoropyrimidine |

-continued

| Ex. No. | Free amine (1) | Free amine (2) | Fluorinated aromatic compound |
|---|---|---|---|
| A26 | 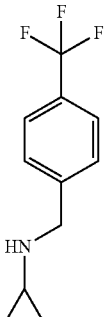 N-[[4-(trifluoromethyl)phenyl]methyl]cyclopropanamine | 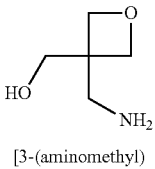 [3-(aminomethyl)oxetan-3-yl]methanol | 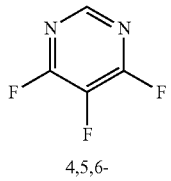 4,5,6-trifluoropyrimidine |
| A27 | 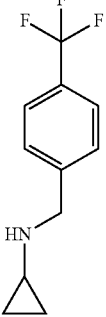 N-[[4-(trifluoromethyl)phenyl]methyl]cyclopropanamine | 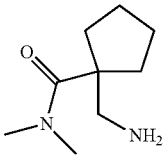 1-(aminomethyl)-N,N-dimethyl-cyclopentanecarboxamide | 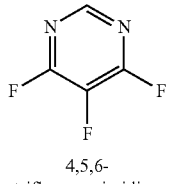 4,5,6-trifluoropyrimidine |
| A28 | 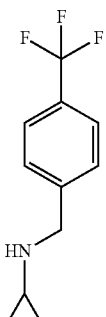 N-[[4-(trifluoromethyl)phenyl]methyl]cyclopropanamine | 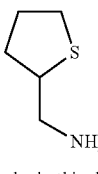 tetrahydrothiophen-2-ylmethanamine | 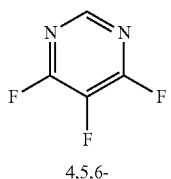 4,5,6-trifluoropyrimidine |

| Ex. No. | Free amine (1) | Free amine (2) | Fluorinated aromatic compound |
|---|---|---|---|
| A29 | 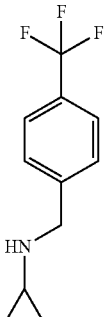<br>N-[[4-(trifluoromethyl)phenyl]methyl]cyclopropanamine | 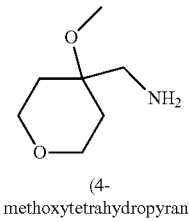<br>(4-methoxytetrahydropyran-4-yl)methanamine | 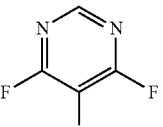<br>4,5,6-trifluoropyrimidine |
| A30 | 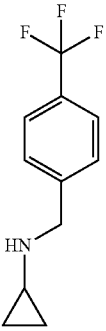<br>N-[[4-(trifluoromethyl)phenyl]methyl]cyclopropanamine | 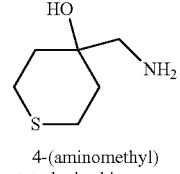<br>4-(aminomethyl)tetrahydrothiopyran-4-ol | 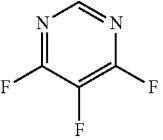<br>4,5,6-trifluoropyrimidine |
| A31 | 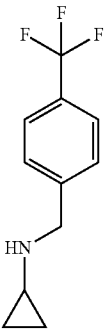<br>N-[[4-(trifluoromethyl)phenyl]methyl]cyclopropanamine | 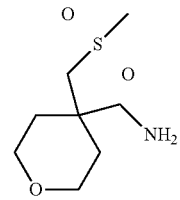<br>[4-(methylsulfonylmethyl)tetrahydropyran-4-yl]methanamine | 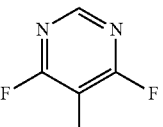<br>4,5,6-trifluoropyrimidine |

-continued

| Ex. No. | Free amine (1) | Free amine (2) | Fluorinated aromatic compound |
|---|---|---|---|
| A32 | 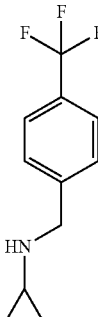<br>N-[[4-(trifluoromethyl)phenyl]methyl]cyclopropanamine | 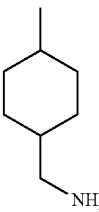<br>(4-methylcyclohexyl)methanamine | 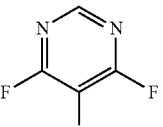<br>4,5,6-trifluoropyrimidine |
| A33 | 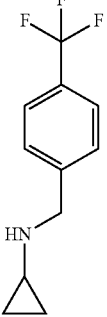<br>N-[[4-(trifluoromethyl)phenyl]methyl]cyclopropanamine | 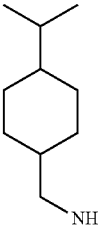<br>(4-isopropylcyclohexyl)methanamine | 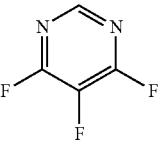<br>4,5,6-trifluoropyrimidine |
| A34 | 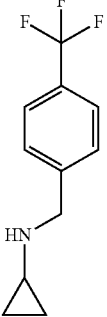<br>N-[[4-(trifluoromethyl)phenyl]methyl]cyclopropanamine | 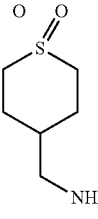<br>(1,1-dioxothian-4-yl)methanamine | 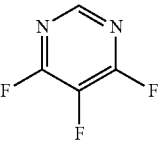<br>4,5,6-trifluoropyrimidine |

| Ex. No. | Free amine (1) | Free amine (2) | Fluorinated aromatic compound |
|---|---|---|---|
| A35 | 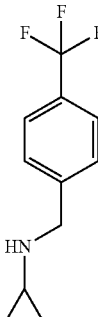<br>N-[[4-(trifluoromethyl)phenyl]methyl]cyclopropanamine | 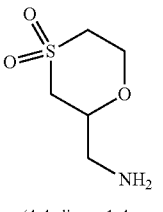<br>(4,4-dioxo-1,4-oxathian-2-yl)methanamine | 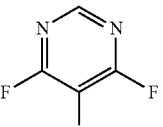<br>4,5,6-trifluoropyrimidine |
| A36 | 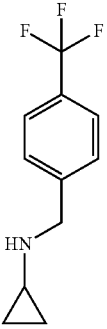<br>N-[[4-(trifluoromethyl)phenyl]methyl]cyclopropanamine | 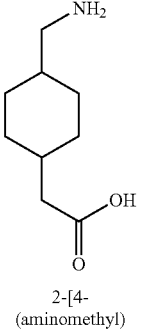<br>2-[4-(aminomethyl)cyclohexyl]acetic acid | 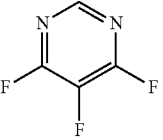<br>4,5,6-trifluoropyrimidine |
| A37 | 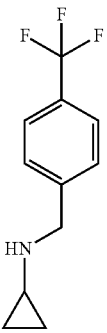<br>N-[[4-(trifluoromethyl)phenyl]methyl]cyclopropanamine | 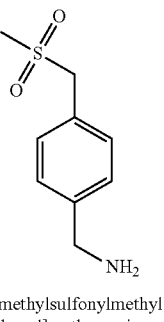<br>[4-(methylsulfonylmethyl)phenyl]methanamine | 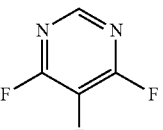<br>4,5,6-trifluoropyrimidine |

-continued

| Ex. No. | Free amine (1) | Free amine (2) | Fluorinated aromatic compound |
|---|---|---|---|
| A38 | 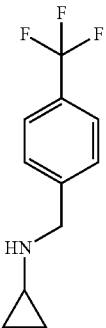<br>N-[[4-(trifluoromethyl)phenyl]methyl]cyclopropanamine | 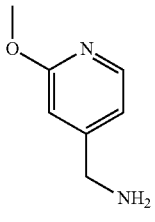<br>(2-methoxy-4-pyridyl)methanamine | 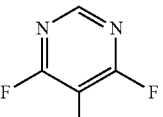<br>4,5,6-trifluoropyrimidine |
| A39 | 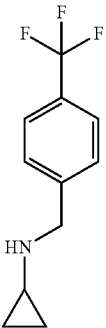<br>N-[[4-(trifluoromethyl)phenyl]methyl]cyclopropanamine | 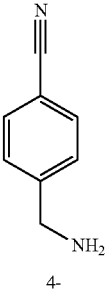<br>4-(aminomethyl)benzonitrile | 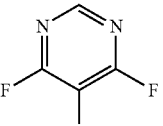<br>4,5,6-trifluoropyrimidine |
| A40 | 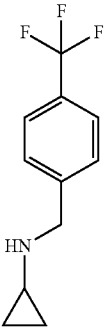<br>N-[[4-(trifluoromethyl)phenyl]methyl]cyclopropanamine | 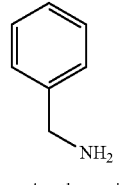<br>phenylmethanamine | 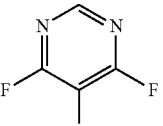<br>4,5,6-trifluoropyrimidine |

-continued

| Ex. No. | Free amine (1) | Free amine (2) | Fluorinated aromatic compound |
|---|---|---|---|
| A41 | 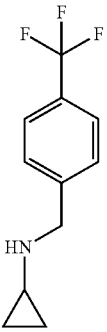<br>N-[[4-(trifluoromethyl)phenyl]methyl]cyclopropanamine | 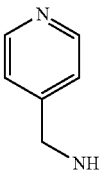<br>4-pyridylmethanamine | 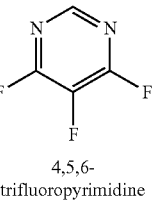<br>4,5,6-trifluoropyrimidine |
| A42 | 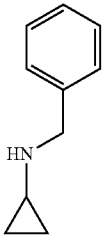<br>N-benzylcyclopropanamine | 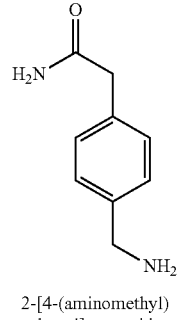<br>2-[4-(aminomethyl)phenyl]acetamide | 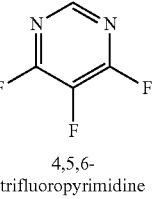<br>4,5,6-trifluoropyrimidine |
| A43 | 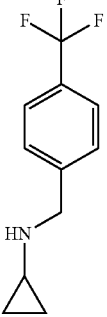<br>N-[[4-(trifluoromethyl)phenyl]methyl]cyclopropanamine | 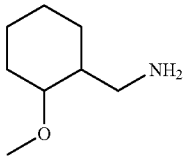<br>(2-methoxycyclohexyl)methanamine | 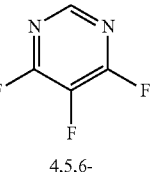<br>4,5,6-trifluoropyrimidine |

-continued

| Ex. No. | Free amine (1) | Free amine (2) | Fluorinated aromatic compound |
|---|---|---|---|
| A44 | 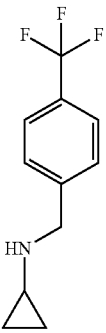<br>N-[[4-(trifluoromethyl)phenyl]methyl]cyclopropanamine | 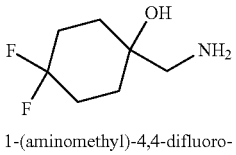<br>1-(aminomethyl)-4,4-difluoro-cyclohexanol | 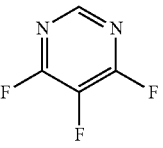<br>4,5,6-trifluoropyrimidine |
| A45 | 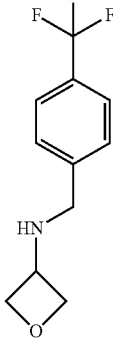<br>N-[[4-(trifluoromethyl)phenyl]methyl]oxetan-3-amine | 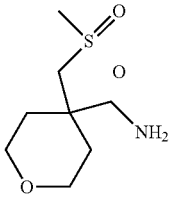<br>[4-(methylsulfonylmethyl)tetrahydropyran-4-yl]methanamine | 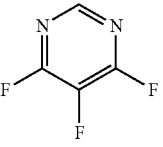<br>4,5,6-trifluoropyrimidine |
| A47 | 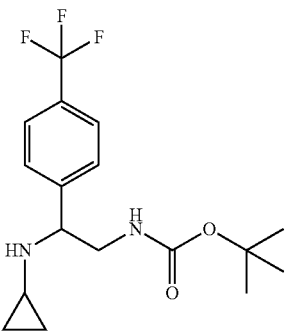<br>tert-butyl N-[2-(cyclopropylamino)-2-[4-(trifluoromethyl)phenyl]ethyl]carbamate | 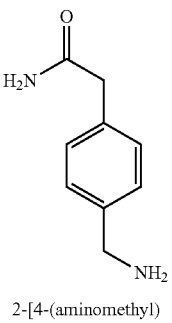<br>2-[4-(aminomethyl)phenyl]acetamide | 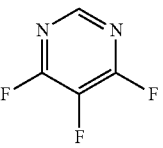<br>4,5,6-trifluoropyrimidine |

-continued

| Ex. No. | Free amine (1) | Free amine (2) | Fluorinated aromatic compound |
|---|---|---|---|
| A49 | N-[[4-(trifluoromethyl)phenyl]methyl]cyclopropanamine | [4-(methylsulfonylmethyl)tetrahydropyran-4-yl]methanamine | 4,5,6-trifluoropyrimidine |
| A52 | N-methyl-1-(4-pyrazol-1-yl)phenyl)methanamine | 2-[4-(aminomethyl)phenyl]acetamide | 4,5,6-trifluoropyrimidine |
| A53 | N-[(4-isopropylphenyl)methyl]cyclopropanamine | 2-[4-(aminomethyl)phenyl]acetamide | 4,5,6-trifluoropyrimidine |
| A54 | N-[(4-ethoxyphenyl)methyl]cyclopropanamine | 2-[4-(aminomethyl)phenyl]acetamide | 4,5,6-trifluoropyrimidine |

-continued

| Ex. No. | Free amine (1) | Free amine (2) | Fluorinated aromatic compound |
|---|---|---|---|
| A55 | N-[(3-methoxyphenyl)methyl]cyclopropanamine | 2-[4-(aminomethyl)phenyl]acetamide | 4,5,6-trifluoropyrimidine |
| A57 | N-[[4-(trifluoromethyl)phenyl]methyl]cyclopropanamine | N-[4-(aminomethyl)cyclohexyl]-1,1,1-trifluoromethanesulfonamide | 4,5,6-trifluoropyrimidine |
| A58 | N-methyl-1-(3-pyrazol-1-ylphenyl)methanamine | 2-[4-(aminomethyl)phenyl]acetamide | 4,5,6-trifluoropyrimidine |
| A59 | N-[[4-(trifluoromethyl)phenyl]methyl]cyclopropanamine | N-[4-(aminomethyl)phenyl]methanesulfonamide | 4,5,6-trifluoropyrimidine |

-continued

| Ex. No. | Free amine (1) | Free amine (2) | Fluorinated aromatic compound |
|---|---|---|---|
| A60 | 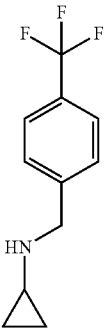<br>N-[[4-(trifluoromethyl)phenyl]methyl]cyclopropanamine | 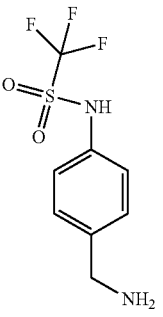<br>N-[4-(aminomethyl)phenyl]-1,1,1-trifluoro-methanesulfonamide | 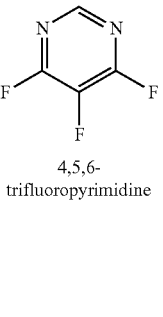<br>4,5,6-trifluoropyrimidine |
| A61 | 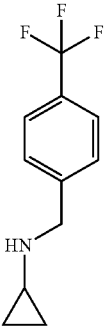<br>N-[[4-(trifluoromethyl)phenyl]methyl]cyclopropanamine | 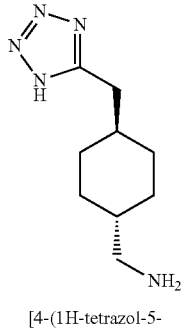<br>[4-(1H-tetrazol-5-ylmethyl)cyclohexyl]methanamine | 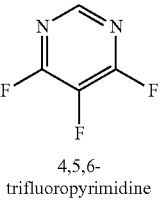<br>4,5,6-trifluoropyrimidine |
| A62 | 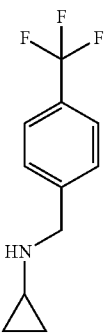<br>N-[[4-(trifluoromethyl)phenyl]methyl]cyclopropanamine | 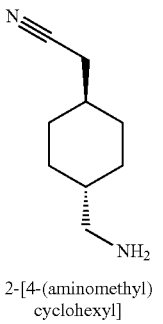<br>2-[4-(aminomethyl)cyclohexyl]acetonitrile | 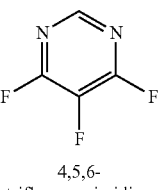<br>4,5,6-trifluoropyrimidine |

-continued

| Ex. No. | Free amine (1) | Free amine (2) | Fluorinated aromatic compound |
|---|---|---|---|
| A63 | N-[[4-(trifluoromethyl)phenyl]methyl]cyclopropanamine | N-[[4-(aminomethyl)tetrahydropyran-4-yl]methyl]methanesulfonamide | 4,5,6-trifluoropyrimidine |
| A64 | 4-[(cyclopropylamino)methyl]benzonitrile | 2-[4-(aminomethyl)phenyl]acetamide | 4,5,6-trifluoropyrimidine |
| A65 | N-[(2-chloro-6-fluorophenyl)methyl]cyclopropanamine | 2-[4-(aminomethyl)phenyl]acetamide | 4,5,6-trifluoropyrimidine |
| A66 | N-[(2-chlorophenyl)methyl]cyclopropanamine | 2-[4-(aminomethyl)phenyl]acetamide | 4,5,6-trifluoropyrimidine |

-continued

| Ex. No. | Free amine (1) | Free amine (2) | Fluorinated aromatic compound |
|---|---|---|---|
| A67 | 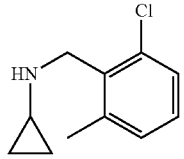<br>N-[(2-chloro-6-methyl-phenyl)methyl]cyclopropanamine | 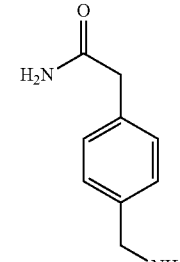<br>2-[4-(aminomethyl)phenyl]acetamide | 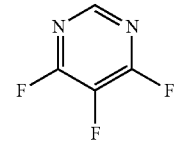<br>4,5,6-trifluoropyrimidine |
| A68 | 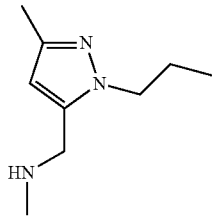<br>N-methyl-1-(5-methyl-2-propyl-pyrazol-3-yl)methanamine | 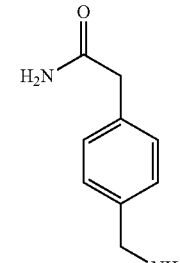<br>2-[4-(aminomethyl)phenyl]acetamide | <br>4,5,6-trifluoropyrimidine |
| A69 | 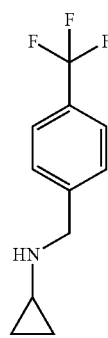<br>N-[[4-(trifluoromethyl)phenyl]methyl]cyclopropanamine | 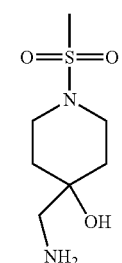<br>4-(aminomethyl)-1-methylsulfonyl-piperidin-4-ol | 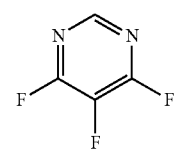<br>4,5,6-trifluoropyrimidine |
| A72 | 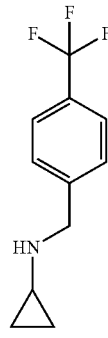<br>N-[[4-(trifluoromethyl)phenyl]methyl]cyclopropanamine | 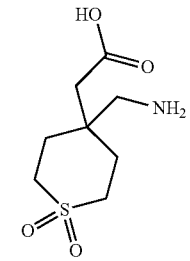<br>2-[4-(aminomethyl)-1,1-dioxo-thian-4-yl]acetic acid | <br>4,5,6-trifluoropyrimidine |

-continued

| Ex. No. | Free amine (1) | Free amine (2) | Fluorinated aromatic compound |
|---|---|---|---|
| A73 | 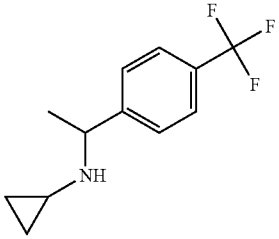<br>N-[1-[4-(trifluoromethyl)phenyl]ethyl]cyclopropanamine | 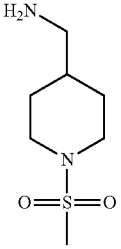<br>(1-methylsulfonyl-4-piperidyl)methanamine | 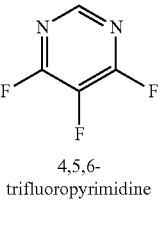<br>4,5,6-trifluoropyrimidine |
| A74 | 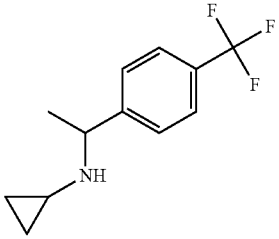<br>N-[1-[4-(trifluoromethyl)phenyl]ethyl]cyclopropanamine | 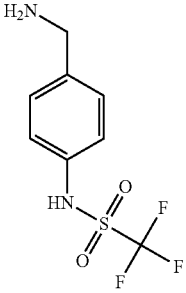<br>N-[4-(aminomethyl)phenyl]-1,1,1-trifluoro-methanesulfonamide | 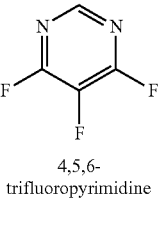<br>4,5,6-trifluoropyrimidine |
| A75 | 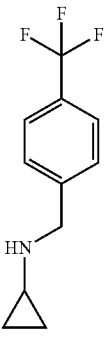<br>N-[[4-(trifluoromethyl)phenyl]methyl]cyclopropanamine | 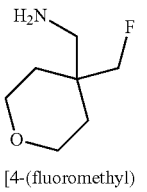<br>[4-(fluoromethyl)tetrahydropyran-4-yl]methanamine | 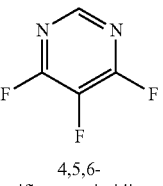<br>4,5,6-trifluoropyrimidine |
| A76 | 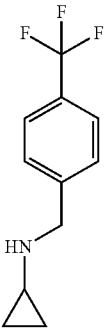<br>N-[[4-(trifluoromethyl)phenyl]methyl]cyclopropanamine | 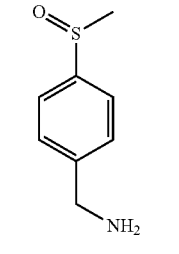<br>(4-methylsulfinylphenyl)methanamine | 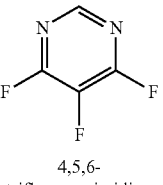<br>4,5,6-trifluoropyrimidine |

| Ex. No. | Free amine (1) | Free amine (2) | Fluorinated aromatic compound |
|---|---|---|---|
| A77 | 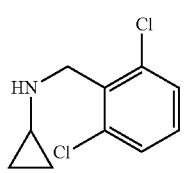<br>N-[(2,6-dichlorophenyl)methyl]cyclopropanamine | 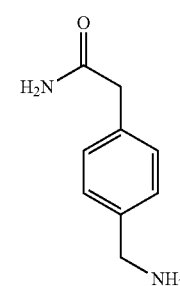<br>2-[4-(aminomethyl)phenyl]acetamide | 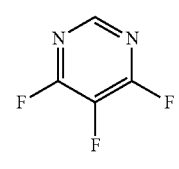<br>4,5,6-trifluoropyrimidine |
| A78 | 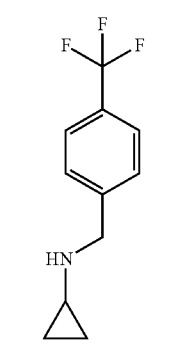<br>N-[[4-(trifluoromethyl)phenyl]methyl]cyclopropanamine | 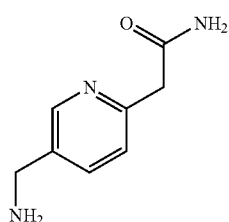<br>2-[5-(aminomethyl)-2-pyridyl]acetamide | 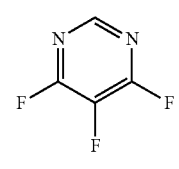<br>4,5,6-trifluoropyrimidine |
| A79 | 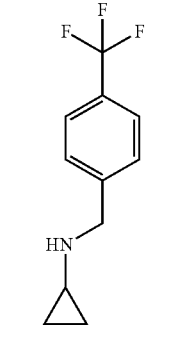<br>N-[[4-(trifluoromethyl)phenyl]methyl]cyclopropanamine | 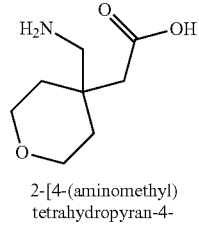<br>2-[4-(aminomethyl)tetrahydropyran-4-yl]acetic acid | 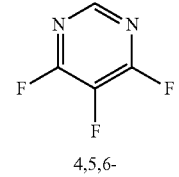<br>4,5,6-trifluoropyrimidine |

-continued

| Ex. No. | Free amine (1) | Free amine (2) | Fluorinated aromatic compound |
|---|---|---|---|
| A82 | 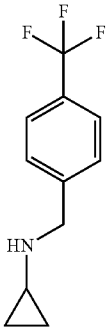<br>N-[[4-(trifluoromethyl)phenyl]methyl]cyclopropanamine | 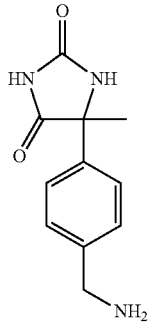<br>5-[4-(aminomethyl)phenyl]-5-methyl-imidazolidine-2,4-dione | <br>4,5,6-trifluoropyrimidine |
| A83 | 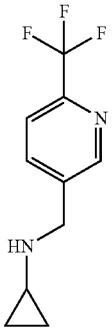<br>N-[[6-(trifluoromethyl)-3-pyridyl]methyl]cyclopropanamine | 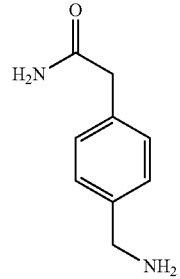<br>2-[4-(aminomethyl)phenyl]acetamide | 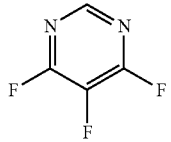<br>4,5,6-trifluoropyrimidine |
| A85 | 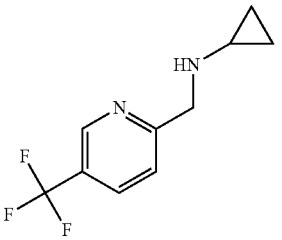<br>N-[[5-(trifluoromethyl)-2-pyridyl]methyl]cyclopropanamine | 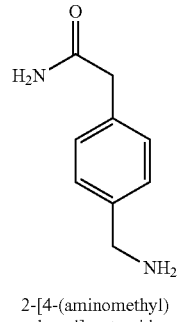<br>2-[4-(aminomethyl)phenyl]acetamide | 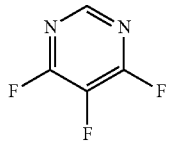<br>4,5,6-trifluoropyrimidine |

-continued

| Ex. No. | Free amine (1) | Free amine (2) | Fluorinated aromatic compound |
|---|---|---|---|
| A88 | 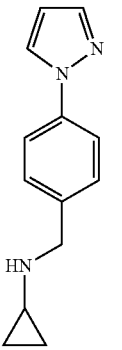<br>N-[(4-pyrazol-1-ylphenyl)methyl]cyclopropanamine | 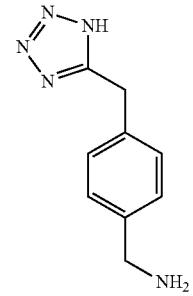<br>[4-(1H-tetrazol-5-ylmethyl)phenyl]methanamine | 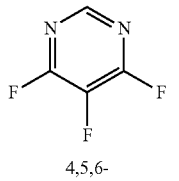<br>4,5,6-trifluoropyrimidine |
| A89 | 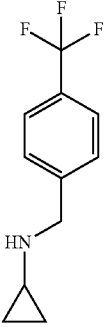<br>N-[[4-(trifluoromethyl)phenyl]methyl]cyclopropanamine | 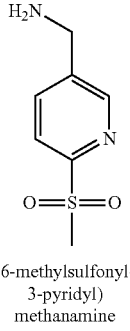<br>(6-methylsulfonyl-3-pyridyl)methanamine | 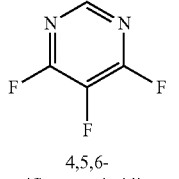<br>4,5,6-trifluoropyrimidine |
| A90 | 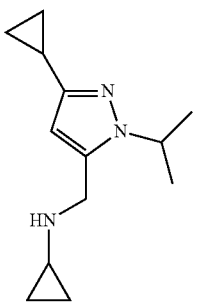<br>N-[(5-cyclopropyl-2-isopropyl-pyrazol-3-yl)methyl]cyclopropanamine | 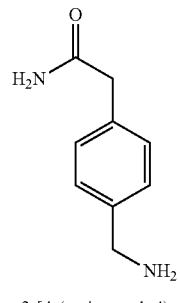<br>2-[4-(aminomethyl)phenyl]acetamide | 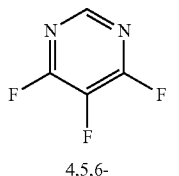<br>4,5,6-trifluoropyrimidine |

-continued

| Ex. No. | Free amine (1) | Free amine (2) | Fluorinated aromatic compound |
|---|---|---|---|
| A91 | N-[[4-(trifluoromethyl)phenyl]methyl]cyclopropanamine | N-[4-(aminomethyl)phenyl]-1,1-difluoro-methanesulfonamide | 4,5,6-trifluoropyrimidine |
| A92 | N-[[4-(trifluoromethyl)phenyl]methyl]cyclopropanamine | 2-[3-(aminomethyl)cyclobutyl]acetic acid | 4,5,6-trifluoropyrimidine |
| A93 | 5-[(cyclopropylamino)methyl]pyridine-2-carbonitrile | 2-[4-(aminomethyl)phenyl]acetamide | 4,5,6-trifluoropyrimidine |
| A97 | N-[(6-isopropyl-3-pyridyl)methyl]cyclopropanamine | 2-[4-(aminomethyl)phenyl]acetamide | 4,5,6-trifluoropyrimidine |

| Ex. No. | Free amine (1) | Free amine (2) | Fluorinated aromatic compound |
|---|---|---|---|
| A98 | 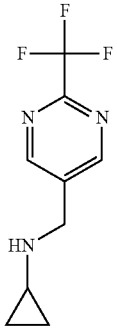<br>N-[[2-(trifluoromethyl)pyrimidin-5-yl]methyl]cyclopropanamine | 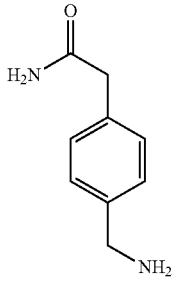<br>2-[4-(aminomethyl)phenyl]acetamide | 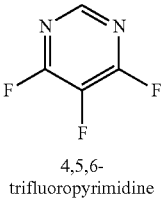<br>4,5,6-trifluoropyrimidine |
| A99 | 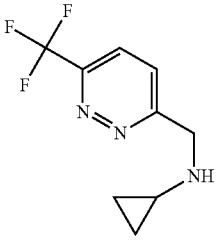<br>N-[[6-(trifluoromethyl)pyridazin-3-yl]methyl]cyclopropanamine | 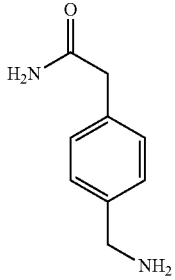<br>2-[4-(aminomethyl)phenyl]acetamide | 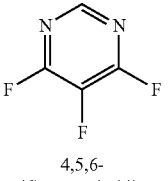<br>4,5,6-trifluoropyrimidine |
| A101 | 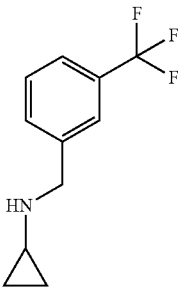<br>N-[[3-(trifluoromethyl)phenyl]methyl]cyclopropanamine | 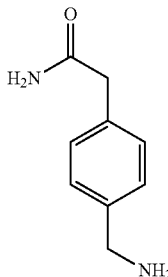<br>2-[4-(aminomethyl)phenyl]acetamide | 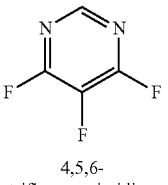<br>4,5,6-trifluoropyrimidine |
| A102 | 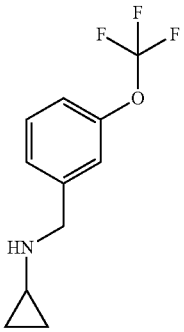<br>N-[[3-(trifluoromethoxy)phenyl]methyl]cyclopropanamine | 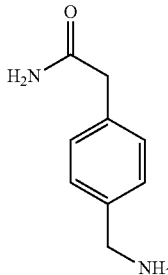<br>2-[4-(aminomethyl)phenyl]acetamide | 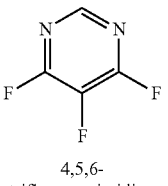<br>4,5,6-trifluoropyrimidine |

-continued

| Ex. No. | Free amine (1) | Free amine (2) | Fluorinated aromatic compound |
|---|---|---|---|
| A103 | 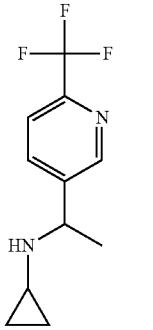<br>N-[1-[6-(trifluoromethyl)-3-pyridyl]ethyl] cyclopropanamine | 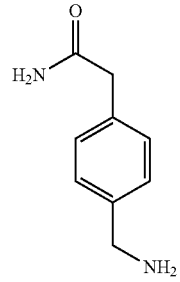<br>2-[4-(aminomethyl) phenyl]acetamide | 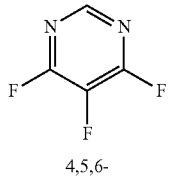<br>4,5,6-trifluoropyrimidine |
| A104 | 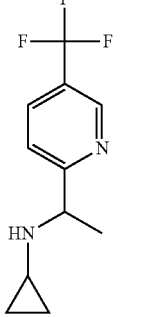<br>N-[1-[5-(trifluoromethyl)-2-pyridyl]ethyl] cyclopropanamine | 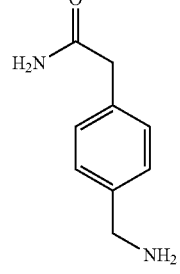<br>2-[4-(aminomethyl) phenyl]acetamide | 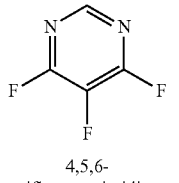<br>4,5,6-trifluoropyrimidine |
| A105 | 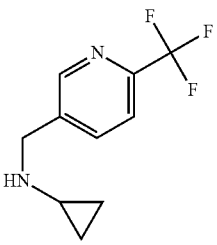<br>N-[[6-(trifluoromethyl)-3-pyridyl]methyl] cyclopropanamine | 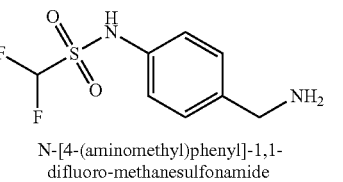<br>N-[4-(aminomethyl)phenyl]-1,1-difluoro-methanesulfonamide | 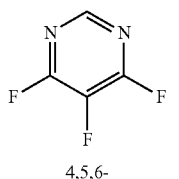<br>4,5,6-trifluoropyrimidine |
| A106 | 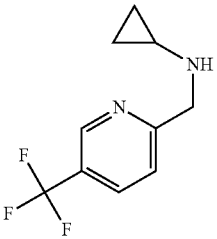<br>N-[[5-(trifluoromethyl)-2-pyridyl]methyl] cyclopropanamine | 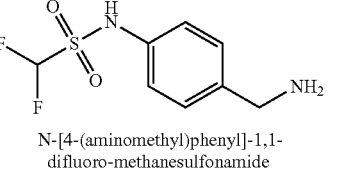<br>N-[4-(aminomethyl)phenyl]-1,1-difluoro-methanesulfonamide | 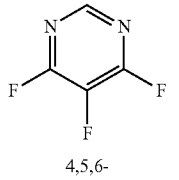<br>4,5,6-trifluoropyrimidine |

| Ex. No. | Free amine (1) | Free amine (2) | Fluorinated aromatic compound |
|---|---|---|---|
| A107 | 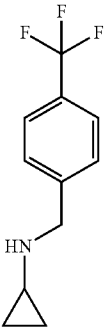<br>N-[[4-(trifluoromethyl)phenyl]methyl]cyclopropanamine | 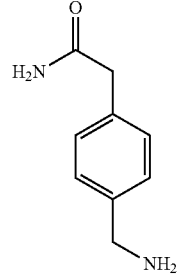<br>2-[4-(aminomethyl)phenyl]acetamide | <br>4,6-difluoropyrimidine |
| A108 | 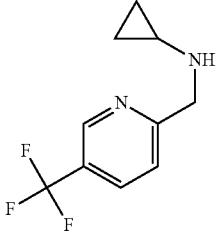<br>N-[[5-(trifluoromethyl)-2-pyridyl]methyl]cyclopropanamine | 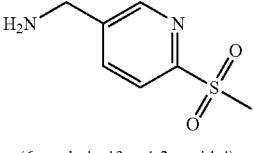<br>(6-methylsulfonyl-3-pyridyl)methanamine | 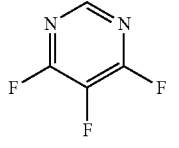<br>4,5,6-trifluoropyrimidine |
| A109 | 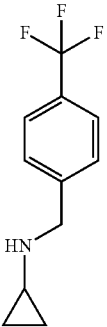<br>N-[[4-(trifluoromethyl)phenyl]methyl]cyclopropanamine | 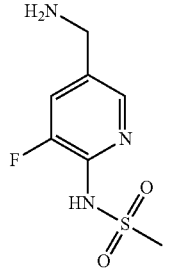<br>N-[5-(aminomethyl)-3-fluoro-2-pyridyl]methanesulfonamide | 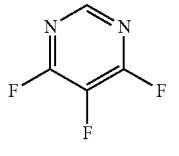<br>4,5,6-trifluoropyrimidine |
| A110 | 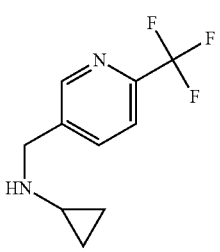<br>N-[[6-(trifluoromethyl)-3-pyridyl]methyl]cyclopropanamine | 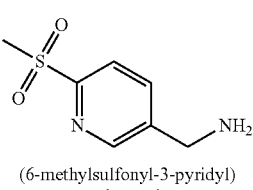<br>(6-methylsulfonyl-3-pyridyl)methanamine | 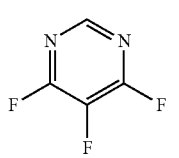<br>4,5,6-trifluoropyrimidine |

| Ex. No. | Free amine (1) | Free amine (2) | Fluorinated aromatic compound |
|---|---|---|---|
| A111 | 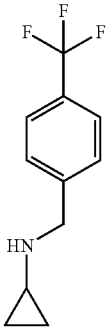<br>N-[[4-(trifluoromethyl)phenyl]methyl]cyclopropanamine | 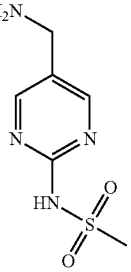<br>N-[5-(aminomethyl)pyrimidin-2-yl]methanesulfonamide | 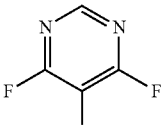<br>4,5,6-trifluoropyrimidine |
| A112 | 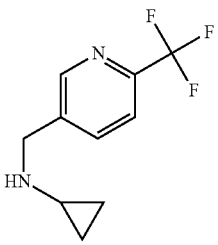<br>N-[[6-(trifluoromethyl)-3-pyridyl]methyl]cyclopropanamine | 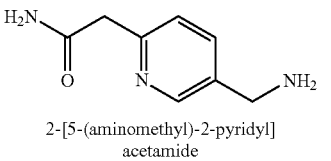 [SMILES: NCc1ccc(CC(N)=O)nc1]<br>2-[5-(aminomethyl)-2-pyridyl]acetamide | 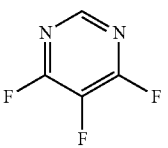<br>4,5,6-trifluoropyrimidine |
| A113 | 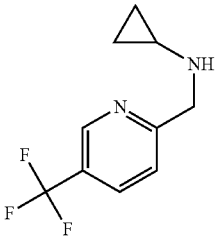<br>N-[[5-(trifluoromethyl)-2-pyridyl]methyl]cyclopropanamine | 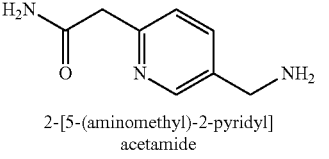 [SMILES: NCc1ccc(CC(N)=O)nc1]<br>2-[5-(aminomethyl)-2-pyridyl]acetamide | 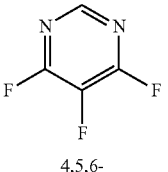<br>4,5,6-trifluoropyrimidine |
| A114 | 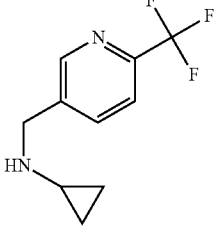<br>N-[[6-(trifluoromethyl)-3-pyridyl]methyl]cyclopropanamine | 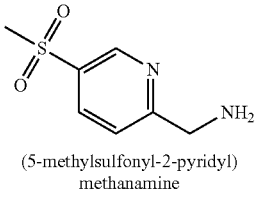<br>(5-methylsulfonyl-2-pyridyl)methanamine | 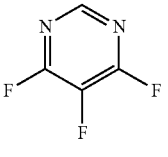<br>4,5,6-trifluoropyrimidine |

-continued

| Ex. No. | Free amine (1) | Free amine (2) | Fluorinated aromatic compound |
|---|---|---|---|
| A115 | 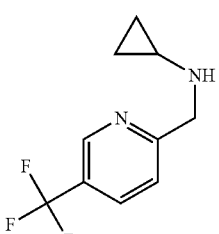<br>N-[[5-(trifluoromethyl)-2-pyridyl]methyl]cyclopropanamine | 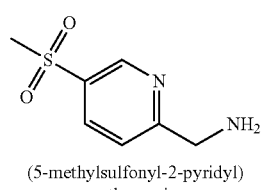<br>(5-methylsulfonyl-2-pyridyl)methanamine | 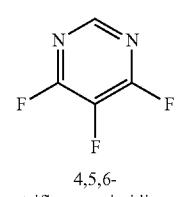<br>4,5,6-trifluoropyrimidine |
| A118 | 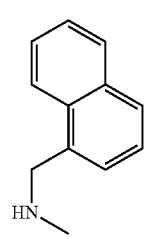<br>N-methyl-1-(1-naphthyl)methanamine | 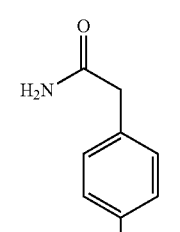<br>2-[4-(aminomethyl)phenyl]acetamide | 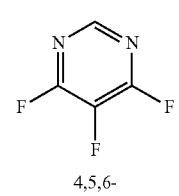<br>4,5,6-trifluoropyrimidine |
| A119 | 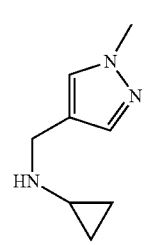<br>N-[(1-methylpyrazol-4-yl)methyl]cyclopropanamine | 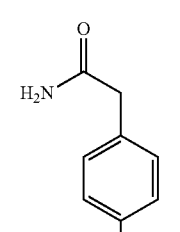<br>2-[4-(aminomethyl)phenyl]acetamide | 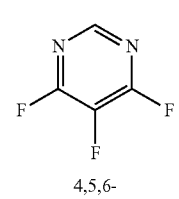<br>4,5,6-trifluoropyrimidine |
| A120 | 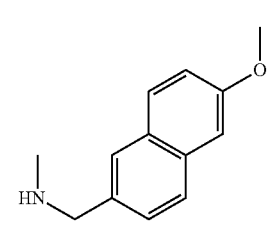<br>1-(6-methoxy-2-naphthyl)-N-methyl-methanamine | 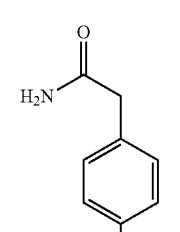<br>2-[4-(aminomethyl)phenyl]acetamide | 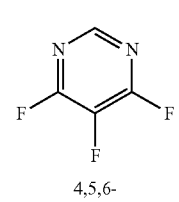<br>4,5,6-trifluoropyrimidine |

| Ex. No. | Free amine (1) | Free amine (2) | Fluorinated aromatic compound |
|---|---|---|---|
| A121 | 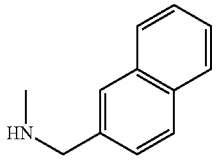<br>N-methyl-1-(2-naphthyl)methanamine | 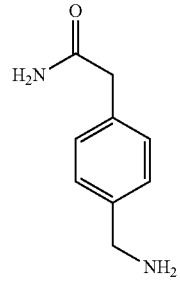<br>2-[4-(aminomethyl)phenyl]acetamide | 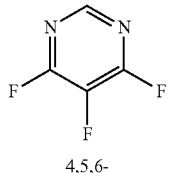<br>4,5,6-trifluoropyrimidine |
| A122 | 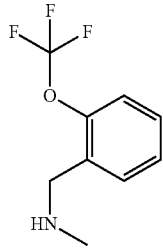<br>N-methyl-1-[2-(trifluoromethoxy)phenyl]methanamine | 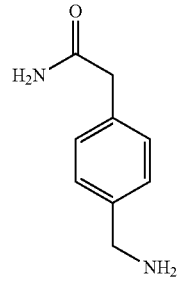<br>2-[4-(aminomethyl)phenyl]acetamide | 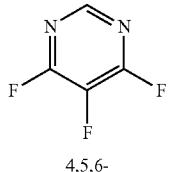<br>4,5,6-trifluoropyrimidine |
| A123 | 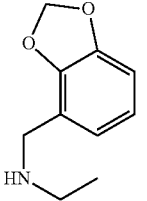<br>N-(1,3-benzodioxol-4-ylmethyl)ethanamine | 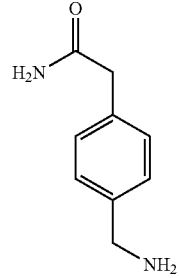<br>2-[4-(aminomethyl)phenyl]acetamide | 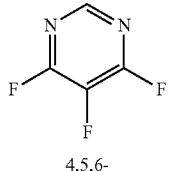<br>4,5,6-trifluoropyrimidine |
| A124 | 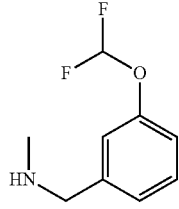<br>1-[3-(difluoromethoxy)phenyl]-N-methyl-methanamine | 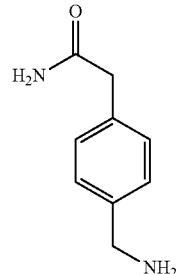<br>2-[4-(aminomethyl)phenyl]acetamide | 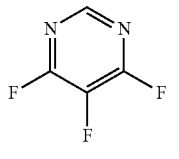<br>4,5,6-trifluoropyrimidine |

-continued

| Ex. No. | Free amine (1) | Free amine (2) | Fluorinated aromatic compound |
|---|---|---|---|
| A125 | 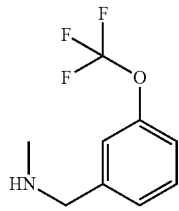<br>N-methyl-1-[3-(trifluoromethoxy)phenyl]methanamine | 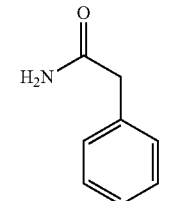<br>2-[4-(aminomethyl)phenyl]acetamide | 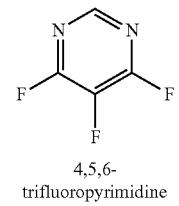<br>4,5,6-trifluoropyrimidine |
| A126 | 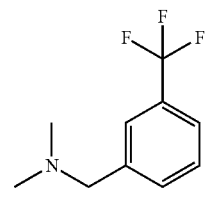<br>N,N-dimethyl-1-[3-(trifluoromethyl)phenyl]methanamine | 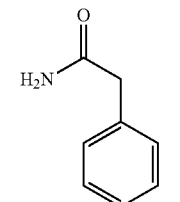<br>2-[4-(aminomethyl)phenyl]acetamide | 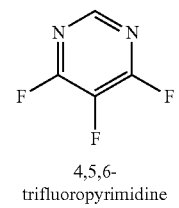<br>4,5,6-trifluoropyrimidine |
| A127 | 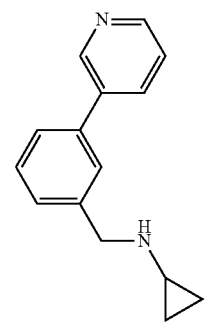<br>N-[[3-(3-pyridyl)phenyl]methyl]cyclopropanamine | 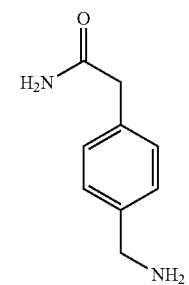<br>2-[4-(aminomethyl)phenyl]acetamide | 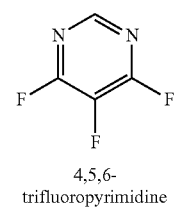<br>4,5,6-trifluoropyrimidine |
| A128 | 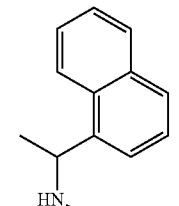<br>N-methyl-1-(1-naphthyl)ethanamine | 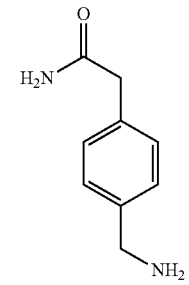<br>2-[4-(aminomethyl)phenyl]acetamide | 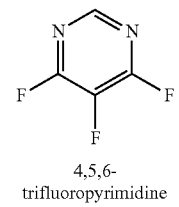<br>4,5,6-trifluoropyrimidine |

-continued

| Ex. No. | Free amine (1) | Free amine (2) | Fluorinated aromatic compound |
|---|---|---|---|
| A129 | 2-[4-(aminomethyl) tetrahydropyran-4-yl]ethanol | N-methyl-1-(4-pyrazol-1-ylphenyl)methanamine | 4,5,6-trifluoropyrimidine |
| A130 | [4-(methylsulfonylmethyl) tetrahydropyran-4-yl]methanamine | N-methyl-1-(4-pyrazol-1-ylphenyl)methanamine | 4,5,6-trifluoropyrimidine |
| A131 | [4-(1H-tetrazol-5-yl)phenyl]methanamine | N-methyl-1-(4-pyrazol-1-ylphenyl)methanamine | 4,5,6-trifluoropyrimidine |
| A132 | 4-(aminomethyl) benzenesulfonamide | N-methyl-1-(4-pyrazol-1-ylphenyl)methanamine | 4,5,6-trifluoropyrimidine |
| A133 | 4-(aminomethyl)-N-(2-methoxyethyl) benzenesulfonamide | N-methyl-1-(4-pyrazol-1-ylphenyl)methanamine | 4,5,6-trifluoropyrimidine |

-continued

| Ex. No. | Free amine (1) | Free amine (2) | Fluorinated aromatic compound |
|---|---|---|---|
| A134 | 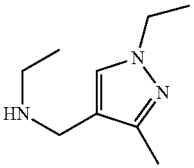<br>N-[(1-ethyl-3-methyl-pyrazol-4-yl)methyl]ethanamine | 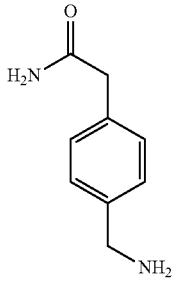<br>2-[4-(aminomethyl)phenyl]acetamide | 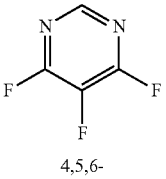<br>4,5,6-trifluoropyrimidine |
| A135 | 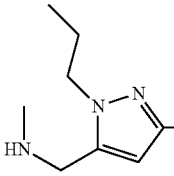<br>N-methyl-1-(5-methyl-2-propyl-pyrazol-3-yl)methanamine | 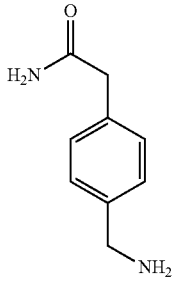<br>2-[4-(aminomethyl)phenyl]acetamide | 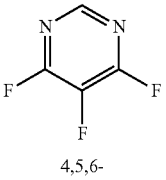<br>4,5,6-trifluoropyrimidine |
| A136 | <br>1-(2,4-dimethylthiazol-5-yl)-N-methyl-ethanamine | 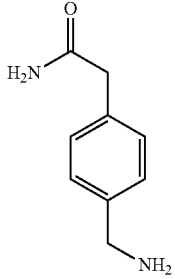<br>2-[4-(aminomethyl)phenyl]acetamide | 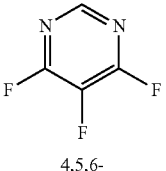<br>4,5,6-trifluoropyrimidine |
| A137 | 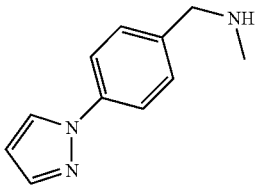<br>N-methyl-1-(4-pyrazol-1-ylphenyl)methanamine | 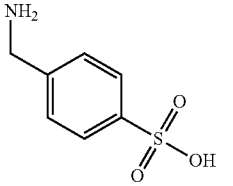<br>4-(aminomethyl)benzenesulfonic acid | 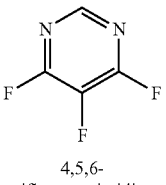<br>4,5,6-trifluoropyrimidine |

-continued

| Ex. No. | Free amine (1) | Free amine (2) | Fluorinated aromatic compound |
|---|---|---|---|
| A138 | 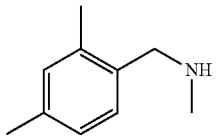<br>1-(2,4-dimethylphenyl)-N-methyl-methanamine | 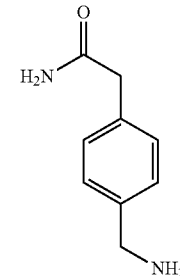<br>2-[4-(aminomethyl)phenyl]acetamide | 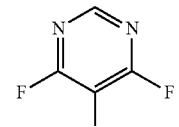<br>4,5,6-trifluoropyrimidine |
| A139 | 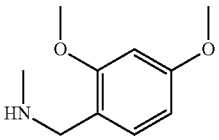<br>1-(2,4-dimethoxyphenyl)-N-methyl-methanamine | 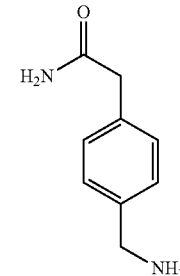<br>2-[4-(aminomethyl)phenyl]acetamide | 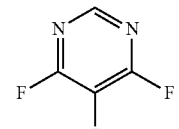<br>4,5,6-trifluoropyrimidine |
| A140 | 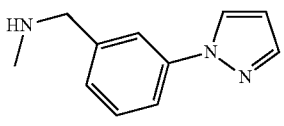<br>N-methyl-1-(3-pyrazol-1-ylphenyl)methanamine | 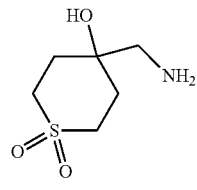<br>4-(aminomethyl)-1,1-dioxo-thian-4-ol | 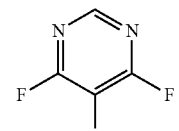<br>4,5,6-trifluoropyrimidine |
| A141 | 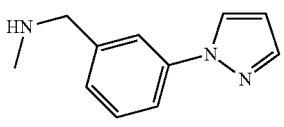<br>N-methyl-1-(3-pyrazol-1-ylphenyl)methanamine | 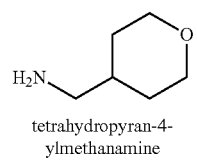<br>tetrahydropyran-4-ylmethanamine | 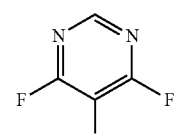<br>4,5,6-trifluoropyrimidine |
| A142 | 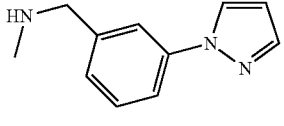<br>N-methyl-1-(3-pyrazol-1-ylphenyl)methanamine | 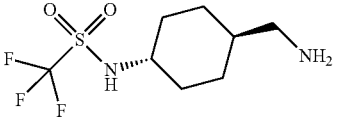<br>N-[4-(aminomethyl)cyclohexyl]-1,1,1-trifluoro-methanesulfonamide | 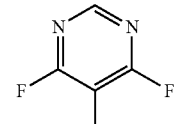<br>4,5,6-trifluoropyrimidine |

-continued

| Ex. No. | Free amine (1) | Free amine (2) | Fluorinated aromatic compound |
|---|---|---|---|
| A143 | N-methyl-1-(3-pyrazol-1-ylphenyl)methanamine | (1-methylsulfonyl-4-piperidyl)methanamine | 4,5,6-trifluoropyrimidine |
| A144 | N-methyl-1-(3-pyrazol-1-ylphenyl)methanamine | [4-(methylsulfonylmethyl)phenyl]methanamine | 4,5,6-trifluoropyrimidine |
| A145 | N-(2,3-dihydro-1,4-benzodioxin-3-ylmethyl)ethanamine | 2-[4-(aminomethyl)phenyl]acetamide | 4,5,6-trifluoropyrimidine |
| A147 | N-[[4-(trifluoromethyl)phenyl]methyl]cyclopropanamine | 2-(4-methylsulfonylphenyl)ethanamine | 4,5,6-trifluoropyrimidine |
| A148 | N-methyl-1-(5-methyl-2-propyl-pyrazol-3-yl)methanamine | (1-methylsulfonyl-4-piperidyl)methanamine | 4,5,6-trifluoropyrimidine |

-continued

| Ex. No. | Free amine (1) | Free amine (2) | Fluorinated aromatic compound |
|---|---|---|---|
| A149 | 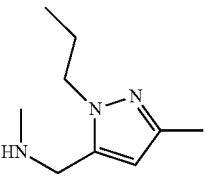<br>N-methyl-1-(5-methyl-2-propyl-pyrazol-3-yl)methanamine | 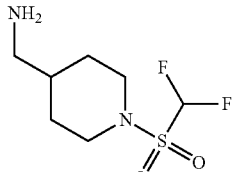<br>[1-(difluoromethylsulfonyl)-4-piperidyl]methanamine | 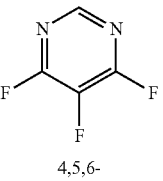<br>4,5,6-trifluoropyrimidine |
| A150 | 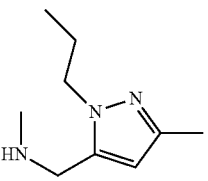<br>N-methyl-1-(5-methyl-2-propyl-pyrazol-3-yl)methanamine | 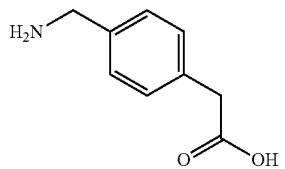<br>2-[4-(aminomethyl)phenyl]acetic acid | 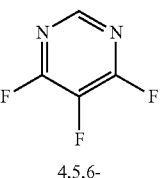<br>4,5,6-trifluoropyrimidine |
| A156 | 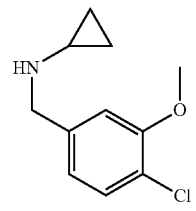<br>N-[(4-chloro-3-methoxy-phenyl)methyl]cyclopropanamine | 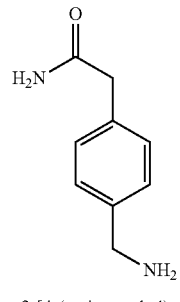<br>2-[4-(aminomethyl)phenyl]acetamide | 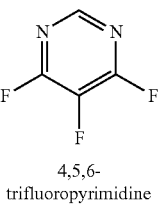<br>4,5,6-trifluoropyrimidine |
| A157 | 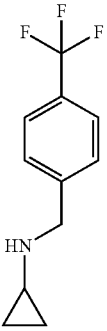<br>N-[[4-(trifluoromethyl)phenyl]methyl]cyclopropanamine | <br>(6-methylpyridazin-3-yl)methanamine | 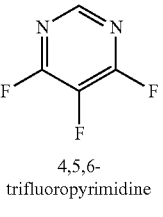<br>4,5,6-trifluoropyrimidine |

| Ex. No. | Free amine (1) | Free amine (2) | Fluorinated aromatic compound |
|---|---|---|---|
| A158 | 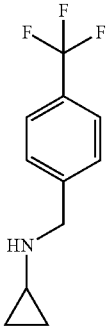<br>N-[[4-(trifluoromethyl)phenyl]methyl]cyclopropanamine | 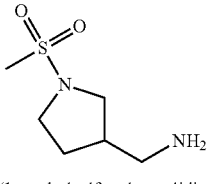<br>(1-methylsulfonylpyrrolidin-3-yl)methanamine | 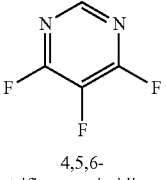<br>4,5,6-trifluoropyrimidine |
| A159 | 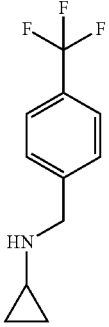<br>N-[[4-(trifluoromethyl)phenyl]methyl]cyclopropanamine | 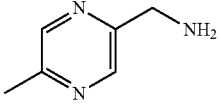<br>(5-methylpyrazin-2-yl)methanamine | 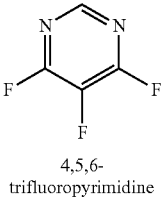<br>4,5,6-trifluoropyrimidine |
| A160 | 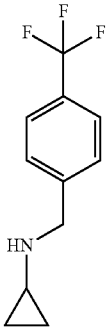<br>N-[[4-(trifluoromethyl)phenyl]methyl]cyclopropanamine | 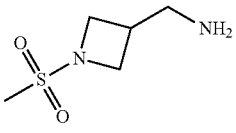<br>(1-methylsulfonylazetidin-3-yl)methanamine | 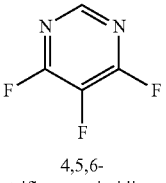<br>4,5,6-trifluoropyrimidine |

-continued

| Ex. No. | Free amine (1) | Free amine (2) | Fluorinated aromatic compound |
|---|---|---|---|
| A161 | 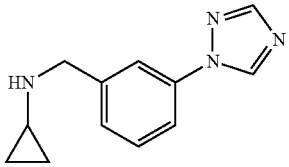<br>N-[[3-(1,2,4-triazol-1-yl)phenyl]methyl]cyclopropanamine | 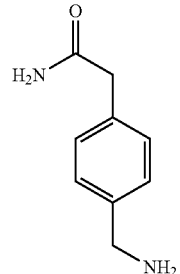<br>2-[4-(aminomethyl)phenyl]acetamide | 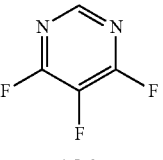<br>4,5,6-trifluoropyrimidine |
| A162 | 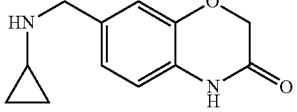<br>7-[(cyclopropylamino)methyl]-4H-1,4-benzoxazin-3-one | 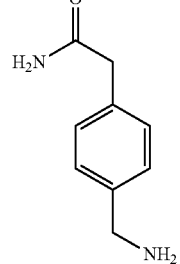<br>2-[4-(aminomethyl)phenyl]acetamide | 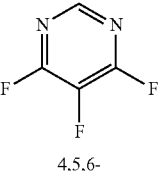<br>4,5,6-trifluoropyrimidine |
| A163 | 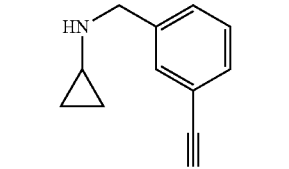<br>3-[(cyclopropylamino)methyl]benzonitrile | 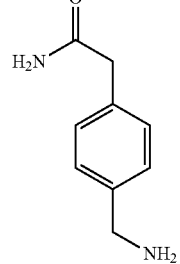<br>2-[4-(aminomethyl)phenyl]acetamide | 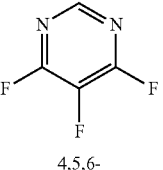<br>4,5,6-trifluoropyrimidine |
| A165 | 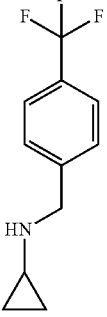<br>N-[[4-(trifluoromethyl)phenyl]methyl]cyclopropanamine | 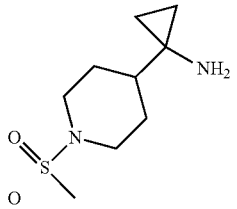<br>1-(1-methylsulfonyl-4-piperidyl)cyclopropanamine | 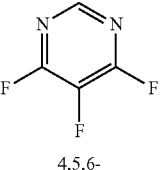<br>4,5,6-trifluoropyrimidine |

-continued

| Ex. No. | Free amine (1) | Free amine (2) | Fluorinated aromatic compound |
|---|---|---|---|
| A166 | 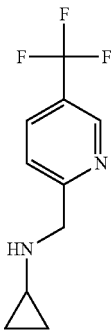<br>N-[[5-(trifluoromethyl)-2-pyridyl]methyl]cyclopropanamine | 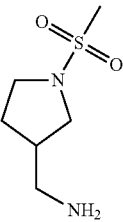<br>(1-methylsulfonylpyrrolidin-3-yl)methanamine | 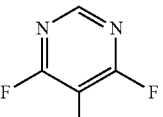<br>4,5,6-trifluoropyrimidine |
| A167 | 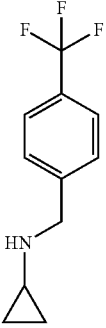<br>N-[[4-(trifluoromethyl)phenyl]methyl]cyclopropanamine | 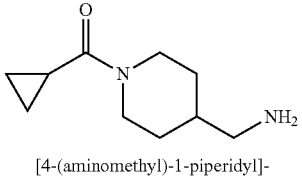<br>[4-(aminomethyl)-1-piperidyl]-cyclopropyl-methanone | 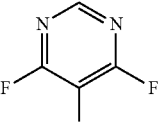<br>4,5,6-trifluoropyrimidine |
| A168 | 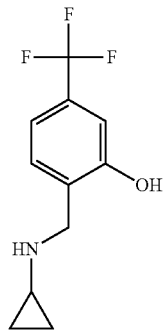<br>2-[(cyclopropylamino)methyl]-5-(trifluoromethyl)phenol | 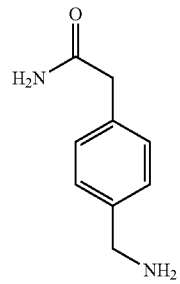<br>2-[4-(aminomethyl)phenyl]acetamide | 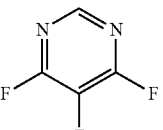<br>4,5,6-trifluoropyrimidine |

| Ex. No. | Free amine (1) | Free amine (2) | Fluorinated aromatic compound |
|---|---|---|---|
| A169 | N-[[4-(trifluoromethyl)phenyl]methyl]cyclopropanamine | 6-methylsulfonyl-6-azaspiro[2.5]octan-2-amine | 4,5,6-trifluoropyrimidine |
| A170 | v | 2-[4-(aminomethyl)phenyl]acetamide | 4,5,6-trifluoropyrimidine |
| A171 | N-[[4-(trifluoromethyl)phenyl]methyl]cyclopropanamine | [(1S,5R)-8-methylsulfonyl-8-azabicyclo[3.2.1]octan-3-yl]methanamine | 4,5,6-trifluoropyrimidine |

| Ex. No. | Free amine (1) | Free amine (2) | Fluorinated aromatic compound |
|---|---|---|---|
| A172 | 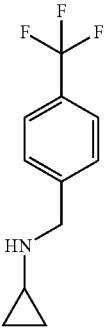<br>N-[[4-(trifluoromethyl)phenyl]methyl]cyclopropanamine | 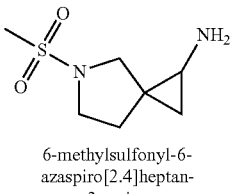<br>6-methylsulfonyl-6-azaspiro[2.4]heptan-2-amine | 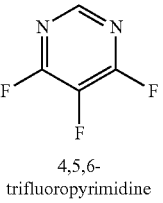<br>4,5,6-trifluoropyrimidine |
| A173 | 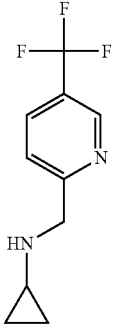<br>N-[[5-(trifluoromethyl)-2-pyridyl]methyl]cyclopropanamine | 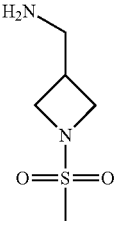<br>(1-methylsulfonylazetidin-3-yl)methanamine | 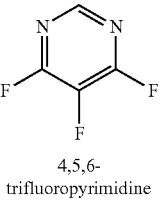<br>4,5,6-trifluoropyrimidine |
| A174 | 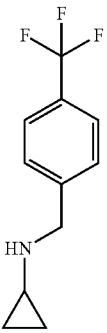<br>N-[[4-(trifluoromethyl)phenyl]methyl]cyclopropanamine | 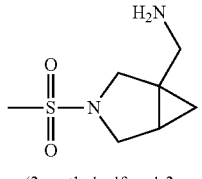<br>(3-methylsulfonyl-3-azabicyclo[3.1.0]hexan-5-yl)methanamine | 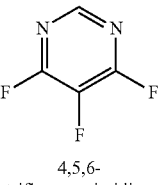<br>4,5,6-trifluoropyrimidine |

-continued

| Ex. No. | Free amine (1) | Free amine (2) | Fluorinated aromatic compound |
|---|---|---|---|
| A175 | N-[[4-(trifluoromethyl)phenyl]methyl]cyclopropanamine | 2-methylsulfonyl-3,3a,4,5,6,6a-hexahydro-1H-cyclopenta[c]pyrrol-4-amine | 4,5,6-trifluoropyrimidine |
| A176 | N-[[6-(trifluoromethyl)-2-pyridyl]methyl]cyclopropanamine | 2-[4-(aminomethyl)phenyl]acetamide | 4,5,6-trifluoropyrimidine |
| A177 | N-[[4-(trifluoromethyl)phenyl]methyl]cyclopropanamine | 2-[6-(aminomethyl)-3-pyridyl]acetamide | 4,5,6-trifluoropyrimidine |
| A178 | N-[[4-(trifluoromethyl)-2-pyridyl]methyl]cyclopropanamine | 2-[4-(aminomethyl)phenyl]acetamide | 4,5,6-trifluoropyrimidine |

-continued

| Ex. No. | Free amine (1) | Free amine (2) | Fluorinated aromatic compound |
|---|---|---|---|
| A179 | 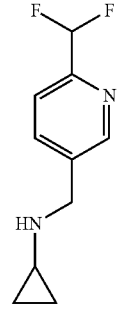<br>N-[[6-(difluoromethyl)-3-pyridyl]methyl] cyclopropanamine | 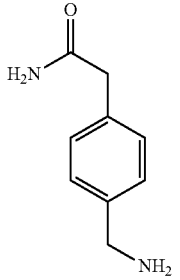<br>2-[4-(aminomethyl) phenyl]acetamide | 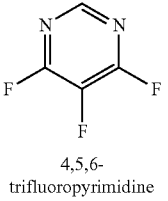<br>4,5,6-trifluoropyrimidine |
| A180 | 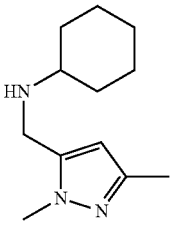<br>N-[(2,5-dimethylpyrazol-3-yl)methyl] cyclohexanamine | 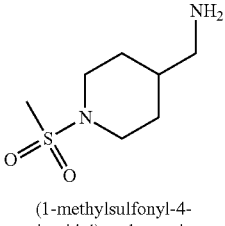<br>(1-methylsulfonyl-4-piperidyl)methanamine | 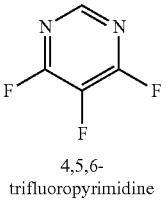<br>4,5,6-trifluoropyrimidine |
| A181 | 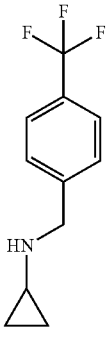<br>N-[[4-(trifluoromethyl) phenyl]methyl] cyclopropanamine | 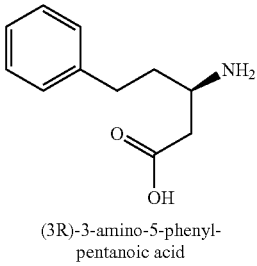 [SMILES: N[C@H](CCc1ccccc1)CC(=O)O]<br>(3R)-3-amino-5-phenyl-pentanoic acid | 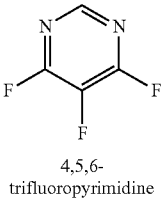<br>4,5,6-trifluoropyrimidine |
| A182 | 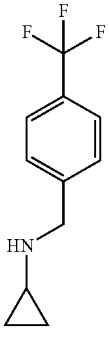<br>N-[[4-(trifluoromethyl) phenyl]methyl] cyclopropanamine | 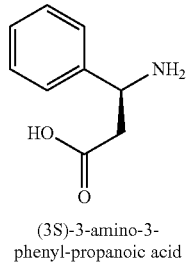 [SMILES: N[C@@H](CC(=O)O)c1ccccc1]<br>(3S)-3-amino-3-phenyl-propanoic acid | 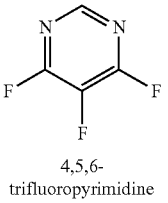<br>4,5,6-trifluoropyrimidine |

-continued

| Ex. No. | Free amine (1) | Free amine (2) | Fluorinated aromatic compound |
|---|---|---|---|
| A183 | 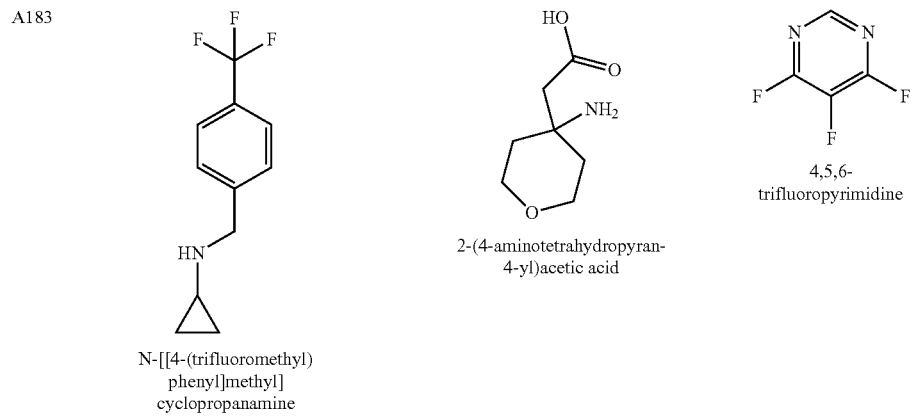 N-[[4-(trifluoromethyl)phenyl]methyl]cyclopropanamine | 2-(4-aminotetrahydropyran-4-yl)acetic acid | 4,5,6-trifluoropyrimidine |
| A184 | 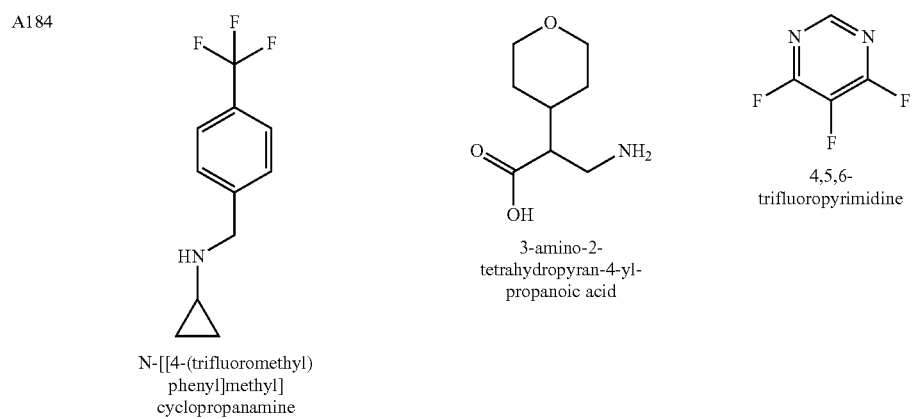 N-[[4-(trifluoromethyl)phenyl]methyl]cyclopropanamine | 3-amino-2-tetrahydropyran-4-yl-propanoic acid | 4,5,6-trifluoropyrimidine |
| A185 | 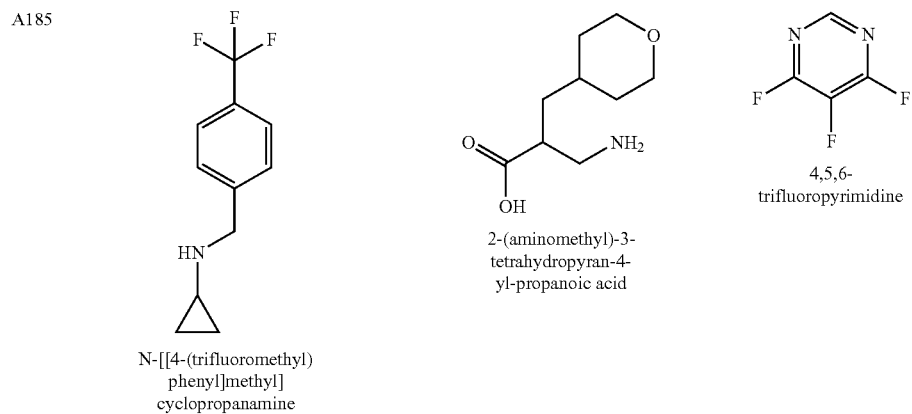 N-[[4-(trifluoromethyl)phenyl]methyl]cyclopropanamine | 2-(aminomethyl)-3-tetrahydropyran-4-yl-propanoic acid | 4,5,6-trifluoropyrimidine |

Synthesis of Selected Free Amines.

Dialkyl Amines were Synthesized Using the Following General Method 2.

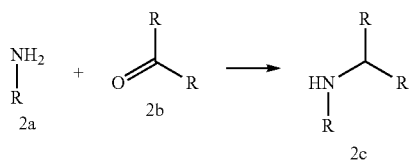

A primary amine 2a, e.g. cyclopropanamine, was coupled to a carbonyl compound 2b, e.g. 4-(trifluoromethyl)benzaldehyde, upon treatment with a suitable reducing agent, e.g. NaBH$_3$CN or NaBH(OAc)$_3$, in an appropriate solvent, e.g. DCM or tetrahydrofuran (THF), with addition of an appropriate acid, e.g. AcOH. Conversion to 2c was typically achieved after stirring at room temperature overnight. The reaction may for example be monitored by thin layer chromatography. The reaction may for example be monitored by thin layer chromatography. The desired product was obtained upon work-up, e.g. by extraction with EtOAc, washing with water at a suitable pH and brine, drying over an appropriate drying agent, e.g. Na$_2$SO$_4$, and purification by flash column chromatography (CC) using an appropriate eluent combination on a suitable column material, e.g. heptane/EtOAc or DCM/MeOH on silica gel, or recrystallization from a suitable solvent or solvent mixture, e.g. toluene/heptane.

Example of Use of Method 2 to Prepare N-[[4-(Trifluoromethyl)Phenyl]Methyl]Cyclopropanamine

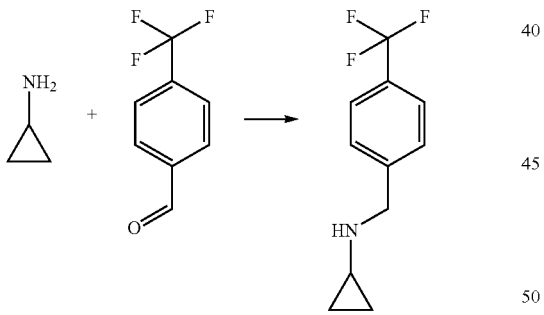

Cyclopropanamine (202 mg, 2.0 mmol) and 4-(trifluoromethyl)benzaldehyde (348 mg, 2.0 mmol) were dissolved in 5 mL DCM and 2 drops of AcOH was added. The mixture was stirred for 15 min at rt, and sodium triacetoxyborohydride (424 mg, 4.0 mmol) was added. The mixture was stirred at room temperature for 4 hours. The mixture was poured into 1M HCl, washed with EtOAc, basicified with 4M NaOH, extracted with EtOAc, washed with brine, dried over Na$_2$SO$_4$, concentrated in vacuo and purified by flash CC (eluent: Heptane/EtOAc, on silica gel), yielding N-[[4-(trifluoromethyl)phenyl]methyl]cyclopropanamine (316 mg, 73%).

General method 2 was used to prepare the following dialkyl amines using the shown starting materials:

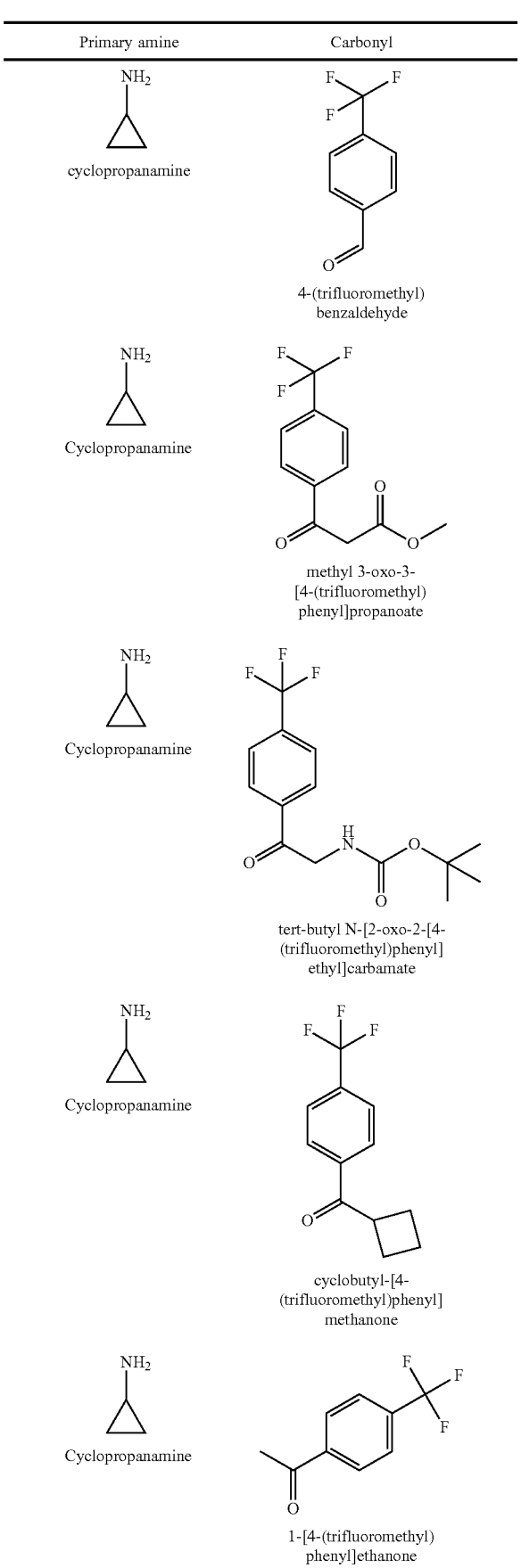

| Primary amine | Carbonyl |
|---|---|
| Cyclopropanamine | 5-(trifluoromethyl)pyridine-2-carbaldehyde |
| Cyclopropanamine | 6-(trifluoromethyl)pyridine-3-carbaldehyde |
| Cyclopropanamine | 5-cyclopropyl-2-isopropyl-pyrazole-3-carbaldehyde |
| Cyclopropanamine | 1-[6-(trifluoromethyl)-3-pyridyl]ethanone |
| cyclopropanamine | cyclopropyl-[4-(trifluoromethyl)phenyl]methanone |
| Cyclopropanamine | 6-isopropylpyridine-3-carbaldehyde |
| Cyclopropanamine | 6-(trifluoromethyl)pyridazine-3-carbaldehyde |
| Cyclopropanamine | 1-[5-(trifluoromethyl)-2-pyridyl]ethanone |
| cyclopropanamine | 4-(trifluoromethyl)pyridine-2-carbaldehyde |

-continued

| Primary amine | Carbonyl |
|---|---|
|  cyclopropanamine | 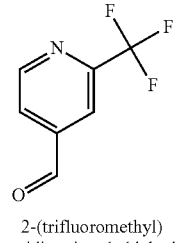 2-(trifluoromethyl) pyridine-4-carbaldehyde |
|  cyclopropanamine | 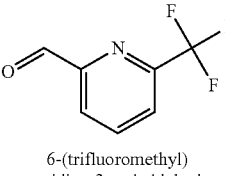 6-(trifluoromethyl) pyridine-2-carbaldehyde |
|  cyclopropanamine | 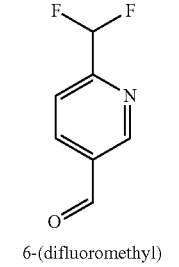 6-(difluoromethyl) pyridine-3-carbaldehyde |
| 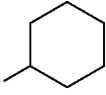 cyclohexanamine |  2,5-dimethylpyrazole-3-carbaldehyde |

N-((2-(trifluoromethyl) pyrimidin-5-yl) methyl) cyclopropanamine

To a solution of 2-(trifluoromethyl) pyrimidine-5-carboxylic acid (700 mg, 3.64 mmol, 1 eq) in dry THF (10 mL) at 0° C. was added borane dimethyl sulfide in THF (828 mg, 10.92 mmol, 3 eq), and the mixture was stirred at room temperature for 16 hours. After completion, the reaction mixture was quenched with MeOH and stirred for another 3 hours at room temperature. The solvent was evaporated and the residue was poured into ice water and extracted with EtOAc (3×75 mL). The combined organic extracts were washed with water (2×40 mL), brine (40 mL), dried over anhydrous $Na_2SO_4$, filtered and evaporated. The crude compound was purified by flash CC (eluent: EtOAc/Pet ether, on silica gel) to afford (2-(trifluoromethyl) pyrimidin-5-yl) methanol (Compound-2) (260 mg, 40%) as yellow liquid.

To a solution of (2-(trifluoromethyl) pyrimidin-5-yl) methanol (0.26 g, 1.46 mmol, 1 eq) in $CH_2Cl_2$ (10 mL) at 0° C. was added pyridinium chlorochromate (PCC, 0.53 g, 2.48 mmol, 1.0 eq), and the mixture was stirred at room temperature for 4 hours. After completion, the reaction mixture was diluted with $CH_2Cl_2$ (30 mL) and filtered through a pad of celite using $CH_2Cl_2$ (50 mL). The filtrate was dried over anhydrous $Na_2SO_4$ and evaporated to afford 2-(trifluoromethyl) pyrimidine-5-carbaldehyde (100 mg, 39%) as yellow liquid. The crude product was used as such without further purification.

To a solution of 2-(trifluoromethyl)pyrimidine-5-carbaldehyde (100 mg, 0.568 mmol, 1 eq) in $CH_2Cl_2$ (2 ml) was added cyclopropanamine (38 mg, 0.68 mmol, 1.2 eq), AcOH (0.5 ml), 4 Å molecular sieves powder (50 mg), and the mixture was stirred at room temperature for 30 min. Then $Na(OAc)_3BH$ (240 mg, 1.36 mmol, 2 eq) was added and stirring was continued at room temperature for 4 hours. After completion, the reaction mixture was diluted with $CH_2Cl_2$ (50 mL) and filtered through a pad of celite. The filtrate was washed with saturated aq. $NaHCO_3$ (25 mL), water (25 mL), brine (20 mL), dried over anhydrous $Na_2SO_4$, filtered and evaporated. The crude compound was purified by flash CC (eluent: EtOAc/Pet ether, on silica gel) to afford N-((2-(trifluoromethyl) pyrimidin-5-yl) methyl) cyclopropanamine (100 mg, 81%) as pale yellow liquid.

[4-(1H-Tetrazol-5-ylmethyl)cyclohexyl]methanamine

To 4-[(tert-butoxycarbonylamino)methyl]cyclohexanecarboxylic acid (0.84 g, 3.2 mmol) a $BH_3$-THF solution in THF (16 mL, 1M) was slowly added. The reaction was allowed to stir for 2.5 hours, concentrated in vacuo and the residue was stirred with an aq. sodium hydroxide solution (1M, 30 mL) for 20 min. Ethyl acetate was added and the mixture was allowed to stir for another 10 min. The phases were separated, the EtOAc phase was concentrated in vacuo and the crude product thereof was purified by flash CC (eluent: EtOAc/heptane, on silica gel) yielding tert-butyl N—[[4 (hydroxymethyl)cyclohexyl]methyl]carbamate (0.76 g, quant yield).

Tert-butyl N-[[4-(hydroxymethyl)cyclohexyl]methyl]carbamate (0.60 g, 2.5 mmol) was dissolved in DCM (20 mL), $Et_3N$ (1 mL) and methanesulfonyl chloride was the added to the solution, and the reaction was stirred over night at room temperature. Concentration under reduced pressure yielded a solid that was mixed with water and EtOAc. The EtOAc phase was separated and washed with brine and dried over sodium sulfate. Filtration and concentration in vacuo of the EtOAC phase gave a solid that was dissolved dry DMSO (10 mL). Potassium cyanide (0.36 g, 5.5 mmol) was added and the reaction was heated to 90° C. for 4 hours. The crude reaction was poured onto water and the resulting mixture was extracted with EtOAc. The organic phase was dried over sodium sulfate, filtered and concentrated in vacuo. The crude product was purified by flash CC (eluent: EtOAc/heptane, on silica gel) yielding tert-butyl N-[[4-(cyanomethyl)cyclohexyl]methyl]carbamate (0.57 g, 88% yield).

To a solution of tert-butyl N-[[4-(cyanomethyl)cyclohexyl]methyl]carbamate (160 mg, 0.60 mmol) in nitrobenzene were added triethylammonium chloride (160 mg, 1.2 mmol) and sodium azide (91 mg, 1.4 mmol). The resulting mixture was heated to 105° C. for 11 hours using microwave irradiation. Some more sodium azide (40 mg, 0.7 mmol) was added and the reaction was heated for another 45 min at 105° C. with microwave irradiation. The reaction was extracted with water and the water phase was washed with ether, made acidic with 1M HCl and extracted with EtOAc. The EtOAc phase was dried using sodium sulfate, filtered and concentrated in vacuo and finally purified by flash CC (eluent: EtOAc/heptane, on silica gel) yielding tert-butyl N-[[4-(1H-tetrazol-5-ylmethyl)cyclohexyl]methyl]carbamate (33 mg, 18% yield).

Tert-butyl N-[[4-(1H-tetrazol-5-ylmethyl)cyclohexyl]methyl]carbamate (33 mg, 0.11 mmol) was dissolved in DCM (2 mL) and trifluoroacetic acid (TFA, 1 mL) was added, and the reaction was stirred for 2 hours. Concentration of the reaction mixture yielded [4-(1H-tetrazol-5-ylmethyl)cyclohexyl]methylammonium 2,2,2-trifluoroacetate that was used without further purification. Using an extra equivalent of the base in the General Method 1 gave [4-(1H-tetrazol-5-ylmethyl)cyclohexyl]methanamine in situ during the reaction.

N-((4-cyanotetrahydro-2H-pyran-4-yl)methyl)methanesulfonamide

To a solution of 4-(aminomethyl) tetrahydro-2H-pyran-4-carbonitrile (0.5 g, 3.57 mmol) in pyridine (5 mL) was added methane sulfonyl chloride (0.4 g, 3.57 mmol), and the mixture was stirred at room temperature for 16 hours. After completion, the reaction mixture was diluted with EtOAc (50 mL) and washed with saturated aq. citric acid (30 mL), water (30 mL), brine (30 mL), dried over anhydrous $Na_2SO_4$, filtered and evaporated. The crude compound was purified by flash CC (Eluent: EtOAc/Pet ether, on silica gel) to afford N-((4-cyanotetrahydro-2H-pyran-4-yl) methyl) methanesulfonamide (370 mg, 48%) as yellow liquid.

A suspension of N-((4-cyanotetrahydro-2H-pyran-4-yl) methyl) methanesulfonamide (0.32 g, 1.46 mmol), Raney Ni (0.82 g, 9.54 mmol), $NH_4OH$ (0.1 mL) in MeOH (6.5 mL) was stirred at room temperature for 16 hours under hydrogen atmosphere. After completion, the reaction mixture was diluted with EtOAc (30 mL) and filtered through a pad of celite. The filtrate was dried over anhydrous $Na_2SO_4$, filtered and evaporated to afford N-((4-(aminomethyl) tetrahydro-2H-pyran-4-yl) methyl) methanesulfonamide (200 mg, 62%). The crude product was used as such without further purification.

4-(aminomethyl)-1-(methylsulfonyl) piperidin-4-ol

To a solution of 1-(methylsulfonyl) piperidin-4-one (1 g, 5.64 mmol) in AcOH (10 mL) was added KCN (0.55 g, 8.57 mmol), and the mixture was stirred at room temperature for 18 hours. After completion, the reaction mixture was diluted with EtOAc (75 mL) and washed with saturated aq. $NaHCO_3$ (40 mL), water (50 mL), brine (40 mL), dried over anhydrous $Na_2SO_4$, filtered and evaporated. The crude compound was purified by flash CC (Eluent: EtOAc/Pet ether, on silica gel) to afford 4-hydroxy-1-(methylsulfonyl) piperidine-4-carbonitrile (500 mg, 43%) as yellow liquid.

A suspension of 4-hydroxy-1-(methylsulfonyl) piperidine-4-carbonitrile (500 mg, 2.45 mmol), Raney Ni (1.35 g, 15.92 mmol), $NH_4OH$ (0.12 mL) in MeOH (10 mL) was stirred at room temperature for 16 hours under hydrogen atmosphere. After completion, the reaction mixture was diluted with EtOAc (30 mL) and filtered through a pad of celite. The filtrate was dried over anhydrous $Na_2SO_4$, filtered and evaporated. The crude product was triturated with diethyl ether to afford 4-(aminomethyl)-1-(methylsulfonyl) piperidin-4-ol (200 mg, 39%) as a pale yellow syrup.

2-(5-(aminomethyl)pyridin-2-yl)acetamide

To a solution of 5-cyanopicolinic acid (1 g, 6.75 mmol) in dry THF (10 mL) at −15° C. was added $Et_3N$ (0.68 g, 6.75 mmol), ethyl chloro formate (0.73 g, 6.75 mmol), and the mixture was stirred for 16 hours at −15° C. Ether (15 mL), $TMSCHN_2$ (1.54 g, 13.5 mmol) was added, and the mixture was stirred overnight while returning to room temperature. After completion, the reaction mixture was diluted with EtOAc (75 mL), washed with water (50 mL), brine (40 mL), dried over anhydrous $Na_2SO_4$, filtered and evaporated. The diazaketone was dissolved in dioxane:$H_2O$ (1:1) (10 mL), added AgCOOPh (cat), and the mixture was stirred at 100° C. for 16 hours. After completion, the reaction mixture was diluted with EtOAc (50 mL), acidified using 1N HCl and extracted using EtOAc (2×50 mL). The combined organic extracts were washed with water (50 mL), brine (50 mL), dried over anhydrous $Na_2SO_4$, filtered and evaporated. The crude compound was purified by triturating with ether (10 mL) and pentane (50 mL) to afford 2-(5-cyanopyridin-2-yl) acetic acid (350 mg, 32%) as yellow solid.

To a solution of 2-(5-cyanopyridin-2-yl)acetic acid (0.35 g, 2.16 mmol) in DMF (3 mL) was added 1-ethyl-3-(3-dimethylaminopropyl)carbodiimide (EDC, 0.82 g, 4.32 mmol), 1-hydroxy-7-azabenzotriazole (HOAt, 0.58 g, 4.32 mmol), DIPEA (1.16 mL, 6.48 mmol), $NH_4Cl$ (0.17 g, 3.24 mmol) and stirred at room temperature for 3 hours.

After completion, the reaction mixture was poured into ice water and extracted with EtOAc (2×50 mL). The combined extracts were washed with water (40 mL), brine (30 mL), dried over anhydrous $Na_2SO_4$, filtered and evaporated. The crude compound was purified by flash CC (Eluent: MeOH/DCM) to afford 2-(5-cyanopyridin-2-yl) acetamide (190 mg, 55%) as yellow solid.

A solution of 2-(5-cyanopyridin-2-yl) acetamide (190 mg, 1.18 mmol), Raney Ni (0.65 g, 7.67 mmol), $NH_4OH$ (0.05 vol) in MeOH (2 mL) was and stirred at room temperature for 16 hours under hydrogen atmosphere. After completion, the reaction mixture was diluted with EtOAc (20 mL) and filtered through a pad of celite. The filtrate was dried over anhydrous $Na_2SO_4$, filtered and evaporated to afford 2-(5-(aminomethyl) pyridin-2-yl) acetamide (80 mg, 41%) as yellow solid.

(6-(methylsulfonyl) pyridin-3-yl) methanamine

A suspension of 6-(methylsulfonyl) nicotinonitrile (500 mg, 2.74 mmol), Raney Ni (1.51 g, 17.85 mmol), $NH_4OH$ (0.12 mL) in MeOH (10 mL) was stirred at room temperature for 16 hours under hydrogen atmosphere. After completion, the reaction mixture was diluted with EtOAc (30 mL) and filtered through a pad of celite. The filtrate was dried over anhydrous $Na_2SO_4$, filtered and evaporated to afford (6-(methylsulfonyl)pyridin-3-yl)methanamine (450 mg) as yellow solid. The crude product was used as such without further purification.

N-[4-(aminomethyl)phenyl]-1,1-difluoro-methanesulfonamide

Tert-butyl N-[(4-aminophenyl)methyl]carbamate (222 mg, 1.0 mmol) was dissolved in 5 mL dry DCM, and the solution was cooled to −78° C. Pyridine (0.24 µL, 3.0 mmol) was added, followed by slow addition of a solution of difluoromethanesulfonyl chloride (150 mg, 1.0 mmol) in 5 mL DCM. The mixture was stirred overnight while returning to rt, poured into $H_2O$, extracted with EtOAc, washed with brine, dried over $Na_2SO_4$ and purified by flash CC (eluent: Heptane/EtOAc, on silica gel), yielding tert-butyl N-[[4-(difluoromethylsulfonylamino)phenyl]methyl]carbamate. The product was dissolved in 2 mL DCM and a solution of 4M HCl in dioxane (2 mL) was added. The mixture was stirred overnight at room temperature, then concentrated in vacuo, and the crude N-[4-(aminomethyl)phenyl]-1,1-difluoro-methanesulfonamide hydrochloride was used in the next step without further purification (55 mg, 23%).

Using the same protocol the following compounds were prepared: 1-(1-methylsulfonyl-4-piperidyl)cyclopropanamine, 6-methylsulfonyl-6-azaspiro[2.5]octan-2-amine, [(1S,5R)-8-methylsulfonyl-8-azabicyclo[3.2.1]octan-3-yl]methanamine, 6-methylsulfonyl-6-azaspiro[2.4]heptan-2-amine, (3-methylsulfonyl-3-azabicyclo[3.1.0]hexan-5-yl)methanamine and 2-methylsulfonyl-3,3a,4,5,6,6a-hexahydro-1H-cyclopenta[c]pyrrol-4-amine.

N-(5-(aminomethyl)-3-fluoropyridin-2-yl) methanesulfonamide A suspension of 5-bromo-3-fluoropyridin-2-amine (2 g, 10.58 mmol), K$_4$FeCN$_6$ (1.78 g, 4.23 mmol) and 1,8-diazabicycloundec-7-ene (DBU, 399 mg, 2.64 mmol) in tBuOH:H$_2$O (1:1) (20 mL) was degassed for 15 min. Then added Pd(PPh$_3$)$_4$ (0.61 g, 0.529 mmol) and the mixture was stirred at 85° C. for 16 hours. After completion, the reaction mixture was diluted with EtOAc (100 mL), washed with water (50 mL), brine (50 mL), dried over anhydrous Na$_2$SO$_4$, filtered and concentrated. The crude compound was purified by flash CC (Eluent: MeOH/DCM, on silica gel) to afford 6-amino-5-fluoronicotinonitrile (600 mg, 42%) as a pale yellow solid.

To a solution of 6-amino-5-fluoronicotinonitrile (600 mg, 4.37 mmol) in pyridine (6 mL) at 0° C. was added methane sulfonyl chloride (0.5 g, 4.37 mmol), and the mixture was stirred at room temperature for 16 hours. After completion, the reaction mixture was diluted with EtOAc (75 mL), washed with water (50 mL), brine (40 mL), dried over anhydrous Na$_2$SO$_4$, filtered and concentrated. The crude compound was purified by flash CC (Eluent: MeOH/DCM, on silica gel) to afford N-(5-cyano-3-fluoropyridin-2-yl) methanesulfonamide (350 mg, 37%) as pale yellow solid.

A suspension of N-(5-cyano-3-fluoropyridin-2-yl) methanesulfonamide (350 mg, 1.627 mmol), Raney Ni (0.9 g, 10.58 mmol), NH$_4$OH (0.1 mL) in MeOH (6.5 mL) was stirred at room temperature for 16 hours under hydrogen atmosphere. After completion, the reaction mixture was filtered through a pad of celite, the filtrate was dried over anhydrous Na$_2$SO$_4$ and evaporated. The crude product was triturated with DCM:pentane (1:5) to afford N-(5-(aminomethyl)-3-fluoropyridin-2-yl) methanesulfonamide (130 mg, 36%) as an off white solid.

5-(aminomethyl) pyrimidin-2-amine

A suspension of 2-aminopyrimidine-5-carbonitrile (0.4 g, 3.33 mmol), Raney Ni (1.8 g, 21.7 mmol), NH$_4$OH (0.2 mL) in MeOH (4 mL) was stirred at room temperature for 16 hours under hydrogen atmosphere. After completion, the reaction mixture was diluted with EtOAc (30 mL) and filtered through a pad of celite. The filtrate was dried over anhydrous Na$_2$SO$_4$, filtered and evaporated to afford 5-(amino methyl) pyrimidin-2-amine (300 mg, 72%) as pale yellow solid.

Synthesis of Example No. A81

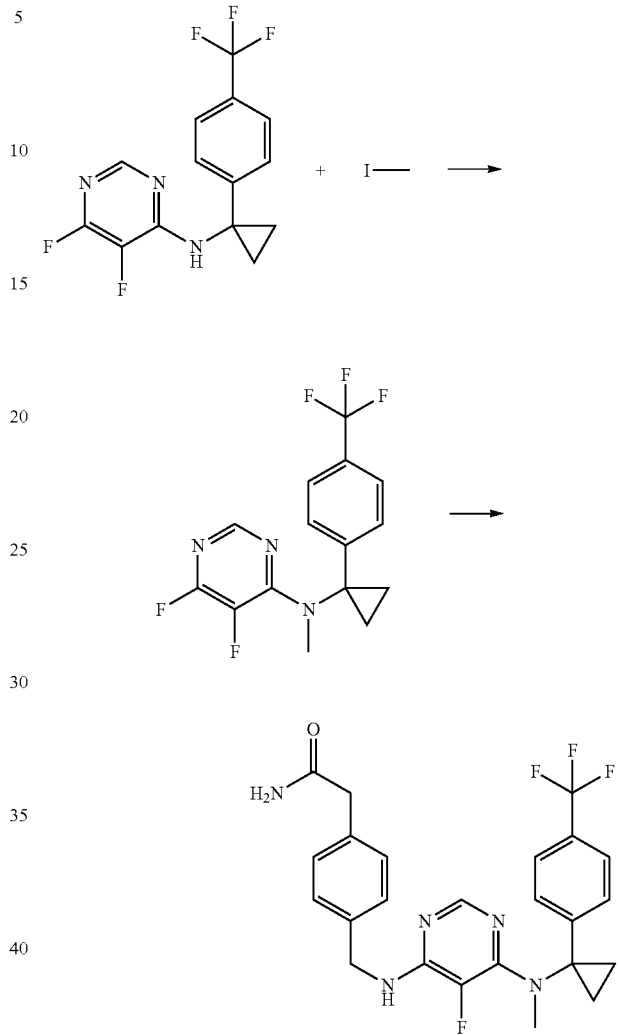

A81

5,6-Difluoro-N-[1-[4-(trifluoromethyl)phenyl]cyclopropyl]pyrimidin-4-amine (100 mg, 0.32 mmol), prepared using Method 1, was dissolved in 1 mL dry DMF and sodium hydride (60% in mineral olie, 13 mg, 0.34 mg) was added. The mixture was stirred at room temperature until gas formation had ceased (30 min). Methyl iodide (45 mg, 0.34 mmol) was added, and the mixture was stirred for 2 hours at room temperature. The mixture was poured into H$_2$O, extracted with EtOAc, washed with brine, dried over Na$_2$SO$_4$ and concentrated in vacuo. The crude product was dissolved in 2 mL dry DMSO and 2-[4-(aminomethyl)phenyl]acetamide (56 mg, 0.34 mmol) and DIPEA (0.12 mL, 0.7 mmol) were added. The mixture was heated at 100° C. in the microwave oven for 30 min, poured into H$_2$O, extracted with EtOAc, washed with brine, dried over Na$_2$SO$_4$, concentrated in vacuo and purified by flash CC (eluent: DCM/MeOH). $^1$H NMR (300 MHz, CD$_3$OD) δ 7.85 (s, 1H), 7.59 (d, J=8.0 Hz, 2H), 7.33-7.21 (m, 6H), 4.57 (s, 2H), 3.49 (s, 2H), 3.21 (s, 3H), 1.61-1.42 (m, 4H). m/z 474 (M+H).

Synthesis of Example No. A100

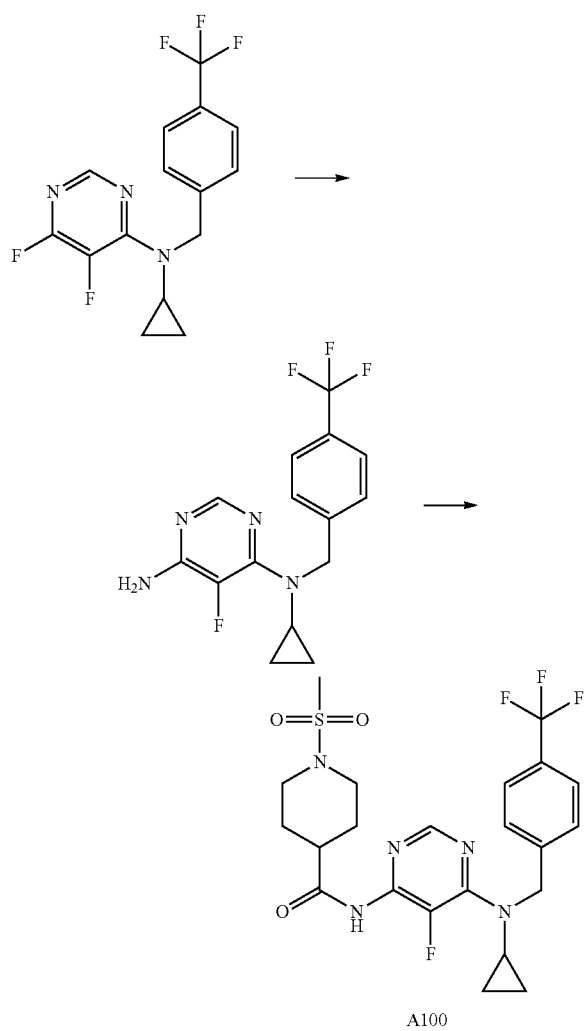

A100

N-Cyclopropyl-5,6-difluoro-N-[[4-(trifluoromethyl)phenyl]methyl]pyrimidin-4-amine (100 mg, 0.3 mmol), prepared using Method 1, was dissolved in 1 mL DMSO. Ammonium chloride (22 mg, 0.4 mmol) and DIPEA (0.14 mL, 0.08 mmol) were added, and the mixture was heated at 100° C. for 2 hours. The mixture was poured into saturated aqueous NaHCO$_3$, extracted with EtOAc, washed with brine, dried over Na$_2$SO$_4$ and concentrated in vacuo, yielding N4-cyclopropyl-5-fluoro-N4-[[4-(trifluoromethyl)phenyl]methyl]pyrimidine-4,6-diamine (40 mg, 41%). The crude product was used in the next step without further purification.

N-Cyclopropyl-5-fluoro-4-[[4-(trifluoromethyl)phenyl]methyl]pyrimidine-4,6-diamine (33 mg, 0.1 mmol), 1-methylsulfonylpiperidine-4-carboxylic acid (21 mg, 0.1 mmol), [dimethylamino(triazolo[4,5-b]pyridin-3-yloxy)methylene]-dimethyl-ammonium hexafluorophosphate (HATU, 38 mg, 0.1 mmol) and DIPEA (40 µL, 0.2 mmol) were dissolved in dry DMSO (1 mL), and the mixture was stirred at 70° C. for 3 days. The mixture was poured into saturated aqueous NaHCO$_3$, extracted with EtOAc, washed with brine, drived over Na$_2$SO$_4$, concentrated in vacuo and purified by flash CC (eluent: DCM/MeOH). $^1$H NMR (300 MHz, CD$_3$OD) δ 8.16 (s, 1H), 7.63 (d, J=8.1 Hz, 2H), 7.48 (d, J=8.1 Hz, 2H), 5.01 (s, 2H), 3.11-3.00 (m, 1H), 2.86 (s, 3H), 2.86-2.80 (m, 4H), 2.76-2.62 (m, 1H), 2.10-1.97 (m, 2H), 1.93-1.76 (m, 3H), 0.94-0.84 (m, 2H), 0.84-0.76 (m, 2H). m/z 516 (M+H).

General Method 3

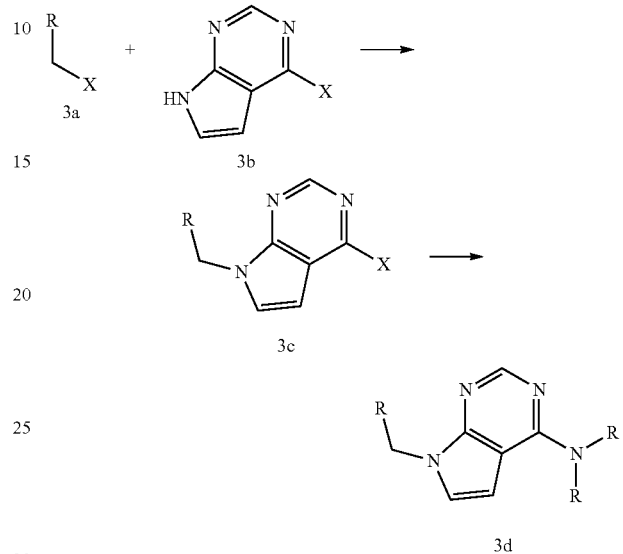

A halogenated pyrrolopyrimidine 3b, e.g. 6-chloro-7-deazapurine, was N-alkylated by addition of an alkyl halide 3a, e.g. [3-(bromomethyl)oxetan-3-yl]methanol, and an appropriate base in a suitable solvent, e.g. cesium carbonate in dry dioxane or sodium hydride in dry tetrahydrofuran. The mixture was stirred at room temperature until completion of reaction, typically overnight. The reaction may for example be monitored by thin layer chromatography. The reaction may for example be monitored by thin layer chromatography. The desired product was obtained upon work-up, e.g. by extraction with EtOAc, washing with water at a suitable pH and brine, drying over an appropriate drying agent, e.g. Na$_2$SO$_4$, and purification by flash column chromatrography (CC) using an appropriate eluent combination on a suitable column material, e.g. heptane/EtOAc or DCM/MeOH on silica gel, or recrystallization from a suitable solvent or solvent mixture, e.g. toluene/heptane. Nucleophilic aromatic substitution of the halogen on intermediate 3c was achieved upon addition of a building block containing a free amino group, e.g. 2-(4-trifluoromethyl-phenyl)-pyrrolidine, and a suitable base in an appropriate solvent, e.g. cesium carbonate in dry DMSO. The reaction was achieved by microwave irradiation at elevated temperatures for a period of time, e.g. at 100-150° C. for 1-4 hours. The reaction may for example be monitored by thin layer chromatography. The desired compound 3d was obtained upon work-up, for example by extraction with EtOAc, washing with water at a suitable pH and brine, drying over an appropriate drying agent, e.g. Na2SO4, and purification by flash column chromatrography (CC) using an appropriate eluent combination on a suitable column material, e.g. heptane/EtOAc or DCM/MeOH on silica gel, or recrystallization from a suitable solvent or solvent mixture, e.g. toluene/heptane.

Use of General Method 3 to Prepare Example No. I1

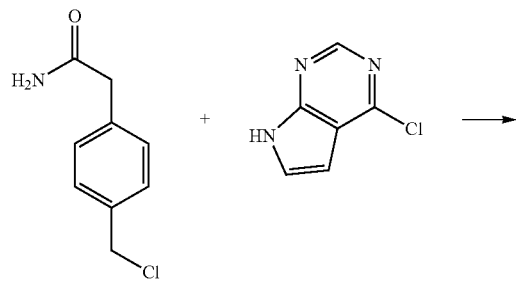

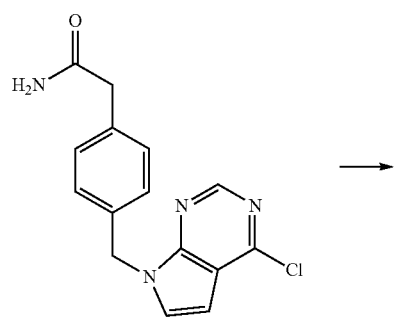

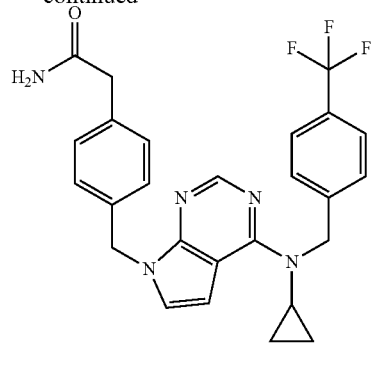

A suspension of 2-(4-(chloromethyl) phenyl) acetamide (1.2 g, 6.54 mmol) 4-chloro-7H-pyrrolo[2,3-d]pyrimidine (1 g, 6.54 mmol), $Cs_2CO_3$ (4.26 g, 13.08 mmol) in DMF (12 mL) was stirred at room temperature for 3 hours. After completion, the reaction mixture was poured into ice water, the solid filtered off and washed with diethyl ether (50 mL) to afford 2-(4-((4-chloro-7H-pyrrolo[2,3-d]pyrimidin-7-yl)methyl)phenyl)acetamide (1.1 g, 56%) as a pale yellow solid.

A solution of 2-(4-((4-chloro-7H-pyrrolo[2,3-d]pyrimidin-7-yl)methyl)phenyl)acetamide (Gemma-Pyrrolopyrimidine) (500 mg, 1.66 mmol), N-(4-(trifluoromethyl)benzyl)cyclopropanamine (358 mg, 1.66 mmol) and DIPEA (0.89 mL, 4.98 mmol) in DMSO (5 mL) was stirred at 150° C. for 4 hours under microwave conditions. After completion, the reaction mixture was poured into ice water and extracted with EtOAc (3×50 mL). The combined extracts were washed with water (2×20 mL), brine (20 mL), dried over anhydrous $Na_2SO_4$, filtered and evaporated. The crude compound was purified by reverse phase chromatography (0.01 M ammonium acetate in water:ACN) to afford 2-(4-((4-(cyclopropyl (4-(trifluoromethyl) benzyl) amino)-7H-pyrrolo[2,3-d] pyrimidin-7-yl)methyl) phenyl)acetamide (75 mg) as an off white solid. $^1H$ NMR (300 MHz, $CDCl_3$): δ 8.36 (s, 1H), 7.54 (d, J=8.1 Hz, 2H), 7.40-7.33 (m, 2H), 7.24 (s, 4H), 6.92 (d, J=3.7 Hz, 1H), 6.83 (d, J=3.7 Hz, 1H), 5.41 (s, 2H), 5.31 (br s, 2H), 5.15 (s, 2H), 3.56 (s, 2H), 3.08 (dt, J=3.5, 6.9 Hz, 1H), 1.02-0.86 (m, 4H). m/z 480 (M+H).

General method 3 was used to prepare the following example numbers using the shown starting materials:

| Ex. No. | Halogenated pyrroloporimidine | Alkyl halide | Free amine |
|---|---|---|---|
| I1 | 4-chloro-7H-pyrrolo[2,3-d]pyrimidine | 2-[4-(chloromethyl)phenyl]acetamide | N-[[4-(trifluoromethyl)phenyl]methyl]cyclopropanamine |

| Ex. No. | Halogenated pyrroloporimidine | Alkyl halide | Free amine |
|---|---|---|---|
| A56 | 4-chloro-7H-pyrrolo[2,3-d]pyrimidine | [3-(bromomethyl)oxetan-3-yl]methanol | N-[[4-(trifluoromethyl)phenyl]methyl]cyclopropanamine |
| A164 | 4-chloro-7H-pyrrolo[2,3-d]pyrimidine | 1-(bromomethyl)-4-(trifluoromethyl)benzene | 2-[4-(aminomethyl)phenyl]acetamide |

Synthesis of 2-[4-(chloromethyl)phenyl]acetamide

To a solution of 2-(4-(hydroxymethyl) phenyl) acetic acid (20 g, 120.48 mmol) in MeOH:toluene (1:1) (200 mL) at 0° C. was added (trimethylsilyl)diazomethane (TMSCHN$_2$, 27.51 g, 240 mmol), and the mixture was stirred at room temperature for 16 hours. After completion, the solvent was evaporated and the crude compound was purified by flash CC (eluent: EtOAc/Pet ether, on silica gel) to afford methyl 2-(4-(hydroxymethyl) phenyl) acetate (18 g, 83%) as an off white solid.

To a solution of methyl 2-(4-(hydroxymethyl) phenyl) acetate (3.4 g, 1.87 mmol) in MeOH (10 vol) was added aqueous NH$_3$ (34 ml), and the mixture was heated at 90° C. for 16 hours in a sealed tube. After completion, the reaction mixture was allowed to room temperature and filtered to afford 2-(4-(hydroxymethyl) phenyl) acetamide (1.1 g, 35%) as an off white solid.

To a solution of 2-(4-(hydroxymethyl) phenyl) acetamide (2 g, 12.12 mmol), Et$_3$N (5.1 mL, 36.36 mmol) in DMF (20 mL) was added methane sulfonyl chloride (1.5 mL, 18.18 mmol), and the mixture was stirred at room temperature for 3 hours. After completion, the reaction mixture was poured into ice water and filtered the solid to afford 2-(4-(chloromethyl) phenyl) acetamide (1.2 g, 54%) as an off white solid.

General Method 4

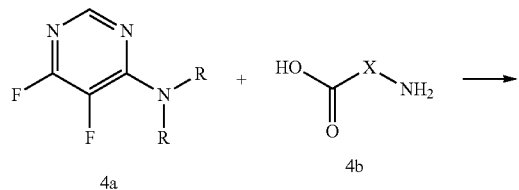

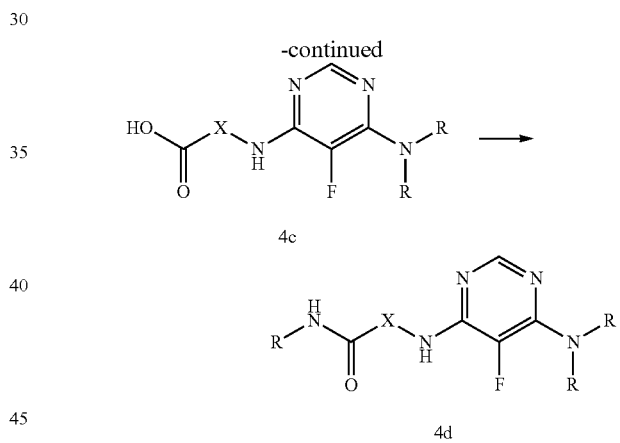

A halogenated pyrimidine 4a, e.g. N-cyclopropyl-5,6-difluoro-N-[[4-(trifluoromethyl)phenyl]methyl]pyrimidin-4-amine, was coupled to an amino acid 4b, e.g. 3-(aminomethyl)cyclobutanecarboxylic acid, upon treatment with a suitable base in an appropriate solvent, e.g. DIPEA or cesium carbonate in dry DMSO or DMF, under microwave irradiation during a period of time, e.g. at 80-150° C. for 1 hour. The reaction may for example be monitored by thin layer chromatography. The reaction may for example be monitored by thin layer chromatography. The desired product was obtained upon work-up, e.g. by extraction with EtOAc, washing with water at a suitable pH and brine, drying over an appropriate drying agent, e.g. Na$_2$SO$_4$, and purification by flash column chromatrography (CC) using an appropriate eluent combination on a suitable column material, e.g. heptane/EtOAc or DCM/MeOH on silica gel, or recrystallization from a suitable solvent or solvent mixture, e.g. toluene/heptane. The free carboxylic acid 4c can be converted to 4d upon acylation with a free amine containing compound, e.g. ammonium chloride, upon treatment with an appropriate coupling reagent or mixture of coupling reagents, e.g. HATU or EDC/HOAt, and a suitable base, e.g. DIPEA, in an appropriate solvent, e.g. DMF or DMSO. Conversion to 4d was typically achieved after stirring at room temperature overnight. The reaction may for example be monitored by thin layer chromatography. The reaction may for example be monitored by thin layer chromatography. The desired product was obtained upon work-up, e.g. by extraction with EtOAc, washing with water at a suitable pH and brine, drying over an appropriate drying agent, e.g. $Na_2SO_4$, and purification by flash column chromatrography (CC) using an appropriate eluent combination on a suitable column material, e.g. heptane/EtOAc or DCM/MeOH on silica gel, or recrystallization from a suitable solvent or solvent mixture, e.g. toluene/heptane. Compounds in which 4d contain a tert-butyl protected acid, e.g. tert-butyl 2-[[2-[4-[[[6-[cyclopropyl-[[4-(trifluoromethyl)phenyl]methyl]amino]-5-fluoro-pyrimidin-4-yl]amino]methyl]tetrahydro-pyran-4-yl]acetyl]amino]acetate, can be hydrolyzed upon treatment with a suitable acid, e.g. HCl in dioxane, prior to purification.

Use of General Method 4 to Prepare Example No. 96:

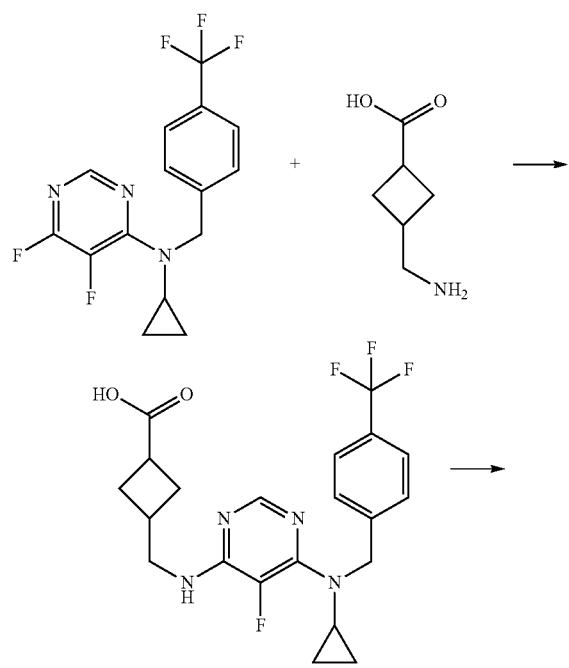

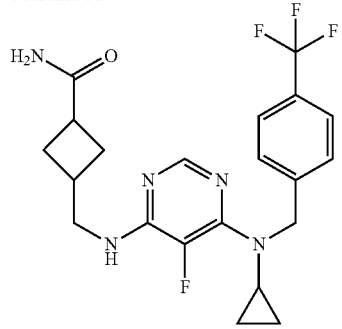

A96

N-Cyclopropyl-5,6-difluoro-N-[[4-(trifluoromethyl)phenyl]methyl]pyrimidin-4-amine (100 mg, 0.3 mmol), prepared using Method 1, was dissolved in 2 mL dry DMSO. 3-(Aminomethyl)cyclobutanecarboxylic acid (39 mg, 0.3 mmol) and DIPEA (0.11 mL, 0.6 mmol) were added, and the mixture was heated at 90° C. for 4 hours. The reaction mixture was poured into 10% aqueous $KHSO_4$, extracted with EtOAc, washed with brine, dried over $Na_2SO_4$ and concentrated in vacuo, yielding 3-[[[6-[cyclopropyl-[[4-(trifluoromethyl)phenyl]methyl]amino]-5-fluoro-pyrimidin-4-yl]amino]methyl]cyclobutanecarboxylic acid (68 mg, 52%).

The crude 3-[[[6-[cyclopropyl-[[4-(trifluoromethyl)phenyl]methyl]amino]-5-fluoro-pyrimidin-4-yl]amino]methyl]cyclobutanecarboxylic acid (66 mg, 0.15 mmol), HATU (57 mg, 0.15 mmol) and DIPEA (60 µL, 0.3 mmol) were dissolved in dry DMF (1 mL), and the mixture was stirred at room temperature overnight. The mixture was poured into saturated aqueous $NaHCO_3$, extracted with EtOAc, washed with brine, dried over $Na_2SO_4$, concentrated in vacuo and purified by flash CC (eluent: DCM/MeOH). $^1H$ NMR (300 MHz, DMSO-$d_6$) δ 7.82 (d, J=1.8 Hz, 1H), 7.67 (d, J=8.2 Hz, 2H), 7.43 (d, J=8.1 Hz, 2H), 7.17-7.00 (m, 2H), 6.66 (s, 1H), 4.83 (s, 2H), 3.43-3.38 (m, 1H), 3.31-3.24 (m, 2H), 2.97-2.83 (m, 1H), 2.46-2.31 (m, 1H), 2.16-1.97 (m, 2H), 1.90-1.74 (m, 2H), 0.78-0.61 (m, 4H). m/z 438 (M+H).

General method 4 was used to prepare the following example numbers using the shown starting materials:

| Ex. No. | Amino acid | Amine | Fluorinated aromatic compound |
|---|---|---|---|
| A80 | 2-[4-(aminomethyl)tetrahydropyran-4-yl]acetic acid | methanamine | 4,5,6-trifluoropyrimidine |

-continued

| Ex. No. | Amino acid | Amine | Fluorinated aromatic compound |
|---|---|---|---|
| A84 | 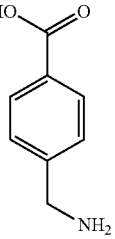<br>4-(aminomethyl)benzoic acid | <br>cyanamide | 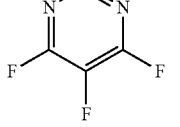<br>4,5,6-trifluoropyrimidine |
| A95 | 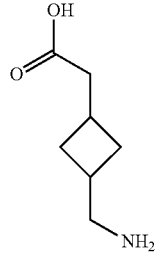<br>2-[3-(aminomethyl)cyclobutyl]<br>acetic acid | NH$_4^+$ Cl$^-$<br>ammonium chloride | 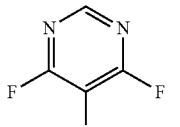<br>4,5,6-trifluoropyrimidine |
| A96 | 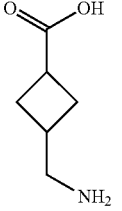<br>3-(aminomethyl)cyclobutane<br>carboxylic acid | NH$_4^+$ Cl$^-$<br>ammonium chloride | 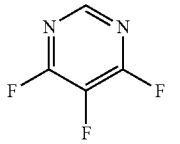<br>4,5,6-trifluoropyrimidine |
| A151 | 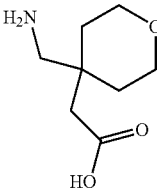<br>2-[4-(aminomethyl)tetrahydro<br>pyran-4-yl]acetic acid | 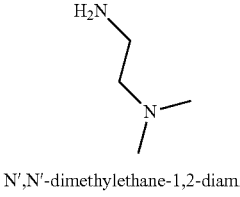<br>N',N'-dimethylethane-1,2-diamine | 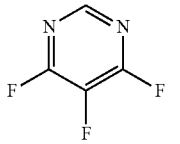<br>4,5,6-trifluoropyrimidine |
| A152 | 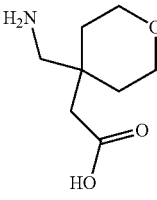<br>2-[4-(aminomethyl)tetrahydro<br>pyran-4-yl]acetic acid | 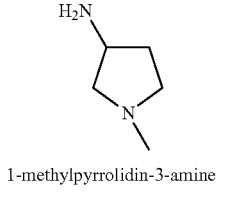<br>1-methylpyrrolidin-3-amine | 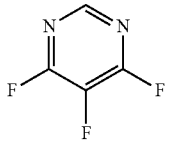<br>4,5,6-trifluoropyrimidine |

| Ex. No. | Amino acid | Amine | Fluorinated aromatic compound |
|---|---|---|---|
| A153 | 2-[4-(aminomethyl)tetrahydro pyran-4-yl]acetic acid | N',N'-dimethylpropane-1,3-diamine | 4,5,6-trifluoropyrimidine |
| A154 | 2-[4-(aminomethyl)tetrahydro pyran-4-yl]acetic acid | tert-butyl 2-aminoacetate | 4,5,6-trifluoropyrimidine |
| A155 | 2-[4-(aminomethyl)tetrahydro pyran-4-yl]acetic acid | tert-butyl 3-aminopropanoate | 4,5,6-trifluoropyrimidine |

Table of $^1$H NMR and MS Data for example compounds.

| Ex. No. | $^1$H NMR or MS Data |
|---|---|
| T1 | $^1$H NMR (300 MHz, CD$_3$OD) δ 7.85 (s, 1H), 7.62 (d, J = 7.7 Hz, 2H), 7.45 (d, J = 8.1 Hz, 2H), 7.39-7.31 (m, 2H), 7.29-7.21 (m, 2H), 4.89 (s, 2H), 4.63 (s, 2H), 4.31 (s, 2H), 3.01-2.85 (m, 1H), 0.88-0.66 (m, 4H). |
| I1 | $^1$H NMR (300 MHz, CDCl$_3$): δ 8.36 (s, 1H), 7.54 (d, J = 8.1 Hz, 2H), 7.40-7.33 (m, 2H), 7.24 (s, 4H), 6.92 (d, J = 3.7 Hz, 1H), 6.83 (d, J = 3.7 Hz, 1H), 5.41 (s, 2H), 5.31 (br s, 2H), 5.15 (s, 2H), 3.56 (s, 2H), 3.08 (dt, J = 3.5, 6.9 Hz, 1H), 1.02-0.86 (m, 4H). |
| X | $^1$H NMR (300 MHz, CDCl$_3$) δ 7.98 (d, J = 1.5 Hz, 1H), 7.59-7.52 (m, 2H), 7.35 (d, J = 7.9 Hz, 2H), 4.9 (s, 1H), 4.85 (s, 2H), 4.52 (d, J = 8.0 Hz, 1H), 3.80 (q, J = 8.9 Hz, 2H), 3.44-3.22 (m, 3H), 2.97-2.81 (m, 1H), 2.23-2.06 (m, 2H), 1.99-1.85 (m, 2H), 1.71-1.52 (m, 1H), 1.40-1.23 (m, 2H), 1.21-1.00 (m, 2H), 0.83-0.65 (m, 4H). |
| A1 | $^1$H NMR (300 MHz, DMSO-d$_6$) δ 8.39 (d, J = 2.3 Hz, 1H), 7.83 (d, J = 1.8 Hz, 1H), 7.70-7.57 (m, 4H), 7.42 (d, J = 7.8 Hz, 2H), 7.18 (d, J = 7.9 Hz, 1H), 4.84 (s, 2H), 4.50 (d, J = 6.1 Hz, 2H), 2.95-2.86 (m, 1H), 2.42 (s, 3H), 0.77-0.64 (m, 4H). |
| A2 | $^1$H NMR (400 MHz, CDCl$_3$) δ 8.02 (d, J = 1.6 Hz, 1H), 7.56 (d, J = 7.9 Hz, 2H), 7.36 (d, J = 7.6 Hz, 4H), 7.28 (d, J = 7.8 Hz, 2H), 5.35 (s, 2H), 5.05 (d, J = 6.7 Hz, 1H), 4.87 (s, 2H), 4.68 (d, J = 5.7 Hz, 2H), 3.59 (s, 2H), 2.90-2.87 (m, 1H), 0.80-0.75 (m, 2H), 0.75-0.70 (m, 2H). |
| A3 | $^1$H NMR (300 MHz, CDCl$_3$) δ 8.05 (d, J = 1.6 Hz, 1H), 7.55 (d, J = 8.1 Hz, 2H), 7.47 (d, J = 8.1 Hz, 2H), 7.37 (d, J = 7.8 Hz, 2H), 7.28 (d, J = 1.9 Hz, 2H), 5.64 (q, J = 7.2 Hz, 1H), 5.34 (s, 2H), 5.07 (s, 1H), 4.69 (d, J = 5.8 Hz, 2H), 3.59 (s, 2H), 2.77-2.63 (m, 1H), 1.79 (d, J = 7.1 Hz, 3H), 0.69-0.50 (m, 3H), 0.33-0.19 (m, 1H). |
| A4 | $^1$H NMR (400 MHz, CDCl$_3$) δ 8.01 (d, J = 1.8 Hz, 1H), 7.56 (d, J = 8.0 Hz, 2H), 7.36-7.29 (m, 4H), 7.24 (s, 2H), 5.24 (s, 3H), 4.95 (s, 1H), 4.80 (s, 2H), 4.64 (d, J = 5.8 Hz, 2H), 4.04-3.93 (m, 1H), 3.86-3.74 (m, |

| Ex. No. | ¹H NMR or MS Data |
|---|---|
| | 2H), 3.68 (q, J = 8.3 Hz, 1H), 3.57 (s, 2H), 2.33-2.20 (m, 1H), 1.98-1.85 (m, 1H). |
| A5 | ¹H NMR (400 MHz, CDCl₃) δ 7.94 (d, J = 1.5 Hz, 1H), 7.56 (d, J = 7.9 Hz, 2H), 7.35 (d, J = 8.0 Hz, 2H), 5.25 (s, 1H), 4.87 (s, 2H), 4.07-3.99 (m, 1H), 3.98-3.89 (m, 1H), 3.79 (d, J = 9.2 Hz, 1H), 3.70-3.61 (m, 3H), 3.18-2.49 (m, 1H), 2.03-1.99 (m, 2H), 0.80 (d, J = 6.6 Hz, 2H), 0.76-0.68 (m, 2H). |
| A6 | ¹H NMR (400 MHz, CDCl₃) δ 8.03 (d, J = 1.7 Hz, 1H), 7.36 (d, J = 7.8 Hz, 2H), 7.33-7.26 (m, 4H), 7.14 (d, J = 8.1 Hz, 2H), 5.33 (s, 2H), 5.04 (s, 1H), 4.81 (s, 2H), 4.68 (d, J = 5.7 Hz, 2H), 3.59 (s, 2H), 2.86 (m, 1H), 0.82-0.66 (m, 4H). |
| A7 | ¹H NMR (300 MHz, DMSO-d₆) δ 7.83 (d, J = 1.8 Hz, 1H), 7.68 (d, J = 8.0 Hz, 2H), 7.43 (d, J = 8.0 Hz, 2H), 7.21-7.12 (m, 1H), 4.83 (s, 2H), 3.60-3.49 (m, 2H), 3.23 (t, J = 6.1 Hz, 2H), 2.96-2.85 (m, 1H), 2.83 (s, 3H), 2.71-2.57 (m, 2H), 1.81-1.65 (m, 3H), 1.28-1.07 (m, 2H), 0.77-0.63 (m, 4H). |
| A8 | ¹H NMR (300 MHz, CD₃OD) δ 7.87 (d, J = 1.5 Hz, 1H), 7.62 (d, J = 7.9 Hz, 2H), 7.45 (d, J = 7.9 Hz, 2H), 4.90 (s, 2H), 3.54 (s, 2H), 3.42-3.34 (m, 2H), 3.01-2.87 (m, 3H), 2.22-2.04 (m, 4H), 0.89-0.67 (m, 4H). |
| A9 | ¹H NMR (300 MHz, CD₃OD) δ 7.87-7.81 (m, 3H), 7.62 (d, J = 8.1 Hz, 2H), 7.55 (d, J = 8.2 Hz, 2H), 7.45 (d, J = 8.1 Hz, 2H), 4.90 (s, 2H), 4.74 (s, 2H), 2.98-2.89 (m, 1H), 2.20-2.09 (m, 1H), 0.86-0.77 (m, 2H), 0.77-0.69 (m, 2H), 0.59-0.44 (m, 4H). |
| A11 | m/z 466 (M + H) |
| A12 | ¹H NMR (300 MHz, CD₃OD) δ 7.85 (s, 1H), 7.59 (d, J = 8.1 Hz, 2H), 7.43 (d, J = 8.0 Hz, 2H), 4.88 (s, 2H), 4.02-3.88 (m, 2H), 3.44-3.27 (m, 4H), 2.95-2.83 (m, 1H), 1.99-1.78 (m, 2H), 1.75-1.63 (m, 2H), 1.40-1.19 (m, 2H), 0.87-0.62 (m, 4H). |
| A13 | ¹H NMR (300 MHz, CDCl₃): δ 8.00 (d, J = 1.6 Hz, 1H), 7.62 (d, J = 8.1 Hz, 2H), 7.55 (d, J = 8.3 Hz, 2H), 7.38 (d, J = 7.9 Hz, 2H), 7.29 (s, 2H), 5.33 (s, 2H), 5.07 (s, 1H), 4.70-4.68 (m, 3H), 3.59 (s, 2H), 3.49 (s, 1H), 2.98 (m, 1H), 1.82-1.64 (m, 1H), 1.36-1.17 (m, 1H), 1.05-0.81 (m, 2H), 0.74-0.68 (m, 3H), 0.54-0.45 (m, 3H), 0.30 (s, 1H). |
| A14 | ¹H NMR (300 MHz, CDCl₃) δ 8.04 (d, J = 1.6 Hz, 1H), 7.61-7.54 (m, 2H), 7.44-7.30 (m, 6H), 5.14 (s, 1H), 4.89 (s, 2H), 4.74-4.67 (m, 2H), 3.76 (s, 2H), 3.03-2.83 (m, 1H), 0.87-0.63 (m, 4H). |
| A15 | ¹H NMR (300 MHz, CDCl₃): δ 8.00 (d, J = 1.8 Hz, 1H), 7.55 (d, J = 8.1 Hz, 2H), 7.38-7.29 (m, 4H), 7.23 (d, J = 1.8 Hz, 2H), 5.34 (s, 2H), 4.95 (s, 1H), 4.83 (d, J = 12.8 Hz, 3H), 4.64 (d, J = 5.8 Hz, 2H), 3.57 (s, 2H), 2.28-1.95 (m, 4H), 1.64 (dq, J = 10.4, 5.9, 5.5 Hz, 2H). |
| A16 | ¹H NMR (300 MHz, CDCl₃): δ 8.06 (s, 1H), 7.61-7.44 (m, 4H), 7.37 (d, J = 7.9 Hz, 2H), 7.29 (s, 2H), 5.92 (t, J = 7.7 Hz, 1H), 5.34 (s, 2H), 5.07 (s, 1H), 4.68 (d, J = 5.8 Hz, 2H), 3.64 (s, 3H), 3.59 (s, 2H), 3.32 (qd, J = 15.6, 7.7 Hz, 2H), 2.72 (d, J = 6.5 Hz, 1H), 0.76-0.49 (m, 3H), 0.29 (s, 1H). |
| A17 | ¹H NMR (300 MHz, CDCl₃): δ 8.11 (d, J = 1.5 Hz, 1H), 7.50 (q, J = 8.5 Hz, 4H), 7.38 (d, J = 7.9 Hz, 2H), 7.29 (s, 2H), 5.56 (d, J = 11.3 Hz, 1H), 5.34 (s, 2H), 5.06 (s, 1H), 4.69 (d, J = 5.8 Hz, 2H), 3.59 (s, 2H), 3.46 (m, 1H), 2.66-2.52 (m, 1H), 2.34-2.08 (m, 2H), 2.09-1.85 (m, 3H), 1.74 (d, J = 9.7 Hz, 1H), 0.62 (d, J = 6.2 Hz, 1H), 0.53-0.38 (m, 2H), 0.05 (d, J = 10.2 Hz, 1H). |
| A18 | ¹H NMR (300 MHz, CD₃OD) δ 7.59 (d, J = 1.5 Hz, 1H), 7.40 (d, J = 7.8 Hz, 2H), 7.25 (d, J = 8.0 Hz, 2H), 7.12-7.00 (m, 4H), 4.76 (s, 2H), 4.38 (s, 2H), 3.28 (s, 2H), 2.62 (s, 2H), 0.98-0.84 (m, 1H), 0.35-0.22 (m, 2H), 0.05-0.01 (m, 2H). |
| A19 | m/z 448 (M + H) |
| A20 | m/z 464 (M + H) |
| A21 | m/z 423 (M + H) |
| A22 | m/z 469 (M + H) |
| A23 | m/z 485 (M + H) |
| A24 | m/z 462 (M + H) |
| A25 | m/z 448 (M + H) |
| A26 | m/z 427 (M + H) |
| A27 | m/z 480 (M + H) |
| A28 | m/z 427 (M + H) |
| A29 | m/z 455 (M + H) |
| A30 | m/z 457 (M + H) |
| A31 | m/z 517 (M + H) |
| A32 | m/z 437 (M + H) |
| A33 | m/z 465 (M + H) |
| A34 | m/z 473 (M + H) |
| A35 | m/z 475 (M + H) |
| A36 | m/z 481 (M + H) |
| A37 | m/z 509 (M + H) |
| A38 | m/z 448 (M + H) |
| A39 | m/z 442 (M + H) |

| Ex. No. | ¹H NMR or MS Data |
|---|---|
| A40 | m/z 417 (M + H) |
| A41 | m/z 418 (M + H) |
| A42 | m/z 406 (M + H) |
| A43 | m/z 453 (M + H) |
| A44 | m/z 475 (M + H) |
| A45 | ¹H NMR (400 MHz, CDCl₃): δ 7.91 (d, J = 1.6 Hz, 1H), 7.58 (d, J = 8.0 Hz, 2H), 7.34 (d, J = 8.0 Hz, 2H), 5.73 (m, 1H), 5.27-5.16 (m, 1H), 4.85 (s, 2H), 4.79 (t, J = 7.1 Hz, 2H), 4.64 (t, J = 6.8 Hz, 2H), 4.00 (d, J = 6.9 Hz, 2H), 3.93-3.85 (m, 2H), 3.75-3.66 (m, 2H), 3.11 (s, 2H), 2.98 (s, 3H), 1.85-1.75 (m, 2H), 1.74-1.63 (m, 2H). |
| A47 | ¹H NMR (300 MHz, DMSO-d₆): δ 7.83 (s, 1H), 7.71-7.53 (m, 5H), 7.41 (br s, 1H), 7.29-7.13 (m, 4H), 7.08 (m, 1H), 6.83 (br s, 1H), 5.53 (m, 1H), 4.57-4.44 (m, 2H), 3.79 (m, 2H), 3.00-2.84 (m, 2H), 2.42 (m, 1H), 1.29 (s, 9H), 0.94 (d, J = 6.2 Hz, 3H), 0.62 (m, 1H), 0.49 (m, 2H), 0.07 (m, 1H). |
| A49 | ¹H NMR (400 MHz, CDCl₃): δ 7.94 (d, J = 1.5 Hz, 1H), 7.55 (d, J = 7.8 Hz, 2H), 7.36 (d, J = 8.3 Hz, 2H), 5.73 (m, 1H), 4.85 (s, 2H), 4.02 (d, J = 6.8 Hz, 2H), 3.91 (ddd, J = 2.9, 9.0, 12.0 Hz, 2H), 3.72 (td, J = 4.5, 12.1 Hz, 2H), 3.15 (s, 2H), 3.01 (s, 3H), 2.88 (dt, J = 2.9, 6.6 Hz, 1H), 1.87-1.79 (m, 2H), 1.76-1.67 (m, 2H), 0.82-0.69 (m, 4H). |
| A52 | ¹H NMR (300 MHz, CD₃OD) δ 8.21 (dd, J = 2.6, 0.6 Hz, 1H), 7.85 (d, J = 1.7 Hz, 1H), 7.78-7.68 (m, 3H), 7.47-7.38 (m, 2H), 7.36-7.23 (m, 4H), 6.54 (dd, J = 2.5, 1.8 Hz, 1H), 4.83 (s, 2H), 4.65 (s, 3H), 4.62 (s, 2H), 3.51 (s, 2H), 3.16 (s, 1.5H), 3.15 (s, 1.5H). NB: peaks at 3.16 ppm and 3.15 ppm are from conformational isomers |
| A53 | ¹H NMR (400 MHz, CDCl₃): δ 8.04 (d, J = 1.0 Hz, 1H), 7.40-7.34 (m, 2H), 7.28 (s, 2H), 7.16 (d, J = 2.4 Hz, 4H), 5.33 (br s, 2H), 5.01 (s, 1H), 4.79 (s, 2H), 4.67 (d, J = 5.9 Hz, 2H), 3.59 (s, 2H), 2.93-2.81 (m, 2H), 1.23 (d, J = 6.8 Hz, 6H), 0.81-0.66 (m, 4H). |
| A54 | ¹H NMR (300 MHz, DMSO-d6): δ 7.83 (d, J = 1.8 Hz, 1H), 7.59-7.49 (m, 1H), 7.40 (br s, 1H), 7.26-7.09 (m, 6H), 6.84 (d, J = 8.8 Hz, 3H), 4.66 (s, 2H), 4.50 (br d, J = 6.2 Hz, 2H), 3.97 (q, J = 7.0 Hz, 2H), 2.77 (m, 1H), 1.30 (t, J = 7.0 Hz, 3H), 0.78-0.59 (m, 4H). |
| A55 | ¹H NMR (400 MHz, CDCl₃): δ 8.03 (d, J = 1.0 Hz, 1H), 7.36 (d, J = 7.8 Hz, 2H), 7.28 (s, 2H), 7.22 (t, J = 7.8 Hz, 1H), 6.86-6.77 (m, 3H), 5.39-5.28 (br s, 2H), 5.01 (s, 1H), 4.79 (s, 2H), 4.67 (d, J = 5.4 Hz, 2H), 3.78 (s, 3H), 3.59 (s, 2H), 2.92-2.86 (m, 1H), 0.79-0.70 (m, 4H). |
| A56 | ¹H NMR (300 MHz, CDCl₃): δ 8.27 (s, 1H), 7.54 (d, J = 8.1 Hz, 2H), 7.34 (d, J = 8.1 Hz, 2H), 6.95 (d, J = 3.3 Hz, 1H), 6.82 (d, J = 3.7 Hz, 1H), 5.95 (br s, 1H), 5.14 (s, 2H), 4.63-4.54 (m, 4H), 4.46 (d, J = 6.2 Hz, 2H), 3.59 (s, 2H), 3.07 (dt, J = 3.1, 6.9 Hz, 1H), 1.00-0.85 (m, 4H). |
| A57 | m/z 570 (M + H) |
| A58 | ¹H NMR (300 MHz, DMSO-d₆) δ 8.47 (d, J = 2.5 Hz, 1H), 7.83 (d, J = 1.9 Hz, 1H), 7.77-7.67 (m, 3H), 7.54-7.39 (m, 3H), 7.25-7.12 (m, 5H), 6.84 (s, 1H), 6.53 (t, J = 2.1 Hz, 1H), 4.80 (s, 2H), 4.51 (d, J = 6.1 Hz, 2H), 3.32 (s, 2H), 3.11 (s, 1.5H), 3.10 (s, 1.5H). NB: Peaks at 3.10 ppm and 3.11 ppm are from conformational isomers |
| A59 | ¹H NMR (300 MHz, CD₃OD) δ 7.85 (d, J = 1.5 Hz, 1H), 7.61 (d, J = 8.2 Hz, 2H), 7.44 (d, J = 8.0 Hz, 2H), 7.33 (d, J = 7.9 Hz, 2H), 7.22 (d, J = 8.0 Hz, 2H), 4.88 (s, 2H), 4.60 (s, 2H), 2.97-2.86 (m, 4H), 0.88-0.65 (m, 4H). |
| A60 | ¹H NMR (300 MHz, CD₃OD) δ 7.85 (d, J = 1.5 Hz, 1H), 7.62 (d, J = 8.1 Hz, 2H), 7.45 (d, J = 8.1 Hz, 2H), 7.35 (d, J = 7.9 Hz, 2H), 7.24 (d, J = 8.0 Hz, 2H), 4.86 (s, 2H), 4.63 (s, 2H), 2.98-2.87 (m, 1H), 0.87-0.75 (m, 2H), 0.75-0.64 (m, 2H). |
| A61 | ¹H NMR (300 MHz, DMSO-d₆) δ 7.81 (d, J = 1.8 Hz, 1H), 7.67 (d, J = 8.0 Hz, 2H), 7.42 (d, J = 8.0 Hz, 2H), 7.09-7.01 (m, 1H), 4.82 (s, 2H), 3.18-3.11 (m, 3H), 2.93-2.83 (m, 1H), 2.79-2.72 (m, 2H), 1.76-1.58 (m, 5H), 1.58-1.43 (m, 1H), 1.03-0.78 (m, 4H), 0.78-0.56 (m, 4H). |
| A62 | ¹H NMR (300 MHz, DMSO-d₆) δ 7.81 (d, J = 1.7 Hz, 1H), 7.67 (d, J = 8.0 Hz, 2H), 7.42 (d, J = 8.0 Hz, 2H), 7.11-7.02 (m, 1H), 4.83 (s, 2H), 3.21-3.11 (m, 2H), 2.96-2.83 (m, 1H), 2.42 (d, J = 6.4 Hz, 2H), 1.85-1.65 (m, 4H), 1.62-1.43 (m, 2H), 1.08-0.84 (m, 5H), 0.77-0.62 (m, 4H). |
| A63 | ¹H NMR (400 MHz, CDCl₃): δ 7.95 (s, 1H), 7.56 (d, J = 8.3 Hz, 2H), 7.36 (d, J = 8.3 Hz, 2H), 7.20 (t, J = 6.6 Hz, 1H), 4.98 (br s, 1H), 4.87 (s, 2H), 3.86-3.74 (m, 2H), 3.74-3.62 (m, 2H), 3.42 (d, J = 6.8 Hz, 2H), 3.05 (d, J = 6.8 Hz, 2H), 2.96-2.83 (m, 4H), 1.70-1.59 (m, 2H), 1.53-1.47 (m, 2H), 0.86-0.77 (m, 2H), 0.73 (br s, 2H). |
| A64 | ¹H NMR (300 MHz, CD₃OD) δ 7.82 (d, J = 1.5 Hz, 1H), 7.68 (d, J = 8.0 Hz, 2H), 7.44 (d, J = 8.2 Hz, 2H), 7.34-7.23 (m, 4H), 4.88 (s, 2H), 4.61 (s, 2H), 3.50 (s, 2H), 2.99-2.89 (m, 1H), 0.88-0.66 (m, 4H). |
| A65 | ¹H NMR (300 MHz, DMSO-d₆) δ 7.84 (d, J = 1.7 Hz, 1H), 7.60-7.52 (m, 1H), 7.45-7.30 (m, 3H), 7.27-7.14 (m, 5H), 6.85 (s, 1H), 4.86 (s, 2H), 4.51 (d, J = 6.2 Hz, 2H), 3.32 (s, 2H), 2.48-2.41 (m, 1H), 0.70-0.59 (m, 4H). |

| Ex. No. | ¹H NMR or MS Data |
|---|---|
| A66 | ¹H NMR (300 MHz, CD₃OD) δ 7.82 (d, J = 1.5 Hz, 1H), 7.44-7.36 (m, 1H), 7.36-7.19 (m, 7H), 4.88 (s, 2H), 4.62 (s, 2H), 3.50 (s, 2H), 2.95-2.83 (m, 1H), 0.84-0.67 (m, 4H). |
| A67 | ¹H NMR (300 MHz, CD₃OD) δ 7.88 (d, J = 1.4 Hz, 1H), 7.35-7.25 (m, 5H), 7.21-7.13 (m, 2H), 4.93 (s, 2H), 4.63 (s, 2H), 3.51 (s, 2H), 2.42-2.34 (m, 1H), 2.33 (s, 3H), 0.73-0.60 (m, 5H). |
| A68 | ¹H NMR (300 MHz, CDCl₃) δ 8.03 (d, J = 1.7 Hz, 1H), 7.37 (d, J = 8.1 Hz, 2H), 7.28 (d, J = 8.1 Hz, 2H), 5.94 (s, 1H), 5.41 (s, 1H), 5.14 (s, 1H), 4.79 (s, 2H), 4.75-4.65 (m, 2H), 4.00 (t, J = 7.4 Hz, 2H), 3.60 (s, 1.5H), 3.15 (s, 1.5H), 3.13 (s, 1H), 2.27 (s, 3H), 1.82 (m, 2H), 0.88 (t, J = 7.4 Hz, 3H). NB: Peaks at 3.15 ppm and 3.13 ppm are from conformational isomers. |
| A69 | ¹H NMR (400 MHz, CDCl₃): δ 7.91 (d, J = 1.0 Hz, 1H), 7.56 (d, J = 7.8 Hz, 2H), 7.35 (d, J = 8.3 Hz, 2H), 5.92 (s, 1H), 5.15 (d, J = 2.9 Hz, 1H), 4.87 (s, 2H), 3.66 (d, J = 11.2 Hz, 2H), 3.49 (d, J = 5.9 Hz, 2H), 3.07 (dt, J = 2.4, 12.0 Hz, 2H), 2.96-2.88 (m, 1H), 2.79 (s, 3H), 1.80 (d, J = 11.7 Hz, 2H), 1.62 (dt, J = 4.9, 12.7 Hz, 2H), 0.85-0.71 (m, 4H). |
| A72 | ¹H NMR (300 MHz, CD₃OD) δ 7.77 (d, J = 1.4 Hz, 1H), 7.51 (d, J = 8.1 Hz, 2H), 7.34 (d, J = 8.1 Hz, 2H), 3.57 (s, 2H), 3.25 (s, 2H), 3.18-3.08 (m, 2H), 3.08-2.94 (m, 2H), 2.89-2.77 (m, 1H), 2.37 (s, 2H), 2.10-1.91 (m, 4H), 0.84-0.75 (m, 1H), 0.75-0.56 (m, 4H). |
| A73 | ¹H NMR (400 MHz, CDCl₃): δ 8.02 (s, 1H), 7.59-7.53 (m, 2H), 7.50-7.43 (m, 2H), 5.62 (q, J = 7.3 Hz, 2H), 4.87 (s, 1H), 3.84 (d, J = 11.7 Hz, 2H), 3.43 (t, J = 6.4 Hz, 2H), 2.78 (s, 3H), 2.73-2.60 (m, 3H), 1.90 (d, J = 11.7 Hz, 2H), 1.78 (d, J = 6.8 Hz, 3H), 1.47-1.32 (m, 2H), 0.75-0.64 (m, 1H), 0.63-0.48 (m, 2H), 0.25 (m, 1H). |
| A74 | ¹H NMR (300 MHz, CDCl₃): δ 8.04 (s, 1H), 7.59-7.52 (m, 2H), 7.50-7.43 (m, 2H), 7.39 (d, J = 8.4 Hz, 2H), 7.25-7.20 (m, 2H), 5.64 (m, 1H), 4.70 (s, 2H), 2.71 (m, 1H), 1.79 (d, J = 7.0 Hz, 3H), 0.69 (m, 1H), 0.60 (m, 2H), 0.27 (m, 1H). |
| A75 | ¹H NMR (300 MHz, CDCl₃): δ 7.98 (s, 1H), 7.55 (d, J = 8.1 Hz, 2H), 7.36 (d, J = 8.1 Hz, 2H), 5.00 (br s, 1H), 4.86 (s, 2H), 4.49 (s, 1H), 4.33 (s, 1H), 3.88-3.76 (m, 2H), 3.76-3.64 (m, 4H), 2.88 (m, 1H), 1.59 (m, 4H), 0.85-0.67 (m, 4H). |
| A76 | ¹H NMR (300 MHz, CD₃OD) δ 7.84 (d, J = 1.6 Hz, 1H), 7.72-7.55 (m, 6H), 7.45 (d, J = 8.1 Hz, 2H), 4.90 (s, 2H), 4.72 (s, 2H), 2.99-2.89 (m, 1H), 2.80 (s, 3H), 0.86-0.67 (m, 4H). |
| A77 | ¹H NMR (300 MHz, DMSO-d₆) δ 7.85 (d, J = 1.7 Hz, 1H), 7.59-7.52 (m, 1H), 7.52-7.47 (m, 2H), 7.42 (s, 1H), 7.35 (dd, J = 8.8, 7.2 Hz, 1H), 7.25-7.15 (m, 4H), 6.85 (s, 1H), 4.94 (s, 2H), 4.51 (d, J = 6.1 Hz, 2H), 3.31 (s, 2H), 2.42-2.31 (m, 1H), 0.71-0.63 (m, 2H), 0.63-0.53 (m, 2H). |
| A78 | ¹H NMR (400 MHz, CDCl₃): δ 8.58 (d, J = 2.0 Hz, 1H), 8.01 (d, J = 1.5 Hz, 1H), 7.69 (dd, J = 2.2, 8.1 Hz, 1H), 7.56 (d, J = 8.3 Hz, 2H), 7.36 (d, J = 7.8 Hz, 2H), 7.24-7.23 (m, 1H), 7.24 (br s, 1H), 7.17 (br s, 1H), 5.33 (br s, 1H), 5.10 (s, 1H), 4.87 (s, 2H), 4.71 (d, J = 6.4 Hz, 2H), 3.74 (s, 2H), 2.90 (dt, J = 2.9, 6.8 Hz, 1H), 0.83-0.75 (m, 2H), 0.71 (d, J = 2.9 Hz, 2H). |
| A79 | ¹H NMR (300 MHz, CDCl₃): δ 7.93 (s, 1H), 7.57 (d, J = 8.1 Hz, 2H), 7.35 (d, J = 8.1 Hz, 2H), 5.14 (m, 1H), 4.90 (s, 2H), 3.89-3.68 (m, 4H), 3.50 (d, J = 7.0 Hz, 2H), 2.94 (tt, J = 3.5, 6.7 Hz, 1H), 2.54 (s, 2H), 1.66-1.48 (m, 4H), 0.89-0.72 (m, 4H). |
| A80 | ¹H NMR (400 MHz, DMSO-d6): δ 8.09 (d, J = 4.4 Hz, 1H), 7.84 (d, J = 1.0 Hz, 1H), 7.68 (d, J = 8.3 Hz, 2H), 7.44 (br d, J = 7.8 Hz, 2H), 7.15 (s, 1H), 4.84 (s, 2H), 3.66-3.53 (m, 4H), 3.50 (d, J = 6.4 Hz, 2H), 2.97-2.86 (m, 1H), 2.59 (d, J = 4.9 Hz, 3H), 2.24 (s, 2H), 1.41 (m, 4H), 0.78-0.64 (m, 4H). |
| A81 | ¹H NMR (300 MHz, CD₃OD) δ 7.85 (s, 1H), 7.59 (d, J = 8.0 Hz, 2H), 7.33-7.21 (m, 6H), 4.57 (s, 2H), 3.49 (s, 2H), 3.21 (s, 3H), 1.61-1.42 (m, 4H). |
| A82 | ¹H NMR (300 MHz, CD₃OD) δ 7.83 (d, J = 1.5 Hz, 1H), 7.62 (d, J = 8.1 Hz, 2H), 7.51-7.42 (m, 4H), 7.38 (d, J = 8.4 Hz, 2H), 4.89 (s, 2H), 4.64 (s, 2H), 2.98-2.87 (m, 1H), 1.77 (s, 3H), 0.87-0.67 (m, 4H). |
| A83 | ¹H NMR (400 MHz, CDCl₃): δ 8.66 (s, 1H), 8.00 (d, J = 1.5 Hz, 1H), 7.77 (d, J = 7.8 Hz, 1H), 7.62 (d, J = 7.8 Hz, 1H), 7.40-7.33 (m, 2H), 7.28 (s, 2H), 5.43-5.29 (br s, 2H), 5.08 (d, J = 2.9 Hz, 1H), 4.89 (s, 2H), 4.68 (d, J = 5.9 Hz, 2H), 3.59 (s, 2H), 2.90 (tdd, J = 3.5, 6.8, 10.1 Hz, 1H), 0.86-0.78 (m, 2H), 0.72 (br s, 2H). |
| A84 | ¹H NMR (300 MHz, CD₃OD) δ 7.91-7.83 (m, 3H), 7.63 (d, J = 8.1 Hz, 2H), 7.53-7.41 (m, 4H), 4.88 (s, 2H), 4.72 (s, 2H), 2.99-2.87 (m, 1H), 0.88-0.69 (m, 4H). |
| A85 | ¹H NMR (300 MHz, DMSO-d6): δ 8.89 (s, 1H), 8.16-8.06 (m, 1H), 7.76 (d, J = 1.8 Hz, 1H), 7.59 (m, 1H), 7.50-7.33 (m, 1H), 7.50-7.33 (m, 1H), 7.20 (q, J = 8.1 Hz, 4H), 6.82 (s, 1H), 4.92 (s, 2H), 4.50 (d, J = 5.9 Hz, 2H), 3.05 (m, 2H), 0.72 (m, 4H). |
| A88 | m/z 497 (M + H) |

| Ex. No. | ¹H NMR or MS Data |
|---|---|
| A89 | ¹H NMR (400 MHz, CDCl₃): δ 8.74 (d, J = 2.0 Hz, 1H), 8.11-8.02 (m, 1H), 8.00-7.94 (m, 2H), 7.56 (d, J = 8.3 Hz, 2H), 7.36 (d, J = 7.8 Hz, 2H), 5.23 (br s, 1H), 4.88 (s, 2H), 4.81 (d, J = 6.4 Hz, 2H), 3.22 (s, 3H), 2.91 (dt, J = 2.9, 6.8 Hz, 1H), 0.84-0.70 (m, 4H). |
| A90 | ¹H NMR (300 MHz, CD₃OD) δ 7.86 (s, 1H), 7.35-7.22 (m, 4H), 5.74 (s, 1H), 4.77 (s, 2H), 4.62 (s, 3H), 4.54-4.40 (m, 1H), 3.50 (s, 2H), 2.85-2.73 (m, 1H), 1.95-1.82 (m, 1H), 1.38 (s, 3H), 1.36 (s, 3H), 0.94-0.76 (m, 4H), 0.76-0.66 (m, 2H), 0.66-0.56 (m, 2H). |
| A91 | ¹H NMR (300 MHz, CD₃OD) δ 7.85 (s, 1H), 7.62 (d, J = 8.0 Hz, 2H), 7.45 (d, J = 8.1 Hz, 2H), 7.32 (d, J = 8.3 Hz, 2H), 7.24 (d, J = 8.0 Hz, 2H), 6.62 (t, J = 53.1 Hz, 1H), 4.87 (s, 2H), 4.61 (s, 2H), 2.97-2.86 (m, 1H), 0.86-0.66 (m, 4H). |
| A92 | m/z 453 (M + H) |
| A93 | ¹H NMR (400 MHz, CDCl₃): δ 8.64 (d, J = 1.5 Hz, 1H), 7.98 (d, J = 1.5 Hz, 1H), 7.73 (dd, J = 2.2, 8.1 Hz, 1H), 7.63 (d, J = 8.3 Hz, 1H), 7.41-7.31 (m, 2H), 7.28 (s, 2H), 5.39 (br s, 2H), 5.10 (d, J = 2.4 Hz, 1H), 4.88 (s, 2H), 4.67 (d, J = 5.9 Hz, 2H), 3.58 (s, 2H), 2.92 (qt, J = 3.5, 6.8 Hz, 1H), 0.87-0.78 (m, 2H), 0.71 (br d, J = 1.5 Hz, 2H). |
| A95 | ¹H NMR (300 MHz, DMSO-d₆) δ 7.82 (s, 1H), 7.67 (d, J = 8.4 Hz, 2H), 7.43 (d, J = 8.2 Hz, 2H), 7.22-6.96 (m, 2H), 6.64 (s, 1H), 4.83 (s, 2H), 3.44-3.35 (m, 1H), 3.31-3.23 (m, 2H), 2.94-2.82 (m, 1H), 2.36 (h, J = 8.4 Hz, 1H), 2.22-2.00 (m, 3H), 1.91-1.64 (m, 2H), 1.47-1.27 (m, 1H), 0.78-0.61 (m, 4H). |
| A96 | ¹H NMR (300 MHz, DMSO-d₆) δ 7.82 (d, J = 1.8 Hz, 1H), 7.67 (d, J = 8.2 Hz, 2H), 7.43 (d, J = 8.1 Hz, 2H), 7.17-7.00 (m, 2H), 6.66 (s, 1H), 4.83 (s, 2H), 3.43-3.38 (m, 1H), 3.31-3.24 (m, 2H), 2.97-2.83 (m, 1H), 2.46-2.31 (m, 1H), 2.16-1.97 (m, 2H), 1.90-1.74 (m, 2H), 0.78-0.61 (m, 4H). |
| A97 | ¹H NMR (300 MHz, CDCl₃): δ 8.46 (d, J = 2.2 Hz, 1H), 8.03 (d, J = 1.5 Hz, 1H), 7.51 (dd, J = 2.2, 8.0 Hz, 1H), 7.42-7.33 (m, 2H), 7.28 (s, 2H), 7.10 (d, J = 8.0 Hz, 1H), 5.33 (br s, 2H), 5.03 (m, 1H), 4.79 (s, 2H), 4.67 (d, J = 5.5 Hz, 2H), 3.59 (s, 2H), 3.04 (td, J = 6.9, 13.9 Hz, 1H), 2.84 (dt, J = 3.1, 6.7 Hz, 1H), 1.29 (d, J = 6.9 Hz, 6H), 0.85-0.69 (m, 4H). |
| A98 | ¹H NMR (300 MHz, DMSO-d₆): δ 8.88 (s, 2H), 7.74 (s, 1H), 7.58 (s, 1H), 7.35 (s, 1H), 7.17-7.07 (m, 4H), 6.77 (s, 1H), 4.79 (s, 2H), 4.44 (d, J = 6.1 Hz, 2H), 3.25 (s, 2H), 3.00-2.90 (m, 1H), 0.72-0.65 (m, 4H). |
| A99 | ¹H NMR (300 MHz, DMSO-d6): δ 8.23-8.09 (m, 1H), 7.83 (d, J = 8.8 Hz, 1H), 7.75 (d, J = 1.5 Hz, 1H), 7.67 (br s, 1H), 7.42 (br s, 1H), 7.20 (q, J = 8.1 Hz, 4H), 6.85 (s, 1H), 5.13 (s, 2H), 4.51 (d, J = 5.9 Hz, 2H), 3.32 (s, 2H), 3.11 (d, J = 2.6 Hz, 1H), 0.75 (d, J = 5.1 Hz, 4H). |
| A100 | ¹H NMR (300 MHz, CD₃OD) δ 8.16 (s, 1H), 7.63 (d, J = 8.1 Hz, 2H), 7.48 (d, J = 8.1 Hz, 2H), 5.01 (s, 2H), 3.11-3.00 (m, 1H), 2.86 (s, 3H), 2.86-2.80 (m, 4H), 2.76-2.62 (m, 1H), 2.10-1.97 (m, 2H), 1.93-1.76 (m, 3H), 0.94-0.84 (m, 2H), 0.84-0.76 (m, 2H). |
| A101 | ¹H NMR (300 MHz, CDCl₃) δ 8.05 (d, J = 1.6 Hz, 1H), 7.64-7.20 (m, 8H), 5.42 (s, 1H), 5.14 (s, 1H), 4.88 (s, 2H), 4.70 (d, J = 5.7 Hz, 2H), 3.60 (s, 2H), 2.98-2.82 (m, 1H), 0.91-0.64 (m, 4H). |
| A102 | ¹H NMR (300 MHz, CDCl₃) δ 8.05 (d, J = 1.6 Hz, 1H), 7.42-7.35 (m, 2H), 7.35-7.25 (m, 3H), 7.23-7.17 (m, 1H), 7.16-7.08 (m, 2H), 5.42 (s, 2H), 5.16 (s, 1H), 4.84 (s, 2H), 4.70 (d, J = 5.7 Hz, 2H), 3.60 (s, 2H), 2.96-2.82 (m, 1H), 0.88-0.66 (m, 4H). |
| A103 | ¹H NMR (300 MHz, DMSO-d₆) δ 8.70 (s, 1H), 7.97 (d, J = 8.4 Hz, 1H), 7.85-7.80 (m, 2H), 7.70-7.62 (m, 1H), 7.42 (s, 1H), 7.20 (q, J = 8.2 Hz, 4H), 6.84 (s, 1H), 5.48 (q, J = 7.0 Hz, 1H), 4.55-4.47 (m, 2H), 3.30 (s, 2H), 2.87-2.77 (m, 1H), 1.78 (d, J = 7.1 Hz, 3H), 0.74-0.55 (m, 3H), 0.24-0.11 (m, 1H). |
| A104 | ¹H NMR (300 MHz, DMSO-d₆) δ 8.90 (d, J = 2.1 Hz, 1H), 8.08 (d, J = 8.0 Hz, 1H), 7.77 (d, J = 1.7 Hz, 1H), 7.70-7.36 (m, 3H), 7.20 (q, J = 8.2 Hz, 4H), 6.84 (s, 1H), 5.46 (q, J = 7.0 Hz, 1H), 4.51 (d, J = 6.0 Hz, 2H), 3.30 (s, 2H), 2.95-2.81 (m, 1H), 1.78 (d, J = 7.1 Hz, 3H), 0.76-0.55 (m, 3H), 0.27 (d, J = 8.8 Hz, 1H). |
| A105 | ¹H NMR (400 MHz, CDCl₃): δ 8.66 (s, 1H), 8.00 (s, 1H), 7.77 (d, J = 8.3 Hz, 1H), 7.62 (d, J = 8.3 Hz, 1H), 7.35 (d, J = 8.3 Hz, 2H), 7.24 (s, 2H), 6.85 (s, 1H), 6.46-6.09 (m, 1H), 5.12 (s, 1H), 4.90 (s, 2H), 4.68 (d, J = 5.9 Hz, 2H), 2.91 (d, J = 2.9 Hz, 1H), 0.88-0.68 (m, 4H). |
| A106 | ¹H NMR (400 MHz, CDCl₃): δ 8.81 (s, 1H), 7.97 (d, J = 1.5 Hz, 1H), 7.84 (dd, J = 2.0, 8.3 Hz, 1H), 7.39-7.29 (m, 3H), 7.24 (s, 2H), 6.68 (br s, 1H), 6.44-6.11 (m, 1H), 5.08 (s, 1H), 4.99 (s, 2H), 4.68 (d, J = 5.9 Hz, 2H), 3.07 (dt, J = 2.9, 6.8 Hz, 1H), 0.85-0.71 (m, 4H). |
| A107 | ¹H NMR (300 MHz, DMSO-d₆) δ 7.99 (s, 1H), 7.64 (d, J = 7.9 Hz, 2H), 7.47-7.30 (m, 4H), 7.22 (q, J = 8.2 Hz, 4H), 6.83 (s, 1H), 5.98 (s, 1H), 4.86 (s, 2H), 4.41 (d, J = 6.0 Hz, 2H), 3.30 (s, 2H), 2.44-2.34 (m, 1H), 0.82-0.71 (m, 2H), 0.63-0.52 (m, 2H). |

-continued

| Ex. No. | ¹H NMR or MS Data |
|---|---|
| A108 | ¹H NMR (400 MHz, CDCl₃): δ 8.81 (s, 1H), 8.73 (s, 1H), 8.08-8.03 (m, 1H), 7.99-7.92 (m, 2H), 7.84 (dd, J = 2.0, 8.3 Hz, 1H), 7.31 (d, J = 7.8 Hz, 1H), 5.25 (br s, 1H), 5.00 (s, 2H), 4.81 (d, J = 6.4 Hz, 2H), 3.22 (s, 3H), 3.13-3.03 (m, 1H), 0.85-0.71 (m, 4H). |
| A109 | ¹H NMR (300 MHz, DMSO-d6): δ 10.54 (s, 1H), 8.13 (s, 1H), 7.85 (s, 1H), 7.73-7.54 (m, 4H), 7.43 (d, J = 8.1 Hz, 2H), 4.85 (s, 2H), 4.52 (d, J = 5.9 Hz, 2H), 3.35 (s, 3H), 2.91 (m, 1H), 0.76-0.65 (m, 4H). |
| A110 | ¹H NMR (400 MHz, CDCl₃): δ 8.73 (s, 1H), 8.66 (s, 1H), 8.05 (d, J = 8.0 Hz, 1H), 7.99-7.92 (m, 2H), 7.77 (d, J = 7.8 Hz, 1H), 7.62 (d, J = 7.8 Hz, 1H), 5.35-5.25 (m, 1H), 4.90 (s, 2H), 4.81 (d, J = 6.4 Hz, 2H), 3.22 (s, 3H), 2.98-2.89 (m, 1H), 0.89-0.82 (m, 2H), 0.77-0.71 (m, 2H). |
| A111 | ¹H NMR (300 MHz, CDCl₃): δ 9.16 (s, 1H), 8.66 (s, 2H), 7.99 (s, 1H), 7.56 (d, J = 8.0 Hz, 2H), 7.35 (d, J = 8.0 Hz, 2H), 5.14 (m, 1H), 4.87 (s, 2H), 4.64 (d, J = 5.8 Hz, 2H), 3.45 (s, 3H), 2.89 (m, 1H), 0.83-0.67 (m, 4H). |
| A112 | ¹H NMR (300 MHz, CDCl₃): δ 8.66 (s, 1H), 8.57 (s, 1H), 7.99 (d, J = 1.5 Hz, 1H), 7.77 (d, J = 8.8 Hz, 1H), 7.69 (dd, J = 2.2, 8.0 Hz, 1H), 7.62 (d, J = 8.0 Hz, 1H), 7.24 (s, 1H), 7.20-7.11 (m, 1H), 5.45-5.28 (m, 1H), 5.17-5.08 (m, 1H), 4.90 (s, 2H), 4.70 (d, J = 6.2 Hz, 3H), 3.74 (s, 2H), 2.96-2.86 (m, 1H), 0.88-0.80 (m, 2H), 0.76-0.69 (m, 2H). |
| A113 | ¹H NMR (400 MHz, CDCl₃): δ 8.81 (s, 1H), 8.57 (s, 1H), 7.96 (s, 1H), 7.84 (d, J = 8.3 Hz, 1H), 7.69 (dd, J = 2.4, 7.8 Hz, 1H), 7.31 (d, J = 8.3 Hz, 1H), 7.24 (s, 1H), 7.19-7.12 (m, 1H), 5.34 (br s, 1H), 5.16-5.06 (m, 1H), 4.99 (s, 2H), 4.70 (d, J = 5.9 Hz, 2H), 3.74 (s, 2H), 3.12-3.02 (m, 1H), 0.85-0.70 (m, 4H). |
| A114 | ¹H NMR (400 MHz, CDCl₃): δ 9.11 (d, J = 2.0 Hz, 1H), 8.66 (s, 1H), 8.20 (dd, J = 2.4, 8.3 Hz, 1H), 7.97 (s, 1H), 7.77 (d, J = 7.8 Hz, 1H), 7.62 (d, J = 7.8 Hz, 1H), 7.55 (d, J = 8.3 Hz, 1H), 5.91 (br s, 1H), 4.94-4.85 (m, 4H), 3.11 (s, 3H), 2.98-2.90 (m, 1H), 0.91-0.81 (m, 2H), 0.78-0.71 (m, 2H). |
| A115 | ¹H NMR (400 MHz, CDCl₃): δ 9.11 (s, 1H), 8.81 (s, 1H), 8.19 (dd, J = 2.4, 8.3 Hz, 1H), 7.95 (s, 1H), 7.84 (dd, J = 2.2, 8.1 Hz, 1H), 7.55 (d, J = 8.3 Hz, 1H), 7.31 (d, J = 8.3 Hz, 1H), 5.89 (br s, 1H), 5 |
| A118 | m/z 430 (M + H) |
| A119 | m/z 410 (M + H) |
| A120 | m/z 460 (M + H) |
| A121 | m/z 430 (M + H) |
| A122 | m/z 464 (M + H) |
| A123 | m/z 438 (M + H) |
| A124 | m/z 446 (M + H) |
| A125 | m/z 464 (M + H) |
| A126 | m/z 448 (M + H) |
| A127 | m/z 483 (M + H) |
| A128 | m/z 444 (M + H) |
| A129 | m/z 441 (M + H) |
| A130 | m/z 489 (M + H) |
| A131 | m/z 457 (M + H) |
| A132 | m/z 468 (M + H) |
| A133 | m/z 526 (M + H) |
| A134 | m/z 469 (M + H) |
| A135 | m/z 426 (M + H) |
| A136 | m/z 426 (M + H) |
| A137 | m/z 429 (M + H) |
| A138 | m/z 408 (M + H) |
| A139 | m/z 440 (M + H) |
| A140 | m/z 461 (M + H) |
| A141 | m/z 397 (M + H) |
| A142 | m/z 542 (M + H) |
| A143 | m/z 474 (M + H) |
| A144 | m/z 481 (M + H) |
| A145 | m/z 452 (M + H) |
| A147 | m/z 509 (M + H) |
| A148 | m/z 454 (M + H) |
| A149 | m/z 490 (M + H) |
| A150 | m/z 427 (M + H) |
| A151 | m/z 553 (M + H) |
| A152 | m/z 565 (M + H) |
| A153 | m/z 567 (M + H) |
| A154 | m/z 540 (M + H) |
| A155 | m/z 554 (M + H) |
| A156 | m/z 470 (M + H) |
| A157 | m/z 433 (M + H) |
| A158 | m/z 488 (M + H) |
| A159 | m/z 433 (M + H) |
| A160 | m/z 474 (M + H) |
| A161 | m/z 473 (M + H) |

-continued

| Ex. No. | ¹H NMR or MS Data |
|---|---|
| A162 | m/z 477 (M + H) |
| A163 | m/z 431 (M + H) |
| A164 | ¹H NMR (300 MHz, CDCl3) δ = 8.42 (s, 1H), 7.56 (d, J = 8.4 Hz, 2H), 7.41 (d, J = 8.1 Hz, 2H), 7.32-7.27 (m, 4H), 6.91 (d, J = 3.3 Hz, 1H), 6.37 (d, J = 2.9 Hz, 1H), 5.46 (s, 2H), 5.41-5.20 (m, 3H), 4.86 (d, J = 5.5 Hz, 2H), 3.59 (s, 2H) |
| A165 | m/z 528 (M + H) |
| A166 | m/z 489 (M + H) |
| A167 | m/z 492 (M + H) |
| A168 | m/z 490 (M + H) |
| A169 | m/z 514 (M + H) |
| A170 | m/z 475 (M + H) |
| A171 | m/z 528 (M + H) |
| A172 | m/z 500 (M + H) |
| A173 | m/z 475 (M + H) |
| A174 | m/z 500 (M + H) |
| A175 | m/z 514 (M + H) |
| A176 | m/z 475 (M + H) |
| A177 | m/z 475 (M + H) |
| A178 | m/z 475 (M + H) |
| A179 | m/z 457 (M + H) |
| A180 | m/z 494 (M + H) |
| A181 | m/z 503 (M + H) |
| A182 | m/z 475 (M + H) |
| A183 | m/z 469 (M + H) |
| A184 | m/z 483 (M + H) |
| A185 | m/z 497 (M + H) |

Biological Evaluation

The activity of the compounds was evaluated using a Fluorescence Polarization (FP) Assay and, RORγ Reporter assay (also referred to as Gal4 assay). The FP assay is an in vitro assay monitoring binding within the ligand binding pocket. The RORγ and the Th17 assays (another suitable assay) are both cell-based assays monitoring functional activity of the compound assayed.

Compounds disclosed herein have also been evaluated in two different mouse in vivo disease models: Experimental Autoimmune Encephalomyelitis (EAE) model (an animal model for multiple sclerosis), and Collagen-induced Arthritis (CIA) model (an animal model for rheumatoid arthritis).

Fluorescence Polarization (FP) Assay

Figure 2:
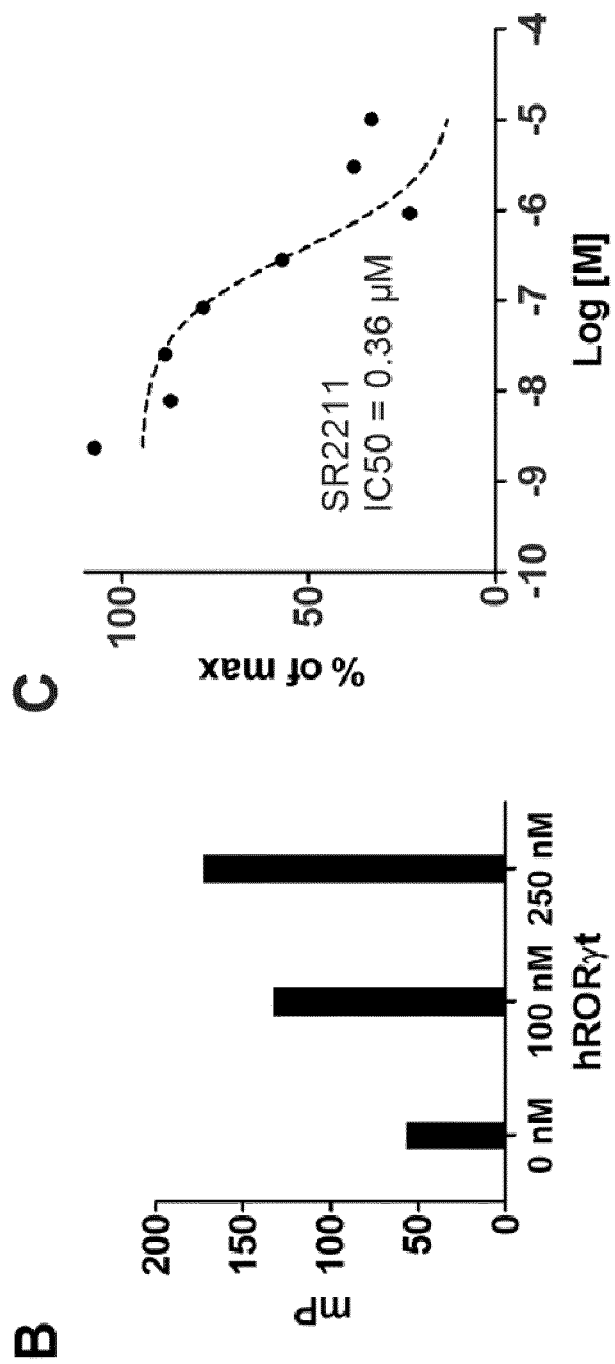
FIG. 2 illustrates the characterisation of the Fluorescence Polarization (FP) assay with the TAMRA-labelled probe used in the FP assay

A buffer containing 10 mM Hepes, 150 mM NaCl, 1 mM DTT, 0.05% Pluronic F-127 detergent (all from Sigma), and 100 nM human RORγt (Ligand Binding Domain obtained from Crelux (Planegg, Germany), batch no PC5032-1) was complemented with 1 μl test compounds diluted in 100% DMSO. The total volume was 25 μl, in a black Perkin Elmer OptiPlate. As negative control, 1 μl DMSO was used. Samples were incubated at room temperature for 30 min, followed by addition 5 μl of probe diluted in assay buffer to a concentration of 125 nM (final concentration of probe is 25 nM). The probe is a fluorescently labeled (TAMRA) RORγt ligand identified by Nuevolution with a total molecular weight of 910 g/mole as shown in Graph A in FIG. 1. Graph (B) in FIG. 2 shows the polarization signal rises with increasing concentration of human RORγt (LBD), using 50 nM TAMRA-labelled probe concentration. Graph (C) of FIG. 2 shows the RORγt inhibitor SR2211 (1,1,1,3,3,3-hexafluoro-2-(2-fluoro-4'-((4-(pyridin-4-ylmethyl)piperazin-1-yl)methyl)-[1,1'-biphenyl]-4-yl)propan-2-ol; see Kumar et al, ACS Chem. Biol., 2012, 7 (4), pp 672-677) inhibits the probe from binding RORγt with an IC50 of 0.36 μM, which is close to the value reported in the literature. The plate was incubated for 10 min at room temperature and fluorescence polarization was read using an Envision 2102 plate reader (Perkin Elmer) with the TAMRA FP optical module installed.

Th17 Assay (Another Suitable Assay)

Human peripheral blood mononuclear cells (PBMCs) were isolated from buffy coats of healthy human volunteers using the Ficoll paque PLUS kit (GE Healthcare, cat no 17-1440-02), as instructed by the manufacturer. Naive CD4+ T cells were isolated with Naive CD4+ T cell kit, human (Milteny Biotec, cat no 130-094-131). The following modifications were made to the manufacturer's protocol: 1) Incubation with Biotin-Antibody Cocktail and Anti-Biotin MicroBeads was prolonged to 30 minutes, and 2) Cells were washed with 40 mL of Miltenyi buffer. Differentiation of Th17 cells in anti-CD3 (BD Pharmingen, 5 μg/ml) coated 96-well plates (400,000 cells/well, 160 μl RPMI 1640+10% Fetal Bovine Serum) containing 5 μg/ml anti-CD28 (BD Pharmingen), 10 ng/ml IL-2 (R&D Systems), 2.5 ng/ml TGFβ-1 (R&D Systems), 20 ng/ml IL-10 (R&D Systems), 20 ng/ml IL-6 (R&D Systems), 30 ng/ml IL-23 (R&D Systems), 2.5 μg/ml anti-IL-4 (R&D Systems) and 1 μg/ml anti-IFNγ (R&D Systems) and with test compound during the entire differentiation (or vehicle, 0.1% DMSO for control). Test compounds were tested in triplicates, diluted 1000-fold in medium (final DMSO concentration is 0.1%). Incubated for seven days at 37° C., 5% $CO_2$, 95% humidity, and 2-fluoro-4'-[[4-(4-pyridinylmethyl)-1-piperazinyl]methyl]-α,α-bis(trifluoromethyl)-[1,1'-biphenyl]-4-methanol (SR2211 Calbiochem, Cat. No. 557353) was used as positive control. As negative control, cells were differentiated into Th0 using 5 μg/ml anti-CD28 (BD Pharmingen), 10 ng/ml IL-2 (R&D Systems), 2 μg/ml anti-IL4 (R&D Systems) and 2 μg/ml anti-IFNγ (R&D Systems) are negative control. IL-17 levels in supernatants were measured with ELISA (R&D Systems).

RORγ Reporter Assay (Gal4)

Cell-based RORγ functional assays were performed using a commercially available assay product (INDIGO Biosciences, State College, Pa., USA; product # IB04001). The RORγ reporter cells are HEK293t cells transfected with one vector that provides high level constitutive expression of a hybrid protein comprised of the yeast Gal4-DNA binding domain fused to the ligand binding domain of human RORγ, and a second vector comprising the firefly luciferase cDNA functionally linked to the upstream activation sequence (UAS) of yeast Gal4. A suspension of RORγ Reporter Cells was prepared using the protocol and culture medium provided in the kit product, and 100 µl of the Reporter Cell suspension was then dispensed into wells of a white, collagen-treated, 96-well assay plate. Concentrated stocks of test compounds were prepared in DMSO, then further diluted using media provided in the kit to generate '2×-concentration' treatment media. 100 µl of medium for each respective treatment concentration dispensed into triplicate assay wells, thereby combining with the reporter cells. All media formulations contained 10% charcoal stripped Fetal Bovine Serum, but are otherwise proprietary to INDIGO Biosciences. Final treatment concentrations for each test compound were 1,000 nM and 100 nM, each with 0.1% residual DMSO. Separate control treatments were media supplemented with vehicle only (0.1% DMSO) to determine the constitutive level of RORγ activity in the reporter cells, and the reference inverse-agonist ursolic acid (f.c. 6,000 nM to 8.2 nM in 3-fold decrements) to establish a positive control inverse-agonist dose response. Assay plates were placed in a 37° C., 5% $CO_2$, 85% humidity incubator for 24 hour. Treatment media were then discarded, 100 µl of luciferase detection reagent was added to each well, and relative light units (RLUs) were quantified from each assay well using a plate reading luminometer. Values of average RLU+/−standard deviation were computed for all treatment sets, followed by the calculations of fold-reduction: [Average $RLU_{Vehicle}$/Average $RLU_{Test\ Cmpd}$]. Percent-reduction of RORγ activity in response to respective test compound treatments was calculated: [100*(1−[Ave $RLU_{Test\ Cmpd}$/Ave $RLU_{Vehicle}$)] where the theoretical minimum reduction (0% reduction) derives from Vehicle treatment only, no treatment compound. In some aspects it may be of interest to provide compounds with selective modulation of RORγ for example compounds that are selective to RORγ over RORα, compounds that are selective for RORγ versus RORPβ, and compounds that are selective for RORγ versus BOTH RORα and RORPβ. It may also be of interest to provide compounds that are selective for RORγ versus further nuclear hormone receptors such as CAR1, FXR, GR, LXRα, LXRβ, PPARα, PXR, RARα, RXRα, TRα, VDR. It is apparent to those skilled in the art that these nuclear hormone receptors are merely examples, and that selectivity against other nuclear receptors may also be of interest. It may for example be of interest to provide compounds that modulate RORγ and one or more further nuclear hormone receptors, as well as compounds that modulate both RORγ and RORα, or RORγ and RORβ. It may also be of interest to provide compounds that modulate RORγ and BOTH RORα and RORP, as well as compounds that modulate both RORγ and one or more further nuclear hormone receptors such as CAR1, FXR, GR, LXRα, LXRβ, PPARα, PXR, RARα, RXRα, TRα, VDR. It is apparent to those skilled in the art that these nuclear hormone receptors are merely examples, and that modulation of even other nuclear receptors may also be of interest. By substituting the ligand binding domain of another nuclear hormone receptor for the ligand binding domain of RORγ, the reporter assay (Gal4) may be modified to provide activity data for compounds against said other nuclear hormone receptor. Those skilled in the art know how to accomplish such modification. By comparing activity against RORγ to activity against another nuclear hormone receptor in this assay, the selectivity of a compound towards RORγ versus said other nuclear hormone receptor can be established. A compound may be said to be selective for RORγ versus another nuclear hormone receptor if the activity of the compound against RORγ is greater than 5, 10, 20, or 100 fold higher for RORγ than for said other nuclear receptor. The compound(s) or pharmaceutical composition(s) described herein may modulate the activity of an RORγ receptor to a larger extent than it modulates the activity of RORα and/or RORβ receptors.

The results of the Fluorescence Polarization (FP) Assay, and RORγ Reporter (Gal4) Assay are shown in Tables 2-4 below.

TABLE 2

Activity Data of Example Compounds obtained from the Fluorescence Polarization (FP) Assay.

| Example. No. | FP activity range (nM) |
|---|---|
| T1 | <500 |
| x | <500 |
| I1 | <500 |
| A1 | <1000 |
| A2 | <500 |
| A3 | <500 |
| A4 | <2000 |
| A5 | <1000 |
| A6 | <500 |
| A7 | <500 |
| A8 | <500 |
| A9 | <500 |
| A11 | <500 |
| A12 | <1000 |
| A13 | <500 |
| A14 | <500 |
| A15 | <500 |
| A16 | <500 |
| A17 | <2000 |
| A18 | <500 |
| A19 | <500 |
| A20 | <2000 |
| A21 | <1000 |
| A22 | <500 |
| A23 | <500 |
| A24 | <500 |
| A25 | <500 |
| A26 | <500 |
| A27 | <1000 |
| A28 | <1000 |
| A29 | <500 |
| A30 | <500 |
| A31 | <500 |
| A32 | <500 |
| A33 | <500 |
| A34 | <500 |
| A35 | <500 |
| A36 | <500 |
| A37 | <500 |
| A38 | <500 |
| A39 | <500 |
| A40 | <1000 |
| A41 | <500 |
| A42 | <500 |
| A43 | <1000 |
| A44 | <500 |
| A45 | <2000 |
| A47 | <10000 |
| A49 | <500 |
| A52 | <500 |
| A53 | <500 |
| A54 | <500 |
| A55 | <500 |
| A56 | <500 |
| A57 | <500 |

TABLE 2-continued

Activity Data of Example Compounds obtained from the Fluorescence Polarization (FP) Assay.

| Example. No. | FP activity range (nM) |
| --- | --- |
| A58 | <500 |
| A59 | <500 |
| A60 | <500 |
| A61 | <500 |
| A62 | <500 |
| A63 | <500 |
| A64 | <500 |
| A65 | <500 |
| A66 | <500 |
| A67 | <500 |
| A68 | <500 |
| A69 | <500 |
| A72 | <10000 |
| A73 | <500 |
| A74 | <500 |
| A75 | <500 |
| A76 | <500 |
| A77 | <500 |
| A78 | <500 |
| A79 | <1000 |
| A80 | <500 |
| A81 | <500 |
| A82 | <1000 |
| A83 | <500 |
| A84 | <500 |
| A85 | <500 |
| A88 | <500 |
| A89 | <500 |
| A90 | <500 |
| A91 | <500 |
| A92 | <10000 |
| A93 | <2000 |
| A95 | <1000 |
| A96 | <10000 |
| A97 | <500 |
| A98 | <500 |
| A99 | <10000 |
| A100 | <10000 |
| A101 | <500 |
| A102 | <500 |
| A103 | <1000 |
| A104 | <1000 |
| A105 | <10000 |
| A106 | <10000 |
| A107 | <1000 |
| A108 | <2000 |
| A109 | <500 |
| A110 | <2000 |
| A111 | <1000 |
| A112 | <2000 |
| A113 | <10000 |
| A114 | <500 |
| A115 | <500 |
| A118 | <500 |
| A119 | <2000 |
| A120 | <500 |
| A121 | <500 |
| A122 | <500 |
| A123 | <10000 |
| A124 | <500 |
| A125 | <500 |
| A126 | <500 |
| A127 | <500 |
| A128 | <500 |
| A129 | <500 |
| A130 | <500 |
| A131 | <500 |
| A132 | <10000 |
| A133 | <2000 |
| A134 | <2000 |
| A135 | <10000 |
| A136 | <2000 |
| A137 | <500 |
| A138 | <500 |
| A139 | <2000 |
| A140 | <10000 |
| A141 | <2000 |
| A142 | <500 |
| A143 | <500 |
| A144 | <10000 |
| A145 | <500 |
| A147 | <500 |
| A148 | <500 |
| A149 | <500 |
| A150 | <2000 |
| A151 | <1000 |
| A152 | <10000 |
| A153 | <10000 |
| A154 | <2000 |
| A155 | <1000 |
| A156 | <500 |
| A157 | <500 |
| A158 | <500 |
| A159 | <500 |
| A160 | <500 |
| A161 | <500 |
| A162 | <500 |
| A163 | <500 |
| A164 | <1000 |
| A165 | <500 |
| A166 | <10000 |
| A167 | <500 |
| A168 | <500 |
| A169 | <500 |
| A170 | <500 |
| A171 | <500 |
| A172 | <2000 |
| A173 | <10000 |
| A174 | <500 |
| A175 | <500 |
| A176 | <500 |
| A177 | <2000 |
| A178 | <500 |
| A179 | <500 |
| A180 | <10000 |
| A181 | <500 |
| A182 | <10000 |
| A183 | <2000 |
| A184 | <10000 |
| A185 | <10000 |

TABLE 3

Activity Data of Example Compounds obtained from the RORγ Reporter Assay (Gal4) at 1 μM.

| Example. No. | Gal4 activity range @ 1 μM (% inhibition) |
| --- | --- |
| T1 | >80 |
| x | >50 |
| I1 | >80 |
| A1 | >80 |
| A2 | >80 |
| A3 | >80 |
| A4 | >50 |
| A5 | >80 |
| A6 | >80 |
| A7 | >80 |
| A8 | >80 |
| A9 | >80 |
| A11 | >80 |
| A12 | >80 |
| A13 | >80 |
| A14 | >80 |
| A15 | >80 |
| A16 | >20 |

TABLE 3-continued

Activity Data of Example Compounds obtained from the RORγ Reporter Assay (Gal4) at 1 µM.

| Example. No. | Gal4 activity range @ 1 µM (% inhibition) |
|---|---|
| A17 | >50 |
| A18 | >80 |
| A19 | >80 |
| A20 | >50 |
| A42 | >50 |
| A49 | >80 |
| A52 | >50 |
| A53 | >80 |
| A54 | >80 |
| A55 | >0 |
| A56 | >80 |
| A57 | >80 |
| A58 | >80 |
| A59 | >80 |
| A60 | >80 |
| A61 | >80 |
| A62 | >80 |
| A63 | >80 |
| A64 | >80 |
| A65 | >50 |
| A66 | >50 |
| A67 | >50 |
| A68 | >50 |
| A73 | >80 |
| A74 | >50 |
| A75 | >80 |
| A76 | >80 |
| A77 | >50 |
| A78 | >80 |
| A79 | >20 |
| A80 | >80 |
| A81 | >80 |
| A82 | >80 |
| A83 | >80 |
| A85 | >80 |
| A88 | >50 |
| A89 | >80 |
| A90 | >0 |
| A91 | >80 |
| A95 | >80 |
| A97 | >80 |
| A98 | >80 |
| A101 | >50 |
| A102 | >80 |
| A103 | >80 |
| A104 | >80 |
| A107 | >50 |
| A108 | >80 |
| A109 | >80 |
| A110 | >50 |
| A120 | >80 |
| A124 | >20 |
| A125 | >50 |
| A138 | >20 |
| A142 | >50 |
| A143 | >80 |
| A145 | >50 |
| A147 | >80 |
| A148 | >20 |
| A149 | >20 |
| A150 | >20 |
| A151 | >50 |
| A164 | >50 |
| A165 | >80 |
| A167 | >80 |
| A168 | >80 |
| A169 | >80 |
| A170 | >50 |
| A171 | >80 |
| A172 | >80 |
| A174 | >80 |
| A175 | >80 |
| A176 | >50 |
| A178 | >20 |

TABLE 3-continued

Activity Data of Example Compounds obtained from the RORγ Reporter Assay (Gal4) at 1 µM.

| Example. No. | Gal4 activity range @ 1 µM (% inhibition) |
|---|---|
| A179 | >80 |
| A181 | >80 |

TABLE 4

Activity Data of Example Compounds obtained from the RORγ Reporter Assay (Gal4) at 0.1 µM.

| Example. No. | Gal4 activity range @ 0.1 µM (% inhibition) |
|---|---|
| T1 | >50 |
| x | >20 |
| I1 | >80 |
| A1 | >20 |
| A2 | >80 |
| A3 | >50 |
| A4 | >0 |
| A5 | >20 |
| A6 | >80 |
| A7 | >80 |
| A8 | >50 |
| A9 | >20 |
| A11 | >50 |
| A12 | >20 |
| A13 | >20 |
| A14 | >50 |
| A15 | >20 |
| A16 | >0 |
| A17 | >20 |
| A18 | >50 |
| A19 | >20 |
| A20 | >20 |
| A42 | >20 |
| A49 | >80 |
| A52 | >0 |
| A53 | >80 |
| A54 | >50 |
| A56 | >80 |
| A57 | >50 |
| A58 | >20 |
| A59 | >80 |
| A60 | >0 |
| A61 | >20 |
| A62 | >80 |
| A63 | >80 |
| A64 | >50 |
| A65 | >20 |
| A66 | >20 |
| A67 | >20 |
| A68 | >0 |
| A73 | >80 |
| A74 | >0 |
| A75 | >80 |
| A76 | >80 |
| A77 | >20 |
| A78 | >50 |
| A80 | >20 |
| A81 | >50 |
| A82 | >20 |
| A83 | >50 |
| A85 | >50 |
| A88 | >0 |
| A89 | >80 |
| A91 | >80 |
| A95 | >20 |
| A97 | >50 |
| A98 | >50 |
| A101 | >50 |
| A102 | >80 |
| A103 | >0 |

TABLE 4-continued

Activity Data of Example Compounds obtained from the RORγ Reporter Assay (Gal4) at 0.1 μM.

| Example. No. | Gal4 activity range @ 0.1 μM (% inhibition) |
|---|---|
| A104 | >50 |
| A107 | >0 |
| A108 | >20 |
| A109 | >0 |
| A110 | >0 |
| A120 | >20 |
| A124 | >0 |
| A125 | >0 |
| A138 | >0 |
| A142 | >0 |
| A143 | >20 |
| A145 | >0 |
| A147 | >50 |
| A148 | >0 |
| A151 | >0 |
| A164 | >20 |
| A165 | >50 |
| A167 | >50 |
| A168 | >50 |
| A169 | >80 |
| A170 | >20 |
| A171 | >80 |
| A172 | >20 |
| A174 | >20 |
| A175 | >50 |
| A176 | >0 |
| A178 | >0 |
| A179 | >20 |
| A181 | >0 |

As can be seen from the tables above, the compounds were found to show beneficial activity across the assays.

According to an embodiment, compounds having inhibition values of greater than 80% in the RORγ Reporter Assay (Gal4) are disclosed herein. According to an embodiment the compounds have inhibition values of greater than 80% in a RORγ Reporter Assay (Gal4) and a FP activity range less than 1000 nM, such as less than 500 nM.

According to an embodiment the compounds are having inhibition values of greater than 50% in a RORγ Reporter Assay (Gal4). According to an embodiment the compounds have inhibition values of greater than 50% in a RORγ Reporter Assay (Gal4), and a FP activity range less than 2000 nM, such as less than 1000 nM, such as less than 500 nM.

According to an embodiment the compounds are having inhibition values of greater than 20% in a RORγ Reporter Assay (Gal4). According to an embodiment the compounds have inhibition values of greater than 20% in a RORγ Reporter Assay (Gal4), and a FP activity range less than 2000 nM, such as less than 1000 nM, such as less than 500 nM.

According to an embodiment the compounds are having inhibition values of greater than 50% in a RORγ Reporter Assay (Gal4) at 1 μM and inhibition values of greater than 20% in a RORγ Reporter Assay (Gal4) at 0.1 μM. According to an embodiment the compounds are having inhibition values of greater than 50% in a RORγ Reporter Assay (Gal4) at 1 μM and inhibition values of greater than 20% in a RORγ Reporter Assay (Gal4) at 0.1 μM, and a FP activity range less than 2000 nM, such as less than 1000 nM, such as less than 500 nM.

Experimental Autoimmune Encephalomyelitis (EAE) Study

EAE is an animal model for multiple sclerosis used to evaluate the efficacy of test compounds. EAE was induced at WuXi AppTec (Shanghai) in female C57BL/6 mice obtained from SLAC Laboratories, Shanghai by injection of 100 μl (100 μg MOG$_{35-55}$ peptide in complete Freund's adjuvant containing 200 μg M. tuberculosis/mouse) emulsion (with a 25-G needle) subcutaneously in the shaved back of the mouse. Each mouse was also given 200 ng PTX in 200 μl of PBS by intraperitoneal injection at 0 and 48 hours after immunization. For treatment, compound or vehicle (2% DMSO, 10% HP-β-CD in MilliQ water) was given orally twice daily at various doses selected from 3, 10, and 30 mg/kg, beginning at the day of EAE induction. Treatment lasted for 25 days, and the animals were scored daily for EAE symptoms using the following scoring system: 0, Normal mouse; no overt signs of disease; 1, Limp tail or hind limb weakness but not both; 2 Limp tail and hind limb weakness; 3 Partial hind limb paralysis; 4 Complete hind limb paralysis; 5 Moribund state; death by EAE: sacrifice for humane reasons. The clinical score can be expressed as the mean score for each treatment group+/−S.E.M.

Results: Example A7 was tested in the EAE study at 30 mg/kg. Example A7 was shown to delay onset and significantly lower the clinical score.

Collagen-Induced Arthritis (CIA) Study

Collagen-induced arthritis is an animal model of rheumatoid arthritis used to evaluate the efficacy of test compounds. CIA was induced at Washington Biotechnology Inc. (Baltimore) in male DBA/1J mice (Jackson Laboratories) by subcutaneous injection at the base of the tail with 50 μl of a bovine collagen/complete Freund's adjuvant emulsion. After 21 days, the mice were further boosted by a further subcutaneous injection of 50 μl of a collagen/incomplete Freund's adjuvant emulsion. For treatment, compound or vehicle (2% DMSO, 10% HP-β-CD in MilliQ water) was given orally twice daily at various doses selected from 3, 10, 30 mg/kg, beginning at the day of CIA induction (Prophylactic setting), or after disease initiation (at day 27, therapeutic setting). Treatment lasted until day 41, and the animals were scored three times weekly. Each paw was scored and the sum of all four scores was recorded as the Arthritic Index (AI). The maximum possible AI was 16.0=no visible effects of arthritis; 1=edema and/or erythema of one digit; 2=edema and/or erythema of 2 joints; 3=edema and/or erythema of more than 2 joints; 4=severe arthritis of the entire paw and digits including limb deformation and ankylosis of the joint. The Arthritis Index for each treatment can be expressed as the mean score for each treatment group+/−S.E.M.

Results: Example A7 was tested in the CIA study at 30 mg/kg in therapeutic setting. Example A7 was shown to decrease rate of disease development and significantly reduce disease severity.

In summary, compounds disclosed herein have been found to at least modulate the activity of RORγ. Additionally it has been found that compounds disclosed herein have in vivo usefulness, and could consequently be useful in treating inflammatory, metabolic and autoimmune diseases.

The invention claimed is:
1. A compound of Formula (I)

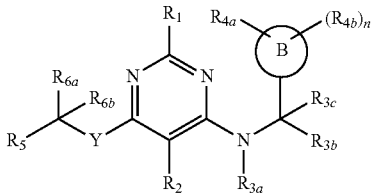

Formula (I)

or a pharmaceutically acceptable salt thereof, wherein:
Y is NR;
R is hydrogen or substituted or unsubstituted $C_{1-4}$ alkyl;
$R_1$ is hydrogen, or substituted or unsubstituted $C_{1-4}$ alkyl;
$R_2$ is halogen;
$R_{3a}$ is selected from the group consisting of $C_{1-4}$ alkyl, $C_{1-4}$ alkylene-$C_{3-6}$ cycloalkyl, $C_{1-4}$ alkylene-$C_{3-6}$-heteroalicyclyl, $C_{3-6}$ cycloalkyl, and $C_{3-5}$ heteroalicyclyl, any of which may be substituted or unsubstituted;
$R_{3b}$ is hydrogen and $R_{3c}$ is selected from the group consisting of hydrogen, substituted or unsubstituted $C_{1-4}$ alkyl, and substituted or unsubstituted $C_{3-6}$ cycloalkyl;
$R_{4a}$ is selected from the group consisting of hydrogen, halogen, —OH, —CN, substituted or unsubstituted $C_{1-6}$ alkyl, substituted or unsubstituted $C_1$-$C_6$ alkoxy, substituted or unsubstituted $C_{2-6}$ alkenyl, substituted or unsubstituted aryl, substituted or unsubstituted aryl-$C_{1-6}$ alkyl, substituted or unsubstituted $C_3$-$C_6$ cycloalkyl, substituted or unsubstituted heteroaryl, and substituted or unsubstituted heteroaryl-$C_{1-6}$ alkyl;
$R_{4b}$ is selected from the group consisting of hydrogen, oxo, halogen, —OH, substituted or unsubstituted $C_{1-4}$ alkyl, substituted or unsubstituted $C_{1-4}$ alkoxy, and —C(=O)$R_{10}$; or
$R_5$ is —(CR$_8$R$_9$)p-CR$_{13}$R$_{14}$R$_{15}$;
n is an integer selected from the group consisting of 0, 1, 2, 3 and 4;
p is an integer selected from the group consisting of 0, 1, and 2;
$R_{6a}$ is selected from the group consisting of hydrogen, halogen, $C_{1-6}$ alkyl, $C_{1-6}$ haloalkyl, $C_{1-6}$ hydroxyalkyl $C_{1-6}$ alkoxy, $C_{1-6}$ haloalkoxy and substituted or unsubstituted aryl,
$R_{6b}$ is selected from the group consisting of hydrogen, substituted or unsubstituted $C_{1-6}$ alkyl, substituted or unsubstituted $C_{1-6}$ alkoxy, substituted or unsubstituted $C_{3-8}$ cycloalkyl, substituted or unsubstituted aryl-$C_{1-6}$ alkyl, substituted or unsubstituted $C_{2-9}$ heteroalicyclyl-$C_{1-6}$ alkyl, substituted or unsubstituted heteroaryl, and substituted or unsubstituted aryl, or
$R_{6a}$ and $R_{6b}$ are taken together to form an oxo group or taken together with the carbon to which they are attached form a ring system selected from substituted or unsubstituted $C_{3-6}$ cycloalkyl, and substituted or unsubstituted $C_{2-9}$ heteroalicyclyl, or $R_{6a}$ and $R_{13}$ are taken together to form a ring system selected from substituted or unsubstituted $C_{3-6}$ cycloalkyl, and substituted or unsubstituted $C_{2-5}$ heteroalicyclyl;
$R_7$, $R_8$, and $R_9$ are independently selected from the group consisting of hydrogen, substituted or unsubstituted $C_{1-6}$ alkyl, substituted or unsubstituted $C_{3-6}$ cycloalkyl, substituted or unsubstituted $C_{2-9}$ heteroalicyclyl; and substituted or unsubstituted aryl;
$R_{10}$ is selected from the group consisting of substituted or unsubstituted $C_{1-6}$ alkyl, substituted or unsubstituted $C_{1-6}$ alkoxy, —OH, —NH$_2$, —NH($C_{1-6}$ alkyl), —N($C_{1-6}$ alkyl)$_2$, and substituted or unsubstituted $C_{3-7}$ cycloalkyl;
$R_{13}$ is absent, or selected from the group consisting of hydrogen, fluorine, —CN, —OH, substituted or unsubstituted $C_{1-6}$ alkyl, substituted or unsubstituted $C_{2-6}$ alkenyl, substituted or unsubstituted $C_{1-6}$ alkoxy, substituted or unsubstituted $C_{3-8}$ cycloalkyl, substituted or unsubstituted $C_{3-8}$ cycloalkenyl, and —(CR$_8$R$_9$)p-C(=O)OR$_7$, —(CR$_8$R$_9$)p-SO$_2$R$_7$, and —(CR$_8$R$_9$)p-C(=O)NR$_8$R$_9$, and when $R_{13}$ is C(=O)NR$_8$R$_9$, $R_8$ and $R_9$ are as defined above or taken together with the nitrogen to which they are attached form a $C_2$-$C_6$ heteroalicyclyl;
$R_{14}$ and $R_{15}$ taken together with the carbon to which they are attached form a ring system selected from the group consisting of substituted or unsubstituted $C_{3-8}$ cycloalkyl, substituted or unsubstituted $C_{3-8}$ cycloalkenyl, substituted or unsubstituted $C_{2-9}$ heteroalicyclyl, substituted or unsubstituted aryl, and substituted or unsubstituted heteroaryl;
B is a ring system selected from the group consisting of aryl, heteroaryl, and, $C_2$-$C_9$ heteroalicyclyl.

2. The compound of claim 1, wherein $R_{3a}$ is selected from the group consisting of methyl, ethyl, cyclopropyl, and cyclobutyl.

3. The compound of claim 1, wherein $R_{3b}$ is hydrogen, and $R_{3c}$ is selected from the group consisting of hydrogen, methyl, cyclopropyl and cyclobutyl.

4. The compound of claim 1, wherein $R_{14}$ and $R_{15}$ taken together with the carbon to which they are attached form a ring system selected from the group consisting of substituted or unsubstituted $C_{3-7}$ cycloalkyl, substituted or unsubstituted $C_{3-7}$ cycloalkenyl, substituted or unsubstituted $C_{2-6}$ heteroalicyclyl, substituted or unsubstituted aryl, and substituted or unsubstituted heteroaryl.

5. The compound of claim 1, wherein $R_{14}$ and $R_{15}$ taken together with the carbon to which they are attached form a ring system selected from the group consisting of substituted or unsubstituted $C_{4-7}$ cycloalkyl, substituted or unsubstituted $C_6$-12 aryl, substituted or unsubstituted 4-membered heteroalicyclyl, substituted or unsubstituted 5-membered heteroaryl, substituted or unsubstituted 5-membered heteroalicyclyl, substituted or unsubstituted 6-membered heteroaryl, a substituted or unsubstituted 6-membered heteroalicyclyl, substituted or unsubstituted 7-membered heteroaryl, and a substituted or unsubstituted 7-membered heteroalicyclyl.

6. The compound of claim 1, wherein $R_{14}$ and $R_{15}$ taken together with the carbon to which they are attached form a ring system selected from the group consisting of phenyl, naphthyl, cyclopropyl, cyclobutyl, cyclopentyl, cyclohexyl, cycloheptyl, azetidinyl, thietanyl, pyrrolyl, pyrazolyl, imidazolyl, pyrrolidinyl, imidazolinyl, pyrazolidinyl, thiazolidinyl, isothiazolidinyl, triazolyl, tetrazolyl, oxazolyl, isoxazolyl, oxadiazolyl, oxathianyl, 1,4-oxathianyl-4,4-dioxide, thiazolyl, isothiazolyl, pyridinyl, pyridazinyl, pyrazinyl, pyrimidinyl, triazinyl, piperidinyl, piperazinyl, morpholinyl, thiomorpholinyl, dioxolanyl, dioxanyl, furyl, dihydrofuranyl, furazanyl, tetrahydrofuryl, pyranyl, tetrahydropyranyl, tetrahydrothiopyranyl, dithiolanyl, dithianyl, thiopyranyl, thianyl, thianyl-1,1-dioxide, thienyl, oxetanyl, quinolyl, isoquinolyl, indolyl, iso-indolyl, and tetrahydrothienyl, any of which may be substituted or unsubstituted.

7. The compounds of claim 6, wherein the ring system is selected from the group consisting of cycloheptyl, cyclohexyl, cyclopentyl, dioxanyl, furyl, imidazolyl, isothiazolyl, isoxazolyl, morpholinyl, oxazolyl, oxetanyl, oxathianyl, phenyl, piperidinyl, pyranyl, pyrazolidinyl, pyrazolyl, pyridinyl, pyrimidinyl, pyrrolidinyl, pyrrolyl, tetrahydrofuryl, tetrahydropyranyl, tetrazolyl, thianyl, thiazolyl, thienyl, thiomorpholinyl, thiopyranyl, and triazolyl, any of which may be substituted or unsubstituted.

8. The compound of 1, wherein the ring system formed by $R_{14}$ and $R_{15}$ taken together with the carbon to which they are attached is substituted with one or more —$(CH_2)q(R_{5a})$ wherein $R_{5a}$ is independently selected from the group consisting of —$CH_2COOR_{20}$, —$CH_2CONR_{21}R_{22}$, oxo, —CN, —$CH_2$—CN, $C_{1-6}$ alkyl, —$CH_2$-imidazolyl, —$CH_2$—$SO_2R_{20}$, —$CH_2C(CH_3)_2(OR_{20})$, —$OR_{20}$, —$CH_2$-triazolyl, —$CF_3$, dimethyl substituted-imidazolyl-2,4-dione, —$CH_2$—$SO_2NR_{21}R_{22}$, morpholinyl, —C(=O)-morpholinyl, piperidyl-$CH_2OR_{20}$, —$OCH_2$-tetrahydrofuryl, piperazinonyl, piperidinyl-$CONR_{21}R_{22}$, —OH, —$COR_{20}$, —$CONR_{21}R_{22}$, —$CH(OR_{20})CH_3$, —$COOR_{20}$, —$CH_2$-pyrrolidyl, $C_{1-6}$ alkylene-OH, cyclopentyl, pyrrolidonyl, tetrazolyl, —$CH_2$-tetrazolyl, —$CH_2OR_{20}$, acyl, —$SOR_{20}$, —$SO_2R_{20}$, —$SO_2NR_{21}R_{22}$, —$NR_{21}SO_2R_{20}$, and halogen;

$R_{20}$, $R_{21}$, and $R_{22}$ are independently selected from the group consisting of hydrogen, substituted or unsubstituted $C_{1-6}$ alkyl, —CN, substituted or unsubstituted $C_{3-6}$ cycloalkyl, substituted or unsubstituted $C_{2-6}$ heteroalicyclyl, or $R_{21}$ and $R_{22}$ are combined to form a $C_{3-6}$ cycloalkyl; and q is an integer selected from 0, 1 or 2.

9. The compound of claim 1, wherein $R_{13}$ is absent or selected from the group consisting of hydrogen, —CN, —$CH_3$, fluorine, —OH, —$CH_2OH$, —$OCH_3$, —$CH_2CH_2OH$, —$CO_2H$, —$CO_2$—$C_{1-4}$-alkyl, —$CH_2$—$SO_2R_{20}$ and —$CONR_8R_9$, wherein $R_8$ and $R_9$ are independently selected from hydrogen, $C_{1-4}$ alkyl, $C_{1-4}$ aminoalkyl, or $R_8$ and $R_9$ taken together with the nitrogen to which they are attached form a $C_2$-$C_6$ heteroalicyclyl, and $R_{20}$ is $C_{1-6}$ alkyl.

10. The compound of claim 1, wherein R is hydrogen.

11. The compound of claim 1, wherein $R_1$ is hydrogen.

12. The compound of claim 1, wherein $R_2$ is fluorine.

13. The compound of claim 1, wherein $R_{4a}$ is selected from the group consisting of hydrogen, halogen, $C_{1-6}$ alkyl, $C_{1-6}$ haloalkyl, $C_{1-6}$ hydroxyalkyl, —CN, $C_1$-$C_6$ alkoxy, $C_{1-6}$ haloalkoxy, $C_3$-$C_5$ cycloalkyl, heteroaryl and aryl.

14. The compound of claim 1, wherein $R_{4a}$ is selected from the group consisting of halogen, $C_{1-4}$ alkyl, $C_{1-4}$ haloalkyl, $C_1$-$C_4$ alkoxy, $C_{1-4}$ haloalkoxy, and heteroaryl.

15. The compound of claim 14, wherein $R_{4a}$ is selected from the group consisting of methyl, ethyl, propyl, isopropyl, tert-butyl, chlorine, fluorine, methoxy, ethoxy, $C_{1-2}$ haloalkyl, $C_{1-2}$ haloalkoxy, and triazolyl.

16. The compound of claim 1, wherein $R_{4a}$ is selected from the group consisting of —$CF_3$, —$CHF_2$, —$OCF_3$, and —$OCHF_2$.

17. The compound of claim 1, wherein $R_{4b}$ is selected from the group consisting of hydrogen, oxo, halogen, $C_{1-4}$ alkyl, $C_{1-4}$ haloalkyl, $C_{1-4}$ hydroxyalkyl, $C_1$-$C_4$ alkoxy, and $C_{1-4}$ haloalkoxy.

18. The compound of claim 1, wherein $R_{4b}$ is selected from the group consisting of methyl, ethyl, propyl, isopropyl, tert-butyl, chlorine, fluorine, methoxy, ethoxy, —OH, $C_{1-2}$ haloalkyl, and $C_{1-2}$ haloalkoxy.

19. The compound of claim 18, wherein $R_{4b}$ is selected from the group consisting of —$CF_3$, —$CF_2CF_3$, —$CHF_2$, —$OCF_3$, —$OCF_2CF_3$, and —$OCHF_2$.

20. The compound of claim 1, wherein $R_{6a}$ is hydrogen.

21. The compound of claim 1, wherein $R_{6b}$ is selected from the group consisting of hydrogen, $C_{1-6}$ alkyl, $C_{1-6}$ haloalkyl, $C_{1-6}$ hydroxyalkyl, $C_1$-$C_6$ alkoxy, $C_{1-6}$ haloalkoxy, $C_{1-6}$-alkoxy-$C_{1-6}$-alkyl, or $R_{6b}$ is selected from the group consisting of —$(CH_2)_q$—$C_{3-6}$ cycloalkyl, —$(CH_2)_q$-aryl, —$(CH_2)_q$—$C_{2-9}$ heteroalicyclyl, —$(CH_2)_q$-heteroaryl, which may be substituted by one or more substituent selected from the group consisting of halogen, $C_{1-4}$ alkyl, $C_{1-4}$ haloalkyl, $C_{1-4}$ alkoxy, $C_{3-5}$ cycloalkyl, —$(CH_2)_q$—$CONR_{23}R_{24}$, —$(CH_2)_q$—$SO_2R_{23}$, and —$(CH_2)_q$—$NR_{23}SO_2R_{24}$, wherein $R_{23}$, and $R_{24}$ are independently selected from the group consisting of hydrogen, substituted or unsubstituted $C_{1-6}$ alkyl, —CN, substituted or unsubstituted $C_{3-6}$ cycloalkyl, substituted or unsubstituted $C_{2-6}$ heteroalicyclyl; and q is an integer selected from 0, or 1.

22. The compound of claim 1, wherein $R_{6b}$ is selected from the group consisting of hydrogen, —$(CH_2)C(CH_3)_3$, phenyl, phenyl substituted with 1 to 3 halogens, —$CH(CH_3)OC(CH_3)_3$, —$CH_2$-phenyl-$OCH_3$, -phenyl-$OCH_3$, —$CH_2$-cyclohexyl-$CH_2CO_2H$, —$CH_2$-cyclohexyl-$CH_2CONH_2$, $CH_2$-cyclohexyl-$CH_2$-tetrazolyl, —$CH_2$-cyclohexyl-$CH_2OH$, —$CH_2$-cyclohexyl-$NHSO_2CH_3$, —$CH_2$-cyclohexyl-$NHSO_2CH_2CF_3$, —$CH_2$-cyclohexyl-$CH_2CN$, —$CH_2$-phenyl-$CH_2CO_2H$, —$CH_2$-phenyl-$CH_2CONH_2$, —$CH_2$-phenyl-$CH_2CONH CH_3$, —$CH_2$-phenyl-$CH_2$-tetrazolyl, —$CH_2$-phenyl-$CONH_2$, —$CH_2$-phenyl-$SO_2NH$-cyclopropyl, —$CH_2$-phenyl-$SO_2CH_3$, —$CH_2$-phenyl-$NHSO_2CF_3$, —$CH_2$-phenyl-$NHSO_2CH_3$, —$CH_2$-phenyl-$NHSO_2CHF_2$, —$CH_2$-pyridyl-$CH_3$, —$CH_2$-pyridyl-$SO_2CH_3$, —$CH_2$-pyridyl-$CH_2CONH_2$, —$CH_2$-pyrimidyl-$NHSO_2CH_3$, —$CH_2$-piperidyl-$COCH_3$, —$CH_2$-piperidyl-$SO_2CH_3$, —$CH_2$-piperidyl-$SO_2CF_3$, —$CH_2$-thienyl-$CH_2CO_2H$, —$CH_2$-cyclobutyl-$CH_2CO_2H$, —$CH_2$-cyclobutyl-$CH_2CONH_2$, —$CH_2$-cyclobutyl-$CO_2H$, —$CH_2$-cyclobutyl-$CONH_2$, —$CH_2$-tetrahydrothiopyranyl, —$CH_2$-cyclopentyl, —$CH_2$-cyclohexyl, —$CH_2$-tetrahydrofuranyl, —$CH_2$-tetrahydropyranyl, —$CH_2$-oxetanyl and —$CH_2$-pyranyl.

23. The compound of claim 22, wherein $R_{6b}$ is hydrogen.

24. The compound of claim 1, wherein $R_{6a}$ and $R_{6b}$ are combined to form a ring system selected from substituted or unsubstituted $C_{3-6}$ cycloalkyl, and substituted or unsubstituted $C_{2-5}$ heteroalicyclyl.

25. The compound of claim 1, wherein $R_7$, $R_8$ and $R_9$ are independently selected from hydrogen, substituted or unsubstituted $C_{1-6}$ alkyl, substituted or unsubstituted aryl-$C_{1-6}$ alkyl, substituted or unsubstituted heteroaryl-$C_{1-6}$ alkyl and substituted or unsubstituted aryl.

26. The compound of claim 25, wherein $R_7$, $R_8$ and $R_9$ are independently selected from hydrogen, $C_{1-6}$ alkyl, $C_{1-6}$ haloalkyl, $C_{1-6}$ hydroxyalkyl, and aryl.

27. The compound of claim 26, wherein $R_7$, $R_8$ and $R_9$ are independently selected from hydrogen, $C_{1-4}$ alkyl, $C_{1-4}$ haloalkyl, and $C_{1-4}$ hydroxyalkyl.

28. The compound of claim 27, wherein $R_7$, $R_8$ and $R_9$ are independently selected from the group consisting of hydrogen, methyl, ethyl and tert-butyl.

29. The compound of claim 1, wherein ring system B is aryl or heteroaryl.

30. The compound of claim 1 wherein at least one of $R_{4a}$ and $R_{4b}$ is not hydrogen.

31. The compound of claim 1, wherein ring system B is a selected from a 6-membered aryl ring with $R_{4a}$ in the para-position or meta-position, a 6-membered heteroaryl ring with $R_{4a}$ in the para-position or meta-position, or a 5-membered heteroaryl with $R_{4a}$ in the 2- or 3-position.

32. The compound of claim 1 wherein ring system B is selected from the group consisting of phenyl, pyridyl, pyrazolyl, pyridazinyl, pyrimidinyl, naphthyl and furanyl.

33. The compound of claim 1, wherein ring system B is a $C_2$-$C_9$ bicyclic heteroalicyclyl ring.

34. The compound of claim 33, wherein the $C_2$-$C_9$ bicyclic heteroalicyclyl ring is selected from 2H-benzo[b][1,4]oxazin-3(4H)-one, 3,4-dihydroquinolin-2(1H)-one, 1,2,3,4-tetrahydroquinoline, 3,4-dihydro-2H-benzo[b][1,4]oxazine, 2,3-dihydrobenzo[d]oxazole, 2,3-dihydro-1H-benzo[d]imidazole, indoline, and 1,3-dihydro-2H-benzo[d]imidazol-2-one, and benzo[d]oxazol-2(3H)-one.

35. The compound of claim 1, wherein n is an integer selected from the group consisting of 1, 2, 3 and 4.

36. The compound of claim 1, wherein n is 0.

37. The compound of claim 1, wherein p is 0.

38. The compound of claim 1, selected from the group consisting of:

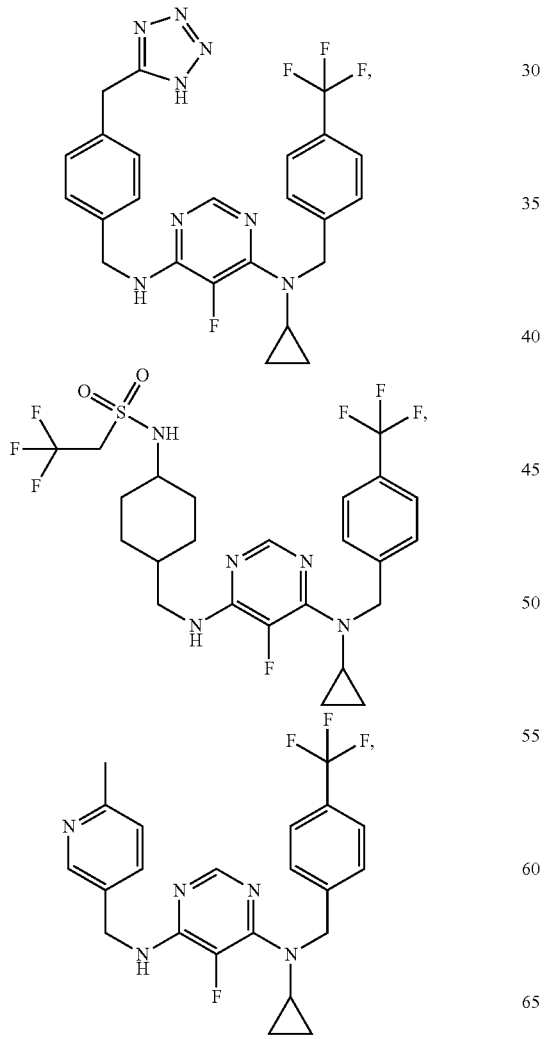

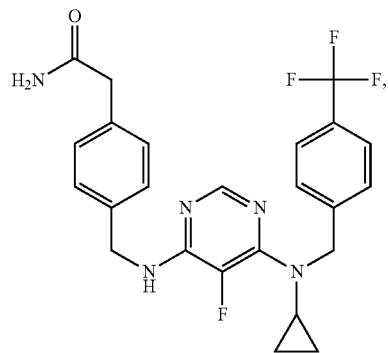

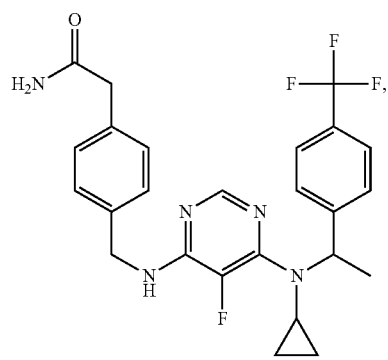

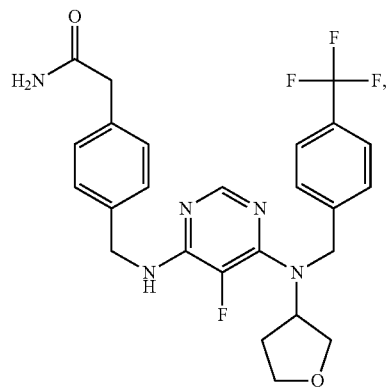

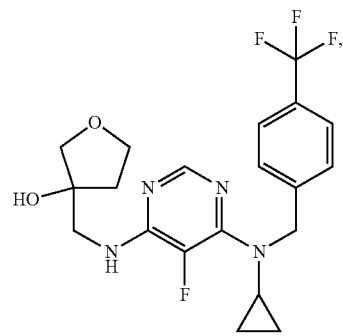

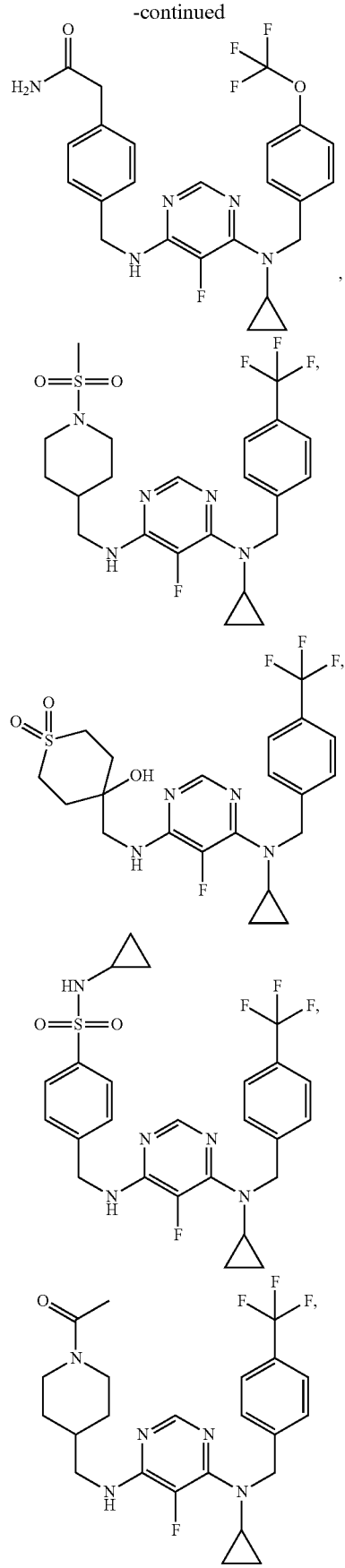
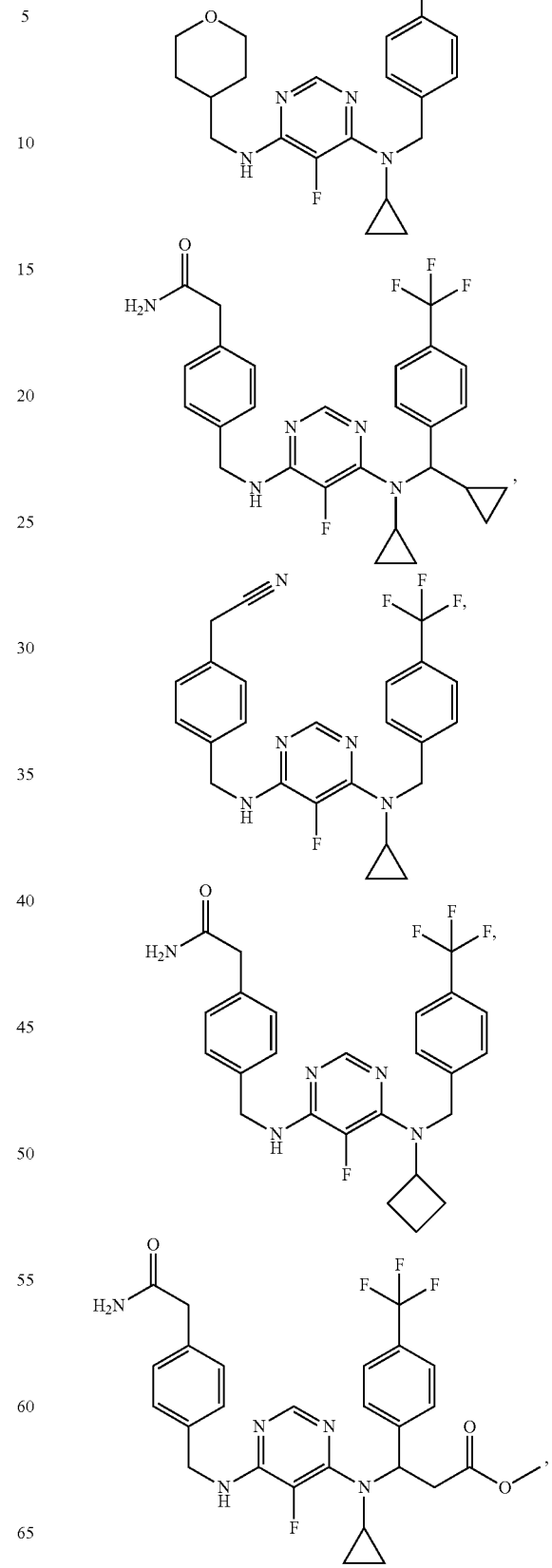

277
-continued
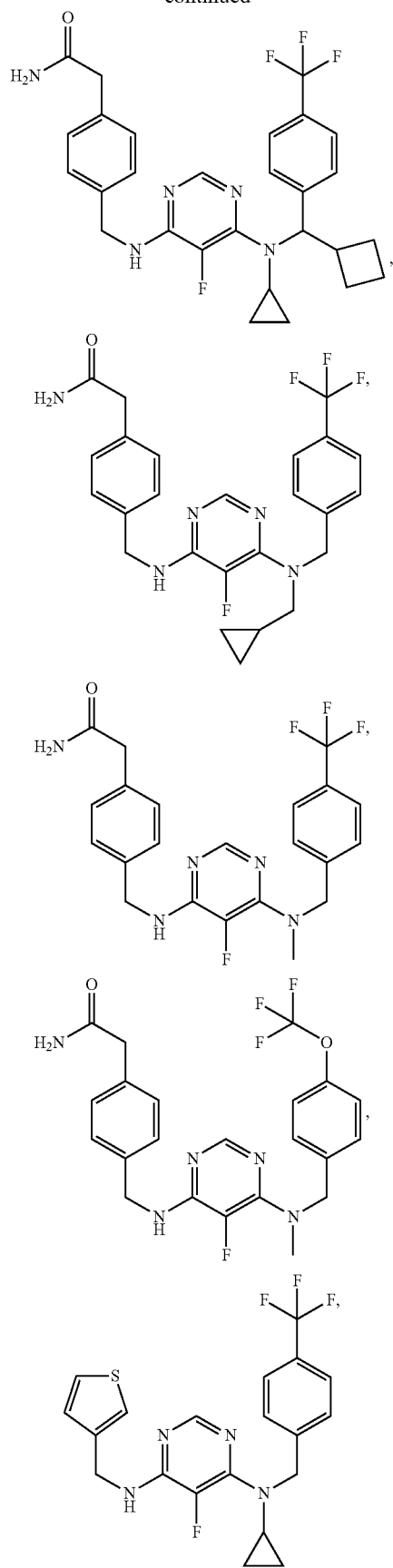
278
-continued
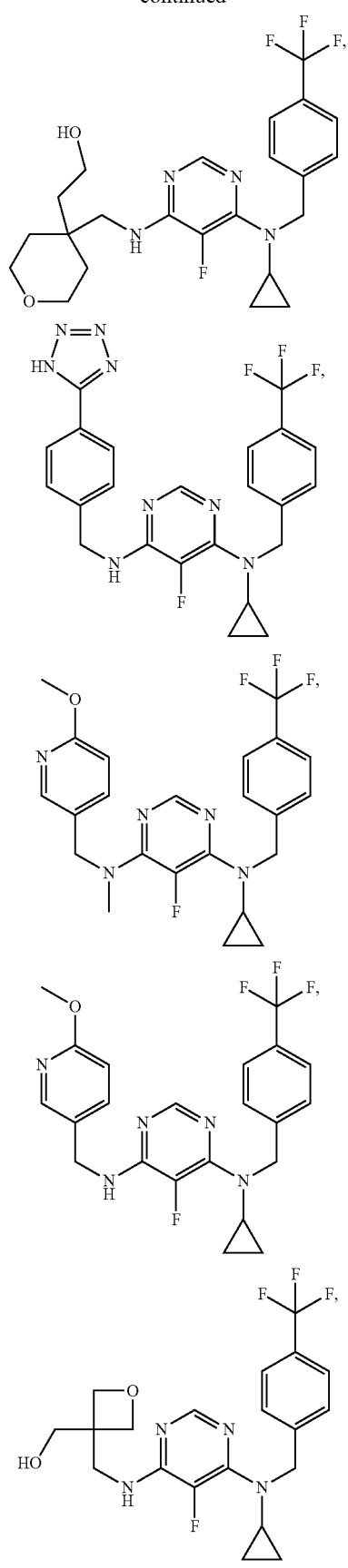

-continued
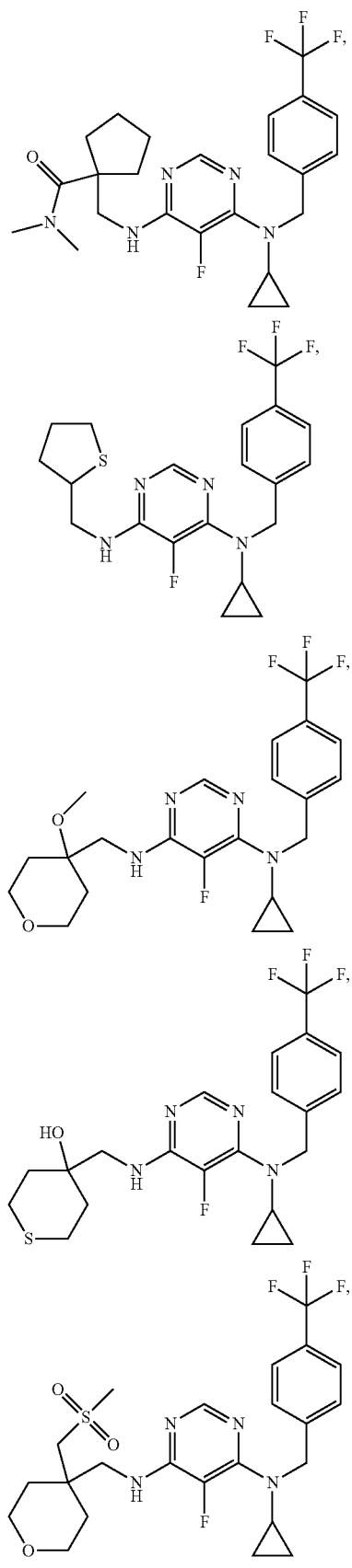
-continued
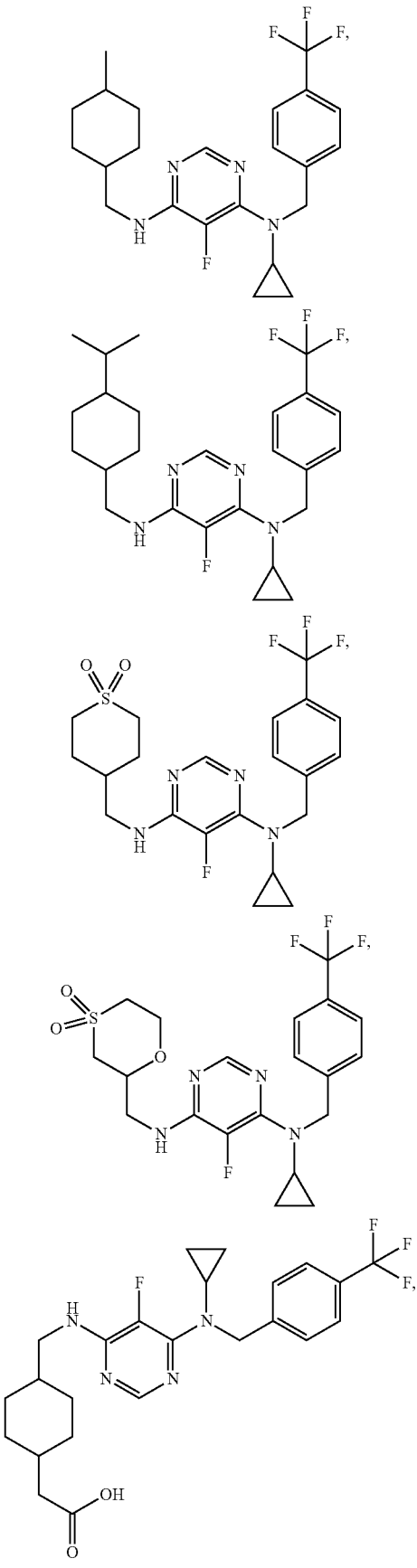

-continued
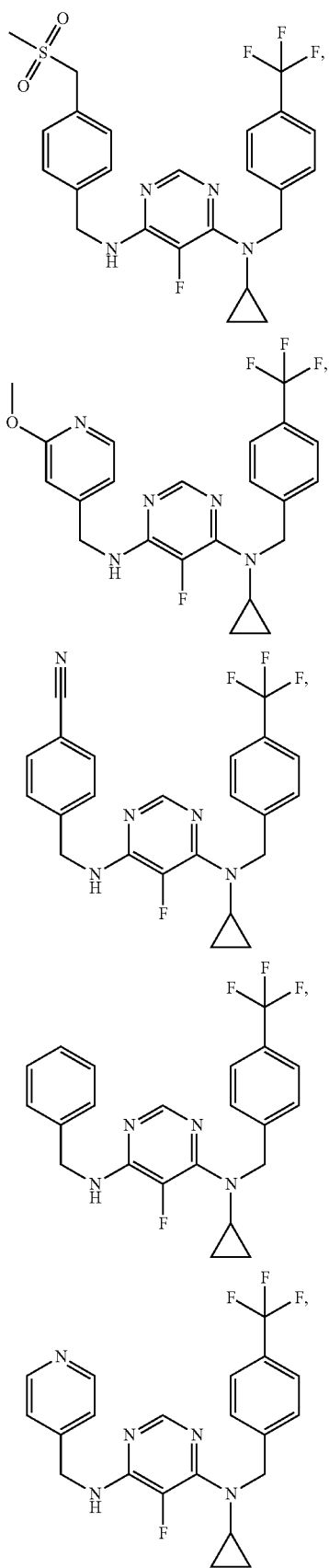
-continued
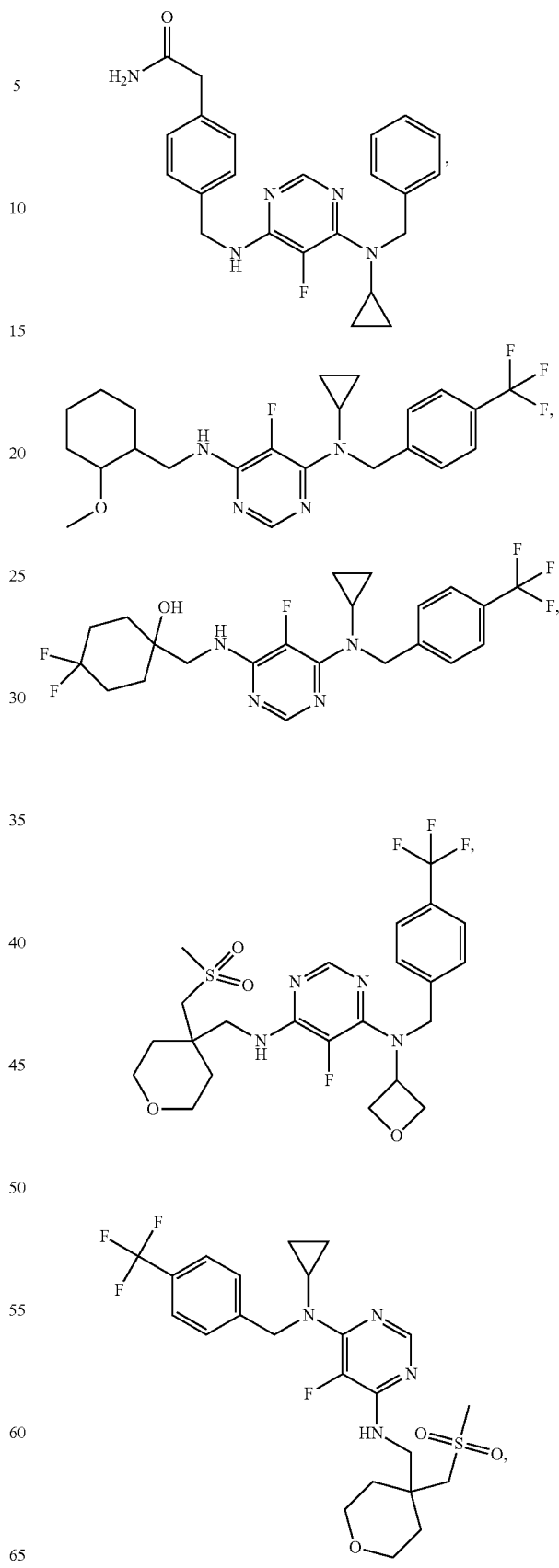

-continued
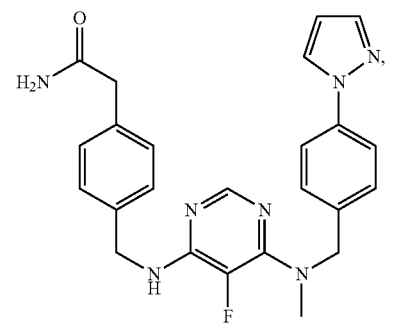
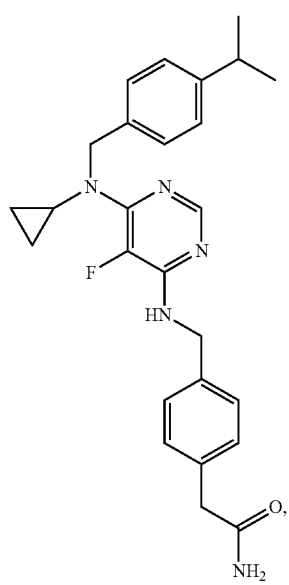
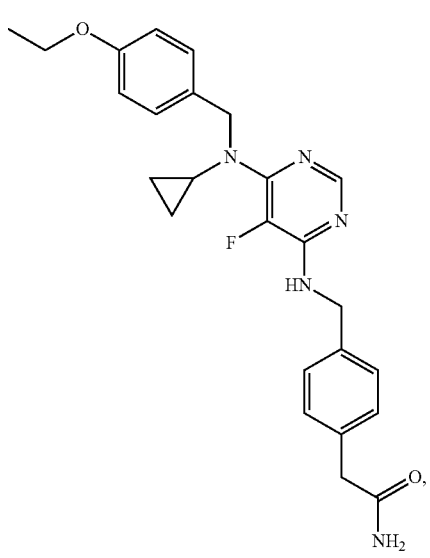
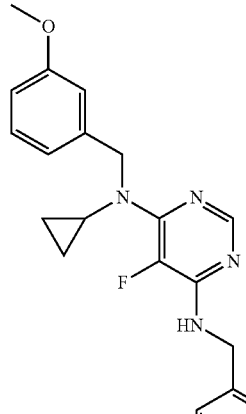
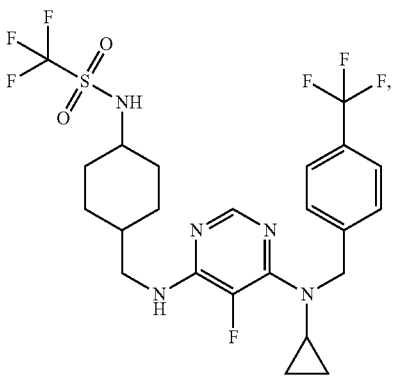
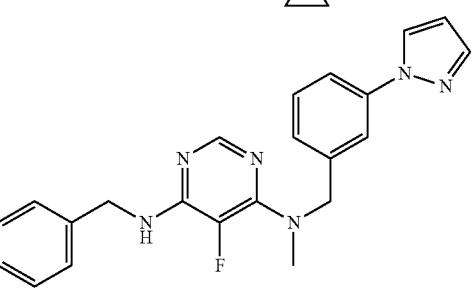
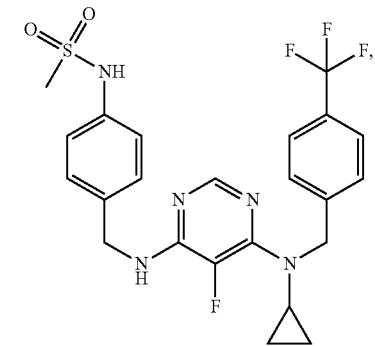

285
-continued
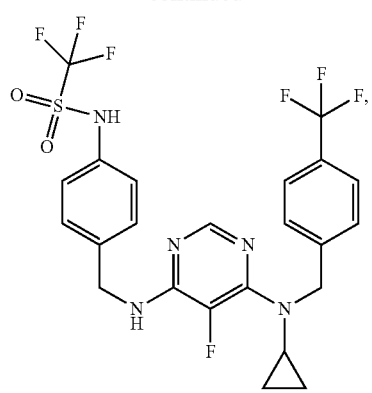
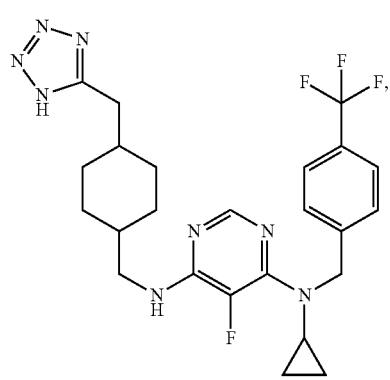
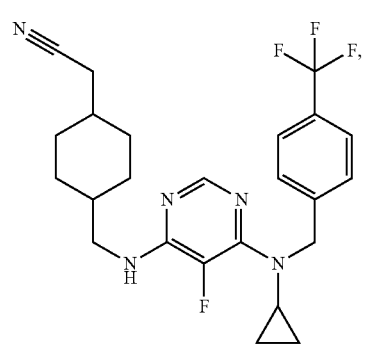
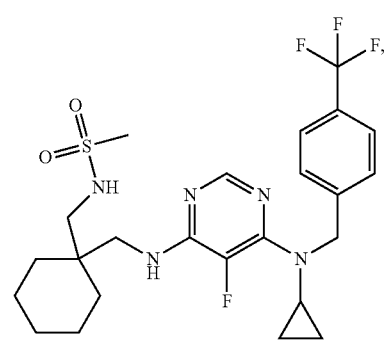
286
-continued
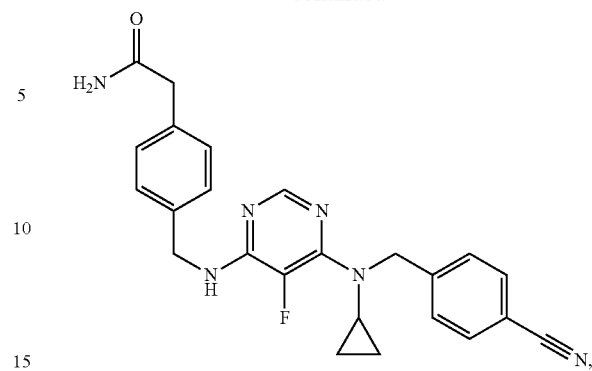
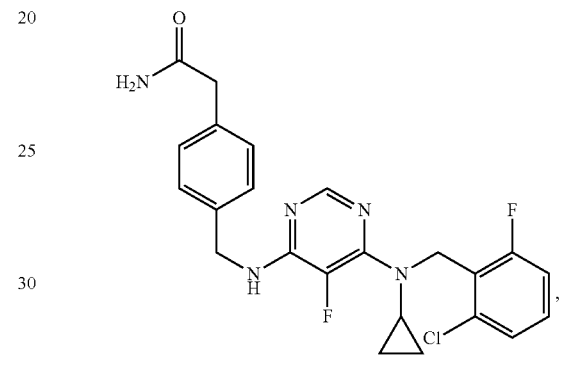
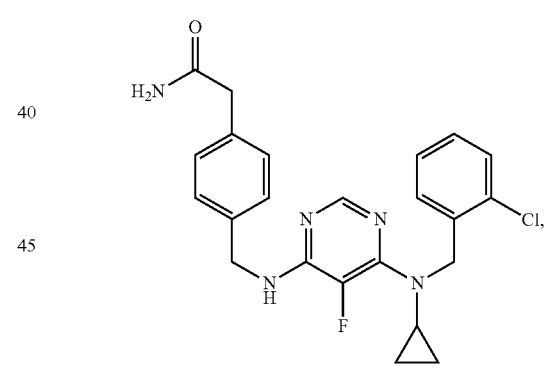
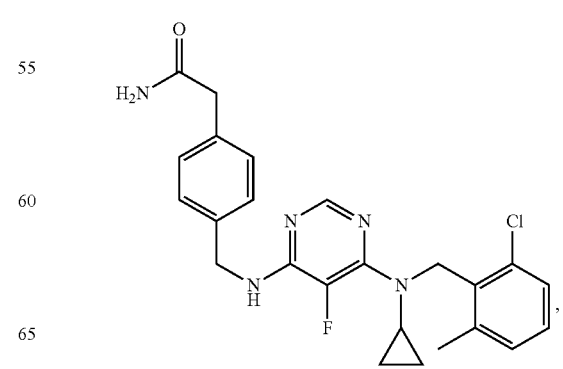

287
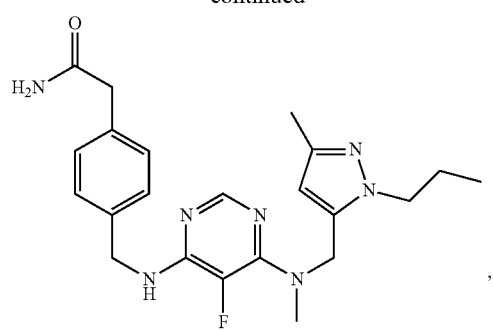
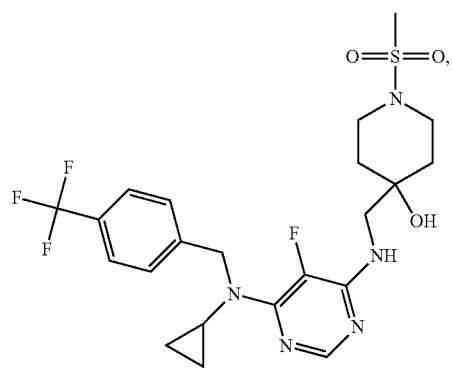
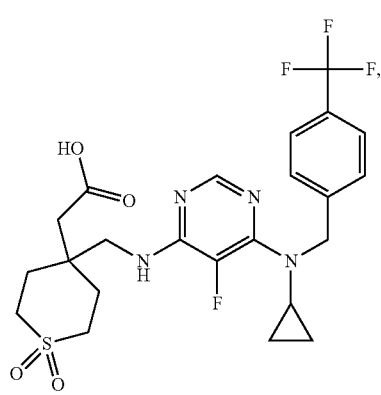
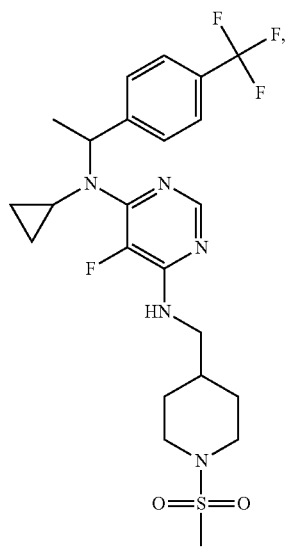
288
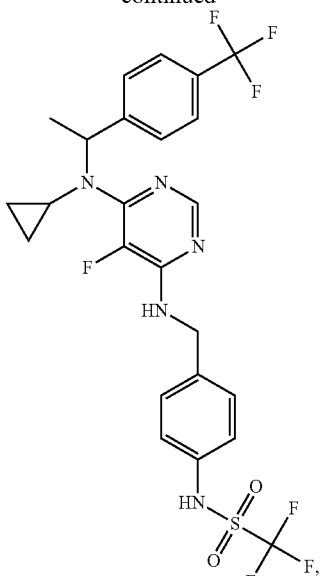
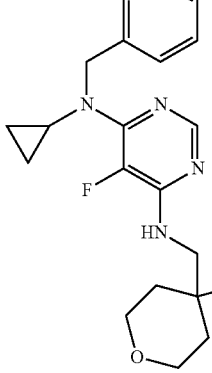
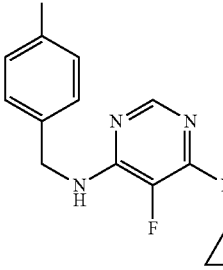
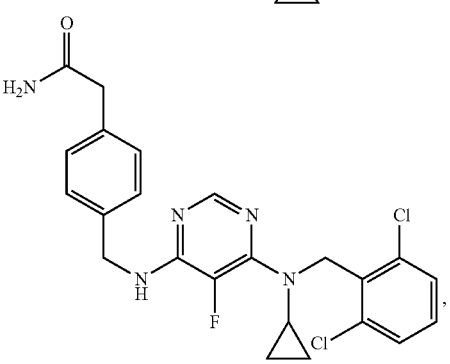

289
-continued
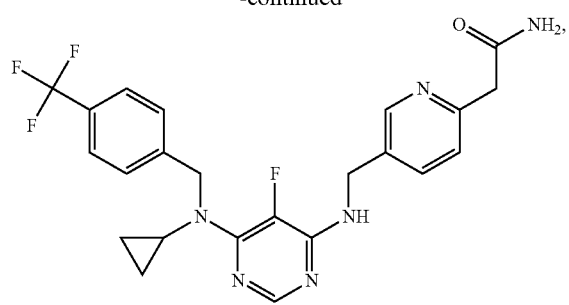
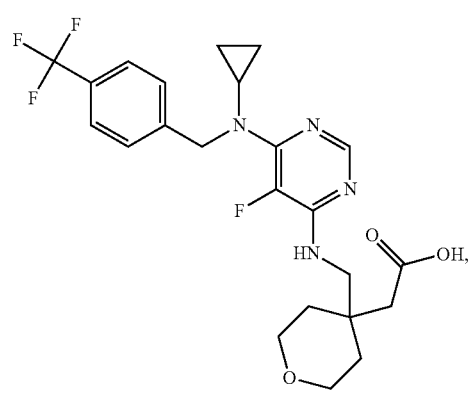
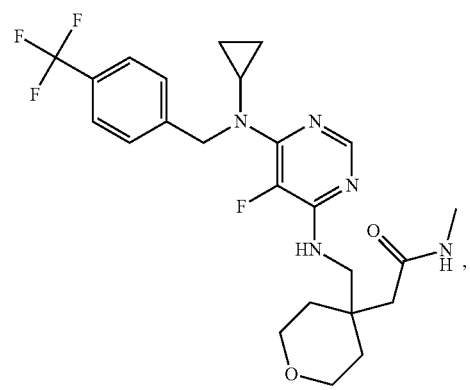
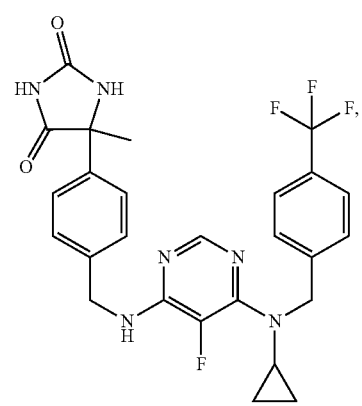
290
-continued
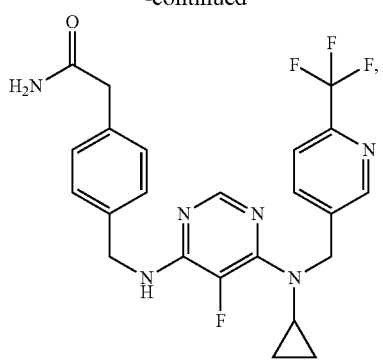
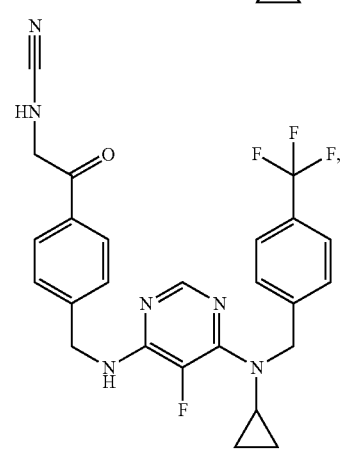
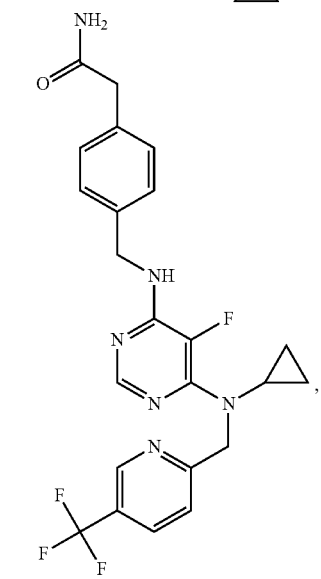
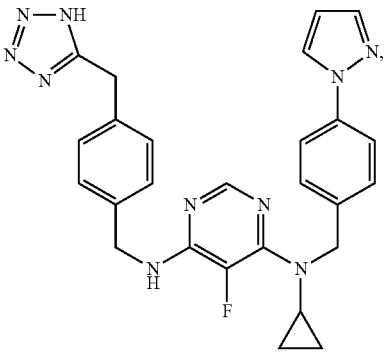

291
-continued
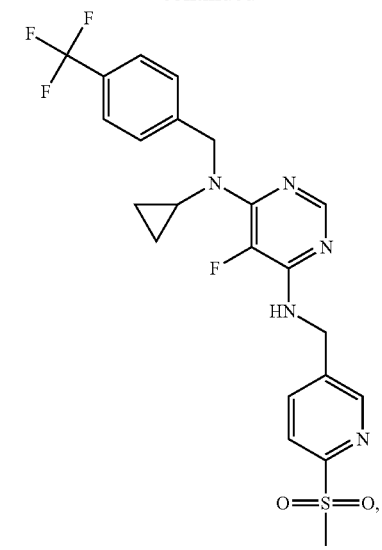
292
-continued
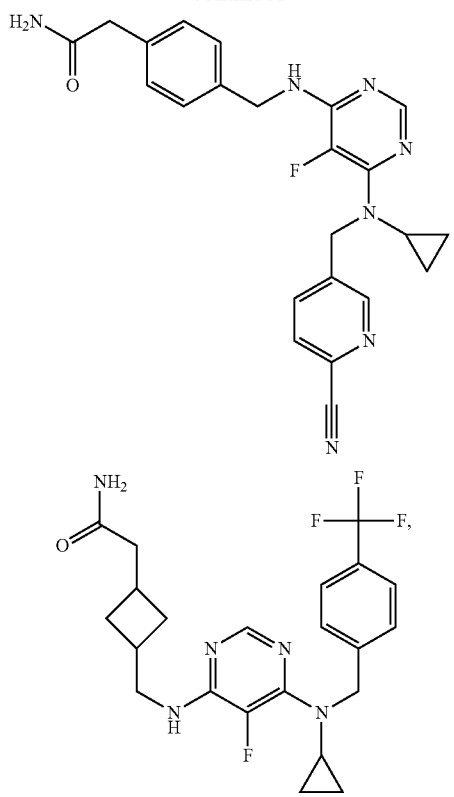
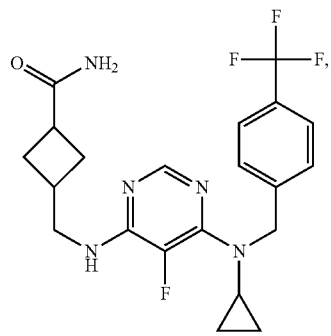
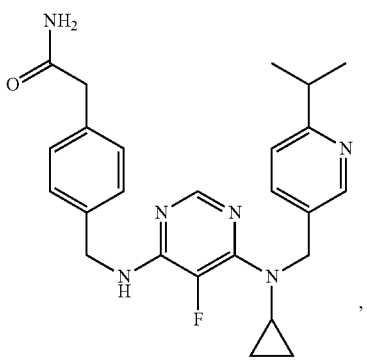

293
-continued
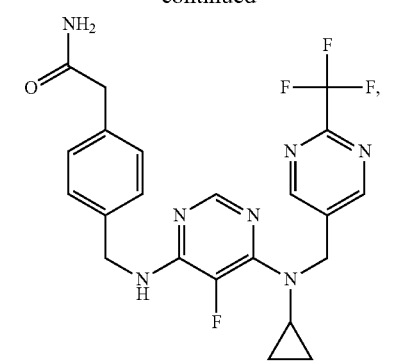
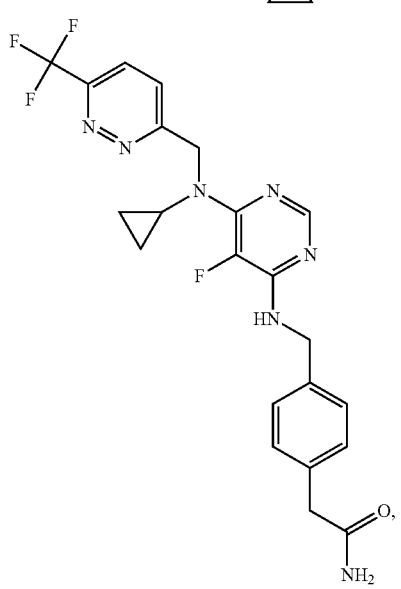
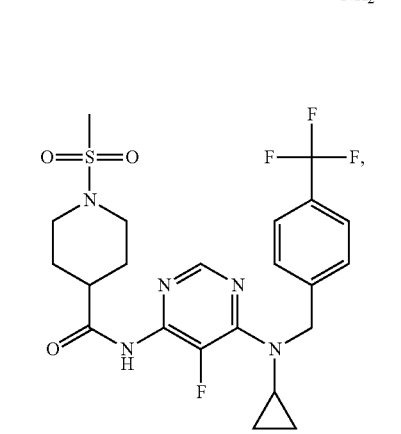
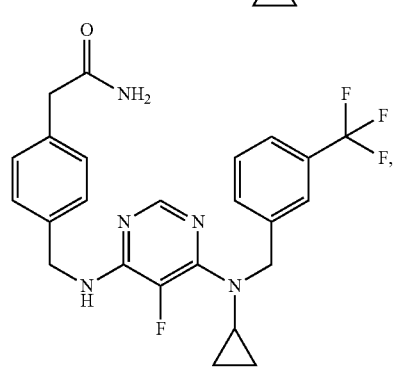
294
-continued
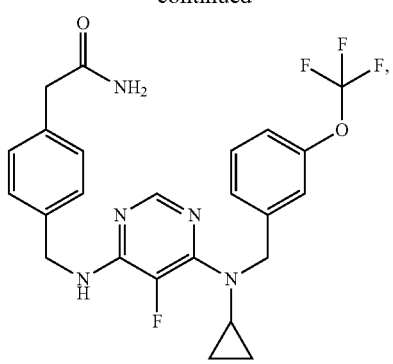
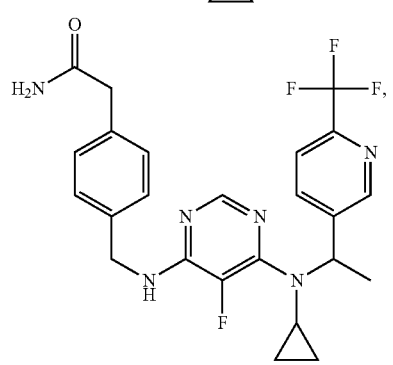
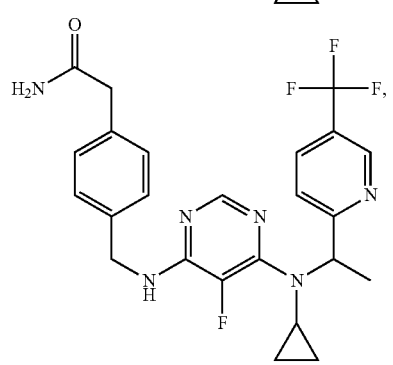
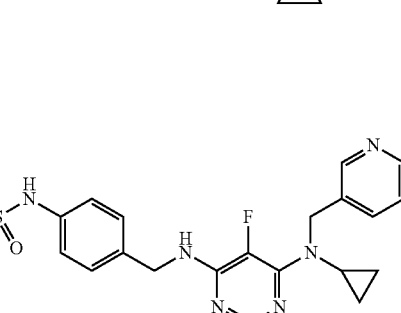
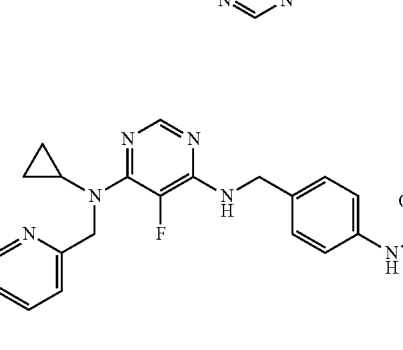

295
-continued
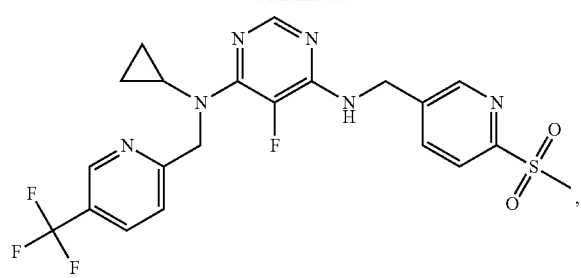
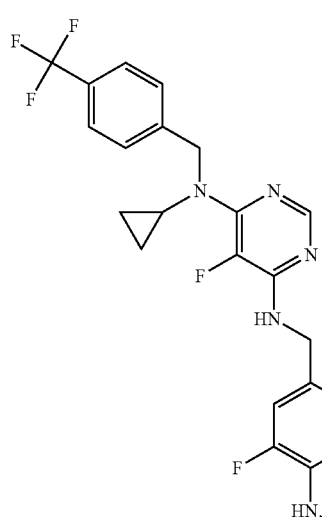
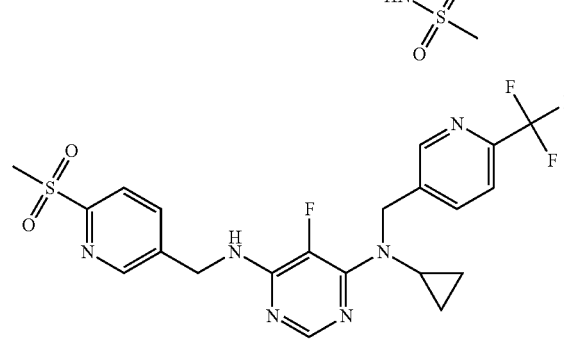
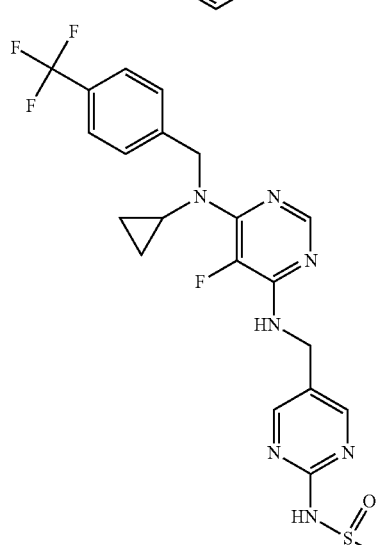
296
-continued
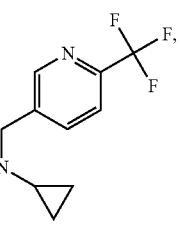
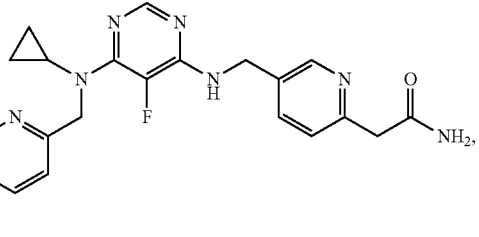
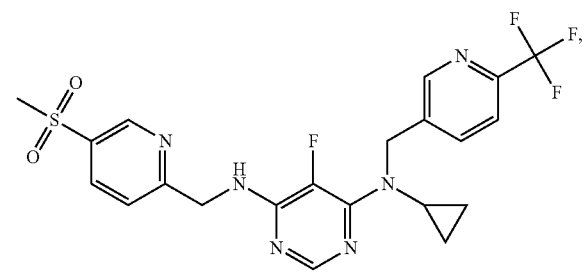
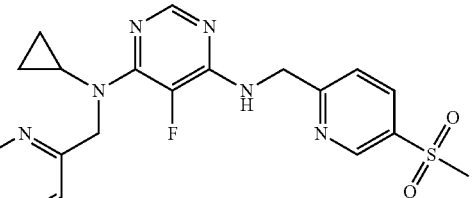
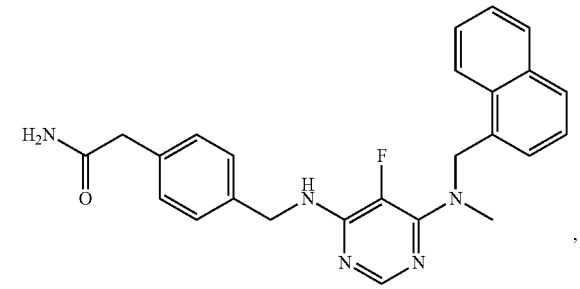
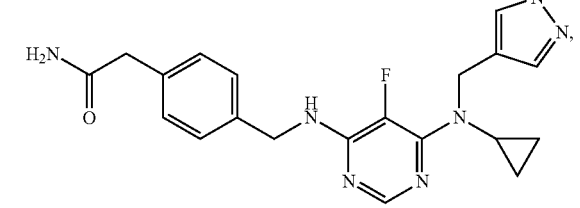

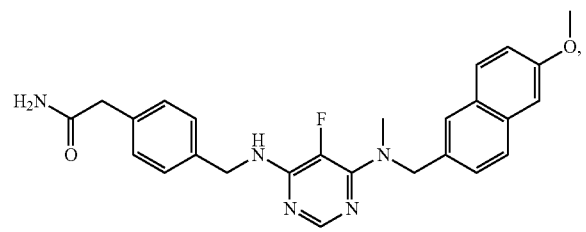
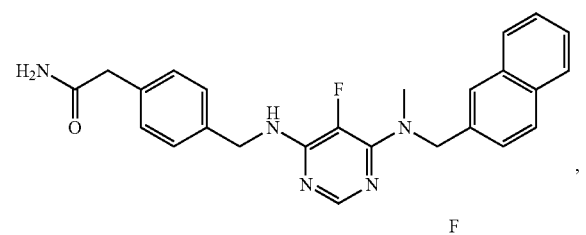
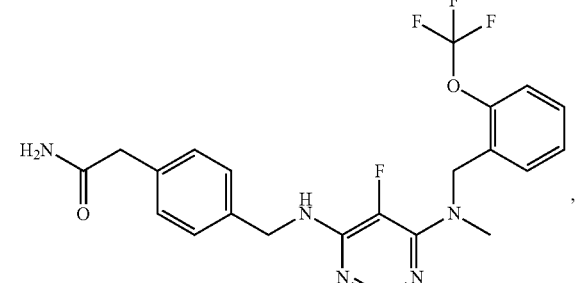
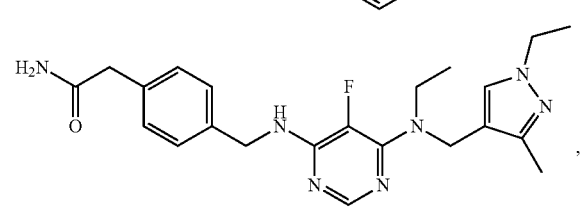
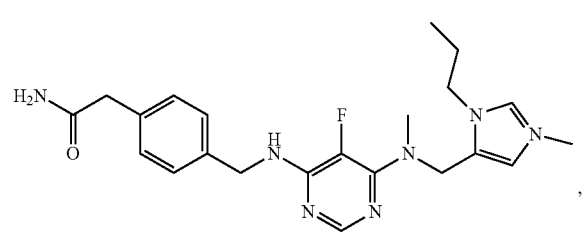
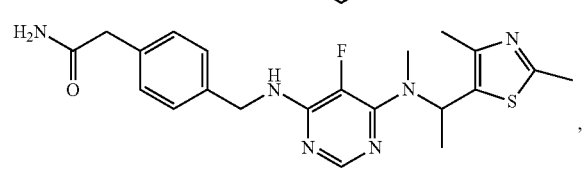
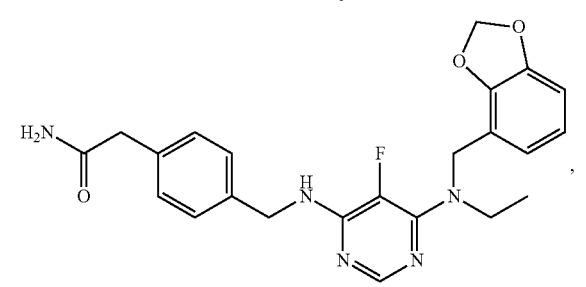
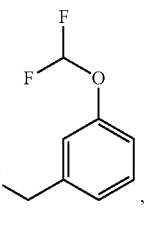
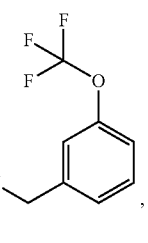
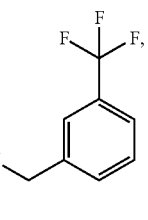
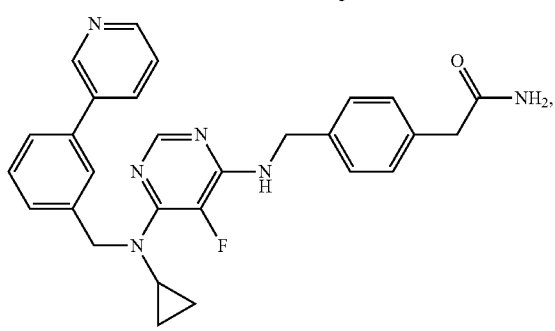
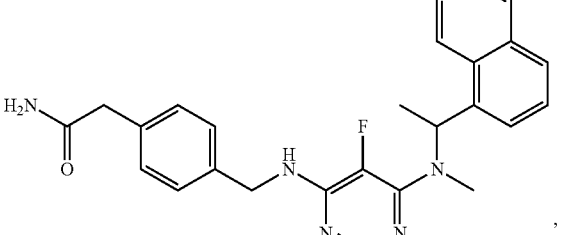
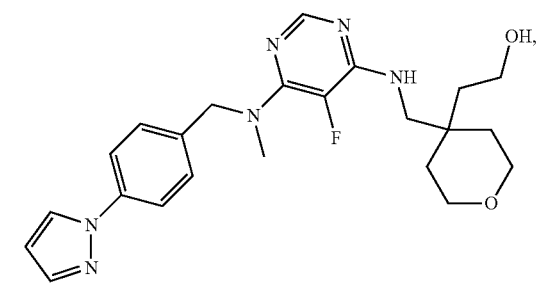

299
-continued
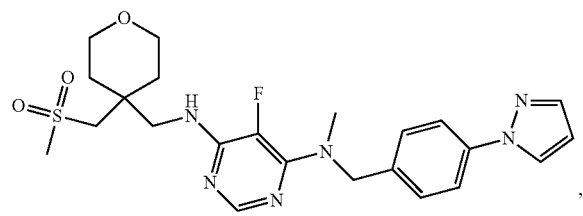
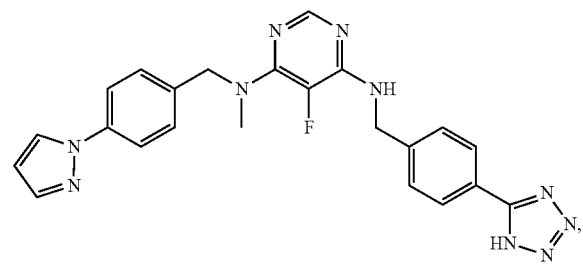
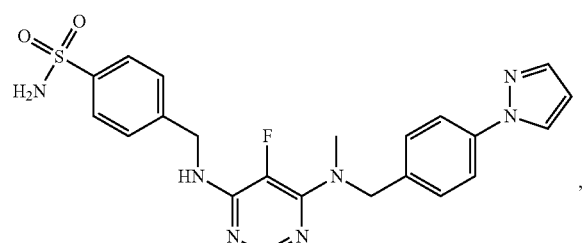
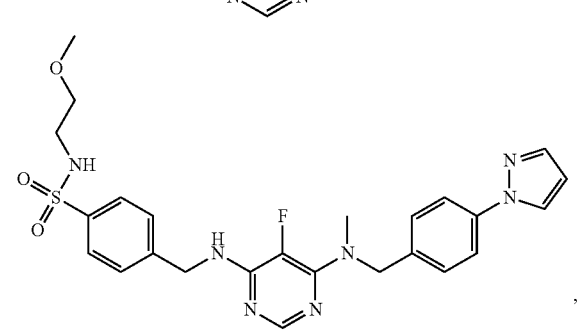
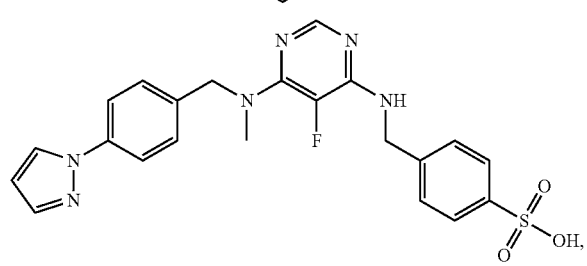
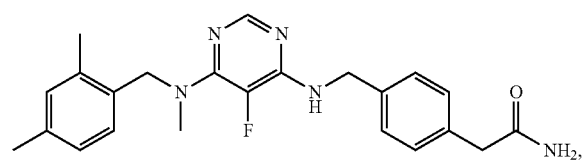
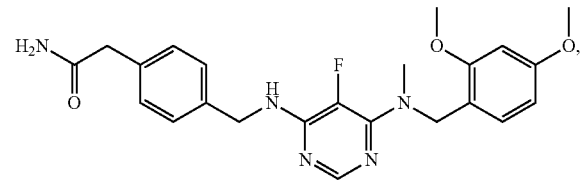
300
-continued
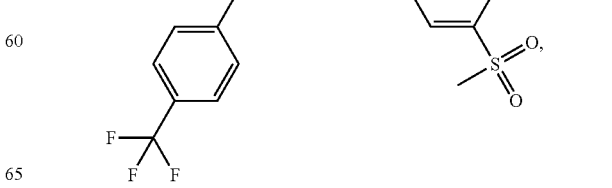

301
-continued
302
-continued
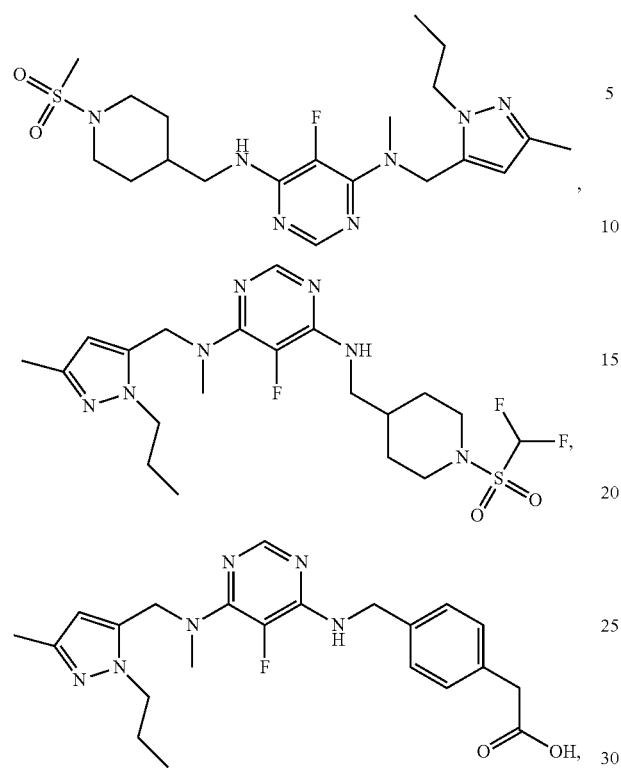
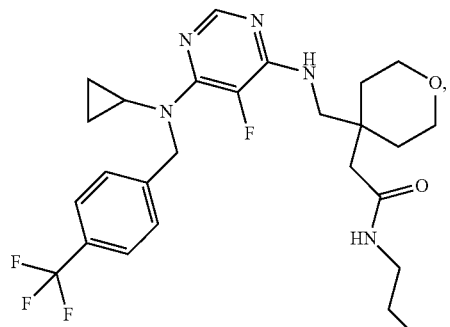
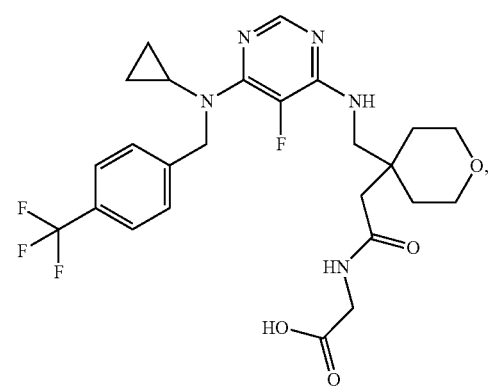
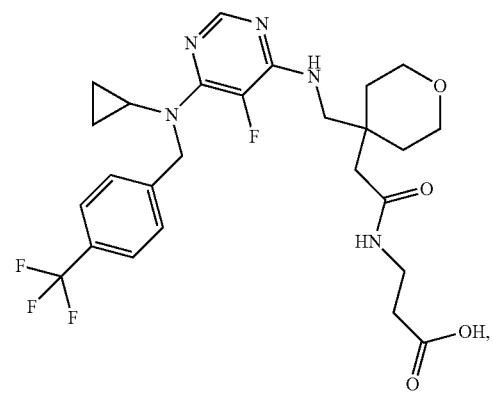
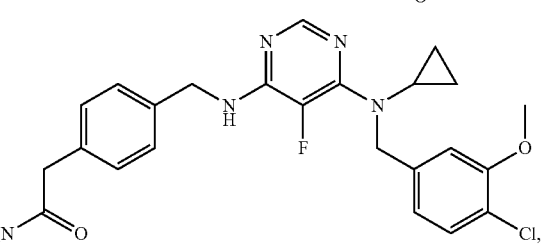
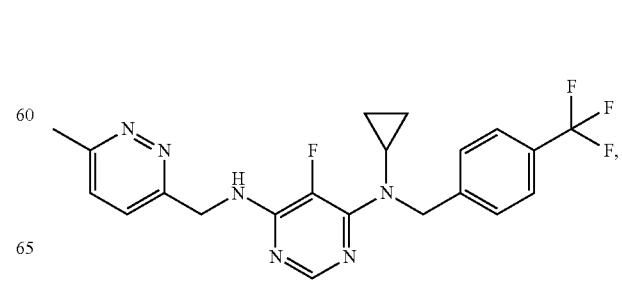

-continued
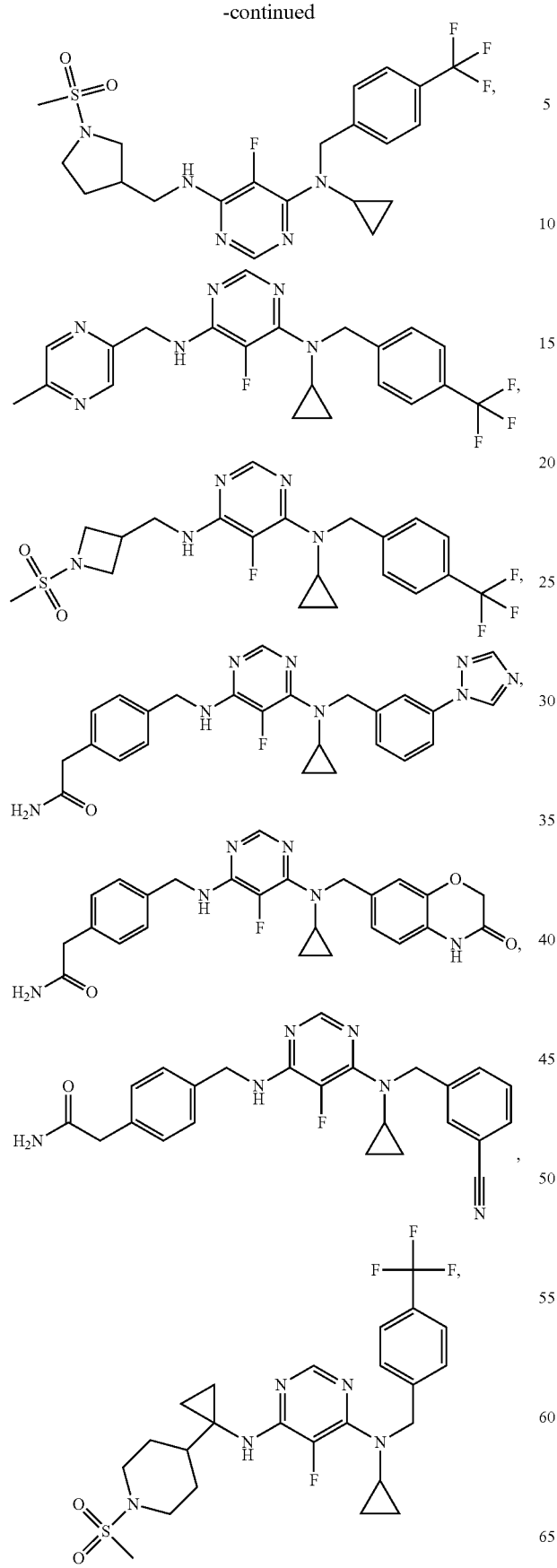
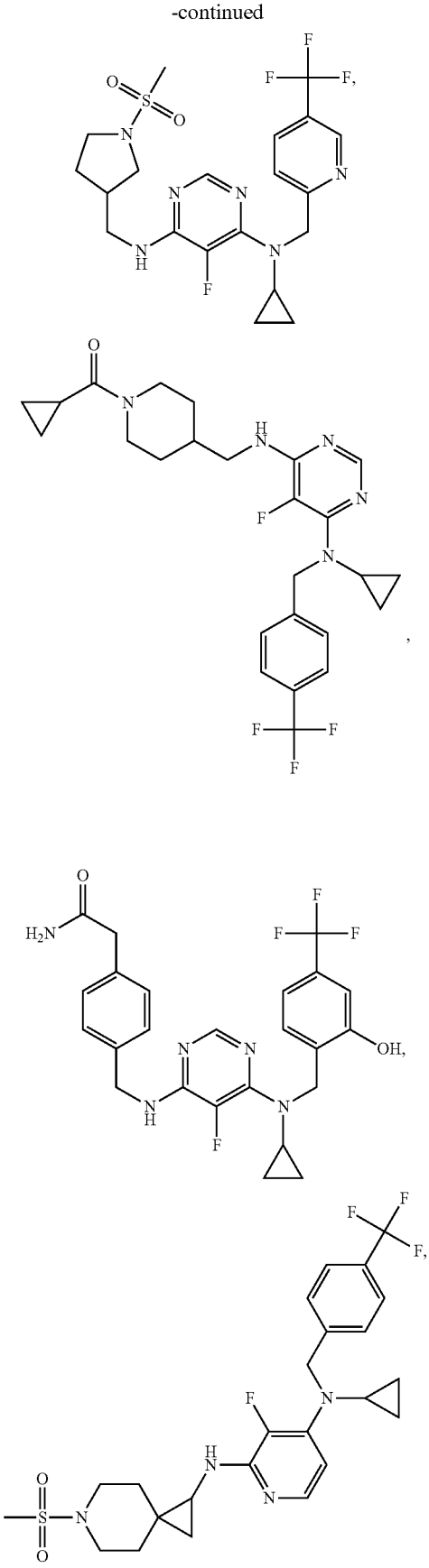

305
-continued
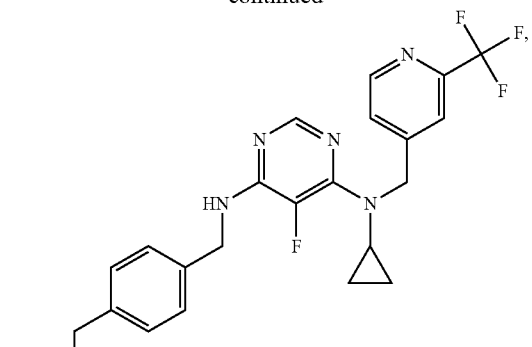
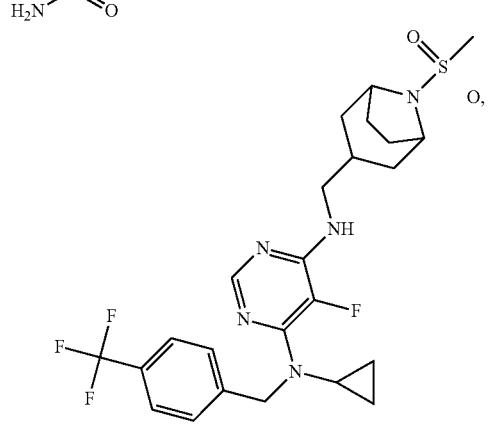
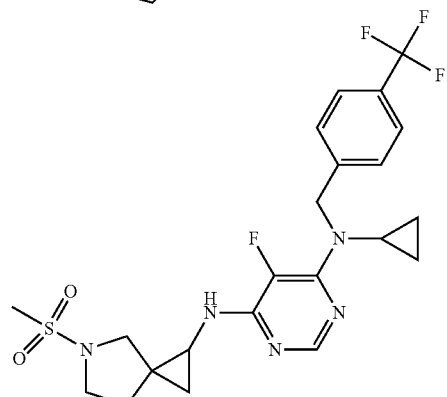
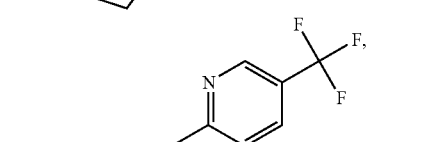
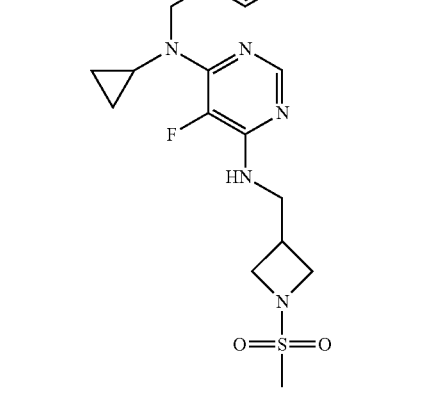
306
-continued
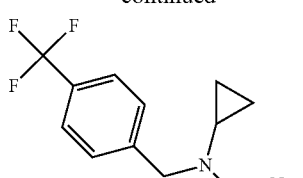
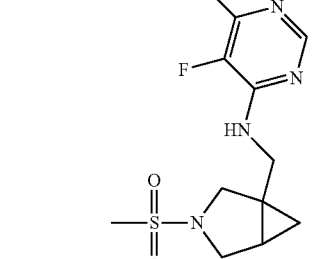
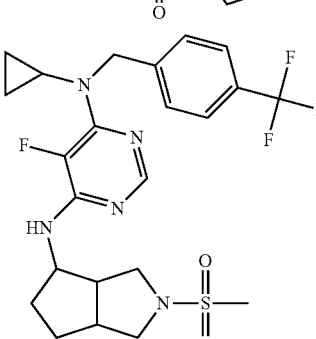
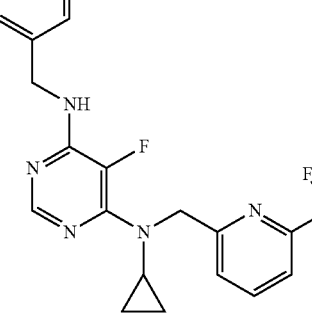
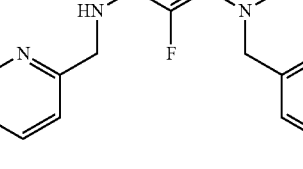

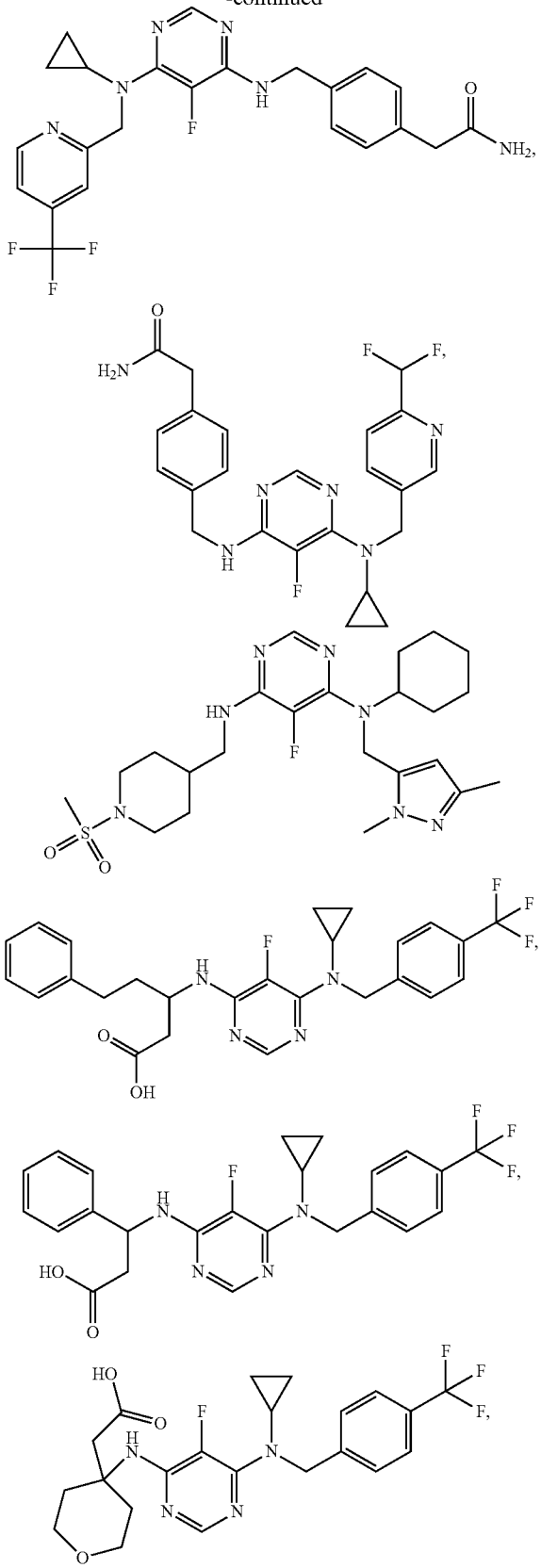
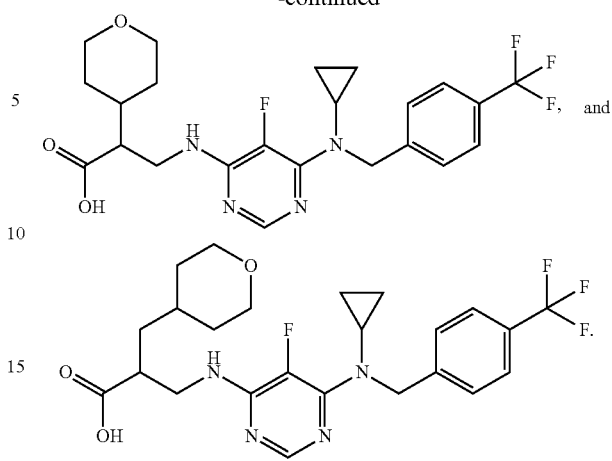

39. A pharmaceutical composition comprising a compound of claim 1 and at least one pharmaceutical acceptable excipient.

40. A method for treating inflammatory, metabolic or autoimmune diseases or disorders selected from the group consisting of asthma, chronic obstructive pulmonary disease (COPD), bronchitis, atherosclerosis, *Helicobacter pylori* infection, allergic diseases including allergic rhinitis, allergic conjunctivitis and uvetis, sprue and food allergy, atopic dermatitis, cystic fibrosis, lung allograph rejection, multiple sclerosis, rheumatoid arthritis, juvenile rheumatoid arthritis, osteoarthritis, ankylosing spondylitis, psoriasis, psoriatic arthritis, steatosis, steatohepatitis, non-alcoholic fatty liver disease (NAFLD), non-alcoholic steatohepatitis (NASH), lupus erythematosus, Hashimoto's disease, pancreatisis, autoimmune diabetes, autoimmune ocular disease, ulcerative colitis, colitis, Crohn's disease, inflammatory bowel disease (IBD), inflammatory bowel syndrome (IBS), Sjogren's syndrome, optic neuritis, type I diabetes, neuromyelitis optica, Myastehnia Gravis, Guillain-Barre syndrome, Graves' disease, scleritis, obesity, obesity-induced insulin resistance and type II diabetes, the method comprising administering a therapeutically effective amount of a compound of claim 1 to a patient in need thereof.

41. The compound of claim 1, wherein $R_{13}$ is absent, or is selected from the group consisting of hydrogen, —CN, —OH, substituted or unsubstituted $C_{1-6}$ alkyl, substituted or unsubstituted $C_{2-6}$ alkenyl, substituted or unsubstituted $C_{1-6}$ alkoxy, substituted or unsubstituted $C_{3-8}$ cycloalkyl, substituted or unsubstituted $C_{3-8}$ cycloalkenyl, and —$(CR_8R_9)p$-$C(=O)OR_7$, —$(CR_8R_9)p$-$SO_2R_7$, and —$(CR_8R_9)p$-$C(=O)NR_8R_9$.

42. The compound of claim 1, wherein $R_{4a}$ is selected from the group consisting of hydrogen, halogen, —OH, substituted or unsubstituted $C_{1-6}$ alkyl, substituted or unsubstituted $C_1$-$C_6$ alkoxy, substituted or unsubstituted $C_{2-6}$ alkenyl, substituted or unsubstituted aryl, substituted or unsubstituted aryl-$C_{1-6}$ alkyl, substituted or unsubstituted $C_3$-$C_6$ cycloalkyl, substituted or unsubstituted heteroaryl, and substituted or unsubstituted heteroaryl-$C_{1-6}$ alkyl.

* * * * *